(12) United States Patent
Sherwood

(10) Patent No.: US 8,465,555 B2
(45) Date of Patent: *Jun. 18, 2013

(54) METHOD AND APPARATUS FOR HIGH VOLTAGE ALUMINUM CAPACITOR DESIGN

(75) Inventor: Gregory J. Sherwood, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,339

(22) Filed: Feb. 27, 2012

(65) Prior Publication Data

US 2012/0151725 A1    Jun. 21, 2012

Related U.S. Application Data

(60) Continuation of application No. 11/684,941, filed on Mar. 12, 2007, now Pat. No. 8,133,286, which is a division of application No. 11/182,707, filed on Jul. 15, 2005, now Pat. No. 7,224,575.

(60) Provisional application No. 60/588,905, filed on Jul. 16, 2004.

(51) Int. Cl.
*H01G 9/00* (2006.01)

(52) U.S. Cl.
USPC ........ 29/25.03; 29/25.41; 29/25.42; 361/508; 361/509; 361/513; 361/517; 361/518; 361/522; 361/535; 361/541; 607/5

(58) Field of Classification Search
None
See application file for complete search history.

(56) References Cited

U.S. PATENT DOCUMENTS

| | | |
|---|---|---|
| 3,010,056 A | 11/1961 | Kurland et al. |
| 3,182,238 A | 5/1965 | Toder et al. |
| 3,211,154 A | 10/1965 | Becker et al. |
| 3,643,168 A | 2/1972 | Manicki |

(Continued)

FOREIGN PATENT DOCUMENTS

| | | |
|---|---|---|
| EP | 0510456 A1 | 10/1992 |
| EP | 0646391 A1 | 4/1995 |

(Continued)

OTHER PUBLICATIONS

"U.S. Appl. No. 09/706,447, Non-Final Office Action mailed Mar. 26, 2003", 5 pgs.

(Continued)

*Primary Examiner* — Julio J Maldonado
*Assistant Examiner* — Yasser Abdelaziez
(74) *Attorney, Agent, or Firm* — Schwegman Lundberg & Woessner, P.A.

(57) ABSTRACT

The present subject matter includes a method of producing an apparatus for use in a patient, the method including etching an anode foil, anodizing the anode foil, assembling the anode foil, at least one cathode foil and one or more separators into a capacitor stack adapted to deliver from about 5.3 joules per cubic centimeter of capacitor stack volume to about 6.3 joules per cubic centimeter of capacitor stack volume at a voltage of between about 465 volts to about 620 volts, inserting the stack into a capacitor case, inserting the capacitor case into a device housing adapted for implant in a patient, connecting the capacitor to a component and sealing the device housing.

20 Claims, 97 Drawing Sheets

U.S. PATENT DOCUMENTS

| | | |
|---|---|---|
| 3,723,926 A | 3/1973 | Thomas et al. |
| 3,742,938 A | 7/1973 | Stern |
| 3,777,570 A | 12/1973 | Thomas et al. |
| 3,803,457 A | 4/1974 | Yamamoto |
| 3,818,177 A | 6/1974 | Needham et al. |
| 3,826,143 A | 7/1974 | Thomas et al. |
| 3,828,227 A | 8/1974 | Millard et al. |
| 3,859,574 A | 1/1975 | Brazier |
| 3,894,210 A | 7/1975 | Smith et al. |
| 3,914,666 A | 10/1975 | Schmickl et al. |
| 3,938,228 A | 2/1976 | Kemkers et al. |
| 3,993,508 A | 11/1976 | Erlichman |
| 4,001,657 A | 1/1977 | Robinson |
| 4,033,848 A | 7/1977 | Strempel et al. |
| 4,047,790 A | 9/1977 | Carino |
| 4,059,216 A | 11/1977 | Meyer |
| 4,086,148 A | 4/1978 | Badia |
| 4,088,108 A | 5/1978 | Hager |
| 4,107,022 A | 8/1978 | Strempel et al. |
| 4,131,935 A | 12/1978 | Clement |
| 4,164,006 A | 8/1979 | Kolkowski |
| 4,169,003 A | 9/1979 | Dangel et al. |
| 4,232,099 A | 11/1980 | Sullivan |
| 4,252,575 A | 2/1981 | Bernard |
| 4,352,145 A | 9/1982 | Stockman |
| 4,384,188 A | 5/1983 | Wright, Jr. |
| 4,425,412 A | 1/1984 | Dittmann et al. |
| 4,481,083 A | 11/1984 | Ball et al. |
| 4,539,999 A | 9/1985 | Mans |
| 4,553,304 A | 11/1985 | Fleuret |
| 4,562,511 A | 12/1985 | Nishino et al. |
| 4,571,662 A | 2/1986 | Conquest et al. |
| 4,604,260 A | 8/1986 | Shimizu et al. |
| 4,614,194 A | 9/1986 | Jones et al. |
| 4,616,655 A | 10/1986 | Weinberg et al. |
| 4,659,636 A | 4/1987 | Suzuki et al. |
| 4,664,116 A | 5/1987 | Shaya et al. |
| 4,683,516 A | 7/1987 | Miller |
| 4,737,068 A | 4/1988 | Mochizuki |
| 4,745,039 A | 5/1988 | Yoshinaka |
| 4,763,229 A | 8/1988 | Ohtuka et al. |
| 4,773,523 A | 9/1988 | Hansen, Jr. et al. |
| 4,782,340 A | 11/1988 | Czubatyj et al. |
| 4,796,638 A | 1/1989 | Sasaki |
| 4,833,719 A | 5/1989 | Carme et al. |
| 4,843,518 A | 6/1989 | Okumura |
| 4,970,626 A | 11/1990 | Kakinoki et al. |
| 5,131,388 A | 7/1992 | Pless et al. |
| 5,142,439 A | 8/1992 | Huggett et al. |
| 5,173,375 A | 12/1992 | Cretzmeyer et al. |
| 5,175,067 A | 12/1992 | Taylor et al. |
| 5,195,019 A | 3/1993 | Hertz |
| 5,214,588 A | 5/1993 | Kaneko et al. |
| 5,227,960 A | 7/1993 | Kunishi et al. |
| 5,230,336 A | 7/1993 | Fain et al. |
| 5,279,029 A | 1/1994 | Burns |
| 5,302,414 A | 4/1994 | Alkhimov et al. |
| 5,306,581 A | 4/1994 | Taylor et al. |
| 5,367,437 A | 11/1994 | Anderson |
| 5,369,547 A | 11/1994 | Evans |
| 5,370,669 A | 12/1994 | Daglow et al. |
| 5,384,685 A | 1/1995 | Tong et al. |
| 5,385,575 A | 1/1995 | Adams |
| 5,414,588 A | 5/1995 | Barbee, Jr. et al. |
| 5,422,200 A | 6/1995 | Hope et al. |
| 5,428,499 A | 6/1995 | Szerlip et al. |
| 5,439,760 A | 8/1995 | Howard et al. |
| 5,448,997 A | 9/1995 | Kruse et al. |
| 5,449,448 A | 9/1995 | Kurihara et al. |
| 5,469,325 A | 11/1995 | Evans |
| 5,471,087 A | 11/1995 | Buerger, Jr. |
| 5,484,452 A | 1/1996 | Persson |
| 5,493,259 A | 2/1996 | Blalock et al. |
| 5,493,471 A | 2/1996 | Walther et al. |
| 5,507,781 A | 4/1996 | Kroll et al. |
| 5,507,966 A | 4/1996 | Liu |
| 5,522,851 A | 6/1996 | Fayram |
| 5,527,346 A | 6/1996 | Kroll |
| 5,554,178 A | 9/1996 | Dahl et al. |
| 5,559,667 A | 9/1996 | Evans |
| 5,584,890 A | 12/1996 | MacFarlane et al. |
| 5,628,801 A | 5/1997 | MacFarlane et al. |
| 5,634,938 A | 6/1997 | Swanson et al. |
| 5,640,756 A | 6/1997 | Brown et al. |
| 5,645,586 A | 7/1997 | Meltzer |
| 5,658,319 A | 8/1997 | Kroll |
| 5,660,737 A | 8/1997 | Elias et al. |
| 5,687,057 A | 11/1997 | Dapo |
| 5,687,851 A | 11/1997 | Schonenberger |
| 5,691,079 A | 11/1997 | Daugaard |
| 5,711,988 A | 1/1998 | Tsai et al. |
| 5,716,729 A | 2/1998 | Sunderland et al. |
| 5,720,767 A | 2/1998 | Amely-Velez |
| 5,737,181 A | 4/1998 | Evans |
| 5,738,104 A | 4/1998 | Lo et al. |
| 5,749,904 A | 5/1998 | Gliner et al. |
| 5,754,394 A | 5/1998 | Evans et al. |
| 5,759,394 A | 6/1998 | Rohrbach et al. |
| 5,774,261 A | 6/1998 | Omori et al. |
| 5,776,632 A | 7/1998 | Honegger |
| 5,779,699 A | 7/1998 | Lipson |
| 5,779,891 A | 7/1998 | Andelman |
| 5,790,368 A | 8/1998 | Naito et al. |
| 5,800,724 A | 9/1998 | Habeger et al. |
| 5,800,857 A | 9/1998 | Ahmad et al. |
| 5,801,917 A | 9/1998 | Elias |
| 5,808,857 A | 9/1998 | Stevens |
| 5,811,206 A | 9/1998 | Sunderland et al. |
| 5,814,082 A | 9/1998 | Fayram et al. |
| 5,821,033 A | 10/1998 | Cromack et al. |
| 5,827,326 A | 10/1998 | Kroll et al. |
| 5,855,995 A | 1/1999 | Haq et al. |
| 5,867,363 A | 2/1999 | Tsai et al. |
| 5,882,362 A | 3/1999 | Muffoletto et al. |
| 5,901,867 A | 5/1999 | Mattson |
| 5,908,151 A | 6/1999 | Elias |
| 5,922,215 A | 7/1999 | Pless et al. |
| 5,926,357 A | 7/1999 | Elias et al. |
| 5,930,109 A | 7/1999 | Fishler |
| 5,949,638 A | 9/1999 | Greenwood, Jr. et al. |
| 5,963,418 A | 10/1999 | Greenwood, Jr. et al. |
| 5,968,210 A | 10/1999 | Strange et al. |
| 5,973,906 A | 10/1999 | Stevenson et al. |
| 5,982,609 A | 11/1999 | Evans |
| 5,983,472 A | 11/1999 | Fayram et al. |
| 6,002,969 A | 12/1999 | Machek et al. |
| 6,004,692 A | 12/1999 | Muffoletto et al. |
| 6,006,133 A | 12/1999 | Lessar et al. |
| 6,009,348 A | 12/1999 | Rorvick et al. |
| 6,010,317 A | 1/2000 | Maget et al. |
| 6,030,480 A | 2/2000 | Face, Jr. et al. |
| 6,032,075 A | 2/2000 | Pignato et al. |
| 6,040,082 A | 3/2000 | Haas et al. |
| 6,042,624 A | 3/2000 | Breyen et al. |
| 6,047,211 A | 4/2000 | Swanson et al. |
| 6,052,625 A | 4/2000 | Marshall |
| 6,094,339 A | 7/2000 | Evans |
| 6,094,788 A | 8/2000 | Farahmandi et al. |
| 6,099,600 A | 8/2000 | Yan et al. |
| 6,104,961 A | 8/2000 | Conger et al. |
| 6,110,233 A | 8/2000 | O'Phelan et al. |
| 6,110,321 A | 8/2000 | Day et al. |
| 6,117,194 A | 9/2000 | Strange et al. |
| 6,118,651 A | 9/2000 | Mehrotra et al. |
| 6,118,652 A | 9/2000 | Casby et al. |
| 6,139,986 A | 10/2000 | Kurokawa et al. |
| 6,141,205 A | 10/2000 | Nutzman et al. |
| 6,148,233 A | 11/2000 | Owen et al. |
| 6,157,531 A | 12/2000 | Breyen et al. |
| 6,162,264 A | 12/2000 | Miyazaki et al. |
| 6,184,160 B1 | 2/2001 | Yan et al. |
| 6,187,028 B1 | 2/2001 | Munshi |
| 6,191,931 B1 | 2/2001 | Paspa et al. |
| 6,204,476 B1 | 3/2001 | Reynolds et al. |
| 6,212,063 B1 | 4/2001 | Johnson et al. |
| 6,225,778 B1 | 5/2001 | Hayama et al. |
| 6,241,751 B1 | 6/2001 | Morgan et al. |

| | | |
|---|---|---|
| 6,246,569 B1 | 6/2001 | Strange et al. |
| 6,249,423 B1 | 6/2001 | O'Phelan et al. |
| 6,249,709 B1 | 6/2001 | Conger et al. |
| 6,256,542 B1 | 7/2001 | Marshall et al. |
| 6,259,954 B1 | 7/2001 | Conger et al. |
| 6,275,371 B1 | 8/2001 | Yoshio et al. |
| 6,275,372 B1 | 8/2001 | Vassallo et al. |
| 6,275,373 B1 | 8/2001 | Marshall et al. |
| 6,275,729 B1 | 8/2001 | O'Phelan et al. |
| 6,297,943 B1 | 10/2001 | Carson |
| 6,299,752 B1 | 10/2001 | Strange et al. |
| 6,321,114 B1 | 11/2001 | Nutzman et al. |
| 6,326,587 B1 | 12/2001 | Cardineau et al. |
| 6,388,284 B2 | 5/2002 | Rhodes et al. |
| 6,388,866 B1 | 5/2002 | Rorvick et al. |
| 6,400,554 B1 | 6/2002 | Shiraishi et al. |
| 6,402,793 B1 | 6/2002 | Miltich et al. |
| 6,404,619 B1 | 6/2002 | Marshall et al. |
| 6,413,283 B1 | 7/2002 | Day et al. |
| 6,421,226 B1 | 7/2002 | O'Phelan et al. |
| 6,426,861 B1 | 7/2002 | Munshi |
| 6,426,864 B1 | 7/2002 | O'Phelan et al. |
| 6,442,015 B1 | 8/2002 | Niiori et al. |
| 6,445,948 B1 | 9/2002 | Somdahl et al. |
| 6,459,566 B1 | 10/2002 | Casby et al. |
| 6,477,037 B1 | 11/2002 | Nielsen et al. |
| 6,477,404 B1 | 11/2002 | Yonce et al. |
| 6,493,212 B1 | 12/2002 | Clarke et al. |
| 6,498,951 B1 | 12/2002 | Larson et al. |
| 6,509,588 B1 | 1/2003 | Barr et al. |
| 6,514,276 B2 | 2/2003 | Munshi |
| 6,522,525 B1 | 2/2003 | O'Phelan et al. |
| 6,555,945 B1 | 4/2003 | Baughman et al. |
| 6,556,863 B1 | 4/2003 | O'Phelan et al. |
| 6,560,089 B2 | 5/2003 | Miltich et al. |
| 6,571,126 B1 | 5/2003 | O'Phelan et al. |
| 6,585,152 B2 | 7/2003 | Farahmandi et al. |
| 6,587,329 B1 | 7/2003 | Feger |
| 6,597,564 B2 | 7/2003 | O'Phelan et al. |
| 6,603,654 B2 | 8/2003 | Rorvick |
| 6,631,072 B1 | 10/2003 | Paul et al. |
| 6,647,290 B2 | 11/2003 | Wuthrich |
| 6,661,644 B2 | 12/2003 | Shimada et al. |
| 6,668,193 B2 | 12/2003 | Ware et al. |
| 6,674,634 B2 | 1/2004 | O'Phelan et al. |
| 6,678,559 B1 | 1/2004 | Breyen et al. |
| 6,684,102 B1 | 1/2004 | O'Phelan et al. |
| 6,687,118 B1 | 2/2004 | O'Phelan et al. |
| 6,699,265 B1 | 3/2004 | O'Phelan et al. |
| 6,705,523 B1 | 3/2004 | Stamm et al. |
| 6,709,946 B2 | 3/2004 | O'Phelan et al. |
| 6,714,818 B1 | 3/2004 | Fishler et al. |
| 6,721,602 B2 | 4/2004 | Engmark et al. |
| 6,736,956 B1 | 5/2004 | Hemphill et al. |
| 6,763,265 B2 | 7/2004 | O'Phelan et al. |
| 6,763,266 B1 | 7/2004 | Kroll |
| 6,778,860 B2 | 8/2004 | Ostroff et al. |
| 6,795,729 B1 | 9/2004 | Breyen et al. |
| 6,799,072 B2 | 9/2004 | Ries et al. |
| 6,815,306 B1 | 11/2004 | Strange et al. |
| 6,819,544 B1 | 11/2004 | Nielsen et al. |
| 6,819,953 B2 | 11/2004 | Yonce et al. |
| 6,833,937 B1 | 12/2004 | Cholewo |
| 6,833,987 B1 | 12/2004 | O'Phelan |
| 6,839,224 B2 | 1/2005 | O'Phelan et al. |
| 6,850,405 B1 | 2/2005 | Mileham et al. |
| 6,853,538 B2 | 2/2005 | O'Phelan et al. |
| 6,881,232 B2 | 4/2005 | O'Phelan et al. |
| 6,885,887 B2 | 4/2005 | O'Phelan et al. |
| 6,957,103 B2 | 10/2005 | Schmidt et al. |
| 6,985,351 B2 | 1/2006 | O'Phelan et al. |
| 6,999,304 B2 | 2/2006 | Schmidt et al. |
| 7,031,139 B1 | 4/2006 | Fayram |
| 7,033,406 B2 | 4/2006 | Weir et al. |
| 7,043,300 B2 | 5/2006 | O'Phelan et al. |
| 7,043,301 B1 | 5/2006 | Kroll et al. |
| 7,157,671 B2 | 1/2007 | O'Phelan et al. |
| 7,224,575 B2 | 5/2007 | Sherwood |
| 7,466,536 B1 | 12/2008 | Weir et al. |
| 7,499,260 B2 | 3/2009 | Schott et al. |
| 7,667,954 B2 | 2/2010 | Lessner et al. |
| 8,133,286 B2 * | 3/2012 | Sherwood .................... 29/25.03 |
| 8,154,853 B2 | 4/2012 | Sherwood |
| 8,170,662 B2 | 5/2012 | Bocek et al. |
| 2001/0011183 A1 | 8/2001 | Munshi |
| 2001/0020319 A1 | 9/2001 | Farahmandi et al. |
| 2002/0035380 A1 | 3/2002 | Rissmann et al. |
| 2002/0067589 A1 | 6/2002 | Marshall et al. |
| 2002/0071240 A1 | 6/2002 | Rorvick et al. |
| 2002/0161406 A1 | 10/2002 | Silvian |
| 2003/0030969 A1 | 2/2003 | Farahmandi et al. |
| 2003/0055460 A1 | 3/2003 | Owen et al. |
| 2003/0056350 A1 | 3/2003 | Yan et al. |
| 2003/0077509 A1 | 4/2003 | Probst et al. |
| 2003/0078620 A1 | 4/2003 | Waltman |
| 2003/0088279 A1 | 5/2003 | Rissmann et al. |
| 2003/0176893 A1 | 9/2003 | Munshi |
| 2003/0199940 A1 | 10/2003 | Nyberg |
| 2003/0204216 A1 | 10/2003 | Ries et al. |
| 2003/0216786 A1 | 11/2003 | Russial |
| 2004/0032698 A1 | 2/2004 | Paul et al. |
| 2004/0127952 A1 | 7/2004 | O'Phelan et al. |
| 2004/0143297 A1 | 7/2004 | Ramsey |
| 2004/0147960 A1 | 7/2004 | O'Phelan et al. |
| 2004/0147961 A1 | 7/2004 | O'Phelan et al. |
| 2004/0173835 A1 | 9/2004 | Schmidt et al. |
| 2004/0174658 A1 | 9/2004 | O'Phelan et al. |
| 2004/0193221 A1 | 9/2004 | O'Phelan et al. |
| 2004/0215281 A1 | 10/2004 | O'Phelan et al. |
| 2004/0220627 A1 | 11/2004 | Crespi et al. |
| 2005/0017888 A1 | 1/2005 | Sherwood et al. |
| 2005/0052825 A1 | 3/2005 | O'Phelan |
| 2005/0264979 A1 | 12/2005 | Breyen et al. |
| 2006/0023400 A1 | 2/2006 | Sherwood |
| 2006/0259082 A1 | 11/2006 | Youker et al. |
| 2007/0088221 A1 | 4/2007 | Stahmann |
| 2007/0162077 A1 | 7/2007 | Sherwood |
| 2008/0029482 A1 | 2/2008 | Sherwood |
| 2008/0030927 A1 | 2/2008 | Sherwood |
| 2008/0032473 A1 | 2/2008 | Bocek et al. |
| 2008/0208270 A1 | 8/2008 | Linder et al. |

FOREIGN PATENT DOCUMENTS

| | | |
|---|---|---|
| GB | 825900 | 12/1959 |
| JP | 52-004051 | 1/1977 |
| JP | 59-083772 | 5/1984 |
| WO | WO-9827562 A1 | 6/1998 |
| WO | WO-9854739 A1 | 12/1998 |
| WO | WO-9951302 A1 | 10/1999 |
| WO | WO-0019470 A1 | 4/2000 |
| WO | WO-2005092436 A1 | 10/2005 |
| WO | WO-2008019141 A1 | 2/2008 |

OTHER PUBLICATIONS

"U.S. Appl. No. 09/706,447, Notice of Allowance mailed Sep. 23, 2003", 5 pgs.

"U.S. Appl. No. 09/706,447, Response filed Jan. 9, 2003 to Restriction Requirement mailed Dec. 11, 2002", 2 pgs.

"U.S. Appl. No. 09/706,447, Restriction Requirement mailed Dec. 11, 2002", 6 pgs.

"U.S. Appl. No. 09/706,447. Response filed Jun. 25, 2003 to Non Final Office Action mailed Mar. 26, 2003", 10 pgs.

"U.S. Appl. No. 11/182,707, Non-Final Office Action mailed Feb. 24, 2006", 15 pgs.

"U.S. Appl. No. 11/182,707, Notice of Allowance mailed Nov. 16, 2006", 7 pgs.

"U.S. Appl. No. 11/182,707, Response filed Aug. 24, 2006 to Non-Final Office Action mailed Feb. 24, 2006", 9 pgs.

"U.S. Appl. No. 11/182,707, Supplemental Notice of Allowance mailed Feb. 12, 2007", 5 pgs.

"U.S. Appl. No. 11/462,281, Final Office Action mailed Mar. 24, 2009", 9 pgs.

"U.S. Appl. No. 11/462,281, Final Office Action mailed Apr. 1, 2010", 12 pgs.

"U.S. Appl. No. 11/462,281, Final Office Action mailed Mar. 21, 2011", 15 pgs.

"U.S. Appl. No. 11/462,281, Non Final Action Mailed Oct. 8, 2008", 14 pgs.
"U.S. Appl. No. 11/462,281, Non Final Office Action Mailed Oct. 1, 2009", 12 pgs.
"U.S. Appl. No. 11/462,281, Non-Final Office Action mailed Aug. 19, 2010", 11 pgs.
"U.S. Appl. No. 11/462,281, Response filed Jun. 30, 2010 to Final Office Action mailed Apr. 1, 2010", 9 pgs.
"U.S. Appl. No. 11/462,281, Response filed Sep. 15, 2011 to Final Office Action mailed Mar. 21, 2011", 11 pgs.
"U.S. Appl. No. 11/462,281, Response filed Jan. 8, 2009 to Non Final Office Action mailed Oct. 8, 2008", 13 pgs.
"U.S. Appl. No. 11/462,281, Response filed Dec. 20, 2010 to Non-Final Office Action mailed Aug. 19, 2010", 13 pgs.
"U.S. Appl. No. 11/462,281, Response filed Dec. 29, 2009 to Non Final Office Action mailed Oct. 1, 2009", 11 pgs.
"U.S. Appl. No. 11/462,281, Response filed Aug. 24, 2009 to Final Office Action mailed Mar. 24, 2009", 8 pgs.
"U.S. Appl. No. 11/462,295, Final Office Action mailed Sep. 17, 2010", 8 pgs.
"U.S. Appl. No. 11/462,295, Non Final Office Action mailed Apr. 5, 2011", 9 pgs.
"U.S. Appl. No. 11/462,295, Non-Final Office Action mailed Aug. 21, 2008", 7 pgs.
"U.S. Appl. No. 11/462,295, Non-Final Office Action mailed Feb. 19, 2010", 9 pgs.
"U.S. Appl. No. 11/462,295, Notice of Allowance mailed Apr. 7, 2009", 6 pgs.
"U.S. Appl. No. 11/462,295, Notice of Allowance mailed Jul. 27, 2009", 6 pgs.
"U.S. Appl. No. 11/462,295, Notice of Allowance mailed Dec. 16, 2008", 7 pgs.
"U.S. Appl. No. 11/462,295, Response filed Jan. 11, 2011 to Final Office Action mailed Sep. 17, 2010", 9 pgs.
"U.S. Appl. No. 11/462,295, Response filed Jun. 21, 2010 to Non Final Office Action mailed Feb. 19, 2010", 11 pgs.
"U.S. Appl. No. 11/462,295, Response filed Sep. 15, 2011 to Non-Final Office Action mailed Apr. 5, 2011", 10 pgs.
"U.S. Appl. No. 11/462,295, Response filed Nov. 18, 2008 to Non Final Office Action mailed Aug. 21, 2008", 14 pgs.
"U.S. Appl. No. 11/462,301, *Ex Parte Quayle* mailed Oct. 14, 2011", 6 pgs.
"U.S. Appl. No. 11/462,301, Final Office Action Mailed Sep. 3, 2009", 11 pgs.
"U.S. Appl. No. 11/462,301, Final Office Action mailed Sep. 16, 2010", 13 pgs.
"U.S. Appl. No. 11/462,301, Non Final office Action mailed Mar. 31, 2011", 6 pgs.
"U.S. Appl. No. 11/462,301, Non-Final Office Action mailed Mar. 1, 2010", 13 pgs.
"U.S. Appl. No. 11/462,301, Non-Final Office Action mailed Dec. 16, 2008", 11 pgs.
"U.S. Appl. No. 11/462,301, Response filed Jan. 4, 2010 to Final Office Action mailed Sep. 3, 2009", 12 pgs.
"U.S. Appl. No. 11/462,301, Response filed Jan. 14, 2011 to Final Office Action mailed Sep. 16, 2010", 13 pgs.
"U.S. Appl. No. 11/462,301, Response filed May 18, 2009 to Non Final Office Action mailed Dec. 6, 2008", 14 pgs.
"U.S. Appl. No. 11/462,301, Response filed Jun. 30, 2010 to Non-Final Office Action mailed Mar. 1, 2010", 14 pgs.
"U.S. Appl. No. 11/462,301, Response filed Jun. 30, 2011 to Non-Final Office Action mailed Mar. 31, 2011", 11 pgs.
"U.S. Appl. No. 11/462,301, Response filed Oct. 14, 2008 to Restriction Requirement mailed Sep. 19, 2008", 8 pgs.
"U.S. Appl. No. 11/462,301, Restriction Requirement mailed Sep. 19, 2008", 7 pgs.
"U.S. Appl. No. 11/684,914, Examiner Interview Summary mailed May 5, 2010", 3 pgs.
"U.S. Appl. No. 11/684,914, Examiner Interview Summary mailed Oct. 14, 2011", 3 pgs.
"U.S. Appl. No. 11/684,914, Final Office Action mailed Jul. 19, 2011", 20 pgs.
"U.S. Appl. No. 11/684,914, Final Office Action mailed Mar. 8, 2010", 20 pgs.
"U.S. Appl. No. 11/684,914, Non-Final Office Action mailed Jul. 8, 2009", 19 pgs.
"U.S. Appl. No. 11/684,914, Non-Final Office Action mailed Sep. 27, 2010", 20 pgs.
"U.S. Appl. No. 11/684,914, Non-Final Office Action mailed Dec. 16, 2010", 20 pgs.
"U.S. Appl. No. 11/684,914, Notice of Allowance mailed Nov. 14, 2011", 7 pgs.
"U.S. Appl. No. 11/684,914, Response filed Jan. 7, 2010 to Non Final Office Action mailed Jul. 8, 2009", 20 pgs.
"U.S. Appl. No. 11/684,914, Response filed Jun. 15, 2011 to Non-Final Office Action mailed Dec. 16, 2010", 14 pgs.
"U.S. Appl. No. 11/684,914, Response filed Sep. 8, 2010 to Final Office Action mailed Mar. 8, 2010", 11 pgs.
"U.S. Appl. No. 11/684,914, Response filed Oct. 18, 2011 to Final Office Action mailed Jul. 19, 2011", 14 pgs.
"Electrolytic Capacitors", Electrochemistry Encyclopedia, [online]. http://electrochem.cwru.edu/encycl/art-c04-electr-cap.htm, (Mar. 2005), 10 pgs.
"PCT Application Serial No. PCT/US2007/017537, International Search Report and Written Opinion mailed Jan. 18, 2008", 13 pgs.
"Ref-06, Energy Stored in a Capacitor,", (Apr. 2000).
Block, Michael, "Biphasic Defibrillation Using a Single Capacitor with Large Capacitance: Reduction of Peak Voltages and ICD Device Size", PACE, Vo. 19, (Feb. 1996), 207-214.
Block, Michael, "Internal Defibrillation with Smaller Capacitors: A Prospective Randomized Cross-Over Comparison of Defibrillation Efficacy Obtained with 90-iF and 125-iF Capacitors in Humans", Journal of Cardiovascular Electrophysiology, vol. 6, No. 5, (May 1995), 333-342.
Brugada, J., "Clinical evaluation of defibrillation efficacy with a new single-capacitor biphasic waveform in patients undergoing implantation of an implantable cardioverter defibrillator", The European Society of Cardiology, vol. 3, (Oct. 2001), 278-284.
Hahn, S. J., et al., "Large Capacitor Defibrillation Waveform Reduces Peak Voltages Without Increasing Energies", PACE, 18(Part II), (Jan. 1995), 203-207.
Morley, A. R., et al., "Electrolytic capacitors: their fabrication and the interpretation of their operations behaviour", The Radio and Electronic Engineer, vol. 43, No. 7, (Jul. 1973), 421-429.
Moynihan, J. D., "Theory, Design and Application of Electrolytic Capacitors", Theory, Design and Application of Electrolytic Capacitors, Copyright by John D. Moynihan, (1982), 139 pgs.
Porter, Mark C, "Handbook of Industrial Membrane Technology", Handbook of Industrial Membrane Technology, Noyes Publications, (1990), 623 Pages.
Shams, A. M, et al., "Titanium hydride formation from Arabian Gulf water", Desalination, vol. 107, (1996), 265-276.
Sherwoood, G. J., "Method and Apparatus for High Voltage Aluminum Capacitor Design", U.S. Appl. No. 11/684,914, filed Mar. 12, 2007, 239 pgs.

\* cited by examiner

1700

```
┌─────────────────────────┐
│ PROVIDING AN ANODE FOIL │─ 1702
└─────────────────────────┘

┌─────────────────────────┐
│   ETCHING THE ANODE FOIL│─ 1704
└─────────────────────────┘

┌─────────────────────────┐
│ FORMING A DIELECTRIC LAYER ON │─ 1706
│       THE ANODE FOIL    │
└─────────────────────────┘
```

Fig. 17A

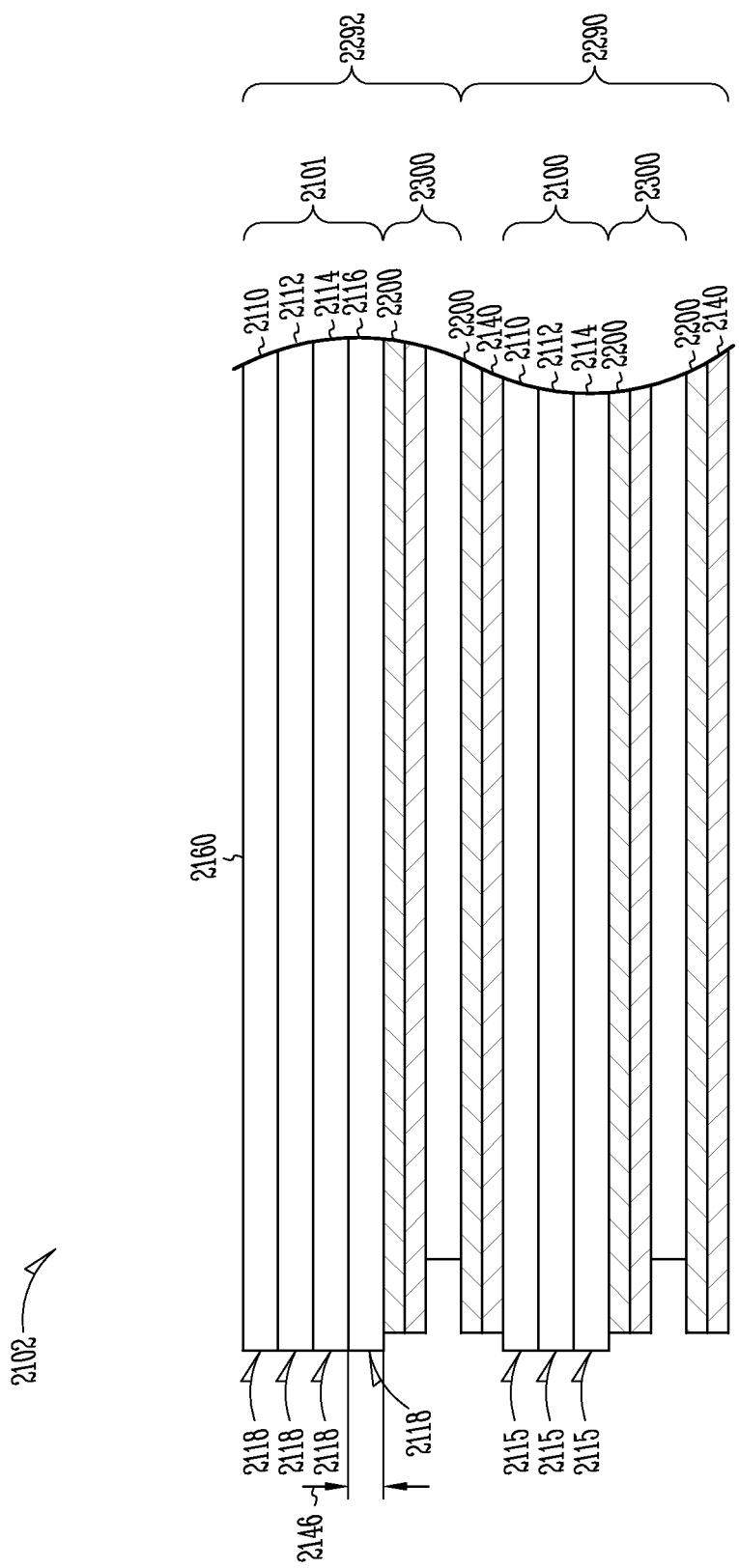

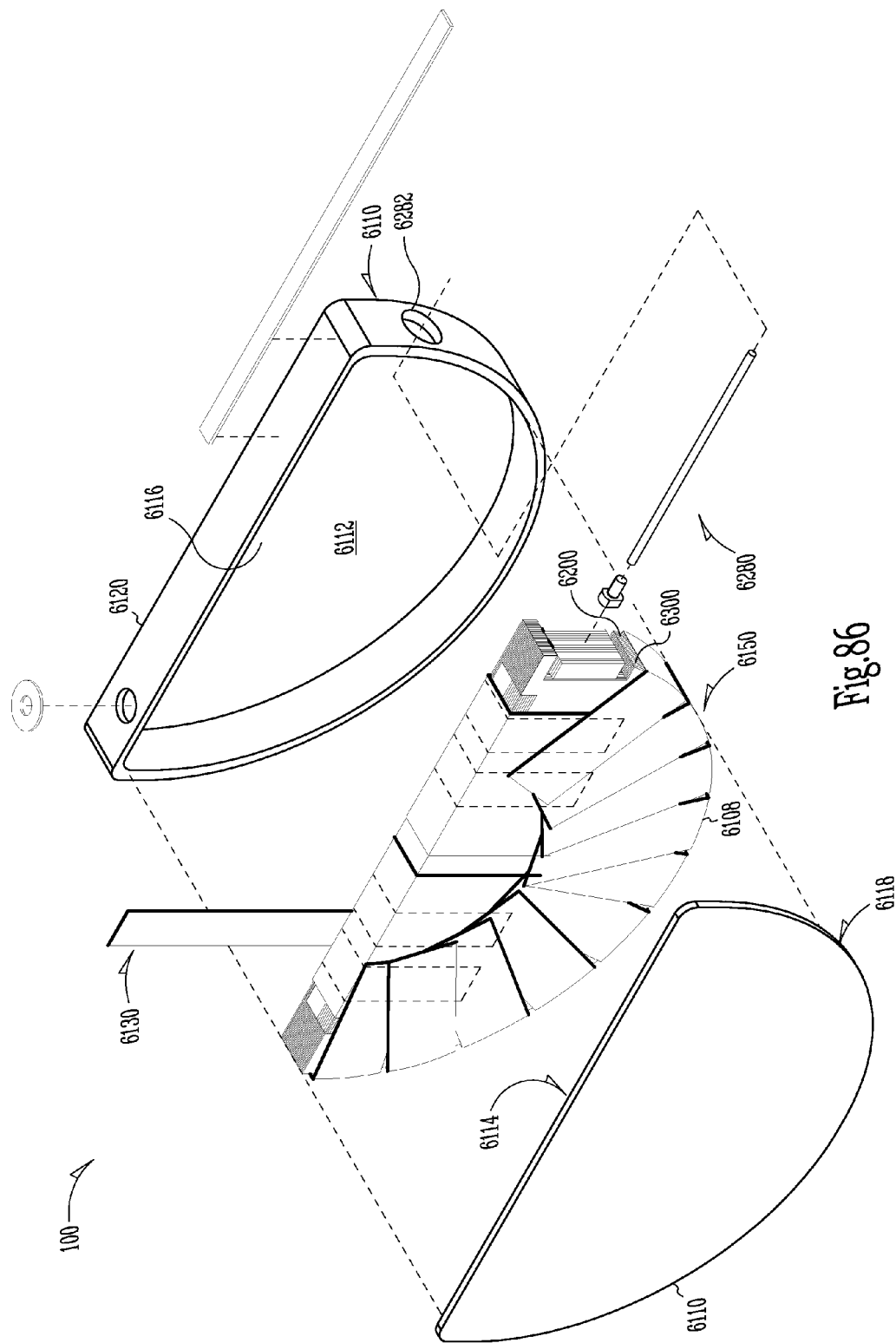

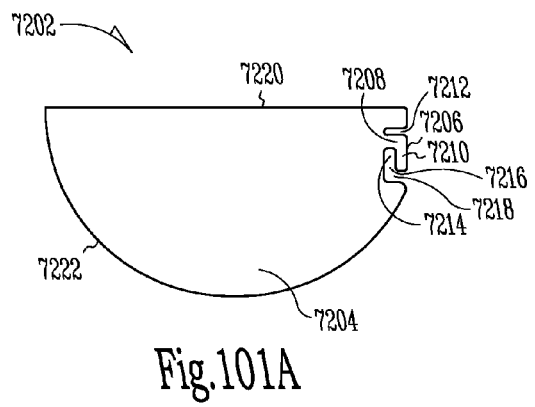
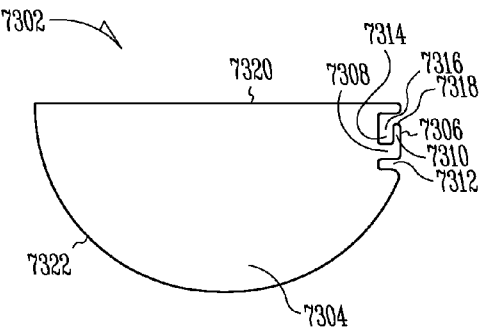
Fig.101A                    Fig.101B
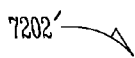
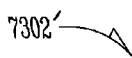
Fig.102A                    Fig.102B

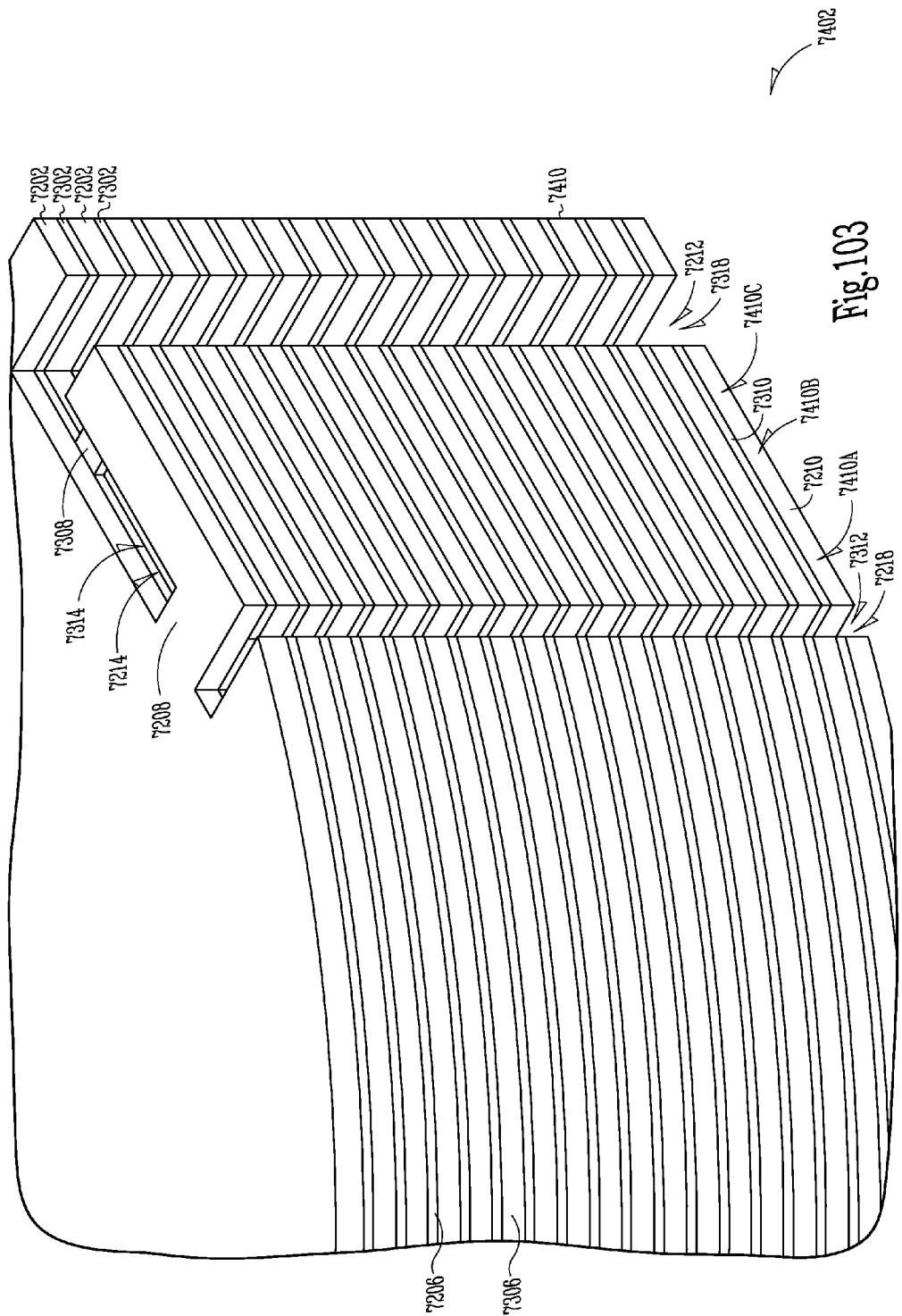

METHOD AND APPARATUS FOR HIGH VOLTAGE ALUMINUM CAPACITOR DESIGN

CLAIM OF BENEFIT OF PRIOR-FILED APPLICATIONS

This patent application is a continuation of U.S. patent application Ser. No. 11/684,914, filed on Mar. 12, 2007, now U.S. Pat. No. 8,133,286, which is a division of U.S. patent application Ser. No. 11/182,707, filed on Jul. 15, 2005, now U.S. Pat. No. 7,224,575, which claims the benefit of priority under 35 U.S.C. 119(e) of U.S. Provisional Application Ser. No. 60/588,905, entitled "Method and Apparatus for High Voltage Aluminum Capacitor Design," filed on Jul. 16, 2004, the specifications of which are incorporated herein by reference.

FIELD OF THE INVENTION

This disclosure relates generally to capacitors, and more particularly, to compact, electrolytic, flat high voltage electrolytic capacitors made from substantially planar layers.

BACKGROUND

A capacitor is an electric circuit element used to store charge temporarily, consisting in general of two metallic plates separated and insulated from each other by a dielectric. Capacitors are useful as a compact source for a high energy pulse.

In many instances, the capacitor takes the form of an aluminum electrolytic capacitor. Existing designs include one or more separators disposed between two or more sheets of aluminum foil. One of the foils serves as the anode of the capacitor, and the other serves as the cathode. Some designs include multiple foils which are interconnected to increase effective size of the anode or cathode.

Electrolytic capacitors often include a dielectric layer formed on one or both of the electrodes. By changing the nature of the dielectric, capacitance can be altered. Higher voltages are possible with improved dielectrics. By improving the design of the dielectric coating, increased capacitor performance is possible.

Varying devices benefit from compact capacitor designs. Implantable cardioverter defibrillators are typically implanted in the left region of the chest or in the abdomen, and include a housing and one or more leads implanted in the patient. Existing implantable cardioverter defibrillator designs include capacitors which can consume 30% of the volume of the housing. A need exists for a smaller device which is capable of delivering patient therapy. One way to obtain a smaller device is to reduce capacitor size.

Thus, implantable cardioverter defibrillators and others devices would benefit from a more compact capacitor. A need exists for an improved capacitor design, including an improved dielectric coating.

SUMMARY

The above-mentioned problems and others not expressly discussed herein are addressed by the present subject matter and will be understood by reading and studying this specification.

The present subject matter includes high voltage capacitors. The high voltage capacitors are used in implantable devices, in various embodiments. Some embodiments are adapted to deliver from about 5.3 joules per cubic centimeter of capacitor stack volume to about 6.3 joules per cubic centimeter of capacitor stack volume. Some of these embodiments deliver energy at a voltage of between about 465 volts to about 620 volts. Some embodiments include an anode layer having a dielectric thickness of less than approximately 1200 nm.

One embodiment of the present subject matter includes a method of producing an apparatus for use in a patient, the method including etching an anode foil, anodizing the anode foil, assembling the anode foil, at least one cathode foil and one or more separators into a capacitor stack adapted to deliver from about 5.3 joules per cubic centimeter of capacitor stack volume to about 6.3 joules per cubic centimeter of capacitor stack volume at a voltage of between about 465 volts to about 620 volts, inserting the stack into a capacitor case, inserting the capacitor case into a device housing adapted for implant in a patient, connecting the capacitor to a component and sealing the device housing.

An additional embodiment of the present subject matter includes a capacitor including a capacitor stack which includes an anode foil, the capacitor stack disposed in a case filled with a capacitor electrolyte, the capacitor including a feedthrough to connect the capacitor stack to electronics, the capacitor being adapted to deliver to the component from about 5.3 joules per cubic centimeter of capacitor stack volume to about 6.3 joules per cubic centimeter of capacitor stack volume, at a voltage of between about 465 volts to about 620 volts, the anode foil made by the process including etching an anode foil to define and etched anode foil, forming a hydrous oxide layer on the etched anode foil, anodizing the etched anode foil and interrupting anodizing the etched anode foil to stabilize the etched anode foil in a mildly alkaline bath, the mildly alkaline bath comprising approximately 10 to approximately 120 grams per liter boric acid and approximately 2 to approximately 50 parts per million phosphate as electrolyte at a pH of approximately 4.0 to approximately 6.0, the aqueous solution being at a temperature of approximately 85 degrees Celsius to approximately 95 degrees Celsius, wherein the anode foil can be anodized to 760 V without scintillation.

An additional embodiment of the present subject matter includes a capacitor having anode means for storing charge, for stacking, and for powering an implantable device, cathode means for storing charge, for stacking, and for powering an implantable device, a case for housing the anode means and the cathode means, feedthrough means for interconnecting the anode means, the cathode means, and implantable device electronics. The anode means and the cathode means are for delivering from about 5.3 joules per cubic centimeter of capacitor stack volume to about 6.3 joules per cubic centimeter of capacitor stack volume, at a voltage of between about 465 volts to about 620 volts.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

FIGS. 17A-B show flowcharts depicting methods of preparing anode foils, according to various embodiments of the present subject matter.

FIG. 38 is a cross-sectional view of a capacitor stack constructed in accordance with one embodiment.

FIG. 86 is an exploded perspective view illustrating a capacitor as constructed in accordance with one embodiment.

FIG. 101A is a top view of an anode foil for use in constructing a capacitor according to one embodiment of the present subject matter.

FIG. 101B is a top view of a cathode foil for use in constructing a capacitor according to one embodiment of the present subject matter.

FIG. 102A is a top view of an anode foil for use in constructing a capacitor according to one embodiment of the present subject matter.

FIG. 102B is a top view of a cathode foil for use in constructing a capacitor according to one embodiment of the present subject matter.

FIG. 103 is a perspective view of a stack of one or more anodes and cathodes of FIGS. 101A and 2B.

FIG. 106E show a top view of FIG. 106D.

FIG. 106F shows a method according to one embodiment.

FIG. 107A is a schematic of a capacitor having a dual-compartment case, according to one embodiment of the present subject matter.

FIG. 107B is a schematic of a capacitor having a dual-compartment case that also serves as a conductor, according to one embodiment of the present subject matter.

FIG. 108 is a schematic of a capacitor having a three compartment case, according to one embodiment of the present subject matter.

FIG. 109 is a perspective view of a flat capacitor including a pressure-relief mechanism according to one embodiment of the present subject matter.

FIG. 110 is a perspective view of a cylindrical electrolytic capacitor including a pressure-relief mechanism according to one embodiment of the present subject matter.

FIG. 111 is a cross-sectional view of a pressure-relief device in accord with one embodiment.

FIG. 112 is a cross-sectional view of a pressure-relief device in accord with one embodiment.

FIG. 113 is a cross-sectional view of a pressure-relief device in accord with one embodiment.

FIG. 114 is a cross-sectional view of a pressure-relief device in accord with one embodiment.

FIG. 115 is a schematic representation of an implantable medical device according to one embodiment of the present subject matter.

Figure 116A:
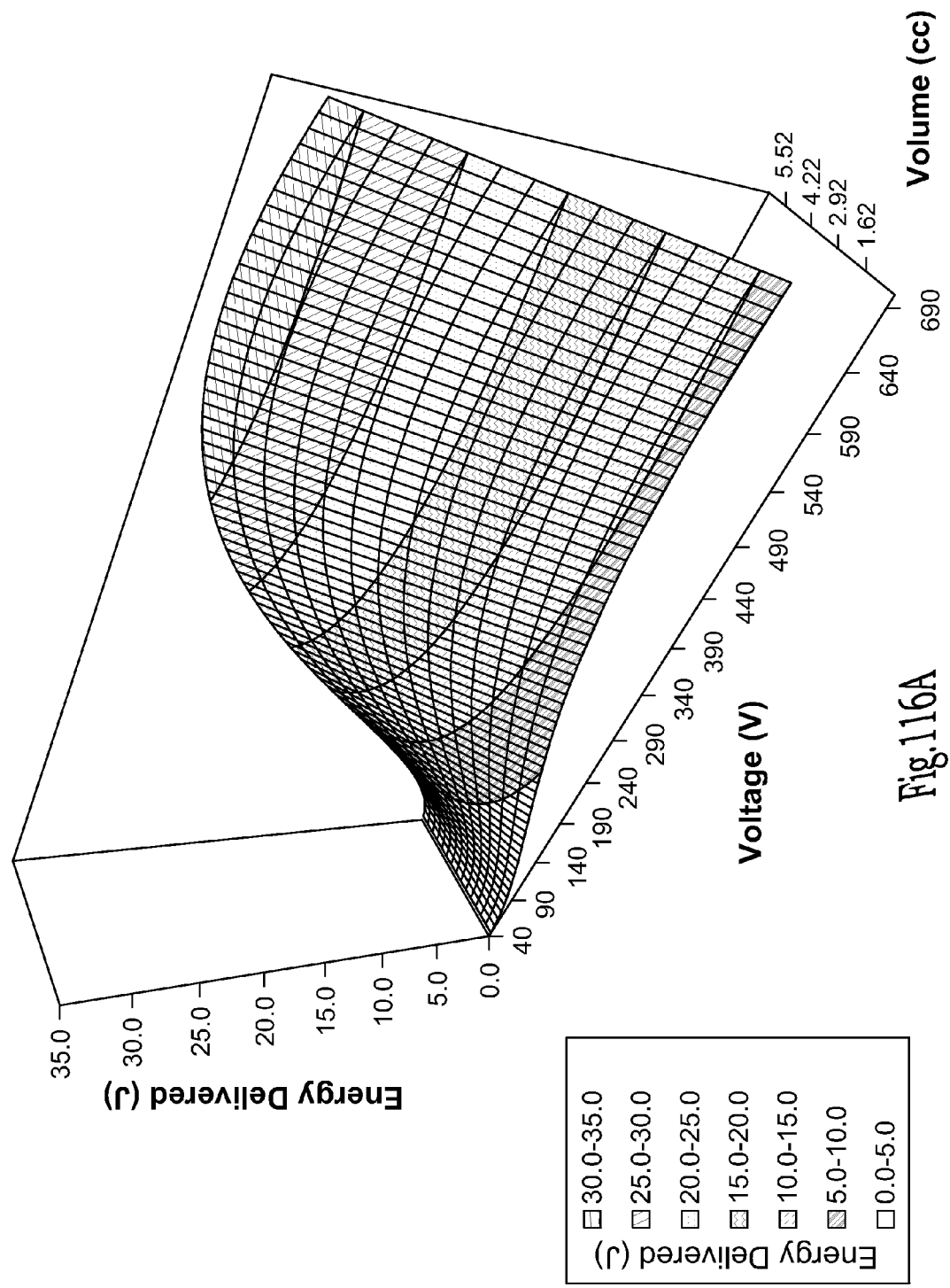

FIG. 116A illustrates a graph representing characteristics of an electrode, according to various embodiments of the present subject matter.

Figure 116B:
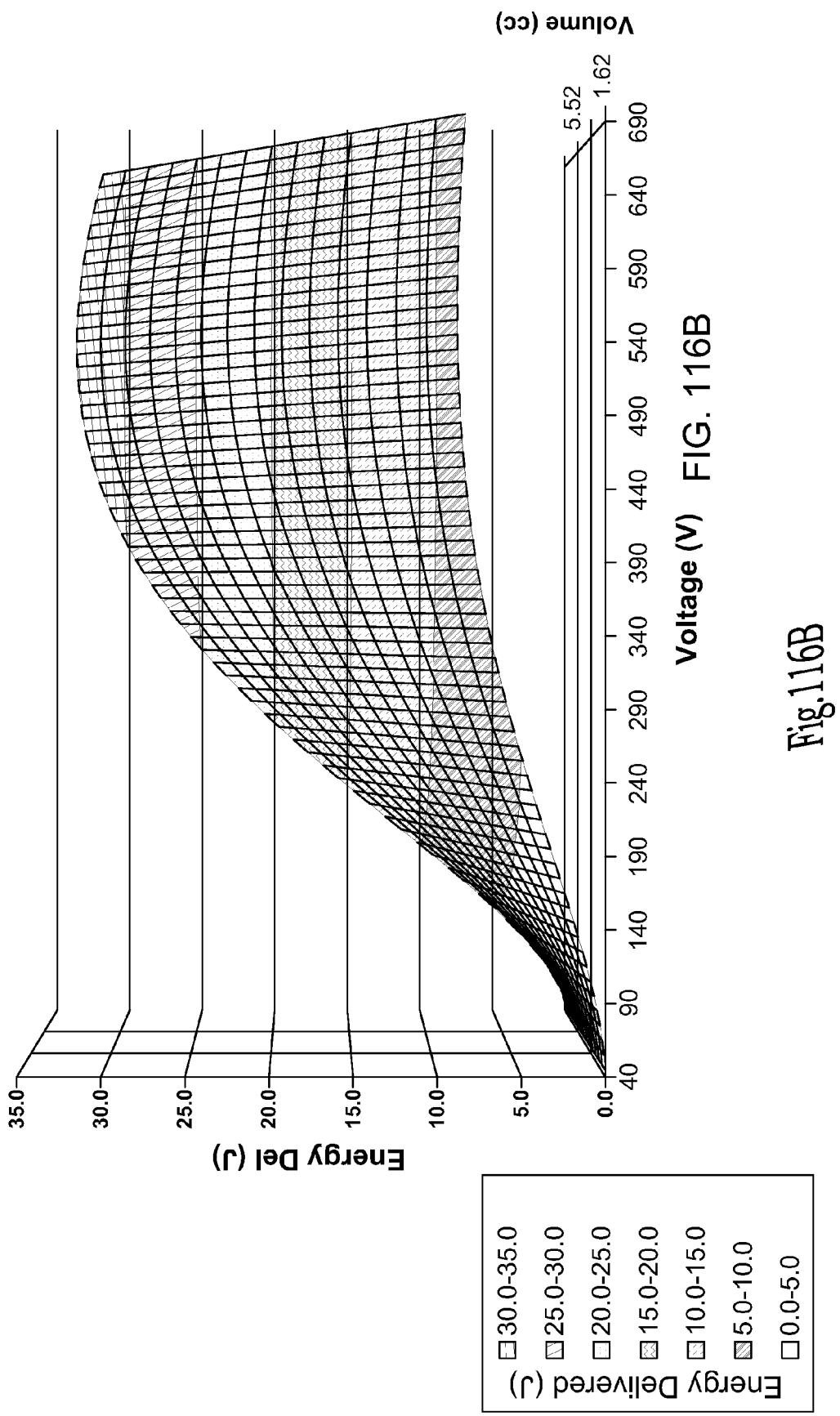

FIG. 116B illustrates a graph representing characteristics of an electrode, according to various embodiments of the present subject matter.

Figure 116C:
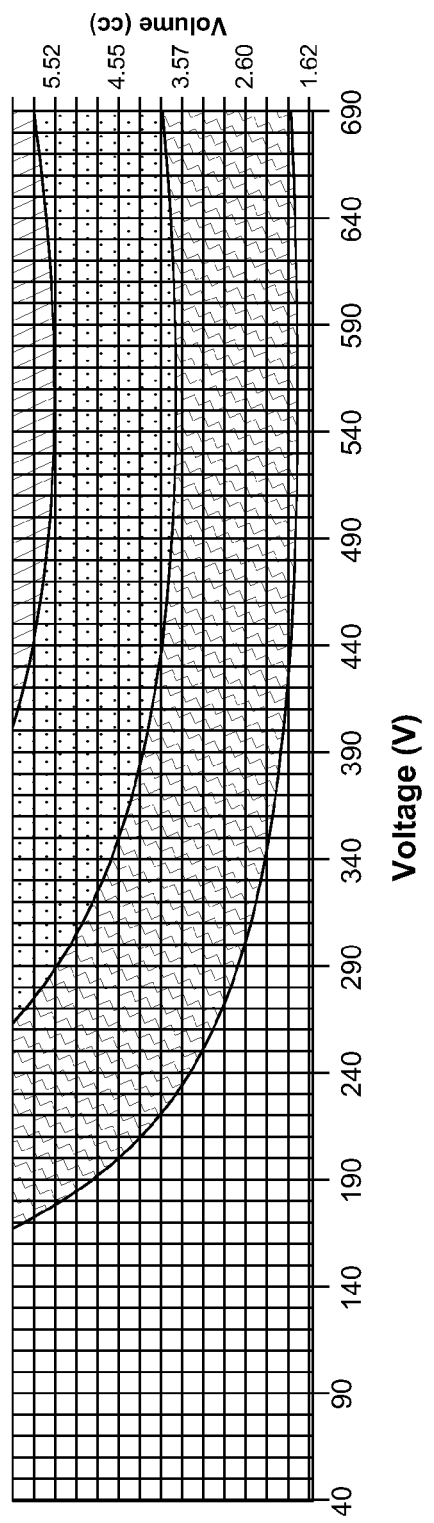

FIG. 116C illustrates a graph representing characteristics of an electrode, according to various embodiments of the present subject matter.

Figure 117:
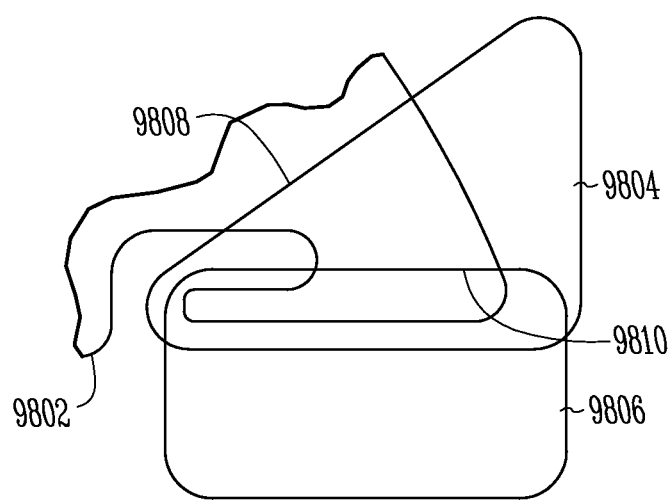

FIG. 117 illustrates one example of a mask applied to the electrode, according to various embodiments of the present subject matter.

Figure 118A:
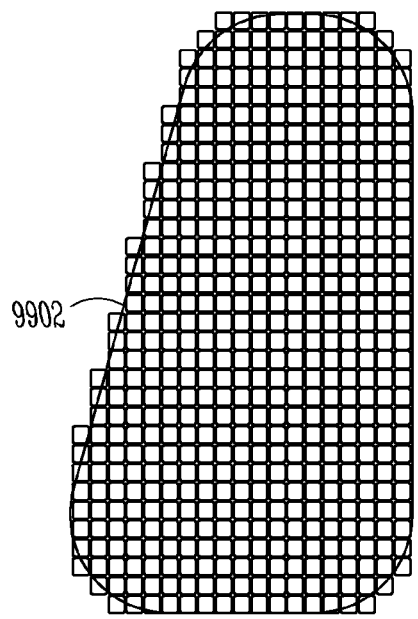

FIG. 118A illustrates a design of a mask applied to an electrode, according to various embodiments of the present subject matter.

Figure 118B:
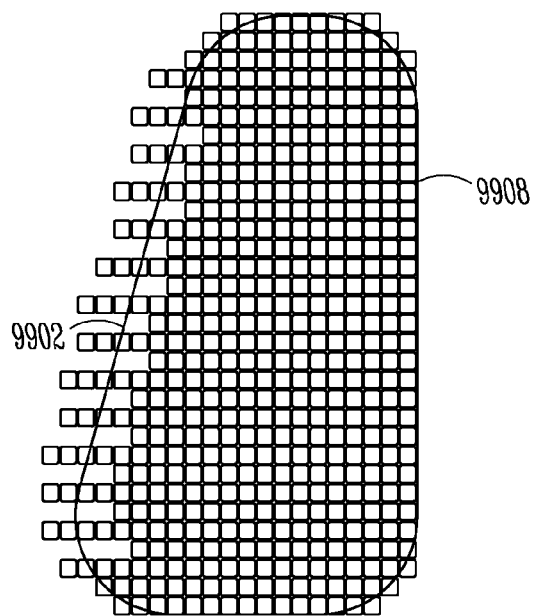

FIG. 118B illustrates a design of a mask applied to an electrode, according to various embodiments of the present subject matter.

Figure 118C:
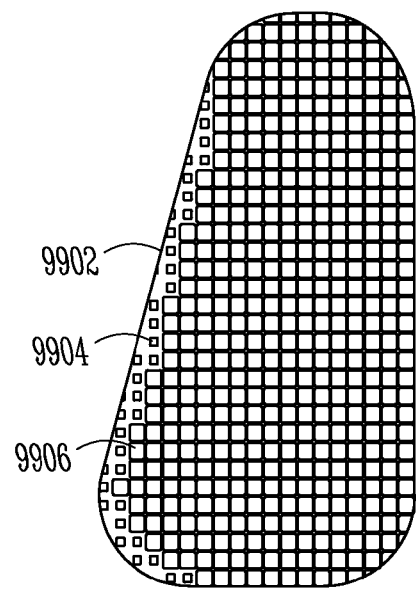

FIG. 118C illustrates a design of a mask applied to an electrode, according to various embodiments of the present subject matter.

Figure 118D:
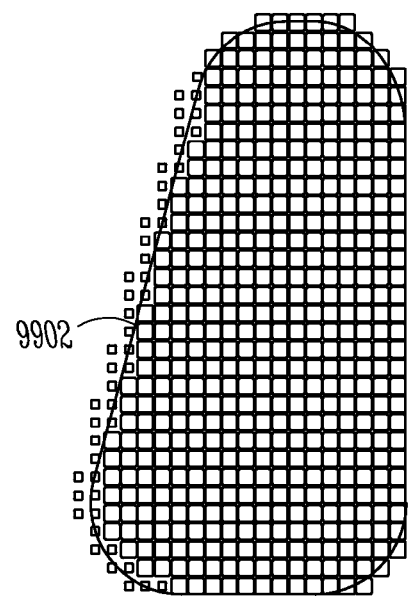

FIG. 118D illustrates a design of a mask applied to an electrode, according to various embodiments of the present subject matter.

Figure 118E:
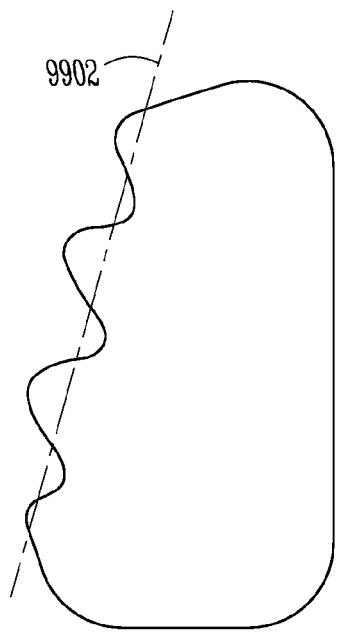

FIG. 118E illustrates a design of a mask applied to an electrode, according to various embodiments of the present subject matter.

Figure 118F:
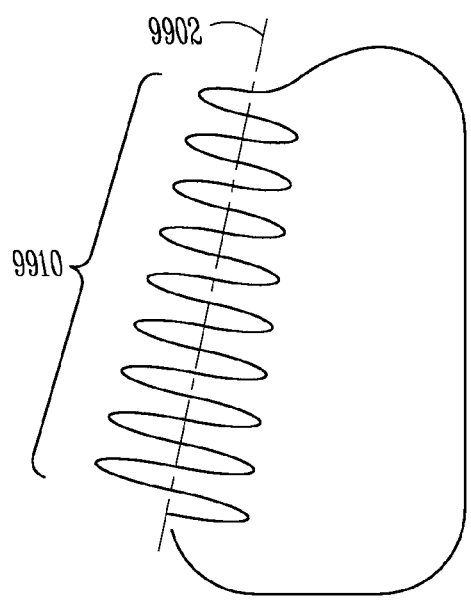

FIG. 118F illustrates a design of a mask applied to an electrode, according to various embodiments of the present subject matter.

Figure 119:
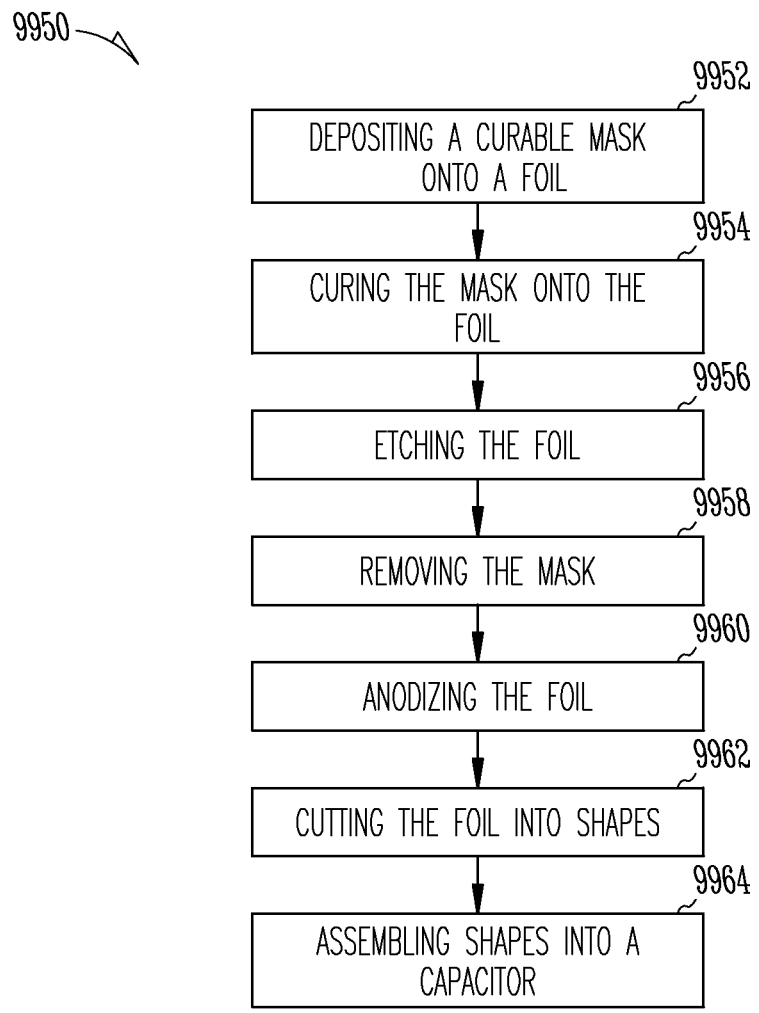

FIG. 119 shows a process for making a foil with a partially etched area, according to various embodiments of the present subject matter.

Figure 120:
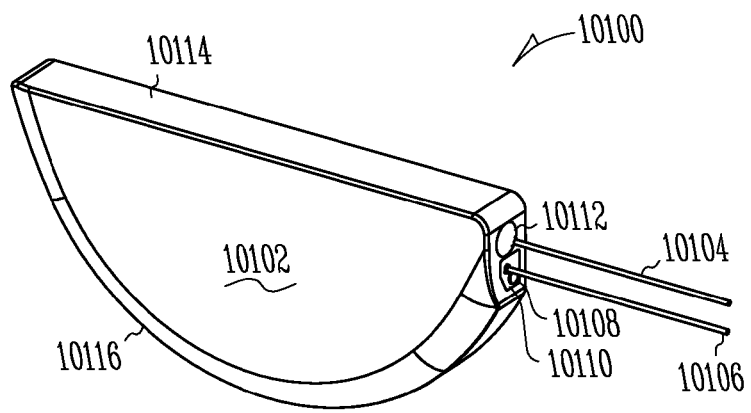

FIG. 120 shows a flat capacitor according to one embodiment of the present subject matter.

Figure 121:
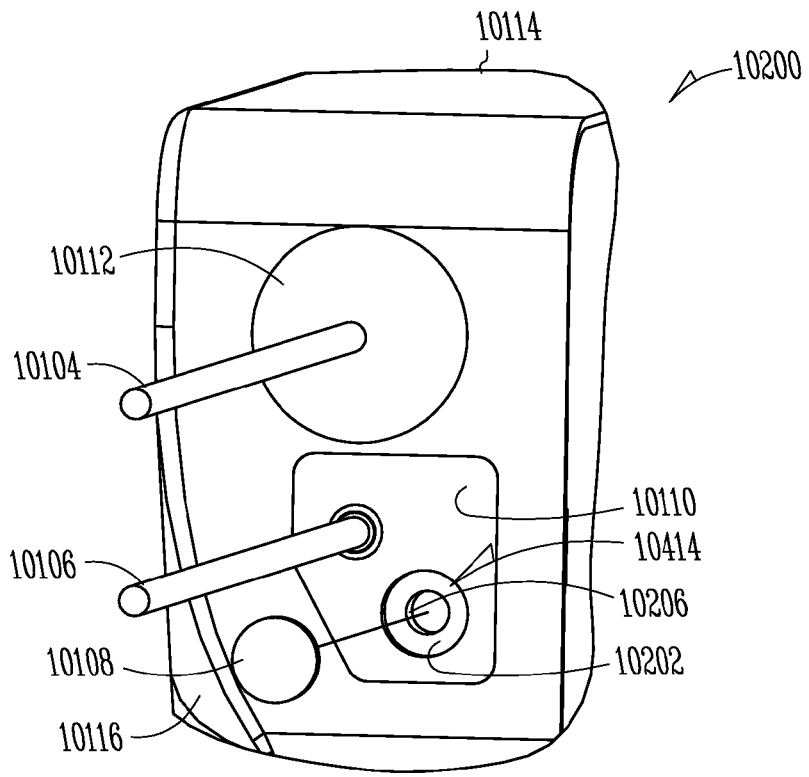

FIG. 121 illustrates a partial view of a capacitor having a plate and plug, according to one embodiment of the present subject matter.

Figure 122:
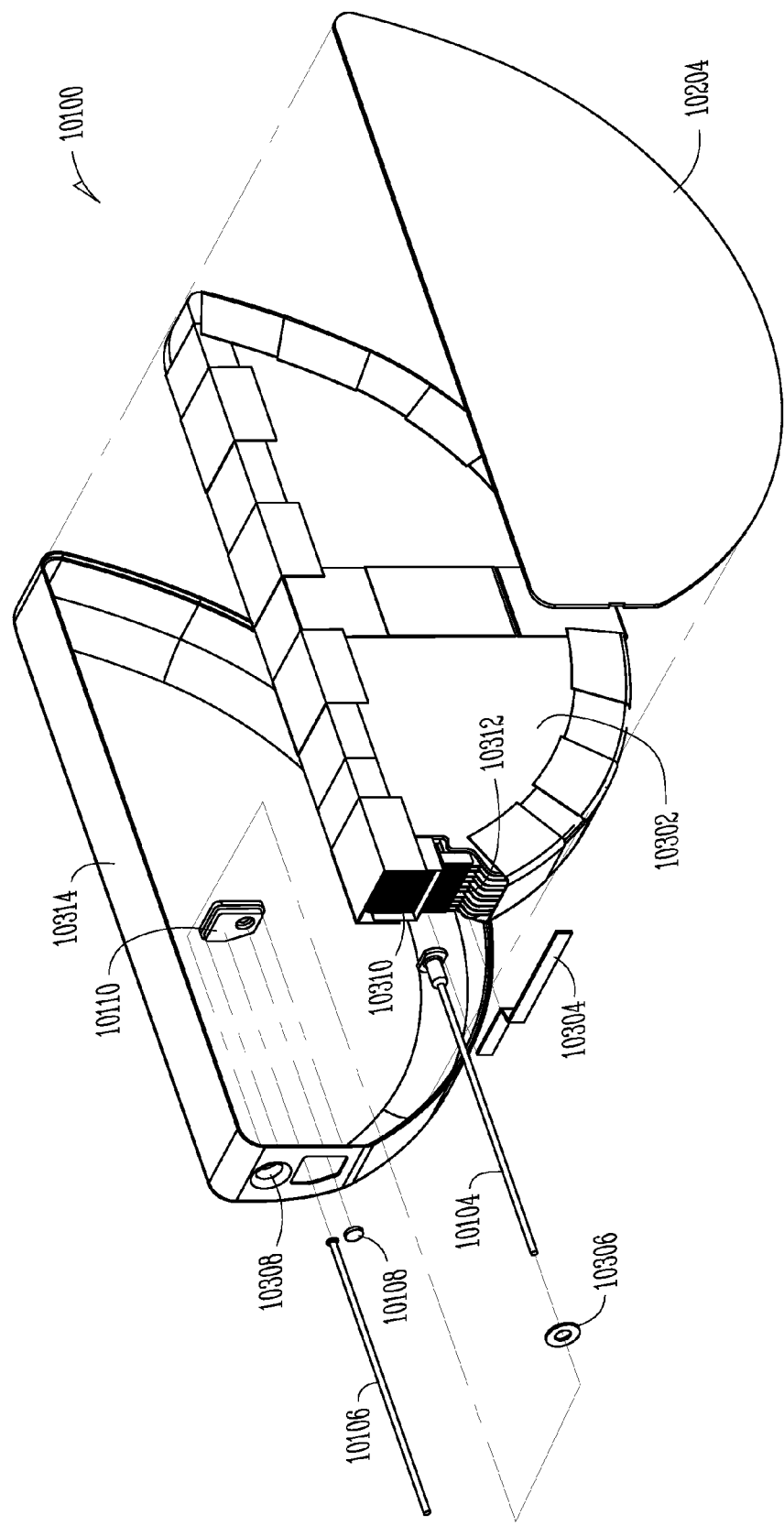

FIG. 122 illustrates an exploded view of a capacitor, according to one embodiment of the present subject matter.

Figure 123A:
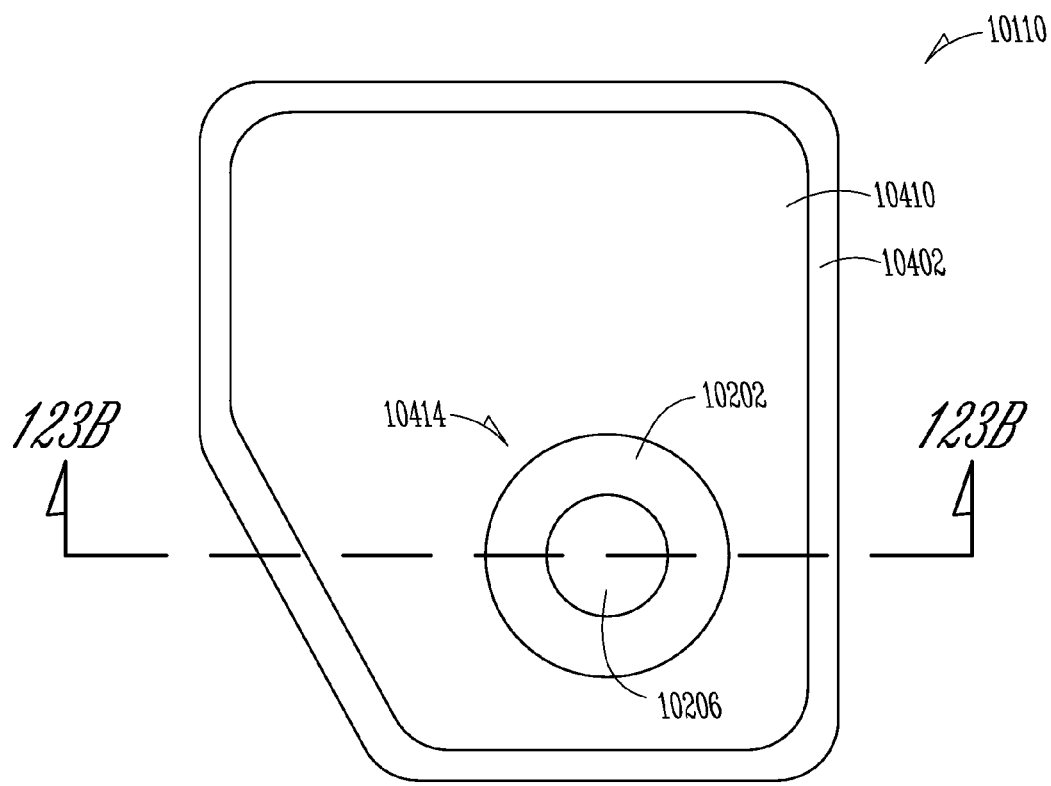

FIG. 123A illustrates a front view of a plate, according to one embodiment of the present subject matter.

Figure 123B:
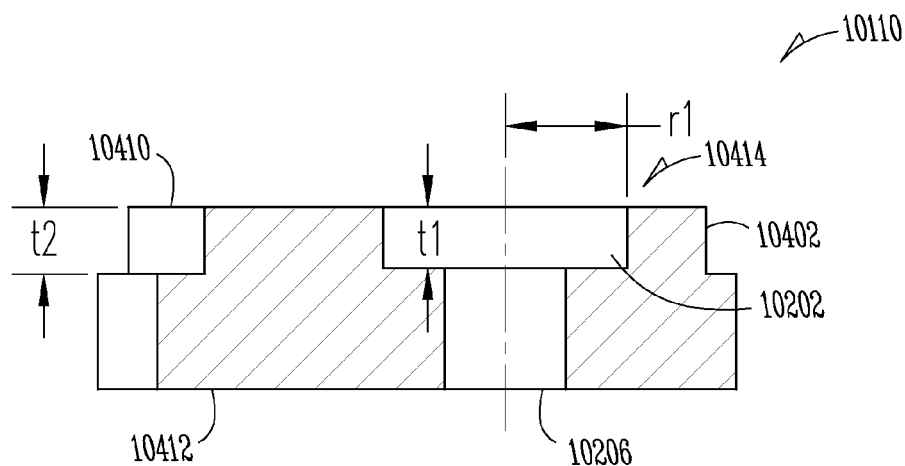

FIG. 123B illustrates a cross section of a side view of a plate taken at line 122B-122B of FIG. 123A.

Figure 124:
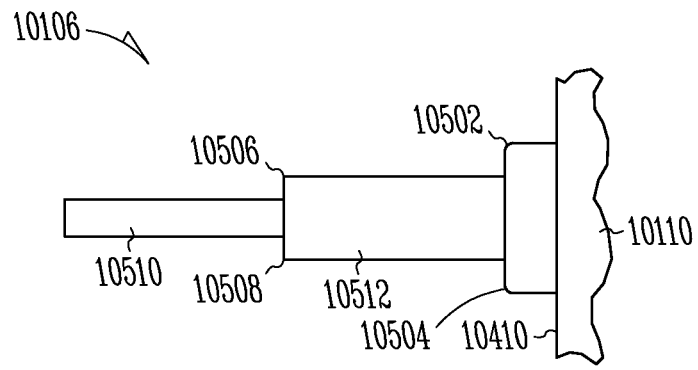

FIG. 124 shows a partial side view of conductor attached to a plate, according to one embodiment of the present subject matter.

Figure 125:
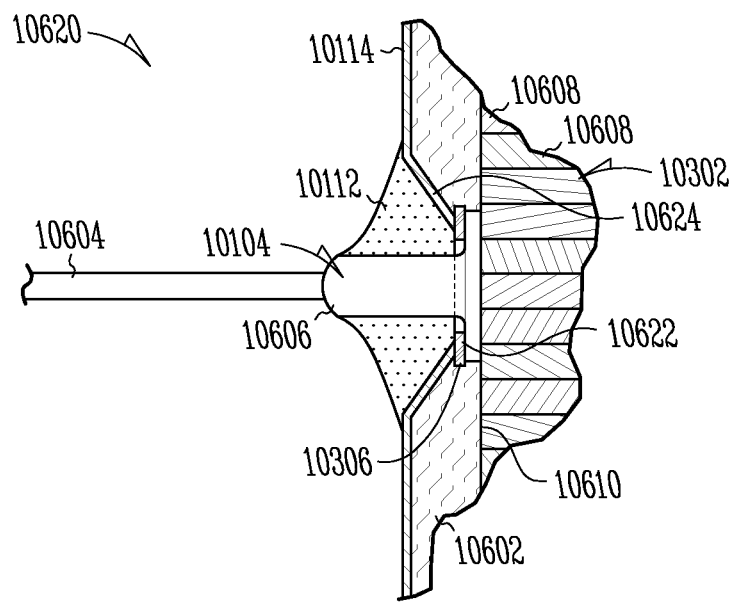

FIG. 125 shows a cross-sectional side view a feedthrough assembly, according to one embodiment of the present subject matter.

Figure 126:
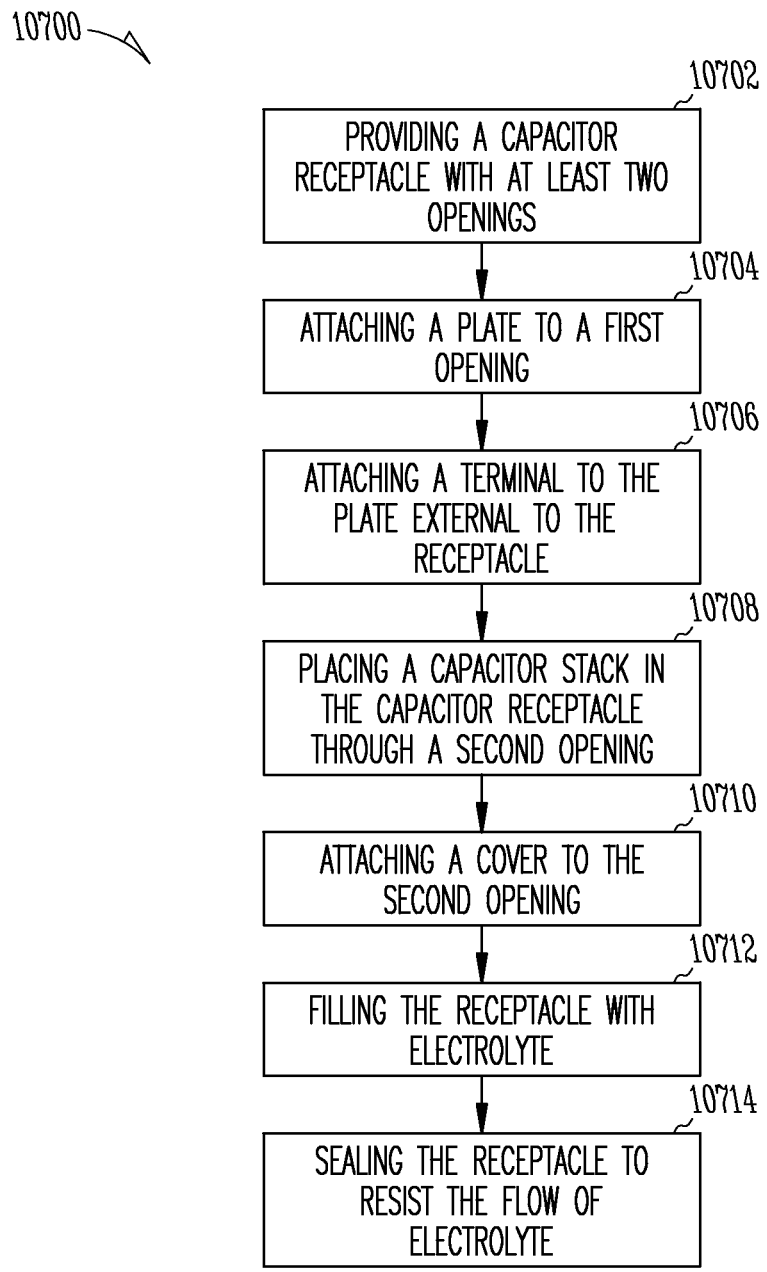

FIG. 126 shows a method for manufacturing an implantable defibrillator, according to one embodiment of the present subject matter.

Figure 127:
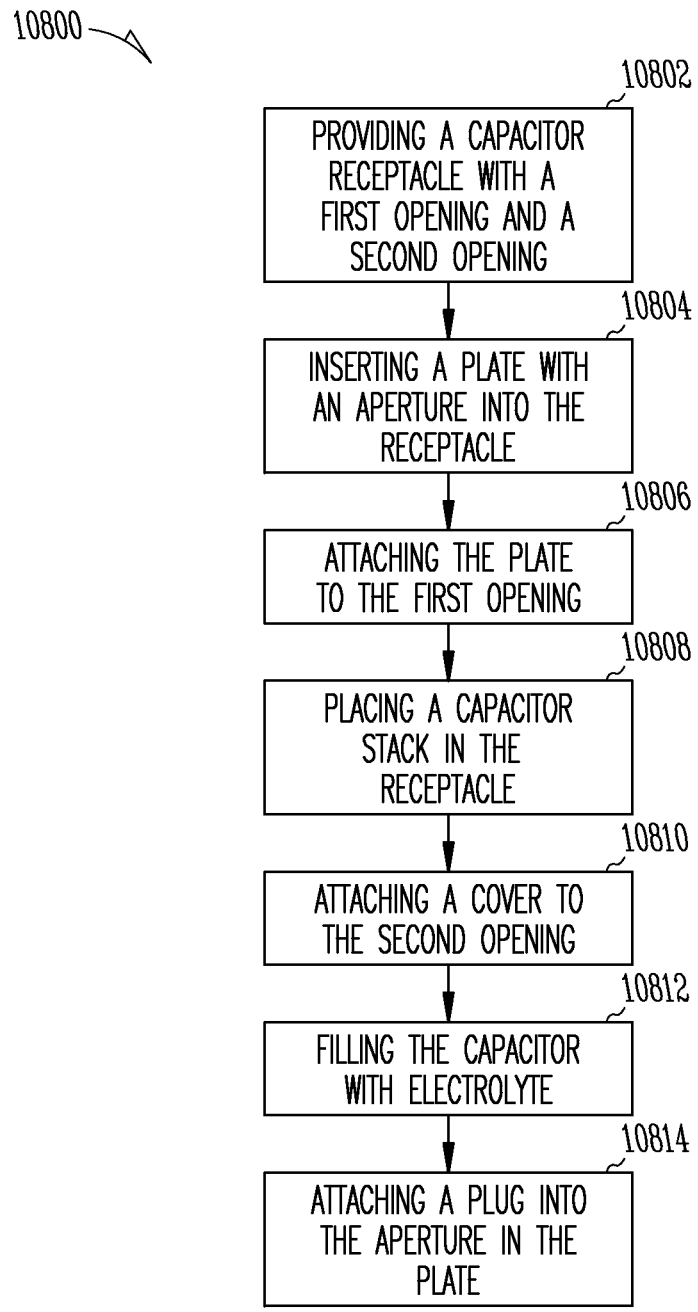

FIG. 127 shows a method for manufacturing an implantable defibrillator, according to one embodiment of the present subject matter.

Figure 128:
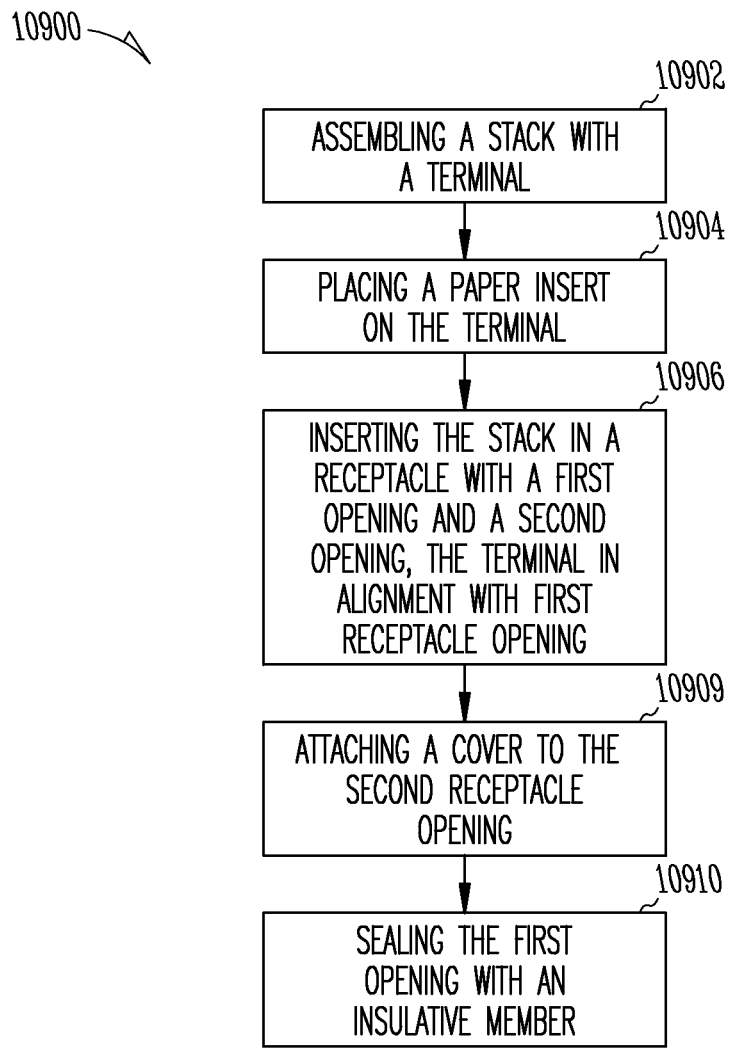

FIG. 128 shows a method for manufacturing an implantable defibrillator, according to one embodiment of the present subject matter.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Figure 1:
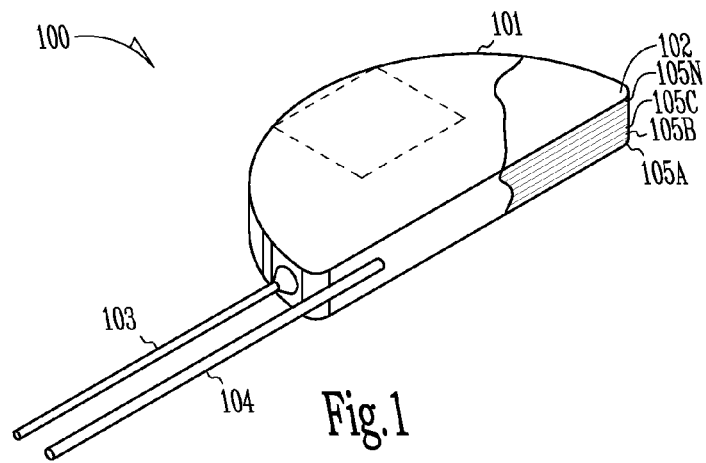
FIG. 1 is an isometric view of a flat capacitor, according to one embodiment of the present subject matter.

FIG. 1 shows a flat capacitor 100 according to one embodiment of the present subject matter. Although capacitor 100 is a D-shaped capacitor, in other embodiments, the capacitor is other desirable shapes, including, but not limited to rectangular, circular, oval, square, or other symmetrical or asymmetrical shape. Capacitor 100 includes a case 101 which contains a capacitor stack 102. In one embodiment, case 101 is manufactured from a conductive material, such as aluminum. In other embodiments, the case is manufactured using a nonconductive material, such as a ceramic or a plastic. One example uses a case 101 which is formed from aluminum which is from about 0.010 inches thick to about 0.012 inches thick. In some examples, the case is electrically connected to an electrode of the capacitor, and one example uses the case as part of the cathode. For example, a conductive material is attached to the cathode and to the case, internal to the housing 101, in various embodiments.

Capacitor 100 includes a first terminal 103 and a second terminal 104 for connecting capacitor stack 102 to an outside electrical component, such as implantable medical device circuitry. In one embodiment, terminal 103 is a feedthrough terminal insulated from case 101, while terminal 104 is directly connected to case 101. Alternatively, the capacitor incorporates other connection methods. For instance, in some embodiments, capacitor 100 includes two feedthrough terminals.

In the present embodiment, capacitor stack 102 includes capacitor modules or elements 105a, 105b, 105c, . . . , 105n.

Figure 2:
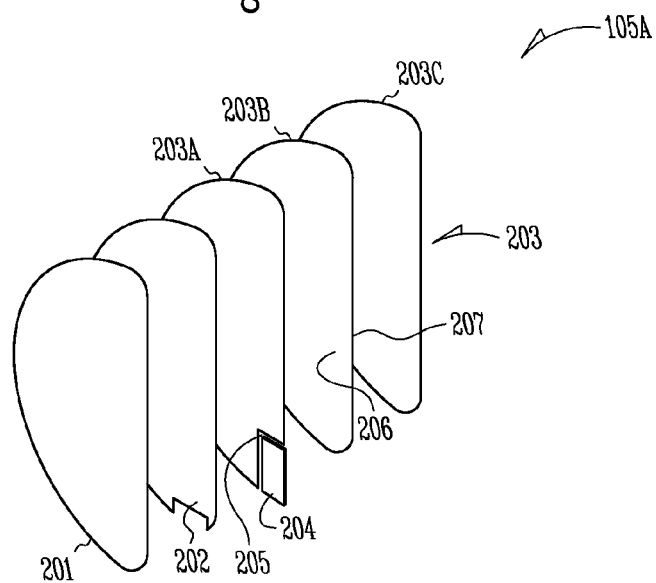
FIG. 2 is an exploded isometric view of portions of the capacitor of FIG. 1.

FIG. 2 shows details of one example of capacitor element 105a, which is representative of capacitor elements 105b-105n. Element 105a includes a cathode 201, a separator 202, and an anode stack 203. In other embodiments, other numbers and arrangements of anodes, cathodes, and separators are utilized.

Cathode 201 is a foil attached to other cathodes of capacitor stack 102 and to terminal 104. In some embodiments, cathode 201 can include aluminum, tantalum, hafnium, niobium, titanium, zirconium, and combinations of these metals. In one embodiment, cathode 201 is constructed by taking an aluminum (98% purity or higher) base metal and coating it with titanium oxide, titanium nitride, or titanium pentoxide using sputtering, plating, vacuum deposition, or other coating techniques. In some embodiments, titanium itself is used with a subsequent processing step used to oxidize the titanium resulting in $TiO$, $TiO_2$, $TiN$, $Ti_2O_5$, or other high dielectric constant oxide.

The resulting titanium-coated cathode material has a higher capacitance per unit area than traditional aluminum electrolytic capacitor cathodes. Traditional cathodes which are 98% aluminum purity or higher generally have capacitance per unit area of approximately 250 $uF/cm^2$ for 30 micron thick foil, with an oxide breakdown voltage in the 1-3 volt range. However, a cathode as described above results in a capacitance per unit area which, in some embodiments, is as high as 1000 $uF/cm^2$ or more.

Advantageously, this provides a single cathode which services several layers of anodic foil without exceeding the oxide breakdown voltage. When using a traditional cathode to service several layers (2 or more) of anodic foil, the cathode voltage may rise as high as 5 or more volts, which is usually greater than the breakdown voltage. When this occurs, the aluminum cathode begins to form oxide by a hydration process which extracts oxygen from the water present in the electrolyte. The reaction produces hydrogen as a byproduct which in turn has the effect of creating an internal pressure within the capacitor causing an undesirable mechanical bulge in the layers from the capacitor stack, or in the case. Therefore, the titanium-coated cathode described above serves as a corrective mechanism for hydrogen generation.

Separator 202 is located between each anode stack 203 and cathode 201. In one embodiment, separator 202 consists of two sheets of 0.0005 inches thick kraft paper impregnated with an electrolyte. In some embodiments, separator 202 includes a single sheet or three or more sheets.

The electrolyte can be any suitable electrolyte for an electrolytic capacitor, such as an ethylene-glycol base combined with polyphosphates, ammonium pentaborate, and/or an adipic acid solute. In one embodiment, the electrolyte includes butyrolactone and ethylene glycol, such as B103AD electrolyte manufactured by Boundary Technologies, Inc. of Northbrook, Ill. 60065 USA.

In one embodiment, each anode stack 203 is a multi-anode stack including three anode foils 203a, 203b, and 203c. In other embodiments, anode stack 203 includes one, two, three or more anode foils having a variety of anode shapes. Each anode foil has a major surface 206 and an edge face 207 generally perpendicular to major surface 206. Anodes 203a, 203b, and 203c are generally foil structures and can include aluminum, tantalum, hafnium, niobium, titanium, zirconium, and combinations of these metals.

In one embodiment, anode foils 203a-203c are high formation voltage anode foils, which will be discussed below. In other embodiments, the anode foils are medium and/or low formation voltage foils. In one embodiment, the major surface of each anode foil 203a-203c is roughened or etched to increase its microscopic surface area. This increases the microscopic surface area of the foil with no increase in volume. Other embodiments use tunnel-etched, core-etched, and/or perforated-core-etched foil structures. Other embodiments utilize other foil compositions and classes of foil compositions.

Depending on which process is used to construct the anode, various surfaces are coated with a dielectric. For example, in embodiments where the anode shapes are punched from a larger sheet which has previously been coated with dielectric, only the surfaces which have not been sheared in the punching process are coated with dielectric. But if the dielectric is formed after punching, in various embodiments, all surfaces are coated. In some embodiments, anodes are punched from a larger sheet to minimize handling defects due to handling during the manufacturing process. For example, if a larger sheet is used as a material from which a number of anode layers are punched, machines or operators can grasp the material which is not intended to form the final anode. Generally, in embodiments where the entire anode is not covered with dielectric, the anode must be aged.

Attachable to anode stack 203 at major surface 206 of anode 203b is a foil connection structure such as a tab or connection member 204, made from aluminum, which electrically connects each anode foil to the other anodes of the capacitor. For instance, in the present embodiment, each tab or connection member 204 of each capacitor element 105a, . . . , 105n is connected to each other connection member 204 and coupled to terminal 103 for electrically coupling the anode to a component or electronic assembly outside the case. In one embodiment, each anode 203a includes a notch 205 which is slightly larger than the width of connection member 204. Connection member 204 fits within notch 205, and this prevents connection member 204 from causing a bulge in anode stack 203. However, other embodiments omit the notch to avoid reducing the surface area of anode 203a. In other embodiments, connection member 204 is omitted and an integrally connected tab connection member is utilized for one or more anode foils.

Figure 3:
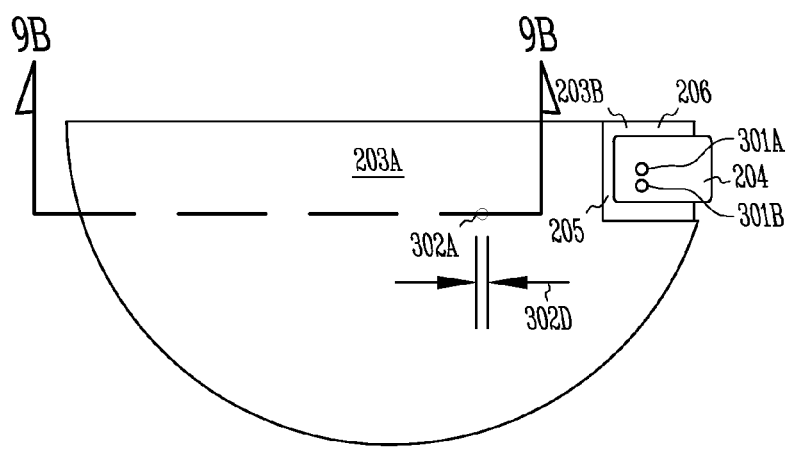
FIG. 3 is a top view of a connection member-to-foil connection and a foil-to-foil connection according to one or more embodiments of the present subject matter.

FIG. 3 shows a top view of capacitor element 105a. In one embodiment, each anode foil 203a-203c of multi-anode stack 203 is interconnected to the other foils 203a-203c of multi-anode stack 203 at a stake weld joint 302a, which will be discussed in more detail below.

In one embodiment, connection member 204 is attached to major surface 206 of anode 203b. Member 204 is attached to anode 203b by a method the inventors call micro-staking. Micro-staking is a cold welding or staking process which uses a small staking point. In one embodiment, each micro-stake joint 301a and 301b is approximately 0.015" (0.381 mm) in diameter. In other embodiments, micro-stake joints 301a and 301b are less than or equal to approximately 0.030" (0.762 mm) in diameter. In some embodiments, joints 301a and 301b can range from approximately 0.005" (0.127 mm) to approximately 0.030" (0.762 mm). In some embodiments, joints 301a and 301b can range from approximately 0.010" (0.254 mm) to approximately 0.020" (0.508 mm).

The small size of joints 301a and 301b allows one to use smaller connection members 204 and to place them closer to an edge 303 of anode 203b than typical capacitors. For instance, in one embodiment, joints 301a and 301b are approximately 0.120" (3.048 mm) from edge 303, and joint 301a is approximately 0.100" (2.54 mm) away from the top edge of foil 206. This in turn allows notch 205 to be smaller than in typical capacitors. For instance, in one embodiment, notch 205 is approximately 0.200" by 0.200" (5.08 mm by 5.08 mm). A smaller notch allows more surface area for anode 203a and thus more capacitance per unit volume. The small size of joints 301a and 301b also allows use of a more highly etched, and hence more brittle, foil since making the small weld joint is less likely to crack the brittle foil than large weld joints.

In one embodiment, member 204 is attached to anode 203b at two micro-stake joints, 301a and 301b. Some embodiments only have a single micro-stake joint 301 and others have three or more micro-stake joints. However, the two welds of this embodiment allow for a redundant weld in case either of the welds fail. In other embodiments, tab 204 is attached by other techniques, such as laser welding or soldering. In one embodiment, tab 204 is attached only to a single anode foil, anode 203b.

Figure 4:
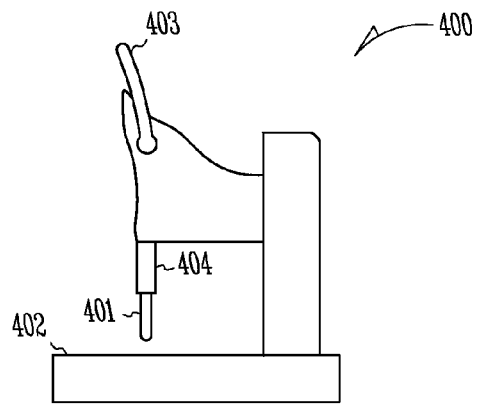
FIG. 4 is a side view of a staking machine having a staking tool for performing staking according to one embodiment of the present subject matter.

FIG. 4 shows a staking machine 400 for making micro-stake joints 301a and 301b according to one embodiment. Machine 400 includes a hardened, planar, anvil surface 402 and a handle 403. A micro-staking tool 401 is shown installed in machine 400. In one embodiment, machine 400 is a hand-operated press manufactured by Gechter Co. of Germany. Alternatively, by way of example, but not limitation, other cold-welding machines, pneumatic presses, electronic solenoid, electro-punch, air over hydraulic, or hydraulic presses can be used to perform the micro-staking process.

Tool 401 is held within a tool holder or collet 404 which is operatively coupled to handle 403. Pulling handle 403 moves collet 404 and tool 401 towards surface 402. Alternatively, as noted above, pneumatic pressure, an electric driver, hydraulic, solenoid, or other actuation means can be used to activate tool 401.

Figure 5:
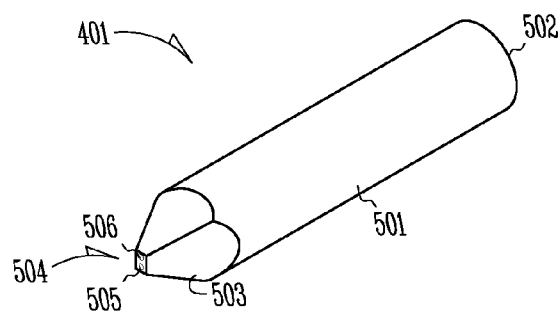
FIG. 5 is an isometric view of the staking tool of FIG. 4.
Figure 6:
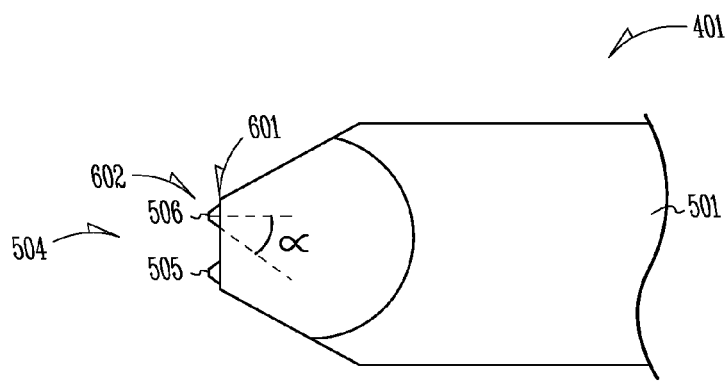
FIG. 6 is a enlarged side view of the staking tool of FIG. 5.

FIGS. 5 and 6 show details of micro-staking tool 401 for performing connection member-to-foil staking according to one embodiment of the present subject matter. Tool 401 is machined from a stainless steel or a tool steel. Tool 401 includes a first end 502 for mounting to collet 404 and a second end 504 for making the micro-staked joints. End 504 includes a first staking pin 505 and a second staking pin 506. In one embodiment, pins 505 and 506 are approximately 0.040" (1.016 mm) apart. In some embodiments, a single pin 505 is used for making a single weld joint.

In one embodiment, each pin 505 and 506 has a generally frustoconical shape rising at an angle α of approximately 30°. Each pin has a circular cross-section having a diameter of approximately 0.028" (0.7112 mm) at its base 601 and a diameter of approximately 0.015" (0.381 mm) at its tip 602. Alternatively, tip 602 can range in diameter from approximately 0.005" (0.127 mm) to approximately 0.030" (0.762 mm); some embodiments range from approximately 0.010" (0.254 mm) to approximately 0.030" (0.762 mm); other embodiments range from equal to or greater than approximately 0.030" (0.762 mm) in diameter. In other embodiments, tip 602 is less than or equal to approximately 0.030" (0.762 mm) in diameter. In some embodiments, tip 602 ranges from approximately 0.010" (0.254 mm) to approximately 0.020" (0.508 mm). By way of example, the pin can have an oval, diamond, elliptical, rectangular, square, or other shaped cross-section. In one embodiment, the tip of each pin 505 and 506 is flat. However, in other embodiments, tips are domed, concave, convex, rounded, or indented and may include a plurality of angles.

Figure 7:
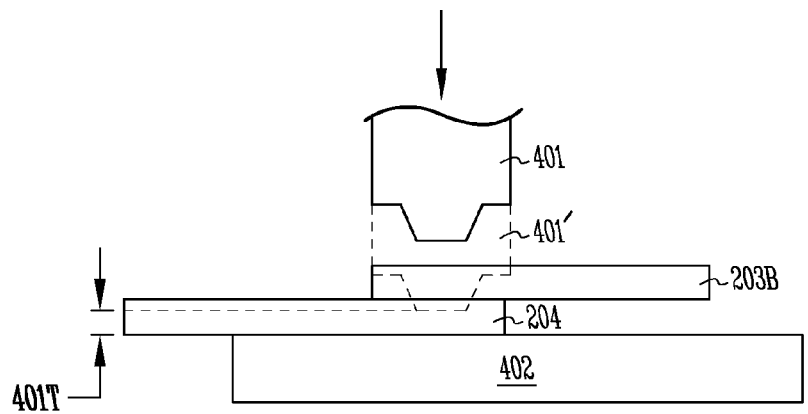
FIG. 7 is an enlarged side view of the staking machine of FIG. 4.

FIG. 7 shows a close-up view of one embodiment of tool 401 being used to micro-stake connection member 204 to anode 203b. In one embodiment, connection member 204 rests against hardened surface 402 and anode 203b lies between connection member 204 and tool 401. Such an arrangement (wherein the connection member rests against the hardened surface and the anode foil is above it) of connection members and foils decreases the likelihood of cracking the brittle foil of anode 203b during micro-staking.

In one embodiment, the hand-operated staking machine is set so that there is a distance 401t of approximately 0.001" (0.0254 mm) between anvil surface 402 and tool 401 when the tool is in its lowest or terminal position 401'. To micro-stake connection member 204 to anode 203b, tool 401 is driven first into anode 203b, which is compressed into connection member 204. In one embodiment, tool 401 is driven to a displacement of 0.001" (0.0254 mm) when micro-staking. In other embodiments, where air, hydraulic, or solenoid force is used, tool 401 is driven under a force in the range of 100 to 1000 pounds until the tool bottoms out. In those embodiments, there is no set clearance.

Figure 8:
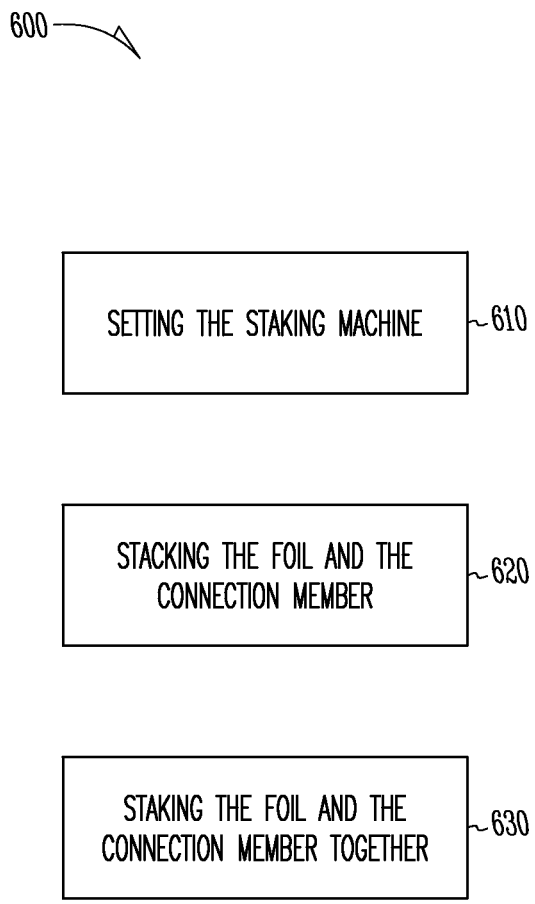
FIG. 8 is a flowchart depicting a method for performing connection member-to-foil staking according to one embodiment of the present subject matter.

FIG. 8 shows a flowchart of one example of a method 600 of joining a connection member and a foil together. Method 600 includes process blocks 610-630. Block 610 entails setting a staking tool; block 620 entails stacking the connection member and the foil; and block 630 entails forcing the foil and connection member together. In one embodiment, a staking machine such as machine 400 having hardened surface 402, and a staking tool such as tool 401 having at least one staking pin 505, are used to perform the method.

Block 610 includes setting staking pin 505 so that there is an approximately 0.001" (0.0254 mm) clearance or displacement between anvil surface 402 and pin 505 when the tool is in its lowest or terminal position. Typically this is done when machine 400 is a hand-operated press.

In some embodiments, block 610 is omitted. For instance, as noted above, pneumatic, hydraulic, air over hydraulic, electric solenoid, electric driver, or other actuation means can be used to activate tool 401. In these embodiments, tool 401 is set to be driven under a force of approximately 100 pounds to 1000 pounds until it bottoms out or until a pre-determined displacement is reached.

Block 620 includes placing a connection member, for instance connection member 204, on hardened surface 402 and stacking or placing a foil, such as foil 203b, on top of connection member 204.

In block 630, the staking machine is activated so that tool 401 drives downward and forces the foil and the connection member together between hardened surface 402 and staking pin 505.

The micro-staking process results in the micro-staked weld joints 301a and 301b as shown in FIG. 3. As described above, in one embodiment, these welds are relatively close to edge 303 of the anode. Thus, a relatively small connection member can be used and a relatively small notch can be used in the notched anode, such as anode 203a. This increases the capacitive surface area of the anode without increasing the volume of the capacitor itself, thus increasing its energy density.

Referring again to FIG. 3, each anode foil 203a-203c of multi-anode stack 203 is interconnected to the other foils 203a-203c of multi-anode stack 203 at a stake weld joint 302a. In one embodiment, foil-to-foil joint 302a has a diameter 302d of approximately 0.025" (0.635 mm). In some embodiments, joint diameter 302d is less than approximately 0.060" (1.524 mm). In various embodiments, joint diameter 302d ranges from approximately 0.015" (0.381 mm) to less than approximately 0.060" (1.524 mm).

Figure 9A:
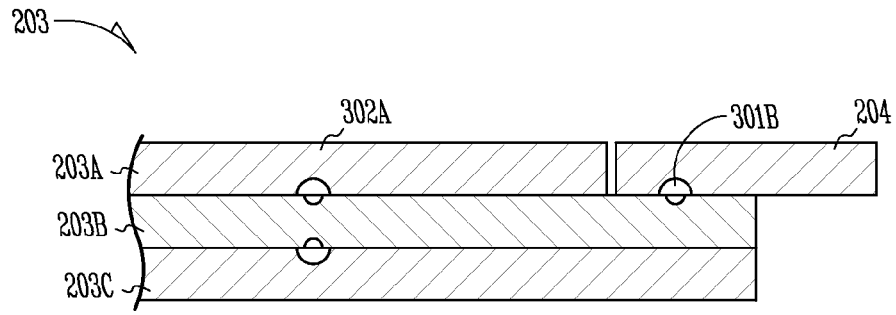
FIG. 9A is a cross-sectional side view of portions of the capacitor stack of FIG. 3.

FIG. 9A shows a cross-sectional view of the foil connection of anode stack 203. Foils 203a-203c are connected by foil-to-foil weld 302a and tab 204 is attached to anode 203b by weld 301b. In various embodiments, foils 203a-203c are different types of etched foils. For example, in one embodiment, all three foils 203a-203c are tunnel-etched foils. In another embodiment, at least one of the foils, for example, foil 203b is a core-etched foil or a perforated core-etched foil. Other embodiments present other permutations of foils. The present joining method is able to successfully join various permutation of materials, thus permitting capacitor manufacturers to design the capacitor with fewer material limitations.

Figure 9B:
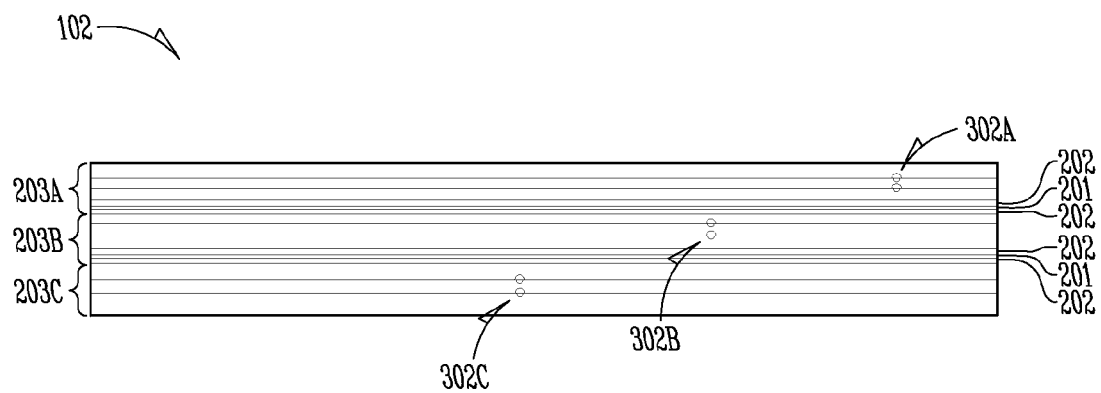
FIG. 9B is a cross-sectional side view of portions of the capacitor stack of FIG. 3.

FIG. 9B shows a cross-sectional view of portions of capacitor stack 102. In the portion shown, capacitor stack 102 includes anode stacks 203a-203c. Between each anode stack is separator 202 and cathode 201. Each anode stack is joined by respective stake welds 302a-302c. In the exemplary capacitor stack, each stake weld 302a-302c of each anode stack 203a-203c is in a different location relative to the major surface of each anode stack. This staggered arrangement of welds provides that the bulges created at any single weld 302a-302c do not cumulate along any single point or vertical line in the capacitor stack. This staggered arrangement helps reduce the overall thickness of capacitor stack 102.

Figure 10:
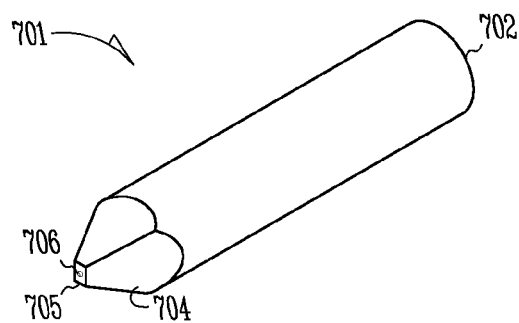
FIG. 10 is an isometric view of a staking tool for performing foil-to-foil staking according to one embodiment of the present subject matter.

FIG. 10 shows a staking tool 701 for staking foils 203a-203c together according to one embodiment of the present subject matter. In one embodiment, a staking machine such as described in FIG. 4 is used. Alternatively, other cold welding machines, pneumatic presses, hydraulic, air over hydraulic or electric solenoid machines are used to perform the staking process.

In some embodiments, such as when the staking machine is hand-operated, tool 701 is driven to a displacement of 0.001" (0.0254 mm) from the hardened surface of the staking machine when the staking is being done. In some embodiments, such as when pneumatic, hydraulic, air over hydraulic or electric solenoid presses are used, tool 701 is driven under a force of approximately 100 pounds to 1000 pounds until it bottoms out or until a pre-determined displacement is reached.

In one embodiment, tool 701 is machined from a stainless steel or a tool steel. Tool 701 includes a first end 702 for mounting to a collet in a staking machine and a second end 704 for making the foil-to-foil staked joints. End 704 includes a stake pin 705 having a tip 706.

In one embodiment, pin 705 has a generally frusto-conical shape rising at an angle α of approximately 30°. The exemplary pin has a circular cross-section. Pin 705 can also have an oval, diamond, elliptical, rectangular, or square shaped cross-section. Pin 705 has a diameter of approximately 0.025" (0.635 mm) at tip 706. Alternatively, in some embodiments, tip 706 is less than approximately 0.060" (1.524 mm). In various embodiments, tip 706 ranges from approximately 0.015" (0.381 mm) to less than approximately 0.060" (1.524 mm). In one embodiment, the tip of pin 705 has a flat surface. However, in other embodiments, the tip is domed, convex, concave, rounded, or may have a plurality of angles.

Figure 11:
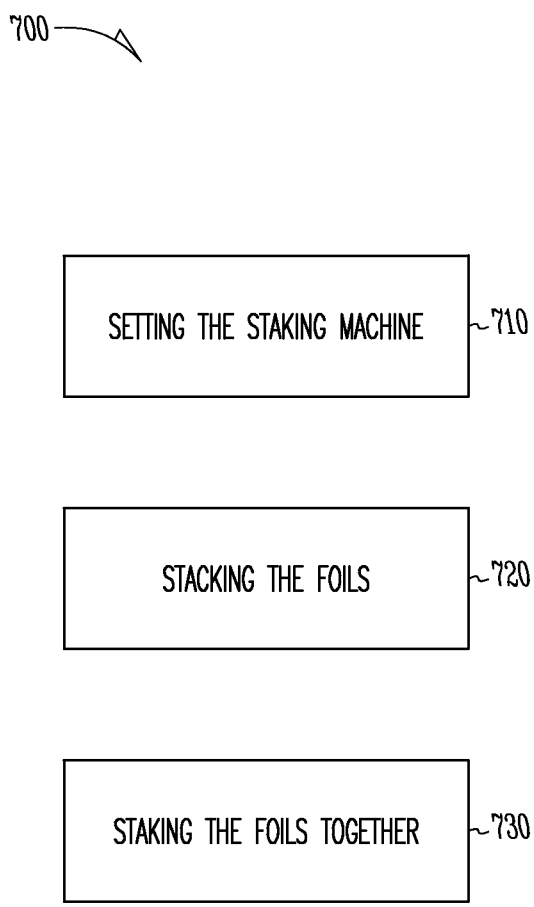
FIG. 11 is a flowchart of a method for performing foil-to-foil staking according to one embodiment of the present subject matter.

FIG. 11 shows a flowchart of one example of a method 700 of assembling two or more anode foils, such as anodes 203a-203c. In one method, three anodes are joined. In other embodiments two, three, four, or more foils are joined using the method. In some embodiments, method 700 joins a stack of foils which includes one or more core-etched foils. However, in various other embodiments, method 700 joins a stack comprising only tunnel-etched foils.

Method 700 includes process blocks 710-730. Block 710 entails setting a staking tool; block 720 entails stacking foils; and block 730 entails forcing the foils together. In one embodiment, a staking machine such as machine 400 having hardened surface 402, and a staking tool such as tool 701 having staking pin 705 are used to perform the method.

Block 710 includes setting staking pin 705 so that there is an approximately 0.001" (0.0254 mm) clearance or displacement between hardened surface 402 and pin 705 when the tool is in its lowest or terminal position. Typically this is done when the staking machine is a hand-operated press.

In some embodiments, block 710 is omitted. For instance, as noted above, pneumatic, hydraulic, air over hydraulic, electric solenoid, electric driver, or other actuation means can be used to activate tool 701. In these embodiments, tool 701 is set to be driven under a force of approximately 100 pounds to 1000 pounds until it bottoms out or until a pre-determined displacement is reached.

Block 720 includes placing a first foil, for instance foil 203c, on hardened surface 402 and stacking or placing one or more foils, such as foils 203b and 203a, on top of foil 203c so that the major surfaces of adjacent foils are in contact with each other and the foils are stacked in a dimension perpendicular to a major surface of each of the foils. After block 720, foil stack 203 is positioned between hardened surface 402 and staking tool 701. In some embodiments, two, three, four or more foils are stacked on the hardened surface.

In block 730, the staking machine is activated so that tool 701 drives downward and forces the anode foils between hardened surface 402 and staking pin 705. In one method, the tool is driven until a displacement of 0.001" (0.0254 mm) between hardened surface 402 and pin 705 is reached. Alternatively, as noted above, if pneumatic, hydraulic, air over hydraulic, electric solenoid, electric driver, or other actuation means are used to activate tool 701, the tool is set to be driven under a force of approximately 100 pounds to 1000 pounds until it bottoms out or until a pre-determined displacement is reached. One embodiment of staking method 700 results in the weld joint 302a as shown in FIG. 3.

Among other advantages of the present method, since joint 302a is small, a more brittle foil can be used and this increases the capacitive surface area of the anode without increasing the volume of the capacitor itself, thus increasing its energy density. Also, a wide variety of foil types can be staked together.

In one embodiment, tab or connection member 204 is staked or micro-staked to anode 203b before the foils 203a-203c are staked together by method 700. Attaching the connection member to only one foil decreases the chance of the highly etched and brittle foil cracking under the stress of the weld. This allows use of foils with greater degrees of etching and thus, smaller volume capacitors.

In assembling capacitor 100, one example method includes assembling two or more anode stacks 203 by method 700. In one embodiment, each anode stack of capacitor 100 has a respective weld 302a-302c in a different location relative to the major surface of the anode stacks. The two or more anode stacks are assembled into capacitor elements 105a-105n. Each anode tab 204 of each element 105a-105n is connected to each adjacent anode tab 204. In one embodiment, the connection members 204 are connected to each other by a method called edge-welding. In other embodiments, the tabs are connected by staking, laser welding, ultrasonic welding, or other methods.

Figure 12:
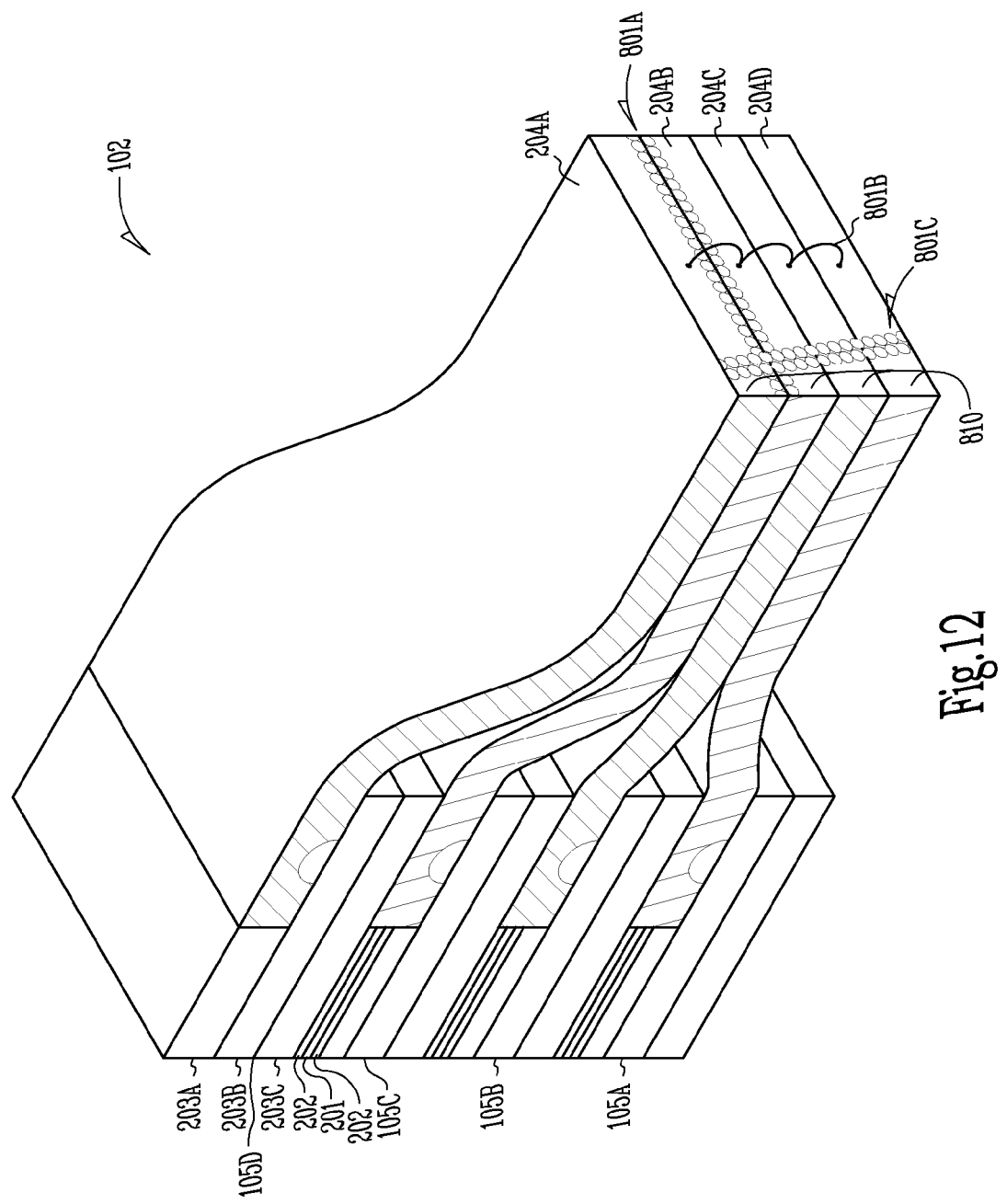
FIG. 12 is a cross-sectional isometric view of a capacitor having edge-connected connection members according to one embodiment of the present subject matter.

FIG. 12 shows a connection member-to-connection member connection according to one embodiment of the present subject matter. In the partial view shown, each capacitor element 105a-105d has a respective tab or connection member 204a-204d attached to it by an attachment method. In one embodiment, micro-staking is used to connect the connection members. In one embodiment, each connection member 204a-204d is approximately 0.004" (0.1016 mm) thick to fill the notch of anode foil 203a, which is 0.004" (0.1016 mm) thick. In other embodiments, the anode foil and the cathode and paper assembly have different thicknesses and so does the connection member. In some embodiments, anode 203a is not notched and each connection member 204a-204d is sandwiched between a pair of foils.

Each connection member 204a-204d is positioned so that an exposed front end face 810 of each connection member is flush with the exposed front end faces of its neighboring connection members, forming a flat frontal surface area. In some embodiments, the end faces 810 are cut to be flush with each other. The exposed face or surface of each connection member is the surface or face of the connection member that is open or revealed on the outside of capacitor stack 102.

Each connection member 204a-204d is connected to its neighboring connection members along their respective front faces 810. Three different embodiments of edge connections 801 are shown. Connections 801 include a laser seam edge-weld 801a, a wire bonded connection 801b, and a laser crosswise edge-weld 801c. However, in the present embodiment only one need be used at any given time. In one embodiment (not shown), edge connection 801 is provided by an ultrasonic edge weld.

In one embodiment, laser edge-weld 801a is provided by a Lumonics JK702 Nd-YAG laser welder using settings of approximately 1.4 Joules at a frequency of 100 hertz. The laser power is approximately 110 Watts, the pulse height is approximately 22%, and the pulse width is approximately 1.4 msec. In various embodiments, the pulse width ranges from about 1.0 ms to about 2.5 ms and the energy level ranges from about 0.8 J to about 2.0 J. In the present process, the connection members are held together in a vice, and the laser beam diameter is approximately 0.011" (0.279 mm). The laser beam is applied along the edge of connection members 204a-204d in a longitudinal manner incrementing to the left or to the right. Alternatively, other welding patterns are used to edge-weld connection members 204a-204d. In some embodiments, the connection members are welded along the horizontal axis, perpendicular to the edges of the connection members 204a-204d. (As shown in cross-wise edge-weld 801c).

Edge-connecting connection members 204a, 204b, 204c, and 204d to each other provides a better electrical connection than crimping them together. Moreover, edge-connection 801 creates a substantially flat, front surface area on the end of the connection members for attachment of a feedthrough terminal or a ribbon connection member (not shown).

Figure 13:
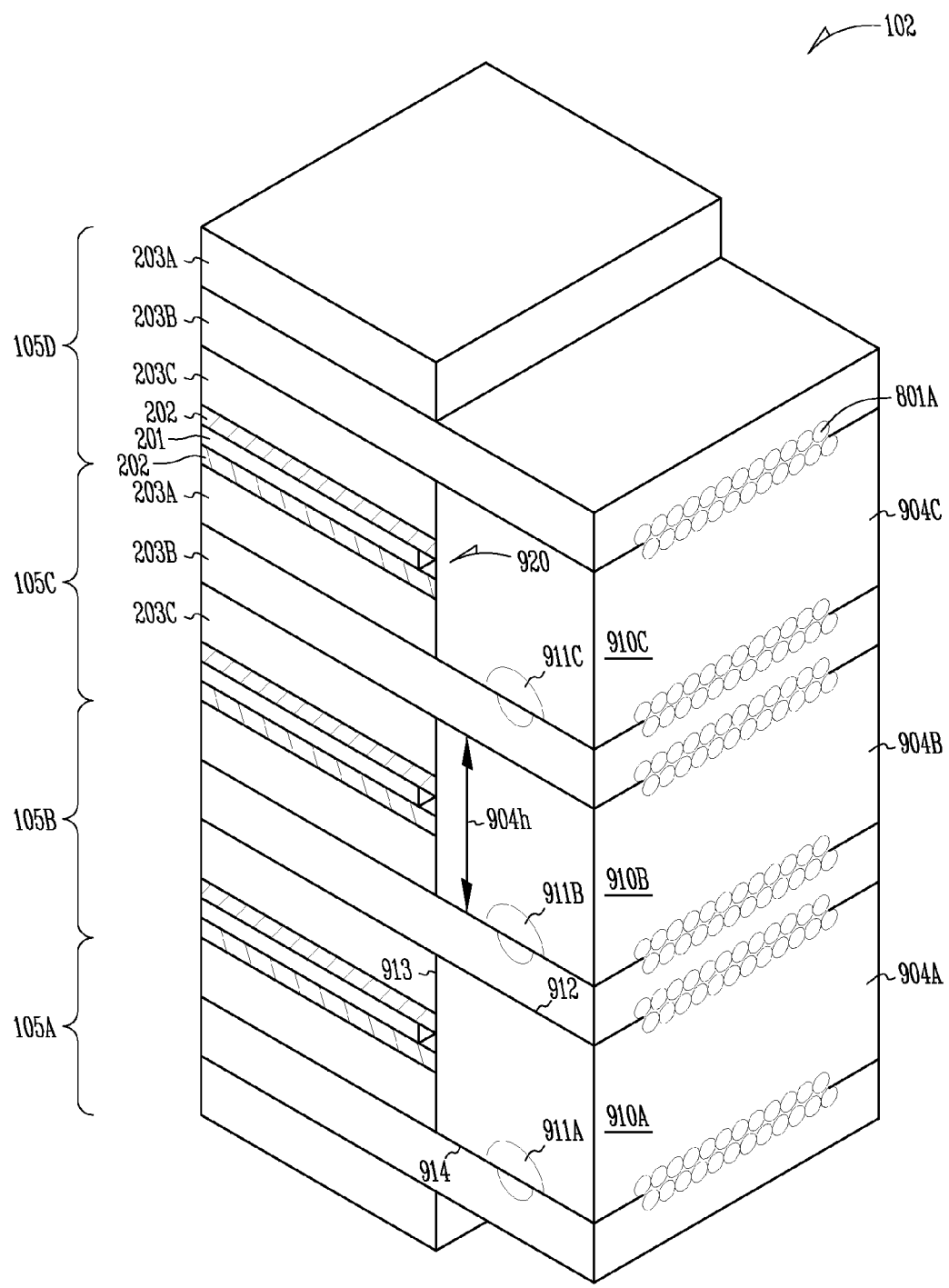
FIG. 13 is a cross-sectional isometric view of a capacitor having edge-connected connection members according to another embodiment of the present subject matter.
Figure 14:
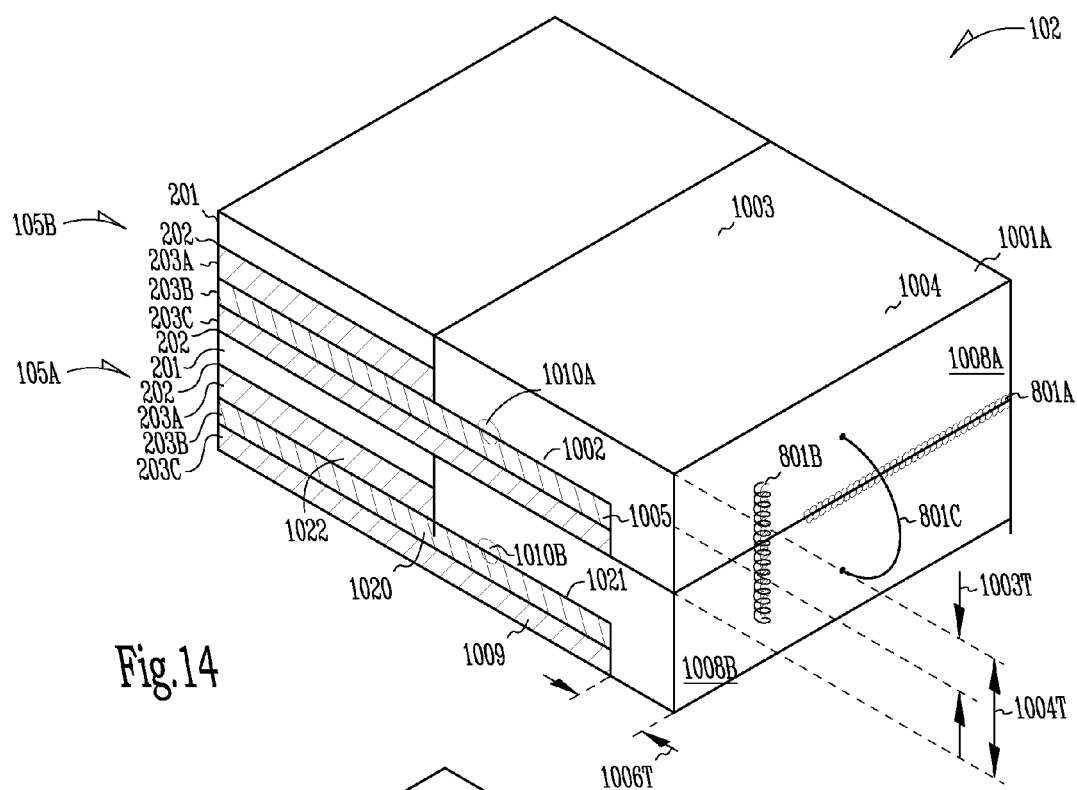
FIG. 14 is a cross-sectional isometric view of a capacitor having edge-connected connection members according to another embodiment of the present subject matter.
Figure 15:
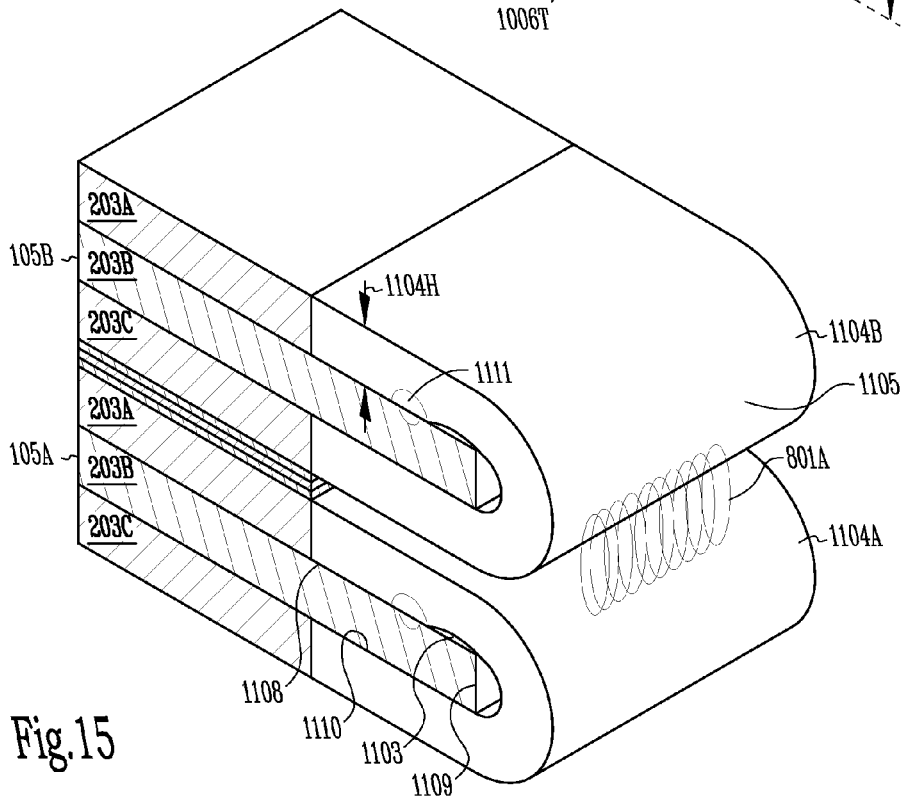
FIG. 15 is a cross-sectional isometric view of a capacitor having edge-connected connection members according to another embodiment of the present subject matter.

FIGS. 13-15 show other embodiments of various connection member structures and anode layouts that are used for edge-connecting as shown in FIG. 12. In each embodiment shown, anode foils 203a-203c each have a thickness of 0.004" (0.1016 mm) and each cathode 202 and paper separator 201 layer has a combined thickness of 0.002" (0.0508 mm). These thicknesses are exemplary and for the purpose of describing the various exemplary connection member structures. In some embodiments, the various structures and features of FIGS. 12-15 are combined with each other.

FIG. 13 shows one embodiment in which each capacitor element 105 includes two notched anodes, anode 203a on the top of the stack and anode 203c on the bottom of the stack and an un-notched middle anode 203b. Some embodiments include two or more top, bottom, and middle anodes. When two or more elements (such as elements 105c and 105d) are stacked, the notch of top anode 203a of lower element 105c and the notch of bottom anode 203c of upper element 105d define a major notch 920. Each major notch, such as major notch 920, receives connection members 904a, 904b, and 904c so that the connection members do not cause a bulge in the anode stack. Each capacitor element 105a-105c has respective connection member 904a-904c attached to it by micro-staking or other attachment method at respective joints 911a-911c.

In this embodiment, each connection member 904a-904c is block-shaped and has a height 904h of approximately 0.014" (0.3556 mm). This allows each connection member to fill the space created by the 0.004" (0.1016 mm) anodes and the 0.0012" (0.0305 mm) cathode 201, and by separators 202. In other embodiments, different thicknesses of anodes, cathodes, paper, and connection members are used.

In one embodiment, each connection member 904a-904c includes four faces 910, 912, 913, and 914. In one embodiment, adjacent faces (such as 912 and 913) are perpendicular to each other. In some embodiments, other angles and shapes are used. Back face 913 abuts or confronts the edge face of top anode 203a of lower capacitor element 105c and the edge face of bottom anode 203c of upper element 105d. Top and bottom faces 912 and 914 abut the major surfaces of adjacent middle anodes 203b.

Each connection member 904a-904c is positioned and sized to fit within the notches of anodes 203a and 203c so that there is no overhang of the connection member over the edge of the anodes (in one embodiment, each connection member is 0.050" (1.27 mm) deep) and so that the exposed front face 910 of each connection member is substantially flush and evenly aligned and substantially co-planar with its neighboring connection members and with the edge of anode 203b, forming a flat frontal surface area. This flat surface provides an excellent surface for performing laser edge-welding or other edge-connecting.

Each connection member 904a-904c is edge-connected to its neighboring connection members at their respective exposed front faces 910a-910c. Since there is no need to squeeze connection members 904a-904c together before they are edge-connected, less stress is put on the connections 911a-911c.

FIG. 14 shows one embodiment in which each capacitor element 105 includes one notched anode 203a for receiving connection members 1001a and 1001b without causing a bulge in anode stack 203. Each capacitor element 105a and 105b has respective connection member 1001a and 1001b attached to it by micro-staking or other attaching method at a weld joint 1010.

In this embodiment, each connection member 1001a and 1001b is a bracket-shaped member and includes a cut-out section 1002, which gives connection members 1001a and 1001b a stepped-shaped or L-shaped body having two surfaces at right angles to each other. The L-shaped body includes a first section 1003 and a second, thicker section 1004. First section 1003 provides a generally planar surface 1020 for attaching to a major surface 1021 of anode 203b, while an upper face of section 1003 abuts the lower major surface of anode 203c. Section 1003 includes a back face 1022 which abuts the edge face of anode 203a. In one embodiment, first section 1003 has a thickness 1003t of approximately 0.004" (0.1016 mm), which is approximately the same thickness as anode 203a. Section 1003 has a length 1007t of approximately 0.050" (1.27 mm).

Second section 1004 provides a surface substantially perpendicular to surface 1020 of section 1003. The inner surface or face 1009 of section 1004 overhangs and confronts the edge faces of anodes 203b and 203c. An outer face 1008 of section 1004 provides an exposed surface for being edge-connected to its neighboring connection members. In one embodiment, second section 1004 has a thickness 1004t of approximately 0.014" (0.3556 mm), which is approximately the same thickness as the total thickness of anodes 203a, 203b, 203c, cathode 201, and separator 202. This provides that each connection member is flush with and abutting the next connection members in the capacitor and that an excellent aluminum surface is exposed for laser edge-welding and other edge-connecting. In one embodiment, second section 1004 has a width 1006t of about 0.020" (0.508 mm).

In other embodiments, the size of cut-out 1002 and the dimensions of sections 1003 and 1004 of connection members 1001a and 1001b are governed by or proportional to the thickness of the anodes of a capacitor. In general, connection members 1001 are designed to permit second section 1004 to overhang and confront the front edge of anodes 203b and 203c and to lie flush with the next adjacent connection member in the capacitor. For example, in one embodiment (not shown), both anodes 203a and 203b are notched and connection member first section 1003 has a thickness of approximately 0.010" (0.254 mm) (thus filling the 0.010" notch) while second section 1004 still has a thickness of approximately 0.014" (0.3556 mm). In other embodiments, different sized anodes, cathodes, paper, and connection members are used.

Each connection member 1001a and 1001b is edge-connected to its neighboring connection members. Since there is no need to squeeze connection members 1001a and 1001b together before they are edge-connected, there is less stress on the connections 1010a and 1010b. Furthermore, each connection member takes up less overall space, thus saving space within the capacitor.

In some embodiments, the connection members have a T-shape cross-section or other shapes which provide a first section for attaching to the anode foil and a second section for confronting the front edge of the foil.

FIG. 15 shows one embodiment in which each capacitor element 105 includes two notched anodes, anode 203a on the top of the stack and anode 203c on the bottom of the stack, and one or more anodes 203b not having notches. Each capacitor element 105a-105b has a respective connection member or connection member 1104a-1104b attached to it by microstaking or other attaching method at respective weld joints 1111a-1111b. In one embodiment, each connection member 1104a-1104b has a height 1104h of approximately 0.004" (0.1016 mm) to approximately match the thickness of the anode foil. This leaves a small gap in the notch between the connection members. In one embodiment, each connection member has a thickness of about 0.005" (0.127 mm) so that the notch is completely filled. In other embodiments, differences in size, anode, cathode, paper, and connection members may be used without departing from the scope of the present subject matter.

In this embodiment, each connection member 1104a-1104b is originally a flat strip and is wrapped around anode 203b to cover and confront the front edge of the anode foil to create a U-shaped cross-section. Alternatively, in some embodiments, each connection member 1104 is originally manufactured with a U-shaped profile or cross section and is placed into a position as shown.

Each connection member 1104a-1104b has an inner surface 1103 and an outer surface 1105. Inner surface 1103 includes a first section 1108 abutting a major top surface of middle anode 203b, a second section 1110 abutting a major bottom surface of anode 203b, and a third section 1109 confronting an edge face of anode 203b. Surface section 1109 is substantially perpendicular to sections 1108 and 1110, while sections 1108 and 1109 are substantially parallel to each other. In one embodiment, surface 1110 is attached to anode 203b.

Each connection member 1104 fits within the notches of anodes 203a and 203c so that outside surface 1105 of each connection member is exposed and aligned with its neighboring connection members, thus forming a frontal surface area which is exposed for being edge-connected.

Each connection member 1104 is edge-connected to its neighboring connection members. Since there is no need to squeeze connection members 1104a-1104b together before they are edge-connected, there is less stress on the connection member-to-anode connection 1111a-1111b.

Referring again to FIG. 2 and as discussed above, in one embodiment anode foils 203a-203c are high formation voltage anode foils. In one embodiment, high formation voltage foils are anode foils having a formation voltage of approximately 441 volts or greater. In one embodiment, the high voltage anode foil comprises an anode foil having a formation voltage between approximately 441 volts and approximately 600 volts. In one embodiment, the high voltage anode foil comprises an anode foil having a formation voltage of approximately 600 volts. In another embodiment, the high voltage anode foil comprises an anode foil having a formation voltage of approximately 600 volts to approximately 880 volts. Other embodiments include other high formation anode foils and will be discussed below. As noted above, some embodiments of the present subject matter include low and medium formation voltage foil.

Figure 16:
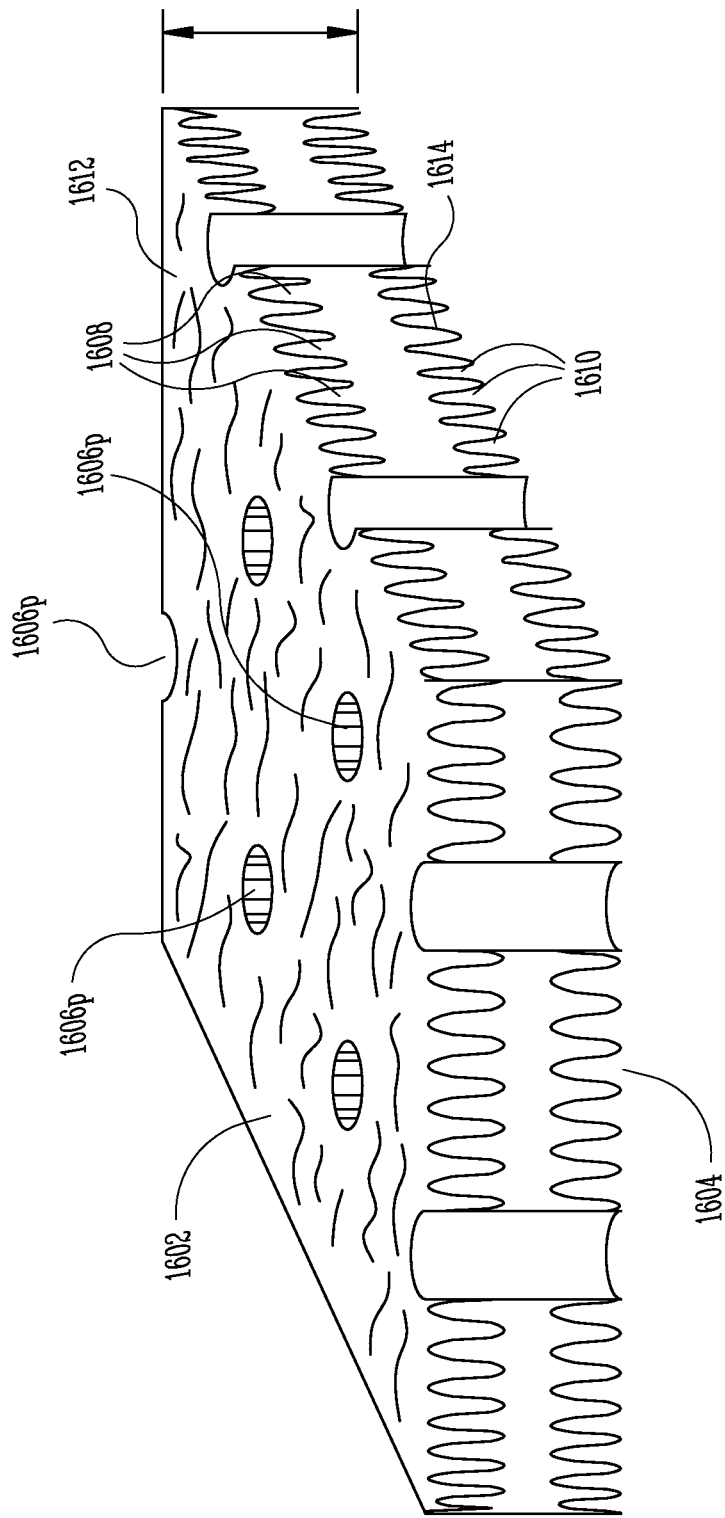
FIG. 16 is an perspective view of an anode foil according to one embodiment of the present subject matter.

FIG. 16 shows an enlarged perspective view of anode foil 203a according to one embodiment of the present subject matter. Anode 203a includes opposing surfaces 1602 and 1604 and a set of perforations 1606p which extend through anode foil 203a from surface 1602 to surface 1604. Surfaces 1602 and 1604 include respective sets of surface cavities (or depressions) 1608 and 1610, which have generally cylindrical, conical, or hemispherical shapes. However, the anode foils are not limited to any particular cavity form, class of cavity forms, or combination of cavity forms. For instance, some embodiments include a porous structure having only cavities. Some embodiments include only perforations. Other embodiments use tunnel-etched, core-etched, and/or perforated-core-etched foil structures. Other embodiments utilize other foil compositions and classes of foil compositions.

On the major surfaces of anode foil 203a are oxide layers 1612 and 1614. Oxide layers 1612 and 1614 are the dielectric layers of the capacitor. The dielectric layer separates the anodes from the cathodes. Examples of suitable oxide layers include metallic oxides such as aluminum oxide ($Al_2O_3$). In one embodiment, layers 1612 and 1614 have a thickness sufficient to withstand approximately 441 volts or greater. In one embodiment, layers 1612 and 1614 have a thickness sufficient to withstand up to 600 volts. Other embodiments withstand 600 volts to 800 volts or greater. In one embodiment, dielectric layers 1612 and 1614 have a thickness conforming to and covering the etched surface to a height of at least 540 nm. In some embodiments, the dielectric layer ranges from approximately 573 nm to approximately 1200 nm. In one embodiment, the anode layers 203*a-c* have a dielectric thickness sufficient to withstand approximately 455 volts to approximately 575 volts during operation. In additional embodiment, layers 203*a-c* have a dielectric thickness sufficient to withstand between about 490 volts and about 540 volts during operation. Other embodiments withstand from about 500 volts to about 530 volts during operation. One example is able to withstand about 515 volts during operation.

In one embodiment, dielectric layers on anodes 203*a-c* have a thickness conforming to and covering the etched surface to a height of between approximately 455 nanometers and about 575 nanometers. In some embodiments, the dielectric layer ranges from approximately 490 nanometers to about 540 nanometers. Other embodiments range between about 500 nanometers and about 530 nanometers. One embodiments includes approximately 515 nm. However, due to the nature of the formation of a dielectric surface, it should be noted that variations in the thickness of coatings are substantial.

The present subject matter is useful to produce a capacitor stack with a high energy density, due in part to the improved surface shape of the anode. An improved surface area increases the surface area of the electrodes without increasing the overall size of the capacitor stack. In various embodiments, the present subject matter is capable of creating a capacitor with a delivered energy density of from about 5.1 joules per cubic centimeter of capacitor stack to about 6.5 joules per cubic centimeter of capacitor stack. Additional embodiments deliver energy density of from about 5.5 joules per cubic centimeter of capacitor stack volume to about 6.1 joules per cubic centimeter of capacitor stack volume. One example delivers about 5.8 joules per cubic centimeter of capacitor stack volume.

FIG. 17A shows a flowchart of a method 1700 for preparing an anode foil for use in a capacitor according to one embodiment of the present subject matter. In block 1702, the method includes providing an anode foil. In block 1704, the method includes etching the anode foil. In block 1706, the method includes forming a dielectric layer on the anode foil.

In various embodiments, the etching of block 1704 includes core-etching the foil, tunnel-etching the foil, perforating the foil and combinations and permutations of these techniques. In some embodiments, perforations such as perforations 1606*p* discussed above are formed using lasers, chemical etchants, or mechanical dies, for example. Exemplary cavities 1608 and 1610 could also be formed using lasers. Some embodiments tunnel-etch the foil, other embodiments provide other known methods of providing a porous or etched foil. In some embodiments, a porous anode structure is constructed using other roughening or etching techniques.

In one embodiment, forming a dielectric layer comprises forming a layer of $Al_2O_3$ having a thickness in the range of 573 nm to 1200 nm on the anode foil (assuming a dielectric growth rate of 1.3-1.5 nm/V). In one embodiment, the dielectric layer is formed on the anode before the capacitor stack is constructed.

In one embodiment, forming the dielectric layer includes applying a current through the anode and raising the voltage to the rated formation voltage. In one embodiment, the formation voltage is 441 volts. In other embodiments, the forming voltage is 450, 500, 550, 600, and 600-800 volts, and other voltages ranging from approximately 441 to approximately 800 volts or greater. The current causes a dielectric $Al_2O_3$ to form on the surface of the foil. Once the formation voltage is reached, the capacitor is held at that voltage until a leakage current stabilizes at a pre-determined level. By monitoring the rising voltage and/or the leakage current, the oxide formation can be estimated. Once the preset voltage is reached, it plateaus, in which case a current drop ensues in order to balance the increasing resistance of oxide film growth. The process is complete when the current drops to a pre-specified value.

Some embodiments combine etching and dielectric forming so that the etching and dielectric forming are done simultaneously.

In one embodiment, method 1700 results in an aluminum anode foil having a formation voltage between approximately 441 volts and approximately 600 volts. In various embodiment, this includes a foil having a formation voltage of approximately 441, approximately 450, approximately 500, approximately 550, approximately 600, and approximately 600 volts to approximately 800 volts or greater. Varying embodiments form a dielectric at approximately 600 volts to approximately 760 volts. In one embodiment, a dielectric thickness sufficient to withstand between about 653 volts and about 720 volts develops during formation. Other embodiments withstand from about 667 volts to about 707 volts during formation. One example is able to withstand about 687 volts during formation.

Figure 17B:
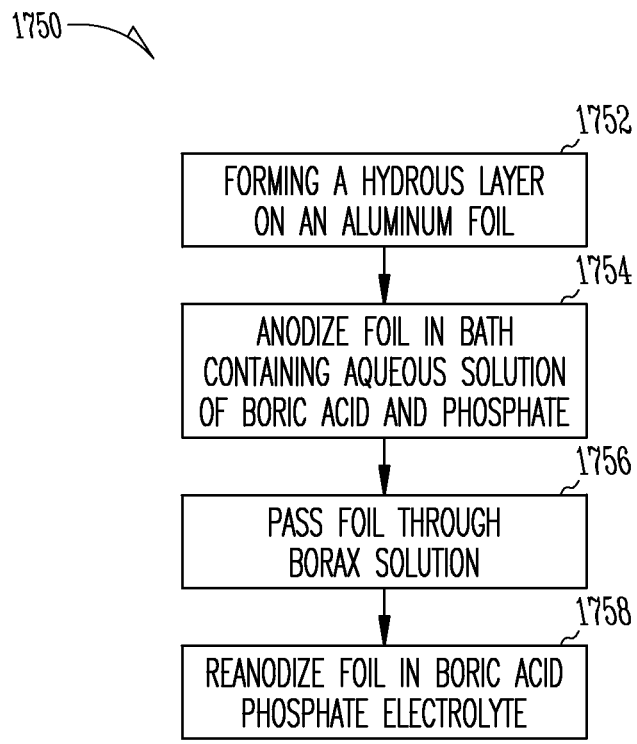

FIG. 17B illustrates an exemplary process for the anodization of aluminum electrolytic capacitor foil, according to one embodiments of the present subject matter. In varying embodiments, the present subject matter is capable of producing anodized aluminum electrolytic capacitor foil at a formation voltage from about 200 volts to about 760 volts, which can result in a capacitor with a working voltage from about 150 volts to about 570 volts. Additionally, the present subject matter is capable of producing an aluminum electrolytic capacitor foil which can deliver about 5.3 joules per cubic centimeter of capacitor stack volume to about 6.3 joules per cubic centimeter of capacitor stack volume, at a voltage of between about 150 volts to about 570 volts.

Varied processes can be utilized to produce the aluminum foil of the present subject matter. For example, one process includes forming a hydrous oxide layer on an aluminum foil by immersing the foil in boiling deionized water 1752. The aluminum foil is also subjected to electrochemical anodization in a bath containing an anodizing electrolyte 1754 composed of an aqueous solution of boric acid, a phosphate, and a reagent. Additionally, the anodizing electrolyte contains a phosphate. In various embodiments, the anodizing electrolyte is at a pH of approximately 4.0 to approximately 6.0. In some examples, the foil is passed through a bath containing a borax solution 1756. Borax, in various embodiments, includes a hydrated sodium borate, $Na_2B_4O_7 \cdot 10H_2O$, and is an ore of boron.

In varying embodiments, the foil is reanodized in the boric acid-phosphate electrolyte previously discussed 1758. In various embodiments of the present subject matter, the process produces a stabilized foil suitable for oxide formation of up to approximately 760 volts.

In various embodiments, the anodizing electrolyte used in block 1754 and 1756 contains about 10 grams per liter to about 120 grams per liter of boric acid and approximately 2 to approximately 50 parts per million phosphate, preferably as phosphoric acid, and sufficient alkaline reagent to lower the resistivity to within approximately 1500 ohm-cm to approximately 3600 ohm-cm and increase the pH from about 4.0 to about 6.0 for best anodization efficiency and foil quality.

In some embodiments, the borax bath contains 0.001 to 0.05 moles/liter of borax. Because the anodizing electrolyte is acidic, in various embodiments, the borax bath is buffered with sodium carbonate to prevent lowering of the pH by dragout of the acidic electrolyte. Additionally, in various embodiments, the borax bath is buffered to lower its resistivity. In one example, the pH of the bath is from about 8.5 to about 9.5, and the temperature is at least approximately 80 degrees Celsius. In varying embodiments, the sodium concentration is approximately 0.005 to approximately 0.05M, preferably about 0.02 M. It should be noted that concentrations of less than approximately 0.005M are too dilute to control properly, and concentrations above approximately 0.05M increase the pH, resulting in a more reactive solution which degrades barrier layer oxide quality.

In varying embodiments of the present subject matter, the presence of at least approximately 2 parts per million phosphate in the acidic anodizing electrolyte is critical. For example, this presence initiates stabilization of the foil so that solely hydrous oxide dissolves in the alkaline borax bath, without damage to the barrier layer dielectric oxide. In varying embodiments, this lowers ESR (equivalent series resistance) of the anodized foil.

Additionally, in various embodiments, when the foil is reanodized following the alkaline borax bath, the foil surface is alkaline and reacts electrochemically with the phosphate, which, in various embodiments, results in the incorporation of phosphate into the dielectric oxide. In varying examples, the alkaline foil surface includes an alkaline metal aluminate, and in one embodiment includes a sodium aluminate. It should be noted that the amount of allowable phosphate in the anodizing electrolyte, in various embodiments, is inversely proportional to the voltage at which the foil is being anodized. For example, in one embodiment, using greater than approximately 24 parts per million results in failure during oxide formation at around 650 volts. In embodiments where approximately 50 parts per million of phosphate is exceeded, the electrolyte scintillates at the foil interface, resulting in damaged, unstable foil. One benefit of the present subject matter is that an electrode is produced which can tolerate a high formation voltage without scintillation at the boundary layer of the foil. It should be noted that anodization temperature should be maintained from about 85 degrees Celsius to about 95 degrees Celsius, as variance outside of these values results in a barrier layer oxide of lower quality, and foil corrosion.

Various aspects of the present subject matter include performance properties which enable the capacitor to function as a single capacitor in an implantable cardioverter defibrillator 1760. For example, by constructing the capacitor stack with the methods and apparatus contained in these teachings, one may construct a capacitor which is suited for use as the sole capacitor used for powering therapeutic pulses in an implantable cardioverter defibrillator. By using a single capacitor, instead of two capacitors which are connected in series, the present subject matter contributes to weight and size reductions.

Figure 18:
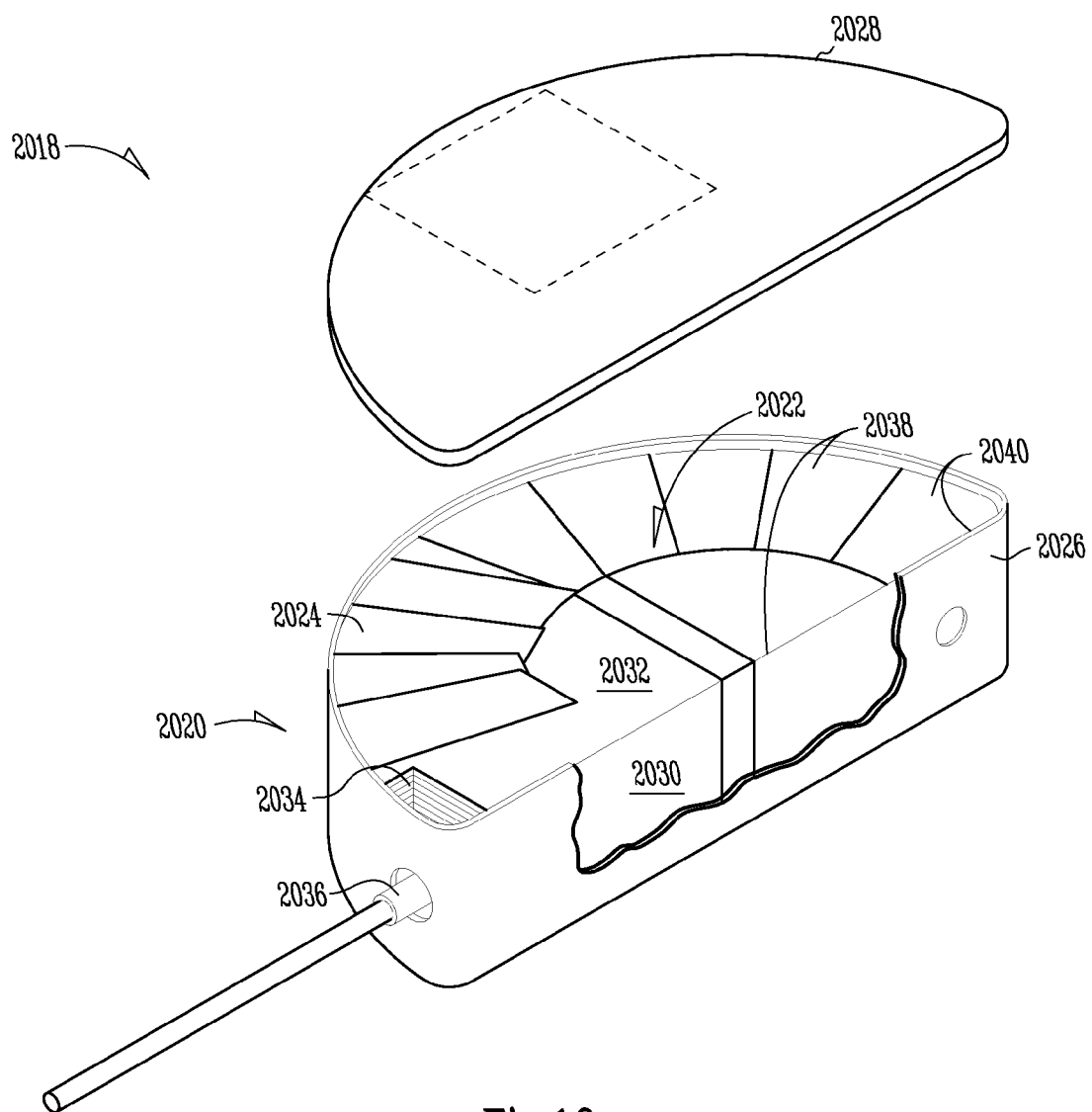
FIG. 18 is a perspective view of a flat capacitor according to one embodiment of the present subject matter.

FIG. 18 shows a partially exploded view of a capacitor 2018 according to one embodiment of the present subject matter. Capacitor 2018 includes one or more features of capacitor 100 of FIG. 1, and some details will be omitted in the present description. In this embodiment, the capacitor includes a case 2020 defining a chamber 2022, in which is placed a capacitor stack 2024.

Case 2020 includes a base 2026 and a lid 2028 overlying and resting on an upper rim of base 2026. Stack 2024 has a face 2030 and a top surface 2032. Stack 2024 has a cutout region 2034 at its periphery, with cutout region 2034 being positioned when the stack 2024 is installed in case 2020 to provide space for electrical connections. An anode feedthrough post 2036 passes through to stack 2024 and is electrically insulated from case 2020. The capacitor stack 2024 is covered with insulating tape 2038. A space 2040 exists between the lid 2028 and the top surface 2032 of the stack 2024 and between the face 2030 of the stack 2024 and a lateral wall of the base 2026 of the case 2020. In some embodiments, space 2040 is a line-to-line interference fit between portions of stack 2024 and case 2020. In other embodiments, space 2040 is a gap or opening within the case and between the stack and the case.

Capacitor stack 2024 includes anode assemblies and cathode assemblies, with separator layers interposed therebetween.

Figure 19:
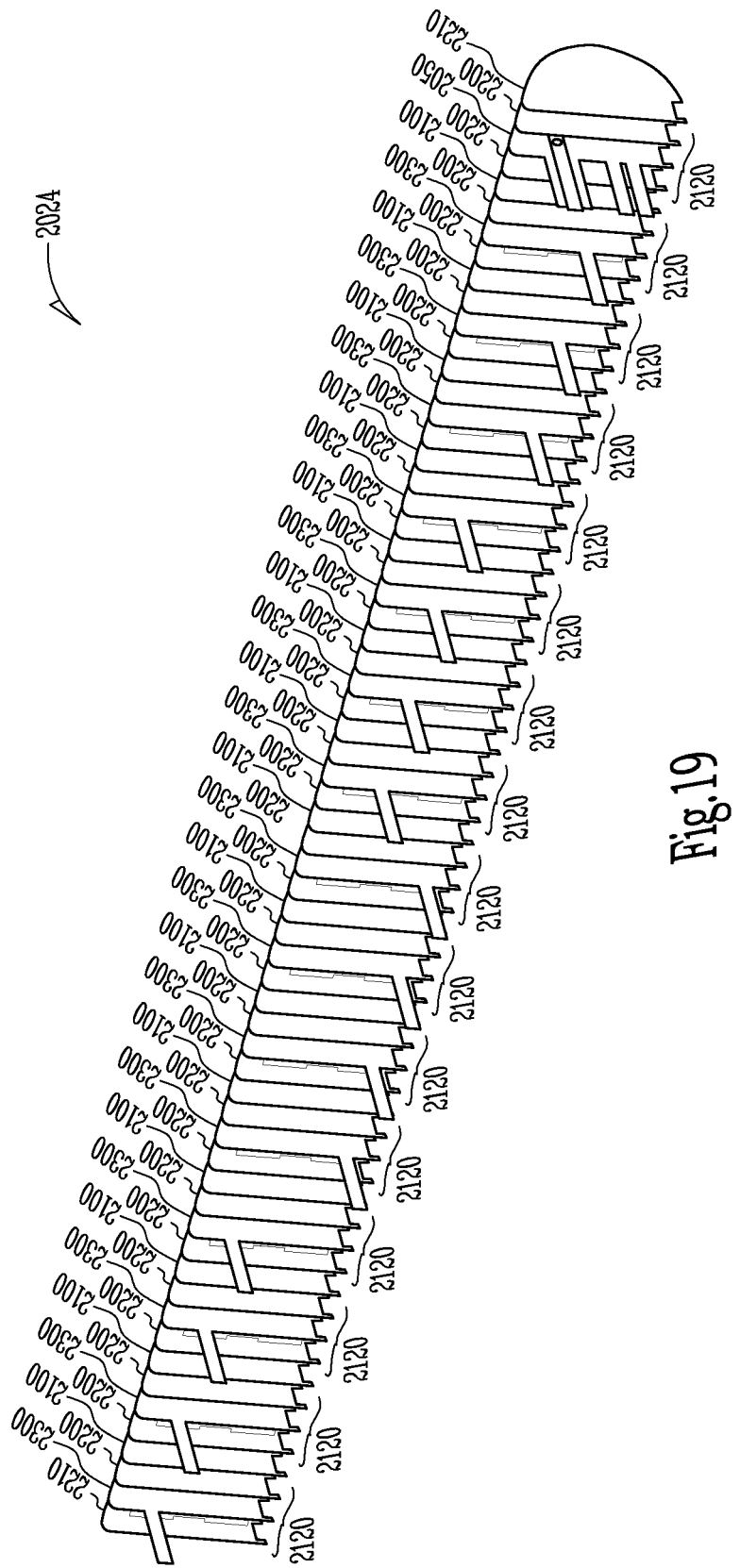
FIG. 19 is an exploded perspective view of a capacitor stack constructed in accordance with one embodiment.

FIG. 19 illustrates an exploded view of capacitor stack 2024 according to one embodiment. Stack 2024 includes a plurality of layers 2120 which include at least one first electrode comprised of an anode stack 2100, at least one separator 2200, and at least one second electrode comprised of one of cathode stacks 2300. The separator 2200 separates each anode stack 2100 from each cathode stack 2300.

Figure 20:
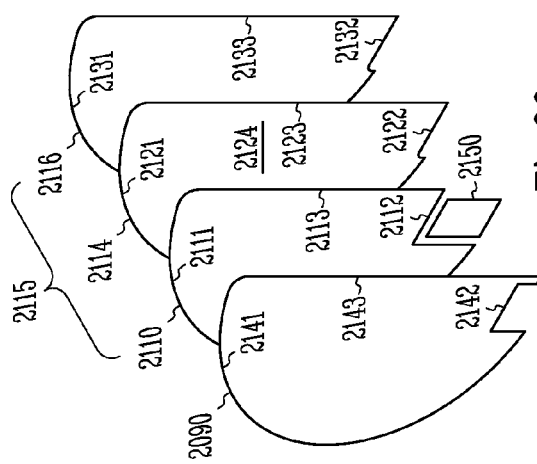
FIG. 20 is an exploded perspective view of an anode stack constructed in accordance with one embodiment.

FIG. 20 illustrates an exploded view of one example of an anode stack 2100. The anode stack 2100 includes a plurality of anode layers including conductive layers 2115 consisting of an upper conductive layer 2110, a middle conductive layer 2114, and a lower conductive layer 2116 as well as an anode-separator layer 2090. Each conductive anode layer has a first edge 2111, 2121, 2131, and 2141, respectively. Each anode layer also includes a clearance area defined by a second edge 2112, 2122, 2132, 2142. Each anode layer also includes an optional second edge 2113, 2123, 2133, 2143, respectively. The anode stack 2100 further includes an edge connection member such as edge clip 2150 for use in interconnecting the anode layers in adjacent layers of the capacitor stack 2024.

Figure 21:
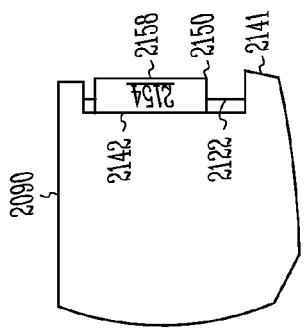
FIG. 21 is a side view of an anode stack and edge connection member constructed in accordance with one embodiment.

FIG. 21 illustrates a portion of an assembled anode stack 2100. The clearance area defined by the second edge 2142 of the anode-separator 2090 leaves the upper surface 2154 of the edge clip 2150 exposed for contact with a connection member such as an adjacent edge clip 2150 of an adjacent layer 2120.

Figure 22:
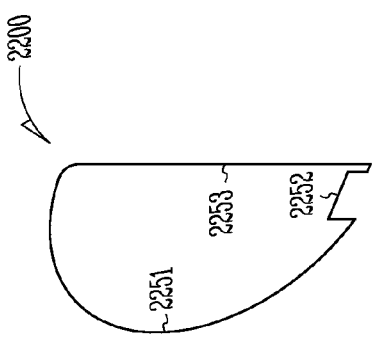
FIG. 22 is a side view of a separator constructed in accordance with one embodiment.
Figure 24:
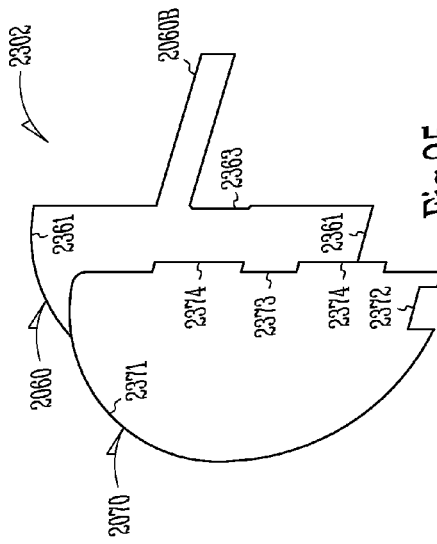
FIG. 24 is an exploded perspective view of a cathode stack constructed in accordance with one embodiment.
Figure 25:
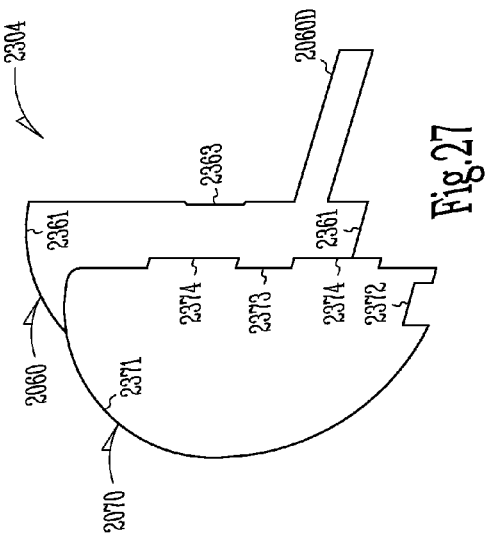
FIG. 25 is an exploded perspective view of a cathode stack constructed in accordance with one embodiment.
Figure 26:
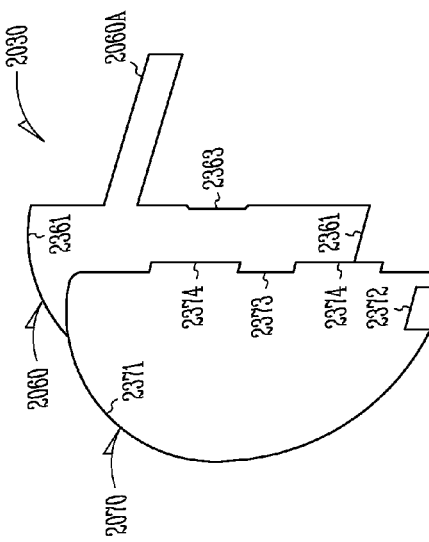
FIG. 26 is an exploded perspective view of a cathode stack constructed in accordance with one embodiment.
Figure 27:
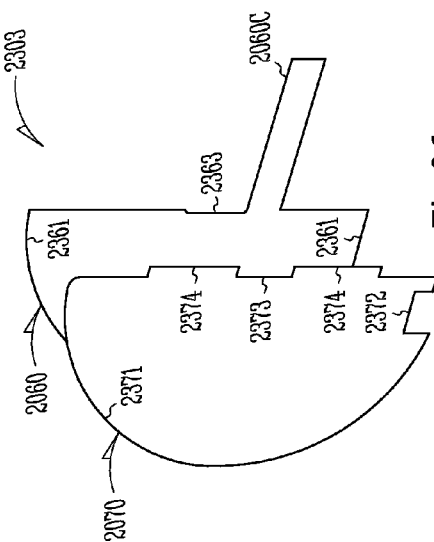
FIG. 27 is an exploded perspective view of a cathode stack constructed in accordance with one embodiment.

FIG. 22 illustrates a separator 2200 which separates the anode stack 2100 from the cathode stack 2300 (FIG. 19). The separator 2200 includes a first edge 2251*a* clearance area defined by a second edge 2252 and a flat edge 2253. The clearance area of the separator 2200 allows a side portion of the edge clip 2150 (FIG. 20) to extend past the separator to reach an edge clip of an adjacent anode stack 2100 (FIG. 19). The separator 2200 is, in one option, made from a roll or sheet of separator material. Suitable materials for the separator material include, but are not limited to, pure cellulose or Kraft paper. Other chemically inert materials are suitable as well, such as porous polymeric materials. The separator 2200 is cut slightly larger than the anode layers (or cathode layers) to accommodate misalignment during the stacking of layers, to prevent subsequent shorting between electrodes of opposite polarity, and to act as an outermost edge for alignment.

Figure 23:
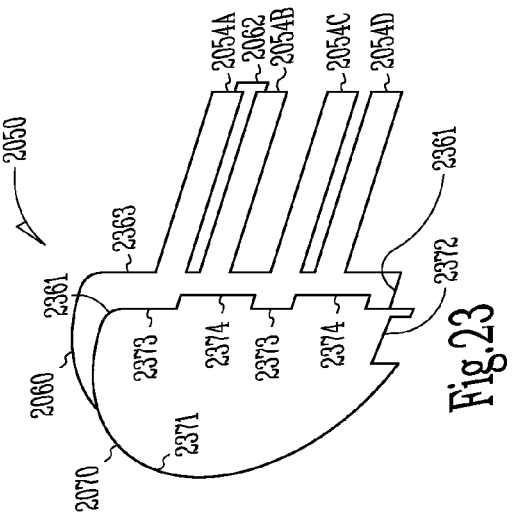
FIG. 23 is an exploded perspective view of a cathode base layer stack constructed in accordance with one embodiment.

FIG. 23 illustrates an exploded view of an embodiment of a cathode base stack 2050 including a cathode conductive layer 2060 and a cathode-separator layer 2070. In this embodiment, cathode conductive layer 2060 includes one or more legs 2054*a*, 2054*b*, 2054*c*, 2054*d* extending from the flat edge 2363. The cathode conductive layer 2060 also includes a cathode extension member 2062 for coupling the capacitor stack 2024 to the case 2020 (FIG. 18). Cathode legs 2054*a*, 2054*b*, 2054*c*, 2054*d* and cathode extension leg 2062 extend beyond the dimensions defined by the inside of the case 2020 during intermediate steps in the manufacturing process and are later formed to fit within the case. The cathode conductive layer 2060 includes a first edge 2361 inset from the first edges of the anode layers 2110, 2114, 2116, and 2090 (FIG. 20) and inset from the second edges of the anode layers 2110, 2114, 2116, and 2090. The conductive layer 2060 also includes a flat edge 2363 inset from the flat edges of the anode layers 2110, 2114, 2116, and 2090.

Cathode-separator layer 2070 is also provided and includes a first edge 2371, a clearance area defined by a second edge 2372, a flat edge 2373 and an extension edge 2374. The cathode conductive layer 2060 includes a first edge 2361 inset from the first edge 2371 of the cathode-separator and inset from the second edges of the cathode-separator layer 2070. The cathode conductive layer 2060 also includes a flat edge 2363 inset from the flat edges of the cathode-separator layer 2070. The inset edge 2361 of the cathode conductive layer 2060 and the clearance area of the cathode-separator layer 2070 allows a portion of the edge clip 2150 (FIG. 20) to extend past the cathode conductive layer 2060 and the cathode-separator layer 2070 to reach an edge clip 2150 (FIG. 20) of an adjacent anode stack.

Referring to FIGS. 24-27, examples of cathode stacks 2300 are shown. Cathode stacks 2300 include in one embodiment, cathode stacks 2301, 2302, 2303, 2304. Each cathode stack 2301, 2302, 2303, 2304 includes cathode layers comprising a cathode conductive layer 2060 and a cathode-separator layer 2070. In this embodiment, each cathode stack 2301, 2302, 2303, 2304 conductive layer 2060 includes an extension member such as a leg 2060a, 2060b, 2060c, or 2060d respectively. Cathode legs 2060a-2060d on each cathode stack 2301, 2302, 2303, 2304 extend beyond the dimensions defined by the case 2020 (FIG. 18) during intermediate steps in the manufacturing process and are later formed to fit within the case. In one embodiment, each leg 2060a-2060d corresponds to leg 2054a, 2054b, 2054c, 2054d, respectively, on the cathode base layer stack 2050, as will be discussed further below. Each cathode stack 2301, 2302, 2303, 2304 includes a cathode conductive layer 2060 having a first edge 2361, which when stacked, is inset from the first edge 2141 of the anode separator 2090 (FIG. 20) and inset from the second edge 2142 of the anode separator. Further details of cathode stacks 2300 will be described below.

In one embodiment of the present subject matter, the capacitor stack 2024 described above is aligned to provide for optimal surface area of the capacitor.

Figure 28A:
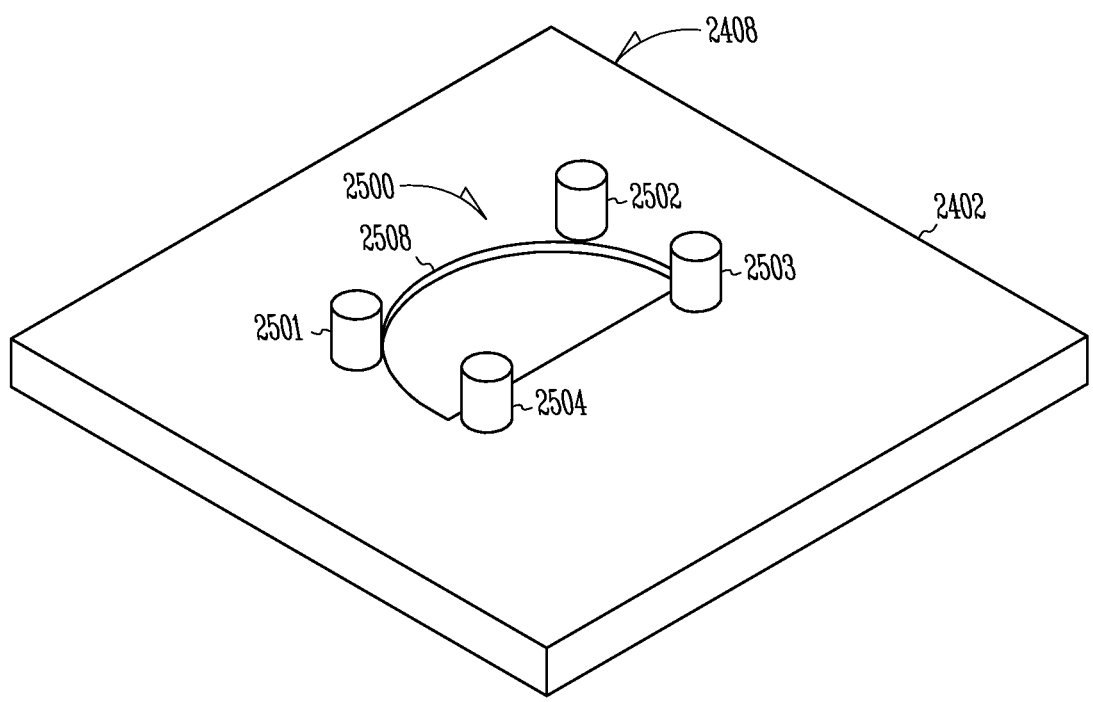
FIG. 28A is a perspective view of an alignment mechanism constructed in accordance with one embodiment.
Figure 28B:
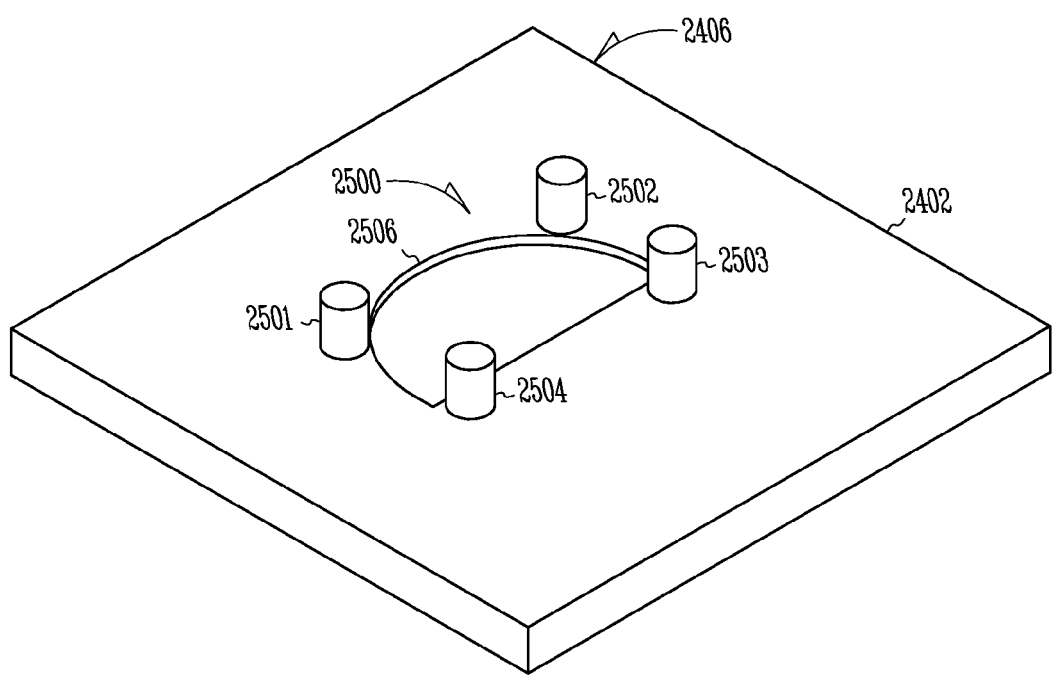
FIG. 28B is a perspective view of an alignment mechanism constructed in accordance with one embodiment.
Figure 29:
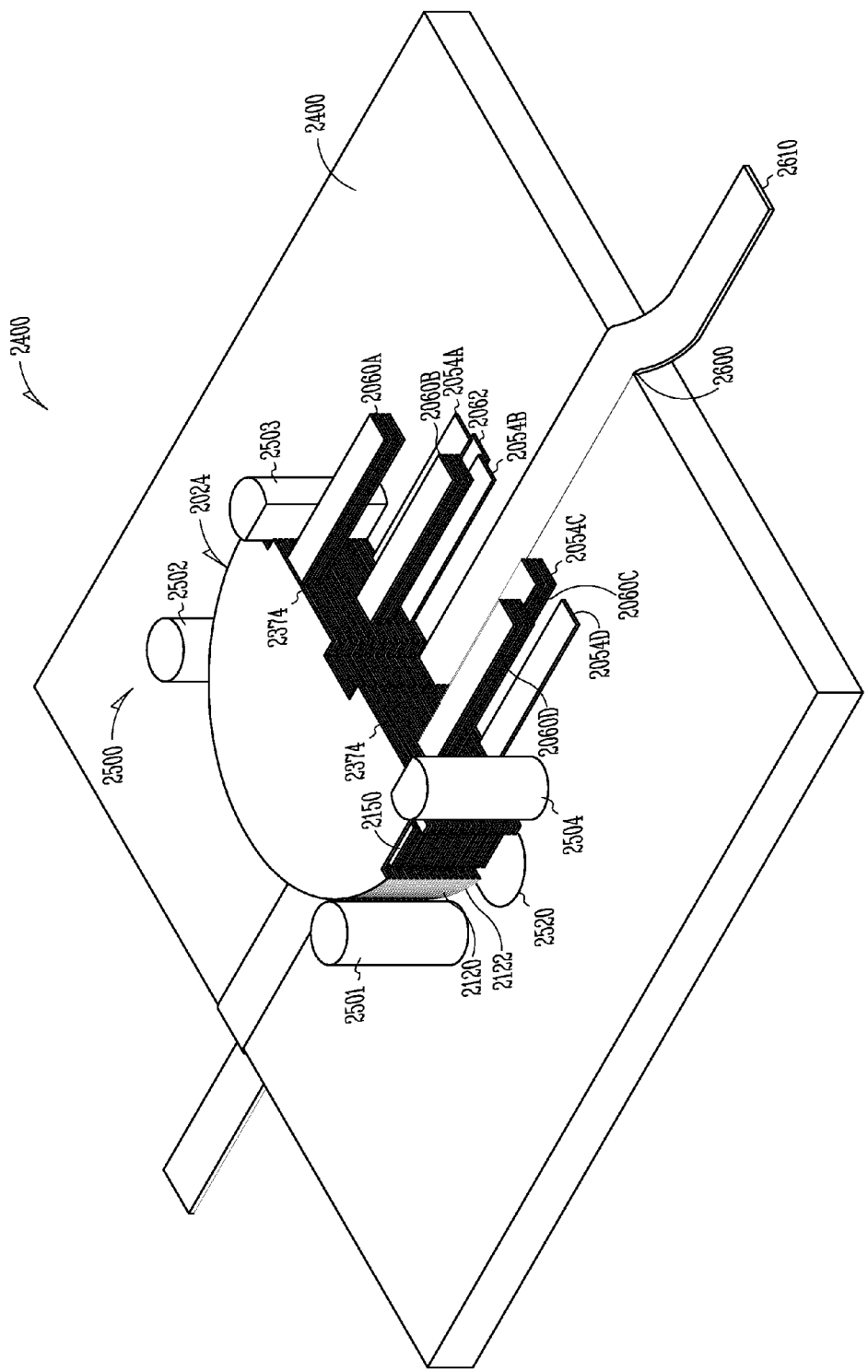
FIG. 29 is a perspective view of a capacitor stack in an alignment mechanism constructed in accordance with one embodiment.

FIGS. 28A, 28B, and 29 illustrate external alignment mechanisms 2408, 2406, 2400 used to assemble anode stack 2100, cathode stack 2300, and capacitor stack 2024, respectively, in accordance with one embodiment. Each of the external alignment mechanisms 2408, 2406, 2400 includes a plurality of precisely placed alignment elements 2500.

The alignment elements 2500 in this embodiment, are vertically placed alignment elements 2501, 2502, 2503, 2504, which extend from a base 2402. The base 2402 supports components thereon, while the alignment elements 2501, 2502, 2503, 2504 align the components while the components are being stacked therein. The external alignment mechanism 2400 optionally includes a first recess 2520, which is sized and positioned to receive a clip, as further discussed below. In another option, the external alignment mechanisms 2406, 2408 each include a second recess 2506, 2508, respectively, in the base 2402, as further discussed below.

Referring to FIG. 29, a capacitor stack 2024 is assembled within the alignment apparatus 2400. The capacitor stack 2024 includes the plurality of layers 2120. Each layer 2122 of the plurality of layers 2120 includes at least one first electrode stack, at least one separator 2200 (FIG. 19) and at least one second electrode stack. Each first electrode stack, second electrode stack and each separator 2200 is aligned relative to the position of the alignment elements 2501, 2502, 2503, and 2504. Optionally positioned within the optional channel 2600 is a fastener 2610, which is for wrapping around a portion of the capacitor stack 2024 once the first electrode stacks, separators 2200 and second electrode stacks have been stacked and aligned. Placing the fastener 2610 in the channel 2600 of the external alignment mechanism 2400 positions the fastener 2610 below the aligned capacitor stack 2024 to maintain flatness of the capacitor stack 2250, for example, for further processing. Alternatively, or in addition to, the optional channel 2600 allows for a gripping device such as pliers to be slipped under the capacitor stack 2250. In addition, precise alignment of the capacitor stack 2250 is maintained by the alignment elements 2500 when wrapping the capacitor stack 2250.

Figure 30:
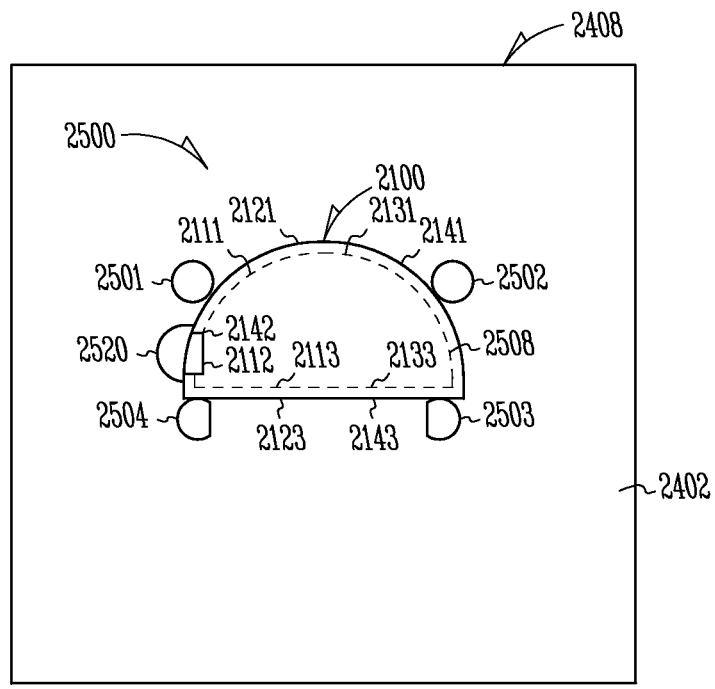
FIG. 30 is a top view of an anode stack aligned within an external alignment mechanism constructed in accordance with one embodiment.

FIG. 30 illustrates a top view of anode stack 2100 within the anode external alignment mechanism 2408, as described in FIG. 28A. To align the anode stack 2100, each conductive layer 2110, 2114, 2116, (FIG. 20) is placed in the recess 2508. The anode separator 2090 (FIG. 20) is placed over the conductive layers 2110, 2114, 2116 and is aligned relative to the alignment elements 2501, 2502, 2503, 2504 by positioning the separator such that the first edge 2141 and the flat edge 2143 extend to contact each of the alignment elements 2501, 2502, 2503, 2504. The second recess 2508 allows the anode separator 2090 to be aligned relative to the conductive layers 2110, 2114, 2116. The alignment elements 2501, 2502, 2503, 2504 concentrically align the separator 2090 relative to the conductive layers 2110, 2114, 2116 (FIG. 20).

In one embodiment, the anode external alignment mechanism 2408 includes a recess 2520. The recess 2520 receives a portion of the edge clip 2150 (FIG. 20) that extends beyond the anode stack 2100 and allows the conductive layers 2115 of the anode stack 2100 to lay flat, one on top of the other within the anode external alignment mechanism 2408. In one embodiment, the anode stack 2100 is staked after being aligned in this manner.

Figure 31:
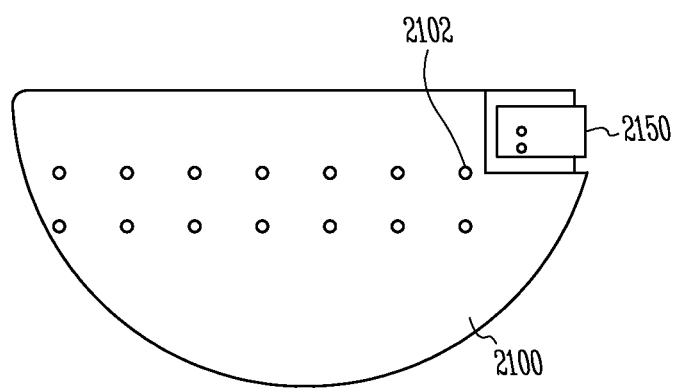
FIG. 31 is a top view of staking locations for a plurality of anode stacks constructed in accordance with one embodiment.
Figure 32:
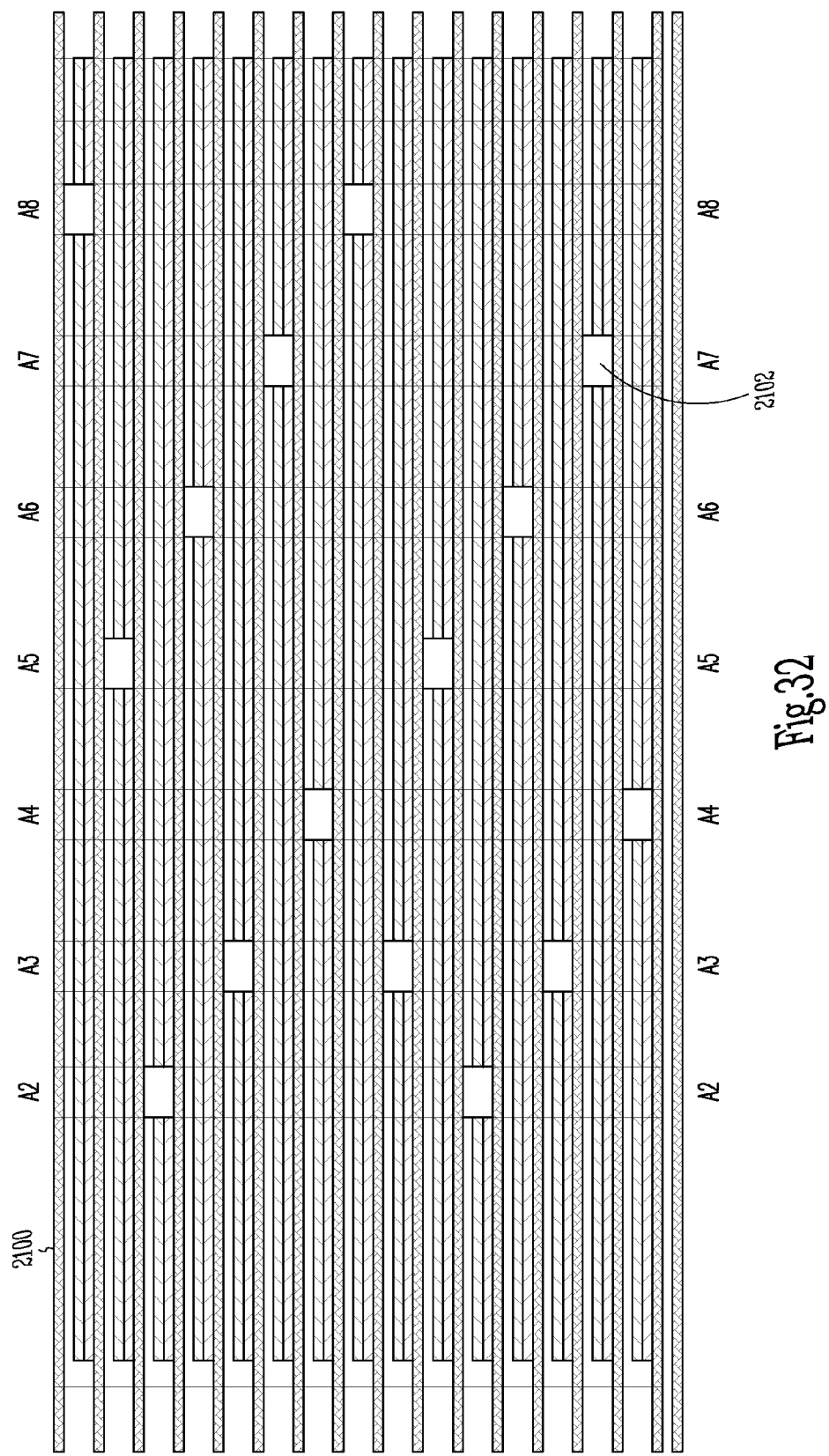
FIG. 32 is a cross-sectional view of the staking locations of FIG. 31.

FIG. 31 illustrates one embodiment in which the anode stack 2100 is removed from the anode external alignment mechanism 2408 (FIG. 30) and staked so that the conductive layers of the anode stack 2100 form an anode chip. In one embodiment, the anode stack is staked as described above, and incorporated herein by reference. In one embodiment, the staking locations 2102 of the anode stacks 2100 in the capacitor stack 2024 (FIG. 18) are distributed so that anode stacks 2100 in adjacent layers have staking locations that are offset from one another, as shown in FIG. 32. In one embodiment, the anode stack 2100 is pressed after being staked to help reduce warpage and to reduce the overall height of the anode stack 2100. In one embodiment, the anode stack 2100 is pressed to a specific, predetermined height.

Figure 33:
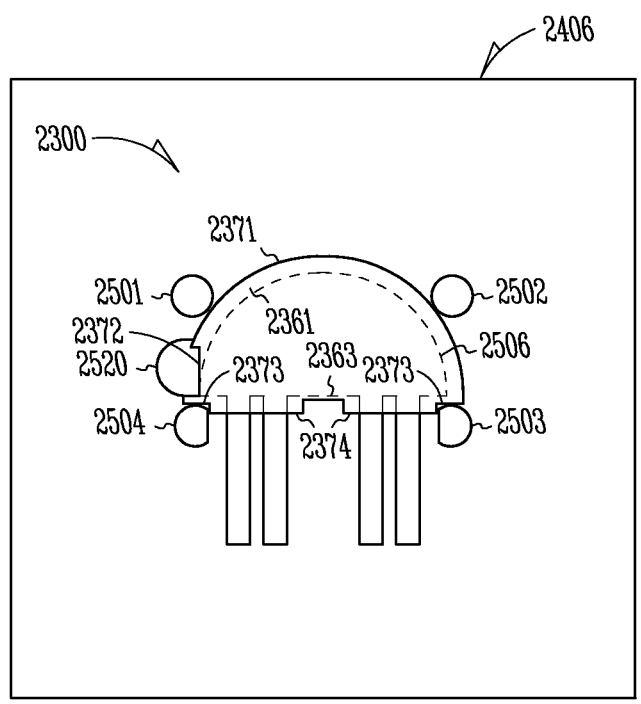
FIG. 33 is a top view of a cathode stack within an alignment mechanism constructed in accordance with one embodiment.

FIG. 33 illustrates a cathode stack 2300 within a cathode external alignment mechanism 2406. The same method is used to align the cathode conductive layer 2060 and cathode separator layer 2070 of the cathode stacks 2050, 2301, 2302, 2303 and 2304, as was used to align the anode stack 2100 (FIG. 30). The cathode conductive layer 2060 is disposed within the recess 2506, and the cathode separator layer 2070 is aligned relative to the alignment elements 2501, 2502, 2503, 2504. Since the alignment elements 2501, 2502, 2503, and 2504 are placed in the same location for the anode external alignment mechanism 2408, the cathode external alignment mechanism 2406, and the external alignment mechanism 2400 (FIG. 29), allows for the stacks 2100, 2300 to be better aligned to one another. This helps to reduce variances in alignment which may result from varying tolerance stack ups between layers of the assembly and the alignment mechanism used.

In one embodiment, the cathode separator layer 2070 is aligned relative to the plurality of alignment elements 2500 by stacking the cathode separator layer 2070 so that edge 2371 and flat edge 2373 extend to contact each of the alignment elements 2501, 2502, 2503, and 2504. While aligned, the cathode separator layer 2070 is coupled to the cathode conductive layer 2060, for example, with adhesive. In one embodiment, each cathode stack 2300 is pressed to help reduce warpage and thus to reduce the overall height of the capacitor stack 2024 (FIG. 18).

Figure 34:
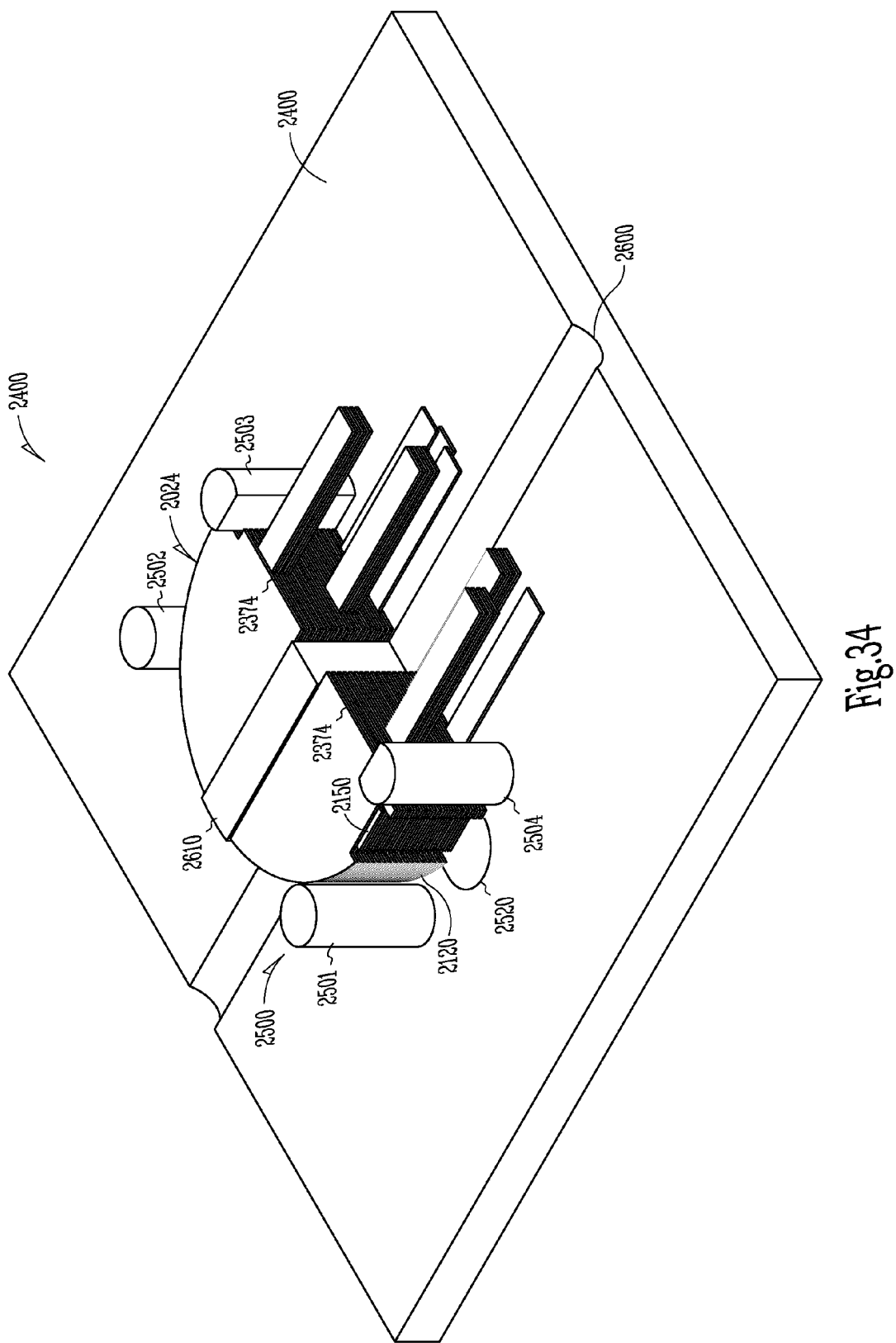
FIG. 34 is a perspective view of a cathode stack in an alignment mechanism constructed in accordance with one embodiment.

FIG. 34 illustrates a capacitor stack 2024 within an external alignment mechanism 2400. In this embodiment, the capacitor stack 2024 includes a plurality of layers 2120, including anode stacks 2100 (FIG. 20), and cathode stacks 2300 (such as cathode stacks 2050, 2301-2304 in FIGS. 23-27), which were each individually aligned with the anode external alignment mechanism 2408 and the cathode external alignment mechanism 2406, respectively. The anode stacks 2100 and the cathode stacks 2050, 2301-2304 are aligned relative to the alignment elements 2500 using one or more outer edges of the cathode separators 2070 (FIGS. 23-27) and one or more outer edges of the anode separators 2090 (FIG. 20). In one embodiment, capacitor stack 2024 includes separators 2200 (FIG. 22) and the alignment elements 2501, 2502, 2503, 2504 further align the separator 2200 relative to the anode stacks 2100 and the capacitor stacks 2300 using an outer edge of the separator 2200 (FIG. 22). In some embodiments, separators 2200 are omitted and capacitor stack 2024 is aligned relative to the alignment elements 2500 using only one or more outer edges of the cathode separators 2070 (FIGS. 23-27) and one or more outer edges of the anode separators 2090 (FIG. 20).

In one embodiment, a fastener 2610 is wrapped around a portion of the stack 2024 to retain the alignment of the layers 2120 relative to one another. In one embodiment, fastener 2610 comprises tape that is wrapped around a central portion of the capacitor stack 2024. Optionally, the capacitor stack 2024 is then clamped and annealed, with or without the fastener 2610. The channel 2600 optionally allows for a tool and/or a robot to be disposed under the stack 2024.

In some embodiments, the anode stack 2100 and the cathode stacks 2050, 2301-2304 are aligned relative to one another within the case 2020, instead of using the external alignment mechanism 2400, and then are coupled to one another in the aligned position. For instance, an outer edge of a separator of the anode stack 2100 (FIG. 20) and an outer edge of a separator of the cathode stacks 2050, 2301-2304 (FIGS. 23-27) would contact an interior surface of the case 2020, and would be aligned therein.

Among other advantages, one or more embodiments of the alignment mechanism described provide for a capacitor making efficient use of space within the case, permit increased anodic surface area, and increased capacitance for a capacitor of a given set of dimensions. Variation in the outer dimensions of one capacitor stack to another capacitor stack is reduced because each is formed within alignment elements positioned the same manner. Dimensional variations in the capacitor stack resulting from variation in the reference points from case to case or alignment apparatus to alignment apparatus are eliminated. This provides improved dimensional consistency in production and allows for reduced tolerances between the capacitor stack and the capacitor case. This allows for more efficient use of space internal to the capacitor case. Each first electrode stack, second electrode stack and each separator is aligned relative to the position of the alignment elements.

Moreover, the example of the capacitor stack structure described above provides for greater anodic surface area since, by aligning to the separator, the anode surface area is optimized by not having to provide extraneous alignment notches or other alignment features on the anode foil itself which decrease the anode surface area.

Since the external alignment mechanism is exterior to the case, better visual observation of the alignment of each electrode stack and separator is provided. Furthermore, multiple points are used to make the alignment, reducing the effect of the tolerance stack up between the conductive layer or separator being aligned and the alignment element at any one position. This also facilitates for alignment of components which during certain steps in the manufacturing process have portions which extend beyond the dimensions defined by the case and are later formed to fit within the case.

In some embodiments, the edges of the cathodes and anodes described above are generally co-extensive or aligned with each other within stack 2024. In other embodiments, capacitor stack 2024 includes anode and cathode layers having at least partially offset edges.

Figure 35:
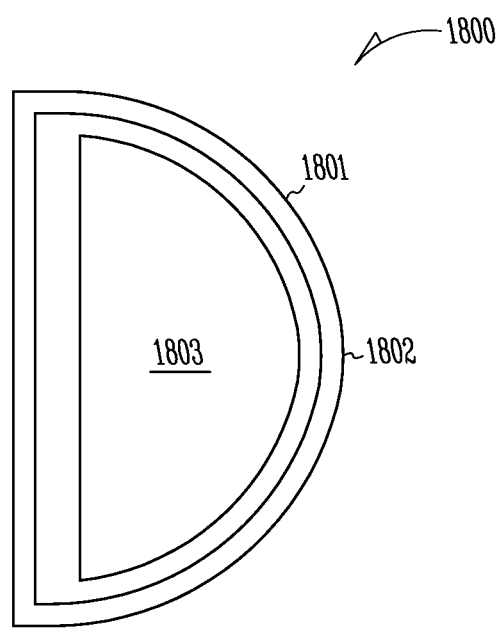
FIG. 35 is a top view of a capacitor stack according to one embodiment.

FIG. 35 shows a planar view of a cathode stack 1800 according to one embodiment. The capacitor stack 1800 includes an anode layer 1801, a separator 1802, and a cathode layer 1803 that are configured in a layered structure analogous to capacitor stack 24 described above. The bottom surface in the FIG. is the anode layer, and the top surface is the cathode layer with the paper separator interposed therebetween. The separator includes two paper separators impregnated with an electrolyte that conducts current between the anode and cathode layers.

Some cutting processes used to make anode and cathode foil layers can produce burrs on the foils that can result in a short circuit if a burr on an anode layer edge portion makes contact with an adjacent cathode layer or vice-versa. When the dimensions of the cathode and anode layers are the same so that the edges of each layer are aligned, a burr on a cathode layer edge portion can then contact a burr on an anode layer edge portion. Burrs on overlapping edge portions of the anode and cathode layers may then make contact and cause a short circuit by traversing only half of the thickness of the paper separator between the two layers.

Accordingly, in one embodiment, the capacitor stack is constructed with layers having edge portions that are offset from one another. In one embodiment, this is done by having a cathode layer with a different dimension than the anode layer so that portions of their edges are offset in the layered structure (i.e., either the anode layer or the cathode layer is smaller than the other). The anode and cathode layers may be of the same general shape, for example, but of different surface areas so that the perimeter of one layer is circumscribed by the perimeter of the other layer.

The capacitance of an electrolytic capacitor results from the charge separation between the electrolyte and the anode layer so that altering the surface area of the cathode layer does not appreciably affect the capacitance of the device. Such an arrangement is shown in FIG. 35 where the cathode layer 1803 is of the same general shape as the anode layer 1801 but with a smaller surface area such that the edge portions of the cathode layer are inwardly offset from the anode layer edges. In this structure, only an edge burr on the cathode layer that traverses the entire thickness of the paper separator can produce a short circuit. This is in contrast to the case where the edge portions of the two layers are aligned rather than being offset. Offsetting the edge portions results in a greater tolerance for edge burrs and allows a less constrained manufacturing process.

Figure 36:
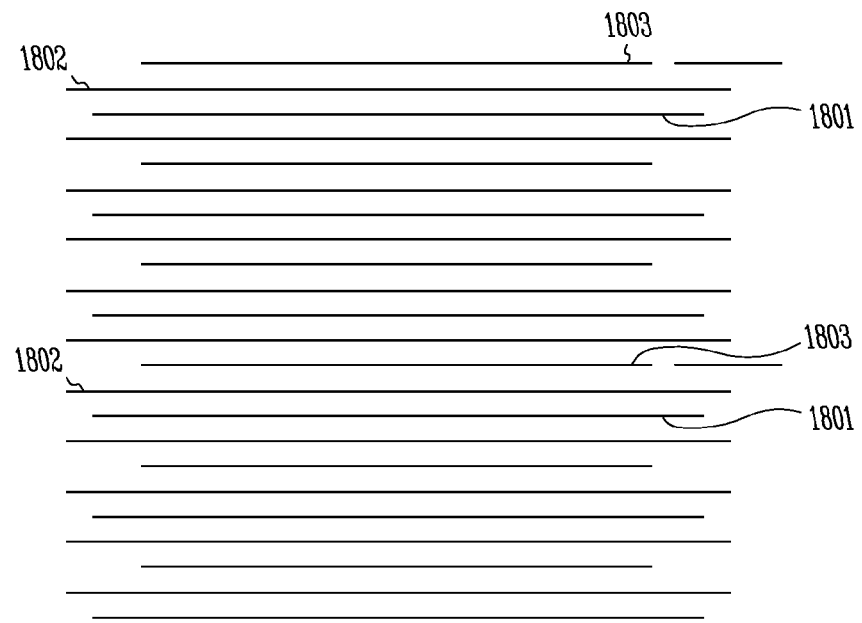
FIG. 36 is a side schematic view of the capacitor stack of FIG. 35.

FIG. 36 shows a cross-sectional schematic of capacitor stack 1800. The capacitor is made up of a plurality of capacitive elements that are stacked on one another with each capacitive element being a layered structure capacitor such as shown in FIG. 35. The anode layers 1801 are stacked on cathode layers 1803 in alternate fashion with paper separator 1802 interposed between each anode layer and each cathode layer.

Varying embodiments use assorted combinations of anodes and cathodes. For example, some embodiments of the capacitor stack include from about 16 planar cathode layers to about 20 substantially planar cathode layers, and from about 52 substantially planar anode layers to about 64 substantially planar anode layers, and one or more substantially planar separator layers. In one example, approximately 58 anode layers are used, and approximately 20 cathode layers are used, with each cathode layer separated from anode stack by approximately 40 separator layers. In this exemplary embodiment, two anode layers have been removed from the example to reduce the thickness of the capacitor stack. In varying examples, this is due to packaging considerations. The example also includes a stack which alternates between one cathode and three anode layers, also called an anode stack. The anode layers are not separated by a separator layer, in various embodiments, to save space.

Figure 37:
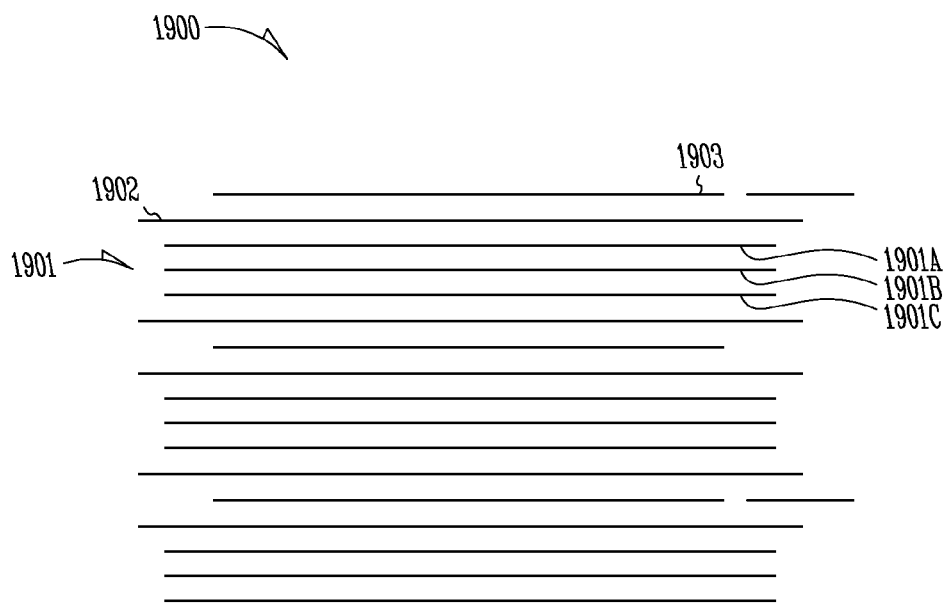
FIG. 37 is a side schematic view of a capacitor stack according to one embodiment.

FIG. 37 shows a capacitor stack 1900 according to one embodiment. Capacitor stack 1900 includes multiple porous anode layers 1901. The multiple layers result in a greater surface area exposed to the liquid electrolyte and a greater capacitance for each element. Three anode layers 1901a-1901c are shown in the FIG. which are stacked together with a paper separator 1902 and cathode layer 1903 on each side of the stack. The liquid electrolyte flows through perforations in the anode layers to reach the oxide layers of each layer. The edge portions of each cathode layer 1903 are inwardly offset from the edge portions of each overlying and underlying anode layer 1901.

In one embodiment, the offset structure described above can be incorporated into a cylindrical capacitor. For instance, the anode and cathode layers are cut from a sheet in a desired width and length. The cathode layer is made narrower than the anode layer so that the edges of the cathode layer are inwardly offset from the anode layer edges. The cylinder configuration is then produced by rolling the layers into concentric anode and cathode layers that are separated by electrolyte.

Offsetting of anode layer and cathode layer edge portions may be accomplished by using a variety of differently shaped and/or dimensioned cathode or anode layers.

In some embodiments, the cathode layer reduction ratio relative to the anode layer is limited. The electrical equivalent circuit of an electrolytic capacitor is the series connection of an anodic capacitance due to the charge separation that occurs between the anode layer and the electrolyte across the dielectric layer, an equivalent series resistance of the capacitor or ESR, and a cathodic capacitance due to the charge separation that occurs between the cathode layer and the electrolyte. When a capacitor is charged to its rated voltage, the voltage is divided and dropped across between the cathodic capacitance Cc and the anodic capacitance Ca. Since the charge stored on cathode layer Qc must equal the charge stored on the anode layer Qa, then:

$$Qa = Qc$$

$$CcVc = CaVa$$

where Vc is the voltage dropped across the cathodic capacitance and Va is the voltage dropped across the anodic capacitance.

The voltage Vc is thus inversely proportional to the cathodic capacitance. The cathodic capacitance should be large enough so that only a small voltage drop occurs across it when a voltage is applied to the capacitor, with most of an applied voltage being dropped across the anodic capacitance. If the cathode layer is made small enough relative to the anode layer, the cathode layer's capacitance may be reduced to such an extent that when the capacitor's rated voltage is applied an overvoltage condition occurs at the cathode layer with the creation of oxide and evolution of hydrogen gas.

Accordingly, in one embodiment the cathode layer is limited to the degree of decrease in surface area relative to the anode layer. In one embodiment, the cathode layer is kept to a size that keeps the overvoltage at tolerable levels when a rated voltage is applied to the capacitor. Such a minimum size for a cathode layer will vary, of course, with the capacitor's geometry and its rated operating voltage, but the size limit can easily be determined empirically.

In one embodiment, for example, flat capacitors used in implantable defibrillators is designed to operate at a rated voltage of 400 volts, and the ratio of the cathode layer surface area to the anode layer surface area is approximately 0.75 or greater. In some embodiments, the ratio is approximately 0.75 to approximately 0.93. In some embodiments, the ratio is approximately 0.93.

In some embodiments, capacitor stack 2024 includes a uniform level of anode foils in each anode stack 2200. In other embodiments, the number of anode foils varies from stack to stack.

For instance, FIG. 38 illustrates a cross-section of a capacitor stack 2160 according to one embodiment. One example of mixed anode stacks 2102 is shown, which includes an anode stack 2100 and a modified anode stack 2101. The anode stack 2100 includes at least one conductive layer 2115 having a height 2146. The modified anode stack 2101 includes a plurality of conductive layers 2118 such that the modified anode stack 2101 includes at least one more conductive layer than included in the anode stack 2100. The anode stack 2100 and the modified anode stack 2101 differ in the quantity of conductive layers in each. In addition, the anode stack 2100 and the modified anode stack 2101 differ in the total surface area of each.

Figure 40:
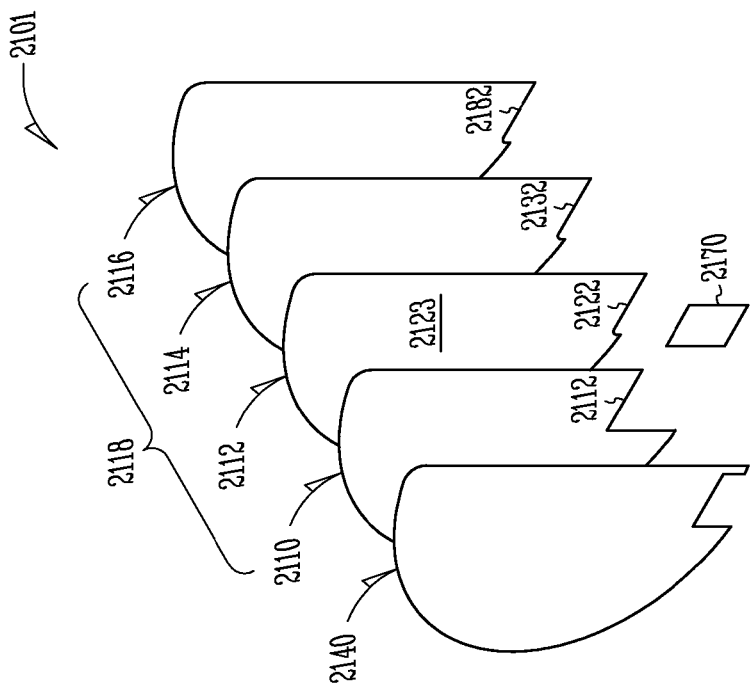
FIG. 40 is an exploded view of a modified anode stack constructed in accordance with one embodiment.
Figure 39:
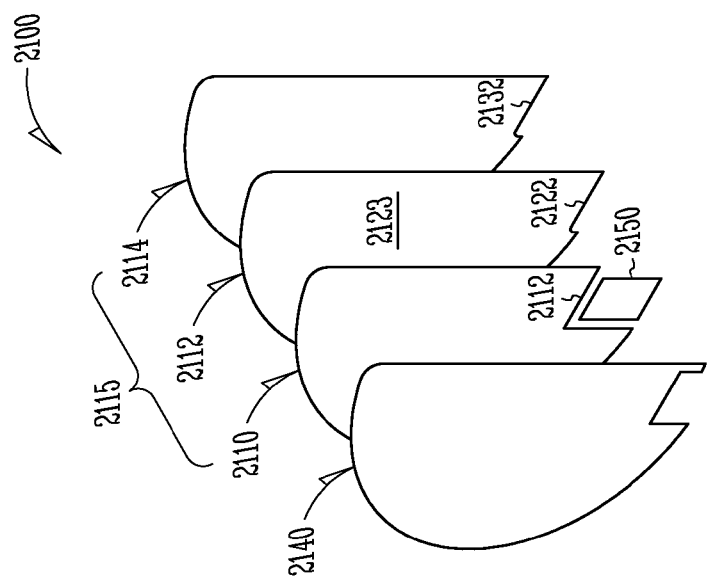
FIG. 39 is an exploded view of an anode stack constructed in accordance with one embodiment.

The anode stack 2100, also shown in FIG. 39 includes a first conductive element 2110, a second conductive element 2112, and a third conductive element 2114, and an anode separator 2140. In one embodiment, as shown in FIG. 40, a modified anode stack 2101 includes a first conductive element 2110, a second conductive element 2112, a third conductive element 2114, and a fourth conductive element 2116, and an anode separator 2140, where the modified anode stack 2101 includes at least one more conductive element than the anode stack 2100. In another option, the modified anode stack 2101 includes one or more less-conductive elements than the anode stack 2100.

Figure 41:
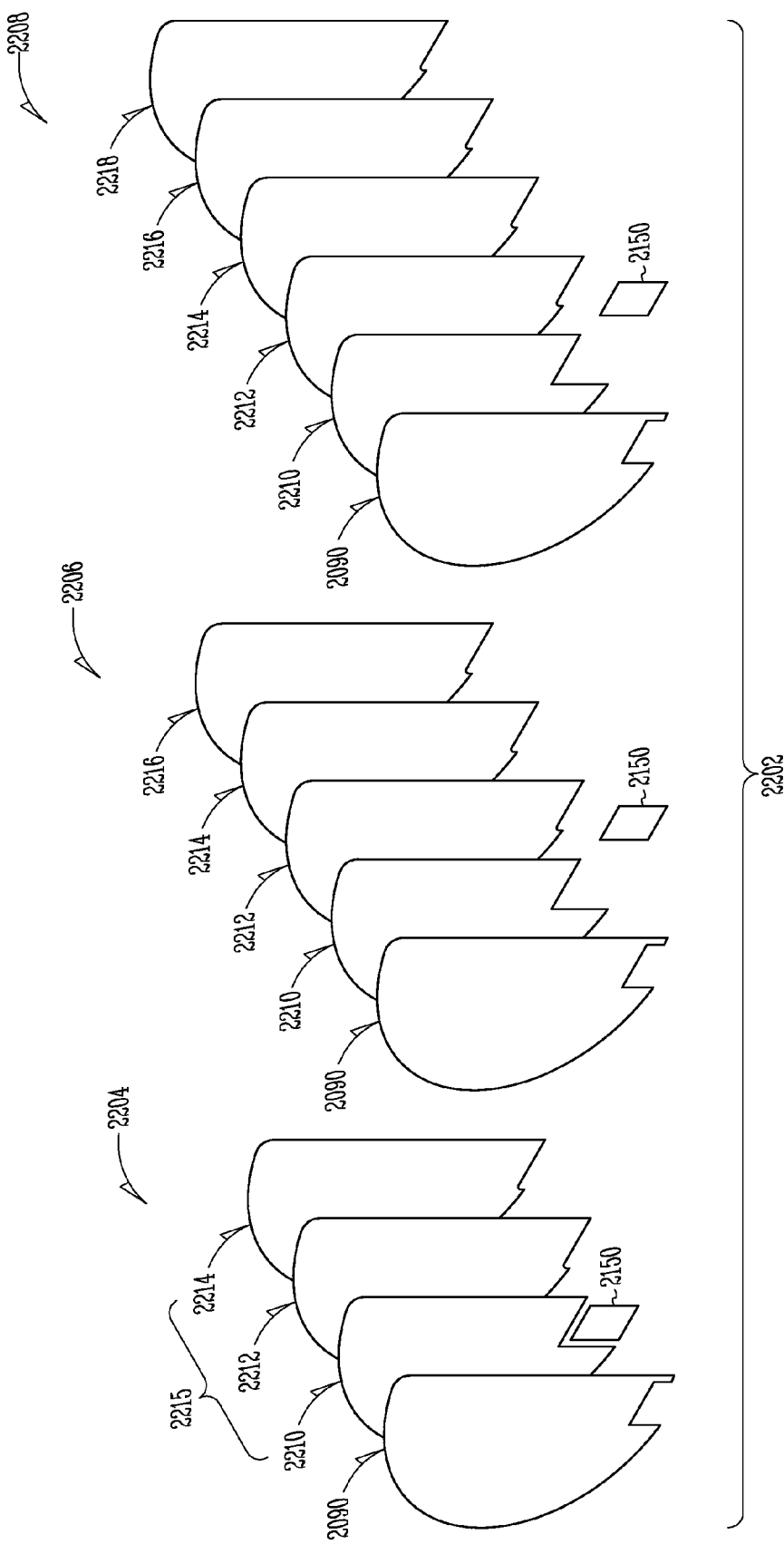
FIG. 41 is an exploded view of a mixed anode stack constructed in accordance with one embodiment.

FIG. 41 illustrates another example of mixed anode stacks 2202, which includes a first anode stack 2204, a second anode stack 2206, and a third anode stack 2208. The first anode stack 2204 has a plurality of conductive layers 2215 including a first conductive element 2210, a second conductive element 2212, and a third conductive element 2214. In one option, the second anode stack 2206 includes a first conductive element 2210, a second conductive element 2212, a third conductive element 2214, and a fourth conductive element 2216. The third anode stack 2208 includes a first conductive element 2210, a second conductive element 2212, a third conductive element 2214, a fourth conductive element 2216, and a fifth conductive element 2218, where the second and third anode stacks 2206, 2208 include a different number of conductive elements than the first anode stack 2204. In another option, the modified anode stack 2201 includes one or more less conductive elements than the anode stack 2200.

In one embodiment, the first anode stack 2204 has a first surface area, and the second anode stack 2206 has a second surface area, and the first surface area is different than the second surface area, for example the second surface area is greater than the first surface area. In a further option, the first anode stack 2204 has a first surface area, the second anode stack 2206 has a second surface area, and the third anode stack 2208 has a third surface area. The third surface area is different than the first surface area and/or the second surface area, for example the third surface area is greater than the first surface area and/or the second surface area. The surface areas can be modified by modifying the surface of the conductive elements, for example, by etching. It should be noted that additional combinations of conductive layers and/or surface areas are contemplated and are considered within the scope of one or more embodiments of the present subject matter.

Figure 42:
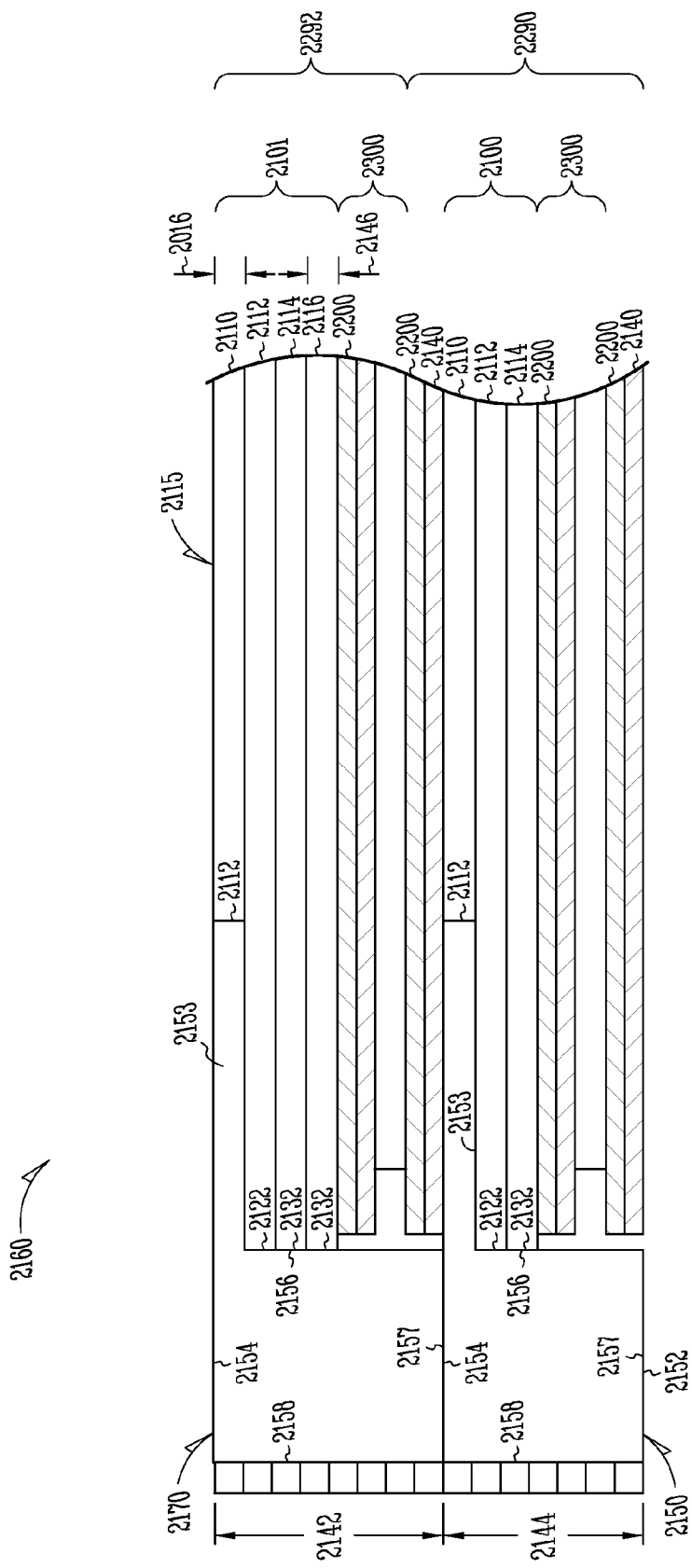
FIG. 42 is a cross-sectional view of a capacitor stack constructed in accordance with one embodiment.

Referring to FIG. 42, the anode stack 2100 is coupled with the modified anode stack 2101, where there are a variety of ways to couple the modified anode stack 2101 with the anode stack 2100. In one example, the stack 2160 includes one or more connection members such as an edge clip 2150 and a modified edge clip 2170, which interconnect the modified anode stack 2101 with the anode stack 2100. The modified edge clip 2170, which is coupled with the modified anode stack 2101, has a height 2142 that is extended for a slightly higher height of the modified anode stack 2101. The edge clip 2150 coupled with the anode stack 2100 has a height 2144 suitable for use with the anode stack 2100. The edge clips 2150, 2170 permit taller anode stacks to be reliably combined. The edge clips 2150, 2170 are anodic and are optionally used to increase anodic surface area of the conductive layers 2115 as the edge clips 2150, 2170 require little space within the capacitor stack 2160. The composition of cells 2290 and modified cells 2292 as further discussed below, can be modified without requiring changes to other components in the capacitor stack 2160 resulting in greater design flexibility.

Referring again to FIG. 38, the capacitor stack 2160 includes at least one cell 290, where each cell 2290 includes an anode stack 2100, an anode separator 2140, a cathode stack 2300, and a cathode separator 2200. In addition, the capacitor stack 2160 includes at least one modified cell 292, where each modified cell 292 includes a modified anode stack 2101, an anode separator 2140, a cathode stack 2300, and a cathode separator 2200. In one option, the cathode stack 2300 and the cathode separator 2200 are substantially the same as included in the cell 2290 and the modified cell 2292, such that the difference in height between the anode stack 2100 and the modified anode stack 2101 is due to the increase in height of the modified anode stack 2101 resulting from the modified anode stack 2101 having a greater number of conductive layers 2115 than included in the anode stack 2100. In another option, the modified anode stack 2101 of the modified cell 2292 has fewer conductive layers 2115 than the anode stack 2100.

In one embodiment, a plurality of modified cells 2292 is distributed throughout the capacitor stack 2160 in a manner to optimize use of existing cathodic area. In one example, the capacitor stack 2160 includes fifteen cells, where at otherwise would be every fifth cell 2290, a modified cell 2292 is disposed instead. Since the modified anode stack 2101 of the modified cell 2292 includes at least one more conductive layer than the anode stack 2100, the resulting example of capacitor stack 2160 includes at least three additional conductive anode layers within the case 20 (FIG. 18), without a substantial increase in the height of the components therein. For instance, for the capacitor stack 2160, instead of adding an additional anode stack 2100, which would have a height of three conductive layers 2115 (FIG. 39), and the height of an anode separator 2140 (FIG. 39), and the height of a separator 2200, and the height of a cathode stack and an additional separator, only the height of the additional conductive layers 2115 in the modified anode stack 2101 is added to the height of the capacitor stack 2160.

In other embodiments the modified anode stack 2101 contains one, two, three, four, five, six or more conductive layers 2115 than is included in each anode stack 2100. Alternatively, more than one type of modified anode stack 2101 is included with the capacitor stack 2160.

Referring again to FIG. 42, a stack 2160 is shown which includes cell 2290, and modified cell 292. An edge clip 2150 is adjacent the edge clip 2170 of an adjacent modified cell 292. The edge clip 2150 is coupled to adjacent modified edge clip 2170. For example, the edge clip 2150 is welded to the modified edge clip 2170. Where a plurality of cells 2290 and modified cells 2292 are provided, a plurality of edge clips 2150, 2170 are also provided. The plurality of edge clips 2150, 2170 stack one on the other such that the bottom surface 2157 of an edge clip 2150 or modified edge clip 2170 contacts the upper surface 2154 of an adjacent modified edge clip 2170, or edge clip 2150. The stacked edge clips 2150, 2170 provide a larger contact surface 2158 increasing ease of attachment thereto. Each anode stack 2100 and modified anode stack 2101 remains essentially flat and do not require the ductility required of other designs to make an electrical connection. The stacked edge clips 2150, 2170 provide for layer designs having higher stack composed of less ductile materials previously used, and further provide for interconnections in less space.

In one embodiment, an upper portion 2153 of the edge clip 2150 or modified edge clip 2170 is positioned within a clearance area 2112 of the first conductive element 2110. A side portion 2152 of the edge clip 2150 extends along the edges 2122, 2132 of the second 2112 and third 2114 conductive elements, and extends along the edges of separators 2200, and further along the edge of the anode separator 2140 of an adjacent modified anode stack 2101. The edge clip 2150 remains separate from the cathode stack 2300. The side portion 2152 of the modified edge clip 2170 extends along the edges 2122, 2132, 2182 of the second 2112, third 2114, and fourth 2116 conductive elements. The side portion 2152 also extends along the edges of separators 2200, as well as along the edge of the anode separator 2140 of an adjacent anode stack 2100 or modified anode stack 2101. The edge clip 2170 remains separate from the cathode stack 2300.

In one or more embodiments, edge clips are utilized and/or connected together as described above for FIGS. 2-15.

In one embodiment, a method is also provided, the method involving aligning an anode stack, including aligning at least one conductive layer having a surface and an edge, and aligning a first separator between the anode stack and a modified anode stack. The method further includes aligning at least one modified anode stack with the anode stack, which includes aligning a plurality of conductive layers, wherein the plurality of conductive layers includes at least one more conductive layer than included in the anode stack and one of the plurality of conductive layers having a surface and an edge, and electrically coupling the anode stack with the modified anode stack.

Several variations for the method are as follows. The method further including welding an edge clip to the modified anode stack. In another embodiment, the method further includes aligning a first modified anode stack and a second modified anode stack, each having a plurality of conductive layers. In yet another embodiment, the method further includes stacking a first number of layers to form the first modified anode stack, and stacking a second number of layers to form the second modified anode stack, and the first number of layers is different than the second number of layers. In yet another embodiment, the method further includes aligning a second separator between the first modified anode stack and the second modified anode stack.

Advantageously, the mixed-anode capacitor stacks described above allow for a reduction in the volume, thickness, and the mass of the stack without a reduction in the deliverable energy, which provides for a smaller overall device size. This results in increased patient comfort, and reduces tissue erosion surrounding the implantable device. In addition, reducing the size of the capacitor allows for other critical component sizes to be increased, for example, the battery, or for other components to be added. A further benefit is that anodic surface area is increased without requiring additional cathodic area to support the added anode conductive layers. This allows a boost in capacitance with a minimal increase in thickness of the capacitor. In empirical studies, capacitors that included the modified anode stack showed capacitance values of 186 µF, 185 µF, and 186 µF, compared to standard devices without the modified anode stack which had capacitance values of 172 µF, 172 µF, and 173 µF.

Referring again to FIG. 34, once stack 2024 is stacked as shown, the anode and cathode layers are interconnected. In one embodiment, one or more layers are constructed and connected as described following.

Figure 43:
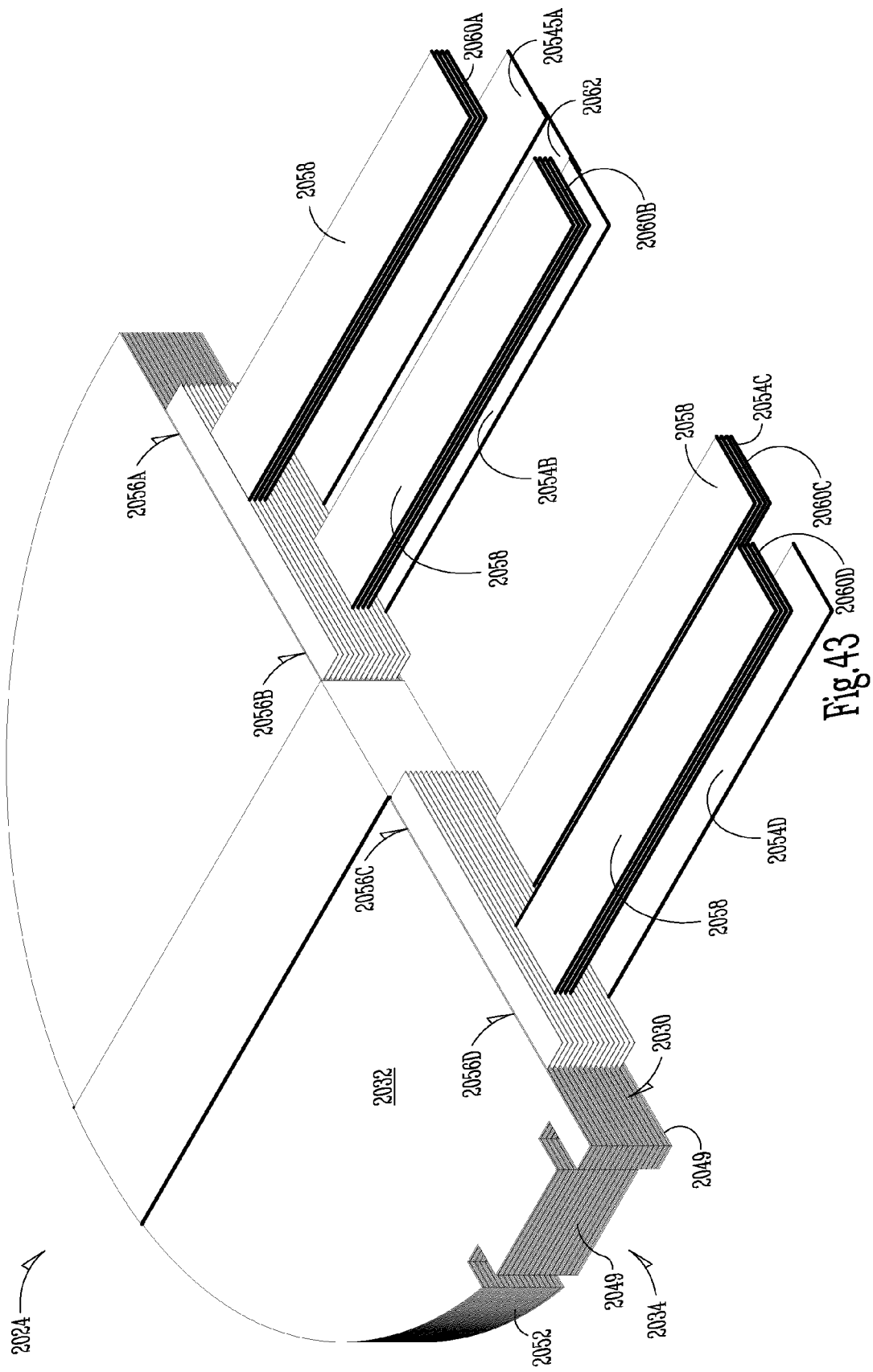
FIG. 43 is a perspective view of a capacitor stack according to one embodiment.

FIG. 43 shows further details of capacitor stack 2024 according to one embodiment of the present subject matter. As described above, the cathode layers 2300 include base foil layer 2050 and a plurality of secondary foil layers 2301-2304, here denoted generally as layers 2052. The base layer has a plurality of base tabs 2054a-2054d including a first base tab 2054a in a first tab position 2056a, a second base tab 2054b in a second tab position 2056b, a third base tab 2054c in a third tab position 2056c, and a fourth base tab 2054d in a fourth tab position 2056d. The present description is an example. Other embodiments include more tabs and fewer tabs with varying numbers of tab positions. Each tab 2054a-2054d is electrically coupled to the other tabs 2054a-2054d through base layer 2050, which includes at least one tab at each tab location. Each secondary layer 2052 has at least one extension member or leg 2060a-2060d positioned to overlay, be co-extensive with, or match with one of the plurality of tab positions 2056a-2056c.

In this embodiment, the cathode layers are positioned to include a first layer group 2060a, a second layer group 2060b, a third layer group 2060c and a fourth layer group 2060d. Other embodiments have more layers or less layers. The layer groups are in electrical contact with each other, but spaced apart from the anode tabs 2049 to allow separate connection of anode layers 2046 without shorting. The layer groups electrically connect to an external cathode connection or cathode lead 2062 which provides an external electrical connection to the case.

Each group of extension members 2060a-2060c is positioned to overlay one of a plurality of tab positions 2056a-2056d. The plurality of secondary layers is portioned into the plurality of the layer groups. The matching tabs of each layer group are located in the same position. For example, each of the matching tabs 2060a of first layer group 2060a are located in first tab position 2056a so that the matching tabs 2060a overlay first base tab 2054a, which is also in first tab position 2056a. In other words, from a top view perspective, tabs 2060a are commonly positioned or co-extensive with base tab 2054a. Secondary layers in each layer group are shown as located in adjacent layers. Alternatively, the layer groups may comprise secondary layers from non-adjacent layers.

Figure 44:
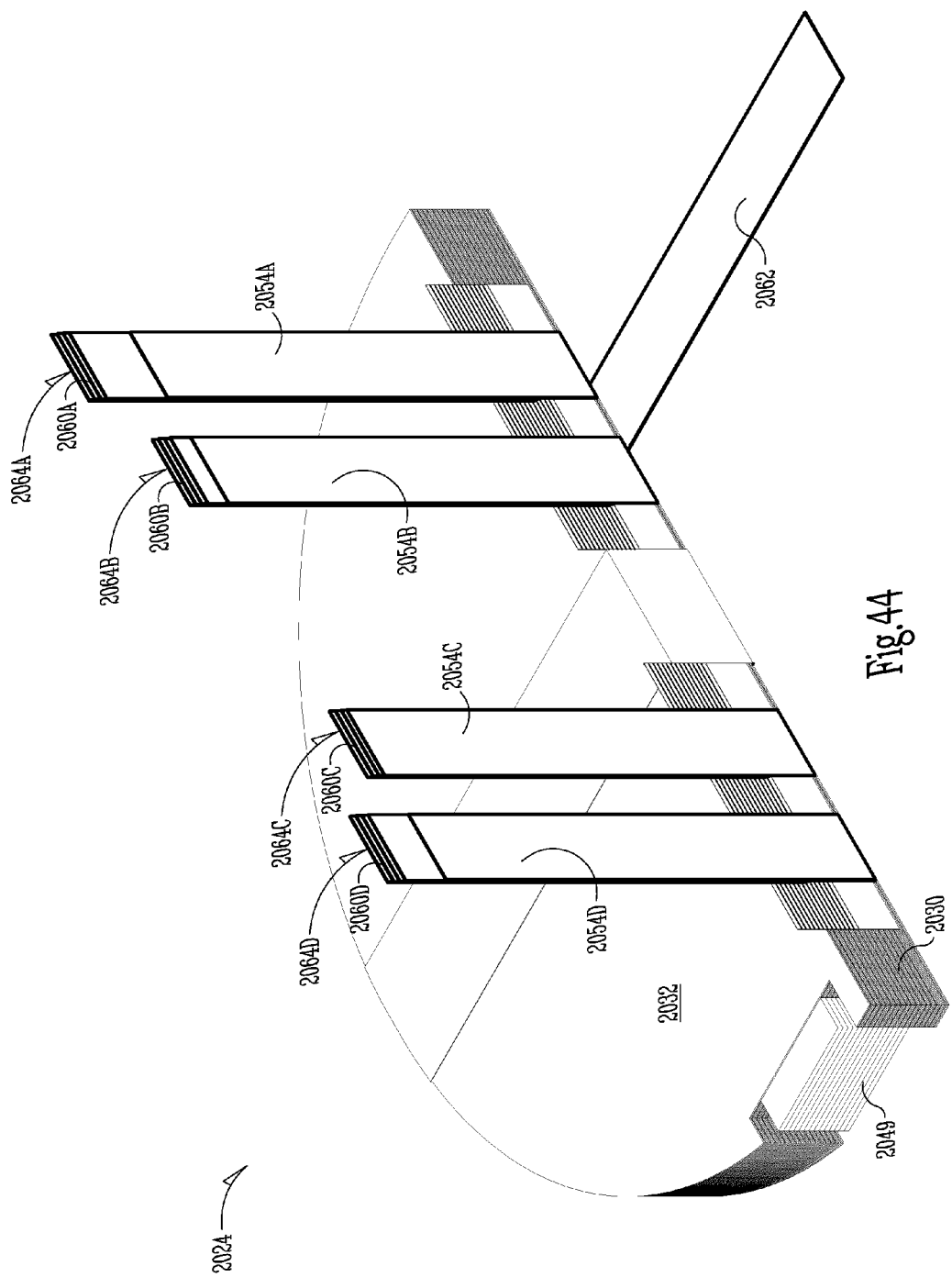
FIG. 44 is a perspective view of the capacitor stack of FIG. 43.

FIG. 44 shows another view of the capacitor stack 2024 having matching tabs of each secondary layer group 2060 folded and welded to the corresponding tab 2054 of the base layer, forming a plurality of tab groups 2064. The tab groups 2064 electrically connect to an external cathode connection or cathode lead 2062 which provides an external electrical connection to the case.

The cathode layers 2044 include a first tab group 2064a, a second tab group 2064b, a third tab group 2064c and a fourth tab group 2064d. The tab groups 2064 are also in electrical contact with each other, but spaced apart from the anode tabs 2049 to allow separate connection from the anode layers 2046 without shorting. The tab groups 2064 are electrically connected to the capacitor case 2020 or alternatively may be insulated from the case 2020.

Figure 45:
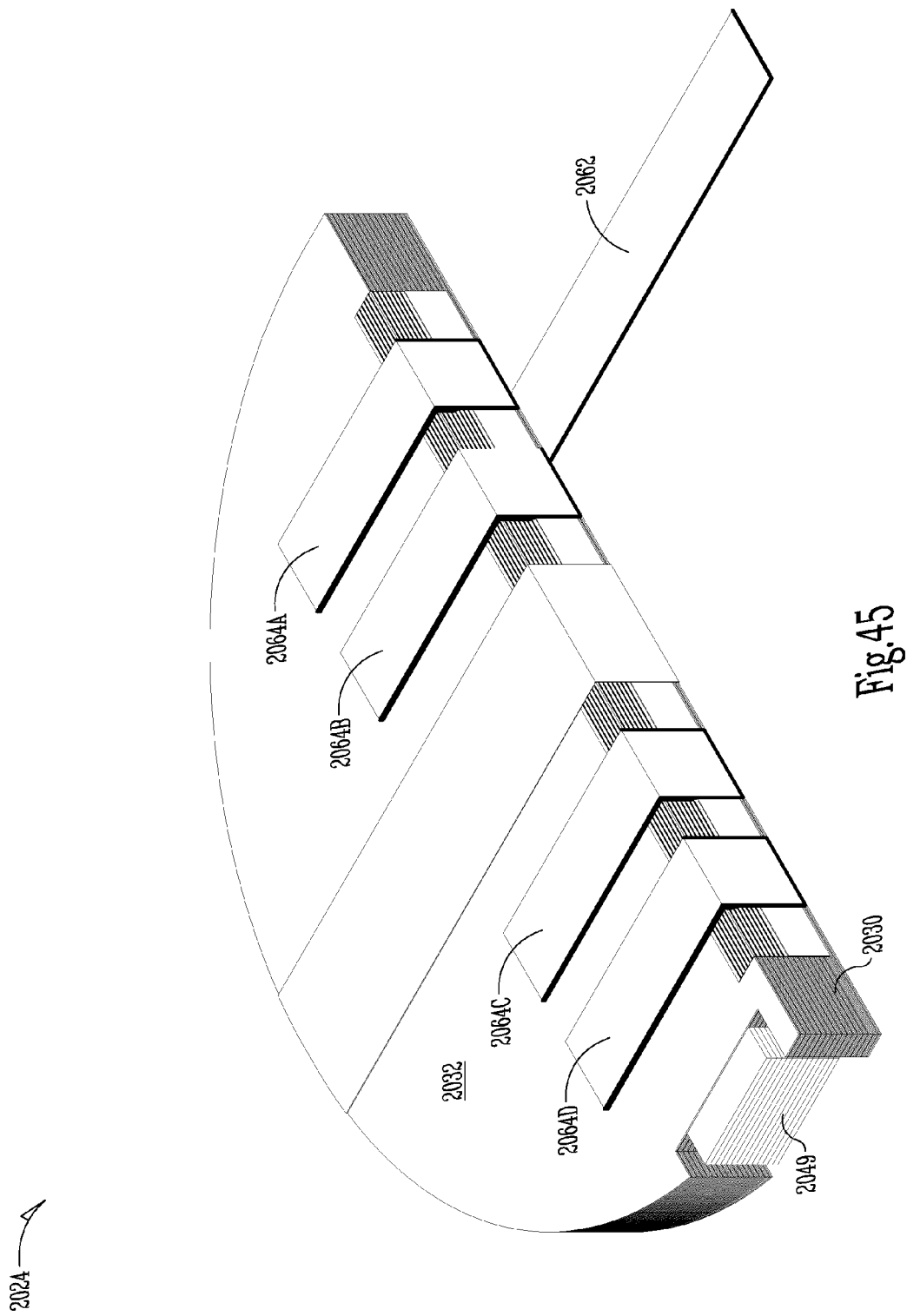
FIG. 45 is a perspective view of the capacitor stack of FIG. 43 with a plurality of tab groups positioned on the top surface of the capacitor stack.

FIG. 45 shows another view of capacitor stack 2024 showing tab groups 2064 folded into position on the top surface 2032 of capacitor stack 2024. The tab groups have a reduced thickness and are folded onto the top of the stack and taped. Alternatively, the tab groups are cut just beyond the weld and taped against the face 2030 of the stack. Each tab group 2064 has a thickness that is less than the sum of the base layer and all the secondary layers.

The thickness of the tab groups are approximately equal to or less than space 2040 as previously shown in FIG. 18. As noted above, in some embodiments, space 2040 is merely a line-to-line interference fit. The present cathode structure provides that the cathode interconnections fit within the limited room available. Alternatively, the tab groups are located in space 2040 between the face 2030 of stack 2024 and the case 2020 or base 2026.

In this embodiment, base layer 2050 has four base tabs 2054a-2054d and each secondary layer 2052 has at least one tab 2058 that matches one of the base tabs 2054a-2054d. The base tabs and matching tabs may be staked to the foil layer or the tabs may be integral with the foil layer. The layers 2050, 2052 may have two or more tabs. The base tabs are shown with four tabs and the secondary tabs are shown with one tab. In some embodiments, the secondary layers include two or more tabs to create redundancy.

The embodiment described above show the base layer and secondary layer as cathode layers. However, the anode layers may also be arranged in a similar fashion. The anode layers may include a base layer with base tabs and secondary layers with matching tabs either alternatively or in addition to the cathode layers. The anode layers and cathode layers may be separated into tab groups and positioned in the space between the top of the stack and the housing and the face of the stack and the housing. The anode layers and cathode layers remain separated from each other such as with paper layers. Insulation may also be required between the anode and cathode layers and the case.

Figure 46:
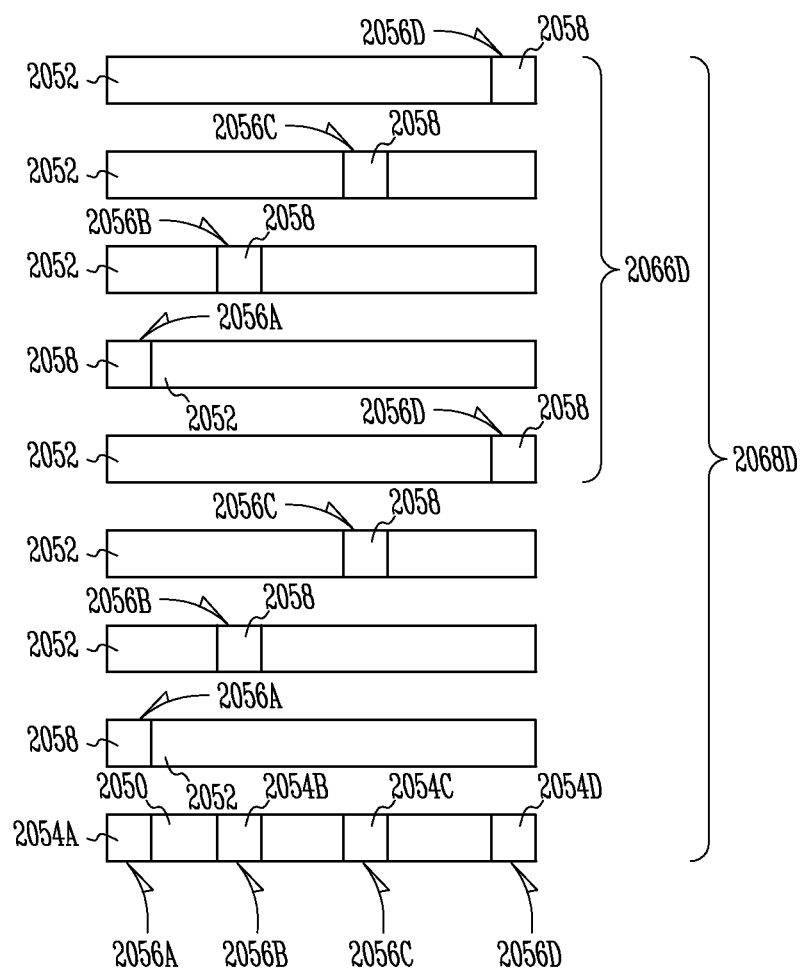
FIG. 46 is a partial exploded side view of the capacitor stack of FIG. 43.

FIG. 46 shows a side view of base layer 2050 and secondary layers 2052 of a capacitor stack including layer groups such as non-adjacent layer group 2066d. The matching tabs 2058 of secondary layers 2052 of non-adjacent layer group 2066*d* are shown mating with base tab 2054*d* to form non-adjacent tab group 2068*d*.

Figure 47:
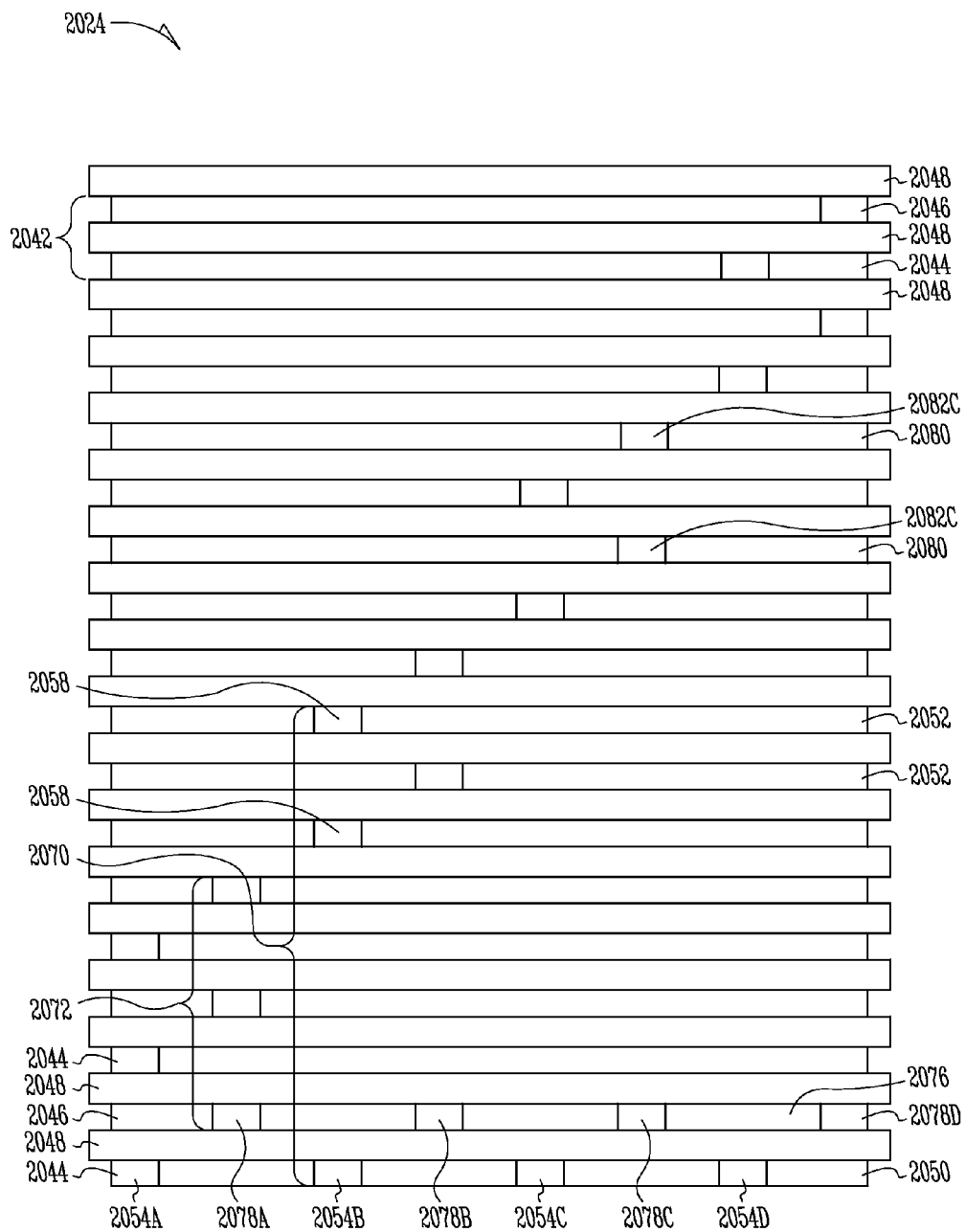
FIG. 47 is a partial side view of a capacitor stack according to one embodiment.

FIG. 47 shows a side view of the foil layers of a capacitor stack 2024 according to one embodiment where both one or more anode layers 2046 and one or more cathode layers 2044 are portioned into cathode tab groups 2070 and anode tab groups 2072.

Capacitor stack 2024 comprises separators 2048 between foil layers of alternating cathode layers 2044 and anode layers 2046. The anode layers and cathode layers form capacitive elements 2042. The cathode layers include a base layer 2050 and secondary layers 2052. The base layer 2050 has base tabs 2054*a*-2054*d* and the secondary layers 2052 have matching tabs 2058. Each matching tab 2058 overlays one of the base tabs 2054*a*-2054*d* of the base layer 2050. The cathode layers 2044 connect to the base layer 2050.

The anode layers 2046 include a secondary base layer 2076 with secondary base tabs 2078*a*-2078*d* and additional secondary layers 2080. Each of the additional secondary layers 2080 has a secondary matching tab 2082 with each secondary matching tab 2082 overlaying one of the secondary base tabs 2078*a*-2078*d* of the secondary base layer 2076. For example, secondary matching tab 2082*c* vertically matches or overlays secondary base tab 2078*c*. Each of the anode layers 2046 connect to the secondary base layer 2076.

In one or more of the embodiments described above, the foil layers are spread out or distributed over multiple locations. For example, the cathode layers may be spread out over four locations with four tab groups, with the thickness of each tab group at each location being about 0.006 inch (assuming that 5 layers at 0.00118 inch per layer are at each location). This thinness of the tab group allows the stacked unit to be placed into the housing with the tab groups occupying the space between the housing and the edge of the stack or the clearance space between the lid and the top of the stack. As a comparison, if the cathode tabs were all brought out at one location, the thickness would be greater than 0.020 inch and make it difficult, if not practically impossible, to fold the tabs collectively over the stack as in FIGS. 44 and 45. Thus, this thickness would require that part of the stack be removed or the case enlarged to allow space for routing and connecting the cathode layer connections, thereby reducing the packing efficiency of the capacitor.

One embodiment of a method to cut foil layers out of etched and unetched aluminum foil using a laser is described below. In one embodiment, the method of preparing aluminum foil layers for electrolytic capacitors includes cutting a capacitor foil layer out of a sheet of aluminum foil with a laser, removing the foil layer from the sheet of aluminum foil, and inserting the foil layer shape in a capacitor. The foil layer may be used as a cathode layer or as an anode layer. In some embodiments, the foil layer includes a plurality of tabs.

In various embodiments, the cutting may be partially through the sheet, the method may include cutting multiple sheets at one time, the method may include cutting multiple layers of sheets including paper separators, and/or the method may include cutting a portion or an entire capacitor stack at one time.

In some embodiments, the method includes laying out a pattern of capacitor foil layer shapes, delivering the aluminum foil to the laser in a roll, cutting different shapes out of the sheet of aluminum foil, and cutting through multiple layered sheets of aluminum foil. The method is used to cut out the intricate shapes of a multi-leg or multi-tab foil layer.

Using the above laser cutting method has one or more of the following advantages: a) rapid prototyping, b) the cut out shape does not drop out of the foil until needed, making for easier handling, c) the method eliminates the need for constant sharpening of expensive dies, d) the method does not produce burrs or particulates. Thus, allowing the use of thinner separators, e) the method allows for optimal pattern layout on the foil reducing the amount of generated waste, f) the foil may be delivered to the laser in several ways including rolls, sheets or small pieces, and g) the laser can be set up to cut out different shapes out of the shame sheet. The method has the advantage of cutting out the intricate shapes of the multiple tab cathode described above without tearing the closely spaced tabs. In addition, the intricate shapes can be formed without developing an expensive die that requires sharpening.

In one embodiment, the foil is cut using a Signature 75 laser manufactured by Control Laser Corporation. In various embodiments, the laser was set at the following setting: current 18-23, 5-8 kHz, and a speed of 0.35 to 1.5 inches/second.

Figure 48:
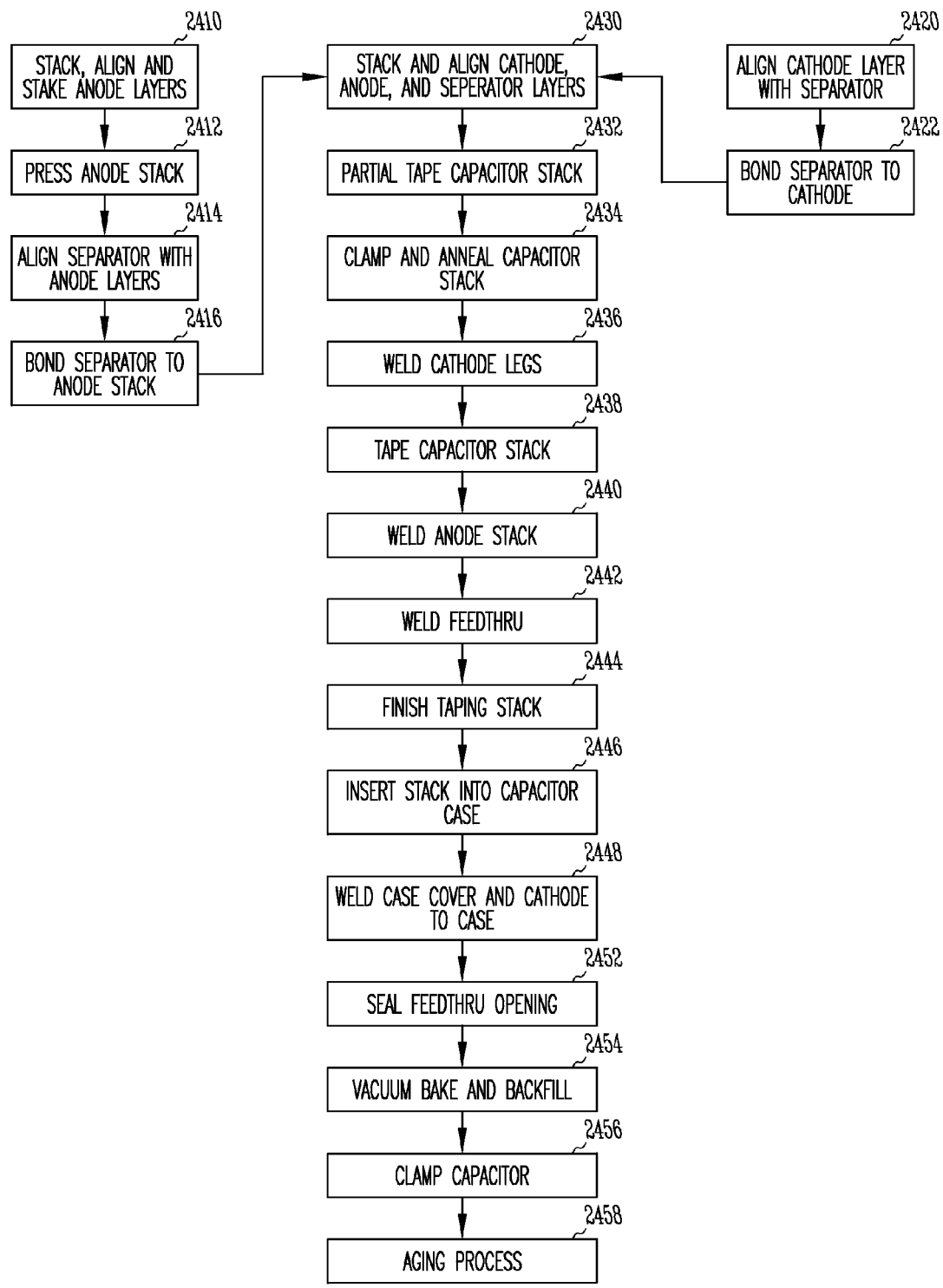
FIG. 48 is a flow-chart of a method for manufacturing a capacitor in accordance with one embodiment.

FIG. 48 illustrates an example of a process flow for a method for manufacturing a capacitor 2018 having a capacitor stack 2024 with one or more of the features described above. The method of FIG. 48 is an example of one embodiment and it is understood that different steps may be omitted, combined, and/or the order changed within the scope of one or more embodiments of the present subject matter.

The method includes, at 2410, stacking the anode conductive layers within an external alignment mechanism 2408 and aligning them therein. In some embodiments, the anode stack is pressed 2412, as further described below. The separator is aligned with the anode layers 2414, and the separator is coupled with the anode stack 2416, for example, by bonding using, for example, an adhesive. The cathode layer is aligned with the cathode separator at 2420, and the cathode separator is coupled with the cathode layer at 2422, for example, by bonding the cathode separator with the cathode layer using, for example, an adhesive.

In one embodiment, the anode stack and cathode stack are individually pressed to improve the flatness of each stack and to reduce or eliminate warpage, and are optionally are pressed to a specific, predetermined height. In another option, the capacitor stack 2024 is pressed to improve the flatness and to reduce or eliminate warpage. In one embodiment, the capacitor stack 2024 is pressed to a specific height to improve the flatness and to reduce or eliminate warpage. Pressing to a specific height helps to maintain consistency in the manufacturing process. Each anode stack 2100, each cathode stack 2300-2304, each layer set, the capacitor stack 2024 of all of the layer sets form, in effect, a spring. The spring rate will vary from capacitor stack 2024 to capacitor stack 2024 due, in part, to variations in the foil supplied and/or in the manufacturing processes associated with cutting the foil as well as the general handling of the part. Pressing the anode stack 2100, the cathode stacks 2300-2304, the layer set, or the capacitor stack 2024 to a controlled height maintains consistency in the assembly process in that each stack 2100, 2300-2304, layer set or capacitor stack 2024 will be maintained at the same height regardless of initial spring rate. Among other things, this assures a consistent fit between the capacitor stack 2024 and the case 2020 (FIG. 18).

Referring again to FIG. 35, at 2430, the cathode, anode, and separator layers are stacked and aligned by the outer edges of the separators using the external alignment mechanism 2400 to form a capacitor stack 2024. The capacitor stack 2024 is optionally partially taped at 2432. Optionally, at 2434 the capacitor stack is clamped and annealed. For example, an anode stack is pressed to a specified height, then assembled into the capacitor stack 2024. The capacitor stack 2024 is clamped to a specified height and annealed. In one example, annealing includes heating to a temperature of about 85 degrees C., soaking for about 12 hours, and cooling to 23 degrees C. degrees for about 1 hour.

In another embodiment, the components are individually annealed. Annealing reduces or eliminates undesired residual stresses which contribute to warpage and can help to provide improved flatness of the overall capacitor stack 2024. Annealing can also be performed after a portion of an electrode has been deformed to retain the deformed shape and reduce effect of material relaxation. In applications where the anode conductive layers are deformed annealing after deforming can also reduce creation of discontinuities of the dielectric layer on the deformed portion of an anode stack Annealing reduces stresses, increases softness and ductility and produces a specific microstructure. A variety of annealing heat treatments can be applied to the components of the capacitor to accomplish the desired result.

Further processing includes welding the cathode legs 2436, taping the capacitor stack 2438, welding the anode stack 2440, and welding the feedthrough 2442, and finish taping the capacitor stack 2444. In addition, the capacitor stack is inserted into the capacitor case 2446, the case cover and the cathode ribbon are welded to the case at 2448. The feedthrough opening is sealed at 2452. The process further includes a vacuum bake and backfill at 2454, clamping the capacitor at 2456, and an aging process at 2458.

Another embodiment for stacking a capacitor stack is described below. In one or more of the embodiments, the capacitor stack includes a curved profile. As used below, the term "profile" refers to the general outline of a portion of an object taken in or projected onto a plane generally perpendicular to a major surface of the object. Thus, for example, in some flat capacitors, profile means the outline of the capacitor case and/or the capacitor stack taken in a plane perpendicular to the major surfaces of the case or the capacitor stack.

Figure 49:
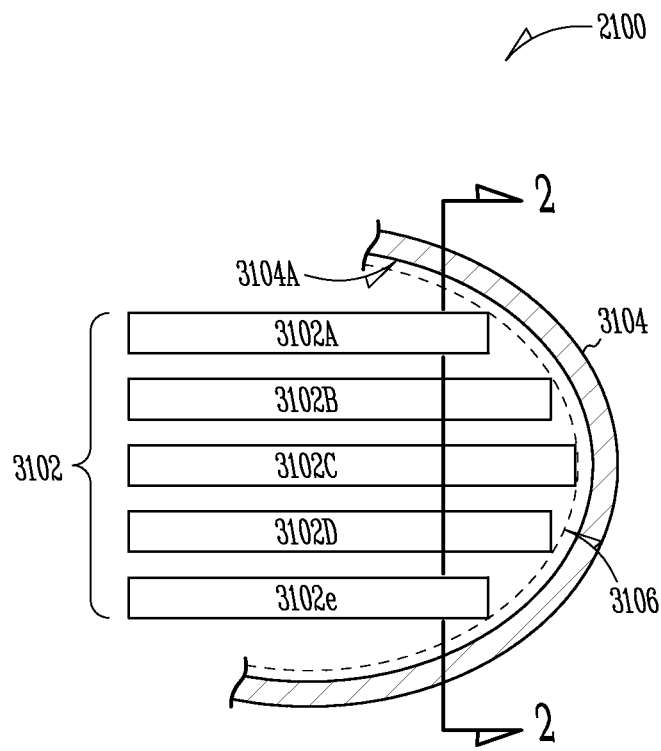
FIG. 49 is a partial cross-sectional view of a capacitor having capacitor modules with edges staggered in a first dimension to define a curved profile.

FIG. 49 shows a portion of a capacitor 3100 according to one embodiment. Capacitor 3100 includes one or more of the features of capacitor 100 of FIG. 1. Accordingly, certain details will be omitted herein. Capacitor 3100 includes a stack 3102 of two or more electrically coupled capacitor modules 3102a, 3102b, 3102c, 3102d, and 3102e within a capacitor case 3104. Modules 3102a-3102e are staggered so that their edges generally (or at least a portion of side of the stack) define a profile 3106 that generally conforms or is substantially congruent to an adjacent curved interior portion 3104a of capacitor case 3104.

Figure 50:
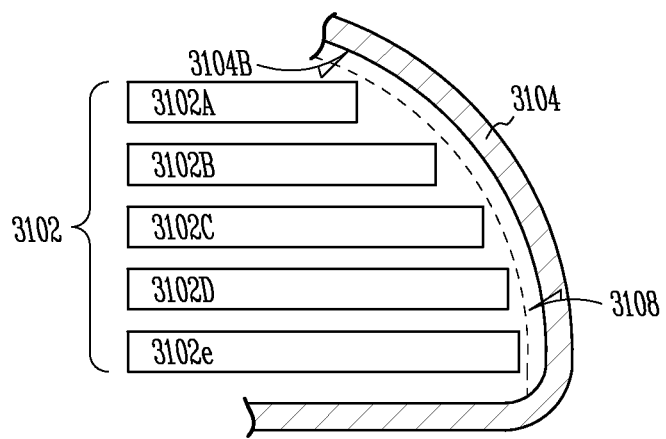
FIG. 50 is a partial cross-sectional view of a capacitor showing that its capacitor modules are staggered in a second dimension to define another curved profile.

FIG. 50, a section view of capacitor 3100 taken along line 2-2, shows that modules 3102a-3102e are staggered in two dimensions. In this view, capacitor modules 3102a-3102e define a profile 3108, which is generally congruent to a curved portion 3104b of case 3104. Although profiles 3106 and 3108 are quite distinct in this exemplary embodiment, other embodiments make profiles 3106 and 3108 substantially congruent.

In one embodiment, each capacitor module includes a three-layer etched and/or perforated anode, a cathode, and at least one electrolyte-carrying separator between the anode and the cathode. The anode and cathode comprise foils of aluminum, tantalum, hafnium, niobium, titanium, zirconium, or combinations of these metals. Additionally, each capacitor module is sandwiched between two pairs of electrolyte-carrying separators, with the separators extending beyond the anode and cathode to prevent undesirable shorting with the case. Alternatively, separate insulative layer can be placed between the capacitor modules and the case interior walls to prevent shorting.

In other embodiments, the capacitor modules take other forms having different numbers of anode layers and separators. For example, in some embodiments, the anodes, cathode, and separators in one or more of the capacitor modules are staggered to define curved module faces that confront the interior surfaces 3104a or 3104b of the case. Also, in some embodiments, one or more of the anodes or cathodes are coupled to the case, making it either anodic or cathodic.

To define the staggered edge faces and thus the curved profile, some embodiments which provide the curved profile in a single dimension, use a set of generally congruent modules of different sizes. For example, one embodiment includes four generally D-shaped modules, each with a common width and height, but with four successively smaller lengths. The modules are stacked, each module having at least one edge aligned vertically with the corresponding edges of adjacent modules.

Figure 51:
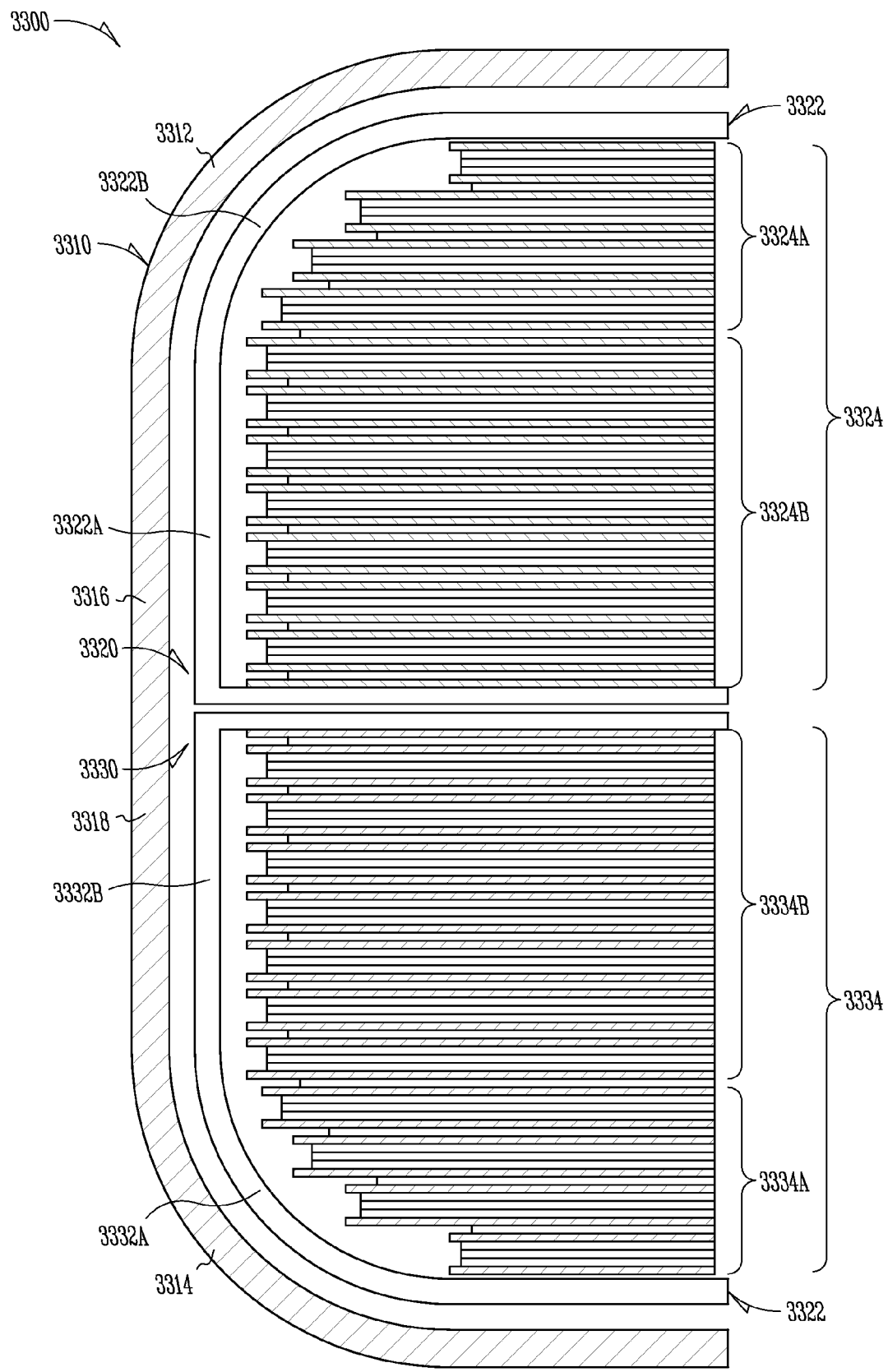
FIG. 51 is a partial cross-sectional view of an implantable heart monitor including a monitor housing and two capacitors having curved profiles that abut interior curved portions of the monitor housing.

FIG. 51 shows an implantable heart monitor 3300 including a monitor housing 3310 and two capacitors 3320 and 3330. Monitor housing 3310 includes two curved portions 3312 and 3314 and adjoining straight portions 3316 and 3318. Capacitor 3320 includes case 3322 and eleven capacitor modules 3324. Case 3322 includes a curved portion 3322a and a straight portion 3322b, respectively confronting curved portion 3312 and straight portion 3316 of housing 3310.

Capacitor modules 3324 include a set of staggered modules 3324a and a set of unstaggered modules 3324b. The set of staggered modules 3324a confront curved portion 3322a of case 3322 and have edges arranged to define a curved profile 3326 generally congruent to the profile of curved portion 3322. Modules 3324b, which are vertically aligned, confront straight portion 3322b of case 3322.

Similarly, capacitor 3330 includes case 3332 and eleven capacitor modules 3334. Case 3332 includes curved portion 3332a and a straight portion 3332b, which confront respective portion 3314 and 3318 of housing 3310. Capacitor modules 3334 include staggered modules 3334a, which confront curved portion 3332a of case 3332, have front edges arranged to define a curved profile 3336 generally congruent to the profile of curved portion 3332a. Modules 3334b confront straight portion 3332b of case 3322.

Notably, the present embodiment provides each of modules 3324 and 3334 with three anodes placed between two separators and at least one cathode placed adjacent one of the separators. (FIG. 51 shows the separators cross-hatched.) However, the subject matter is not limited to any particular module arrangement. Indeed, some embodiments of the subject matter use other (greater or lesser) numbers of anodes as well as modules. Moreover, some embodiments mix modules of different arrangements within the same capacitor case. This allows greater flexibility in exploiting the space available in the case as well as the housing. For more details, see FIGS. 21-25 and the accompanying discussion.

Additionally, other embodiments of the subject matter construct capacitor cases 3322 and 3332 as a single case having two adjacent compartments with a common wall. Modules 3324 and 3334 are each placed in a respective one of compartments. The cathodes in modules 3324 and the anodes of modules 3334 are electrically coupled to the case; an external anode terminal is coupled to the anodes of module 3324; and an external cathode terminal is coupled to the cathodes of module 3334, thereby effecting a series connection of the two capacitors using two external terminals instead of the four that are conventionally provided.

This arrangement can be made by providing two (first and second) aluminum case bodies having the desired curved portions, placing capacitor modules in the first case body, and welding a cover to the first case body. Other capacitor modules can then be stacked and placed in the second case body. The cover of the first case body is then put on the opening of the second case body and welded in place. For further details, see FIGS. 106-108 which will be discussed below.

Figure 52:
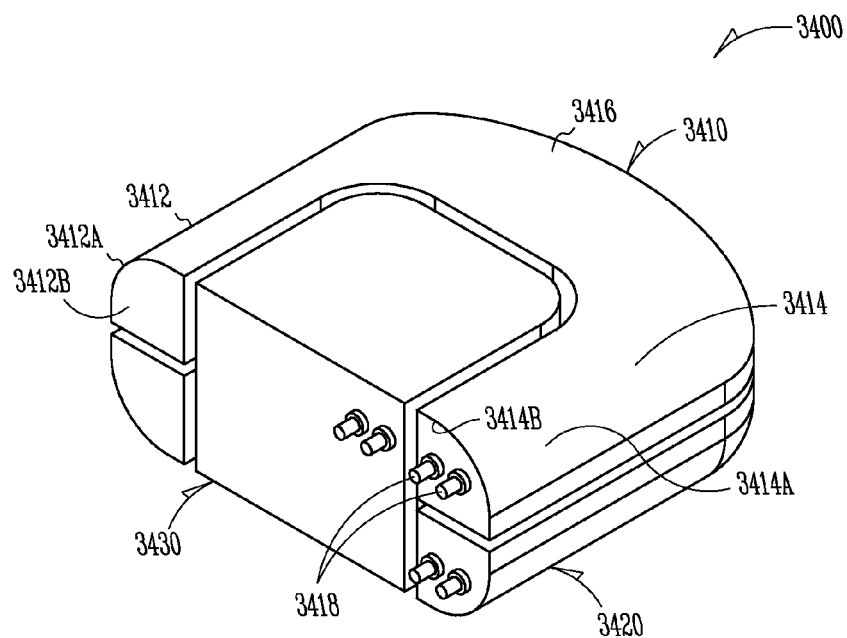
FIG. 52 is a perspective view of a capacitor-battery assembly including two stacked U-shaped capacitors and a battery nested within the capacitors.

FIG. 52 shows a perspective view of a capacitor-battery assembly 3400 including two stacked U-shaped capacitors 3410 and 3420 and a battery 3430 nested within the capacitors. For sake of brevity, capacitor 3420, which is of substantially identical size, shape, and structure as capacitor 3410 in this exemplary assembly, is not described separately. Capacitor 3410 includes legs 3412 and 3414, respective middle (or intermediate) portions 3416, and terminals 3418. Legs 3412 and 3414 are parallel, and include respective curved surfaces 3412a and 3414a, and respective flat end surfaces 3412b and 3414b.

Figure 53:
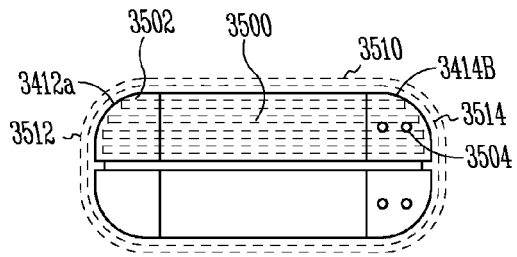
FIG. 53 is a front view of the FIG. 52 assembly without the battery.

FIG. 53, a front view of assembly 3400 without battery 3430, shows that curved surfaces 3412a and 3414b are generally congruent to each other and to respective curved profile 3502 and 3504 defined by capacitor modules 3500. Further, it shows a housing 3510 (in phantom) having a curved or concave portions 3512 and 3514 generally congruent with or conformant to curved or convex surfaces 3412a and 3414a. (Some embodiments insulate and/or separate case 3606 from housing 3602.)

Figure 54:
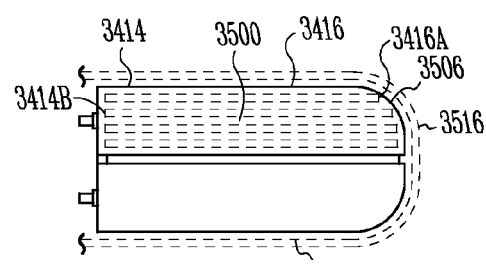
FIG. 54 is a side view of the FIG. 52 assembly.

FIG. 54, a side view of assembly 3400 without battery 3430, shows that the curved surfaces 3412a and 3414b are generally perpendicular to end surfaces 3412a and 3412b. Middle portion 3416 is also shown as having a curved portion 3416a which is congruent to a curved profile 3506 defined by capacitor modules 3500 and a curved portion of 3516 of monitor housing 3510.

Figure 55:
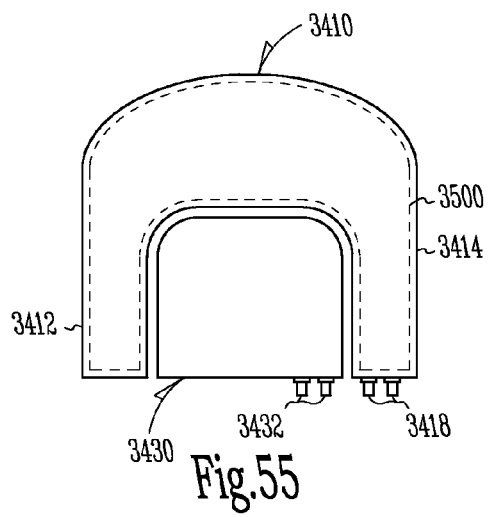
FIG. 55 is a top view of the FIG. 52 assembly.

FIG. 55 is a top view of assembly 3400, showing the general outline of capacitor modules 3500. This FIG. also shows that battery 3430 includes terminals 3432.

In one embodiment, the cathodes of the capacitor are coupled as described above for FIGS. 43-47 and the accompanying discussion. Other embodiments couple the cathodes using tabs which are connected to each cathode layer and then coupled together. Some embodiments couple the tabs as discussed below for FIGS. 101-105 and the accompanying discussion. In another embodiment, the cathodes are coupled as discussed below.

Figure 56:
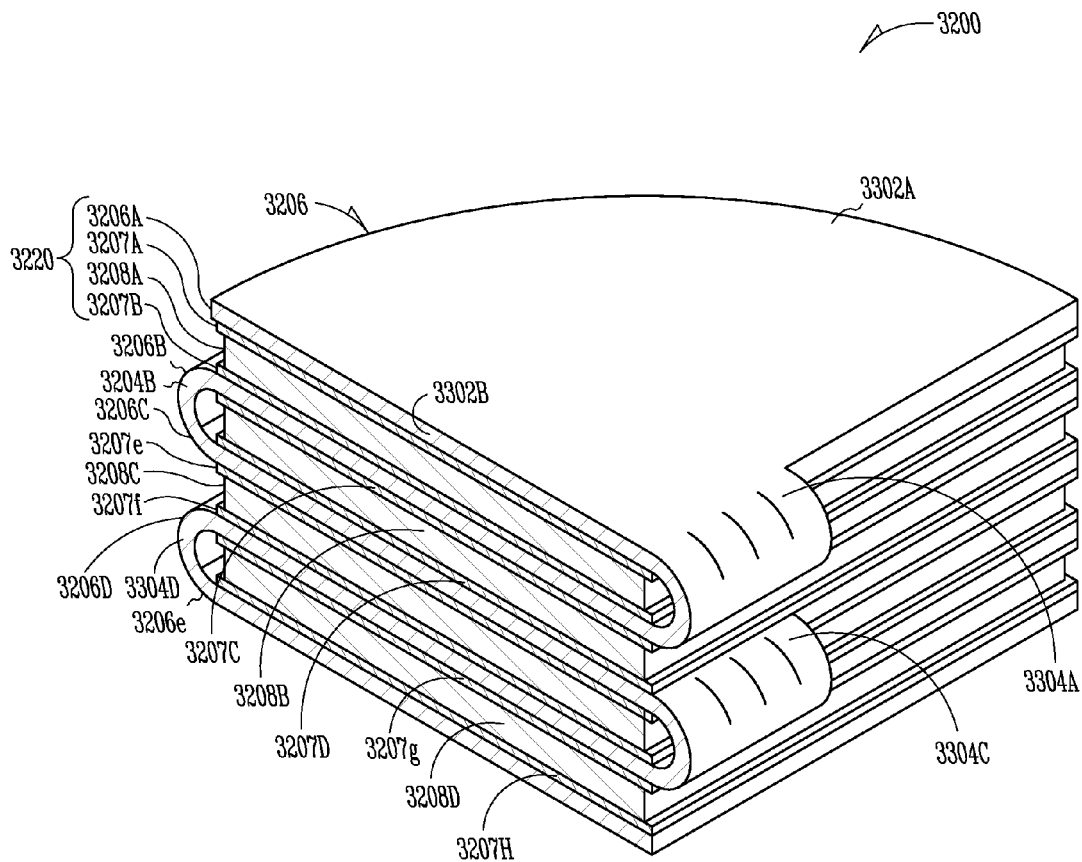
FIG. 56 is an isometric cross-section view of portions of a capacitor stack according to one embodiment.

FIG. 56 shows an isometric cross-section view of a portion of a capacitor stack 2300 according to one embodiment. For sake of clarity, the vertical portion of stack 3200 is shown at a larger scale than the horizontal and axial portions. Stack 3200 includes a plurality of anodes 3208a-3208d, a plurality of cathode plates 3206a-3206e, and respective separators 3207a-3207h located between each anode 3208a-3208d and cathode plate 3206a-3206e adjacent thereto. Each cathode, anode, and separator assembly comprises a capacitor element 3220.

In this embodiment, each of the anodes has a D-shape and includes a top major surface, a bottom major surface, and one or more edge faces generally perpendicular to each of the major surfaces. In some embodiments, the anodes are circular, square, rectangular, octagonal, or other desirable shape. In the exemplary embodiment, each anode foil is approximately 0.004" (0.1016 mm) thick. Other embodiments use other size foils.

Cathode structure 3206 includes a plurality of cathode plates 3206a-3206e. Each plate 3206a-3206e is integrally connected by respective fold areas 3304a-3304d. The cathode includes first major surface 3302a and an opposing major surface 3302b.

Cathode structure 3206 is folded so that, in cross-section, it has a serpentine, z-shaped, or s-shaped profile, interweaving under and over each anode 3208a-3208d. In one embodiment, the major surface of each cathode plate 3206a-3206e is substantially parallel to and faces the major surface of an adjacent cathode plate.

In one embodiment, each anode 3208a-3208d is sandwiched between an adjacent pair of cathode plates. The bottom major surface of each anode 3208a-3208d confronts a major surface of a first cathode plate (with a separator between the two surfaces), and the top major surface of each anode 3208a-3208d confronts a major surface of a second cathode plate (with a separator between the two surfaces) which is adjacent to the first cathode plate. Each fold area 3304a-3304d confronts a portion of an edge face of each anode 3208a-3208d. In the exemplary embodiment, cathode structure 3206 does not include a plurality of tabs as do anodes 3208a-3208d. Instead, the present cathode is a single, integral structure folded over and under each anode. Thus, the cathode-to-cathode connection of the present flat capacitor is provided by the integral structure of the cathode itself.

Figure 57:
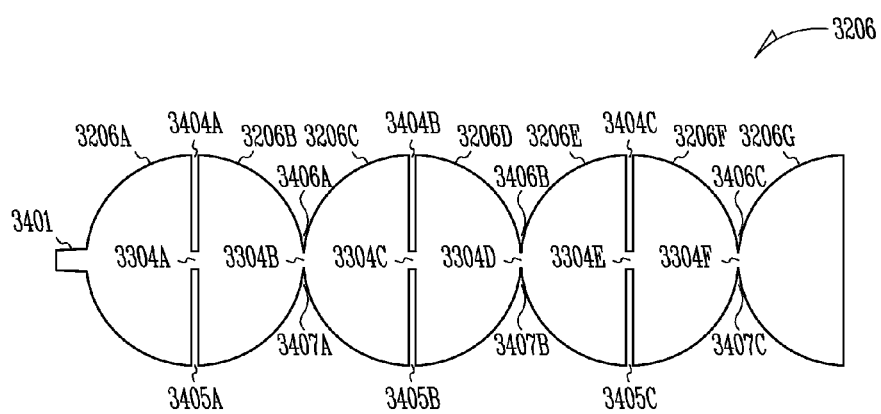
FIG. 57 is a top view of a cathode structure according to one embodiment.

FIG. 57 shows an unfolded cathode structure 3206 in accord with one embodiment. In this embodiment, cathode structure 3206 is laser-cut from a single aluminum sheet. One laser-cutting method is discussed above. In some embodiments, cathode structure 3206 is cut using high-precision dies. In various embodiments, cathode 3206 is aluminum, tantalum, hafnium, niobium, titanium, zirconium, and combinations of these metals. However, the exemplary embodiment is not limited to any particular foil composition or class of foil compositions.

In one embodiment, the aluminum sheet is cut so that cathode plates 3206a-3206g are formed. The number of plates shown in the embodiment is simply exemplary and in no way limits the present subject matter. Each plate 3206a-3206g is similar to the other plates of the cathode, having a D-shape. In some embodiments, the cathode plates are circular, rectangular, square, octagonal, and other desirable symmetrical or asymmetrical shapes. In some embodiments, each plate has a different shape than the other plates, and the assorted shapes are varied to allow for defining an arbitrary lateral face of the capacitor stack, such as described above regarding the curved profile capacitor.

In one embodiment, each plate 3206a-3206g is defined by one or more cut-outs. For instance, plate 3206b is defined by an opposing pair of cut-outs 3404a and 3405a. Cut-outs 3404a and 3405a are opposing, slit-shaped cut-outs which have fold area 3304a between them. Fold area 3304a integrally connects cathode plate 3206b to cathode plate 3206a while also providing a fold section to allow the plates to be folded upon each other. The other plates in cathode 3206 include slit cut-outs 3404b-3404c and 3405b-3405c.

Plate 3206b also is defined by another pair of cut-outs, cut-outs 3406a and 3407a. In one embodiment, cut-outs 3406a and 3407a are opposing, rounded V-shaped cut-outs which provide for the resultant D-shape when cathode 3206 is folded. In some embodiments, the cut-outs have other shapes providing for many possible flat capacitor shapes. Possible shapes, by way of example and not limitation, include circular, rectangular, square, octagonal, and other desirable shapes. Cut-outs 3406a and 3407a have a fold area 3304b between them. Fold area 3304b integrally connects cathode plate 3206b to cathode plate 3206c, while also providing a fold section to allow the plates to be folded upon each other. The other plates of cathode 3206 also include V-shaped cutouts 3406b-3406c and 3407b-3407c, so that each cathode plate is partially separated from its neighboring cathode plates by at least one cutout.

In constructing a capacitor, cathode structure 3206 is folded in an alternating manner along fold areas 3304a-3304f so that a serpentine structure is formed. An anode is inserted within each fold (that is, between each neighboring cathode plate). A separator is inserted between each cathode plate and each anode. In one embodiment, each of the separators has a slightly larger surface area than the surface area of each of cathode plates 3206a-3206g.

In one embodiment, the cathode structure is coupled to case 3110 by a single tab 3401 which is integral with a single one of the cathode plates. In one embodiment, a single one of the plurality of cathode plates, plate 3206a, for example, includes an integral tab 3401 for connecting to case 3110. In other embodiments, more than one cathode plate can include a tab 3401. In one embodiment, terminal 3112 is directly connected to case 3110. In some embodiments, tab 3401 is coupled to a feedthrough wire or terminal such as terminal 3111.

In one or more embodiments, the foldable, integral cathode structure described herein provides the cathode-to-cathode connections required by flat capacitors without requiring the manufacturer to attach separate tabs to each cathode. This cathode structure minimizes the space which is required by the joints and the tabs. Furthermore, the foldable cathode structure also helps increase reliability of the capacitor since the stress caused by welding tabs to the cathodes is eliminated, and the number of interconnects is reduced.

Figure 58:
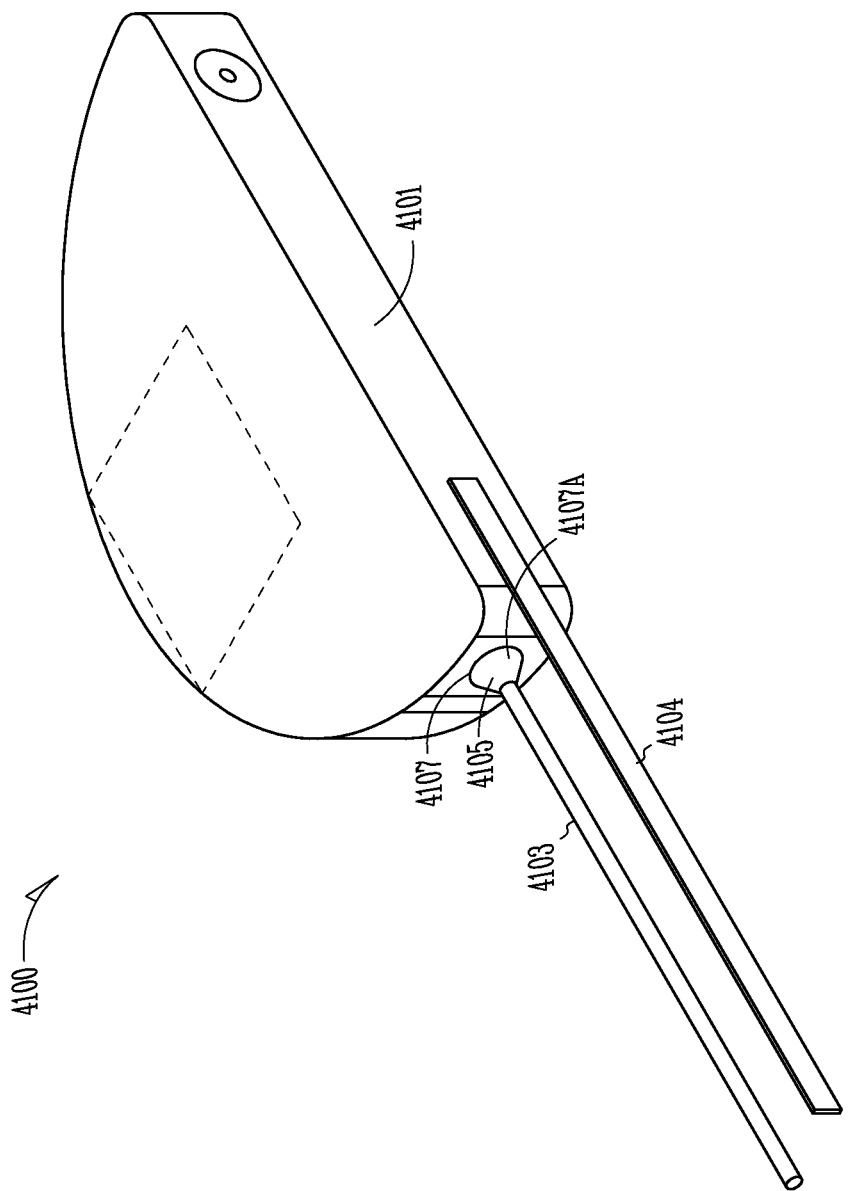
FIG. 58 is an isometric view of a flat capacitor in accord with one embodiment of the present subject matter.

FIG. 58 shows a flat capacitor 4100 in accord with one embodiment of the present subject matter. Capacitor 4100 includes one or more of the features of capacitor 100 of FIG. 1. Thus the present discussion will omit some details which are referred to above regarding FIG. 1. Capacitor 4100 includes a case 4101, a feedthrough assembly 4103, a terminal 4104, and a sealing member 4105.

Case 4101 includes a feedthrough hole 4107 which is drilled, molded, or punched in a portion of a wall of case 4101. Feedthrough hole 4107 is in part defined by an edge 4107a which outlines the feedthrough hole within case 4101. Feedthrough hole 4107 provides a passage for connecting feedthrough assembly 4103 to circuitry outside of case 4101. In some embodiments, case 4101 includes two or more feedthrough holes for providing a second or third feedthrough assembly.

Feedthrough assembly 4103 and terminal 4104 connect capacitor elements to outside circuitry. In the exemplary embodiment, feedthrough assembly 4103 extends through feedthrough hole 4107 and is insulated from case 4101. Terminal 4104 is directly connected to case 4101. Alternatively, in some embodiments, the capacitor incorporates other connection methods, depending on other design factors. In various embodiments, two or more insulated feedthrough assemblies are employed.

In one embodiment, sealing member 4105, such as an epoxy, is deposited around feedthrough hole 4107 and feedthrough assembly 4103 to insulate feedthrough assembly 4103 from case 4101 and to seal an electrolyte within the case. An exemplary epoxy is a two-part epoxy manufactured by Dexter Hysol. This includes a casting resin compound (manufacturer No. EE 4183), a casting compound (manufacturer No. EE 4215), and a hardener (manufacturer No. HD 3404). The exemplary two-part epoxy is mixed in a ratio of hardener=0.055*casting resin. The mixture is cured at 0.5 hours at 60 degrees Celsius or 1.5 hours at room temperature. Another epoxy is a UV cure epoxy such as manufactured by Dymax, Inc., which can be cured using an Acticure (manufactured by GenTec) ultraviolet curing system at 7 W/cm$^2$ at a distance of 0.25" for approximately 10 seconds. In one embodiment, sealing member 4105 is a plug, as will be discussed below.

In one embodiment, the sealing member provides a non-hermetic seal. In one embodiment, the sealing member includes an elastic plug which will be discussed in further detail below.

Figure 59:
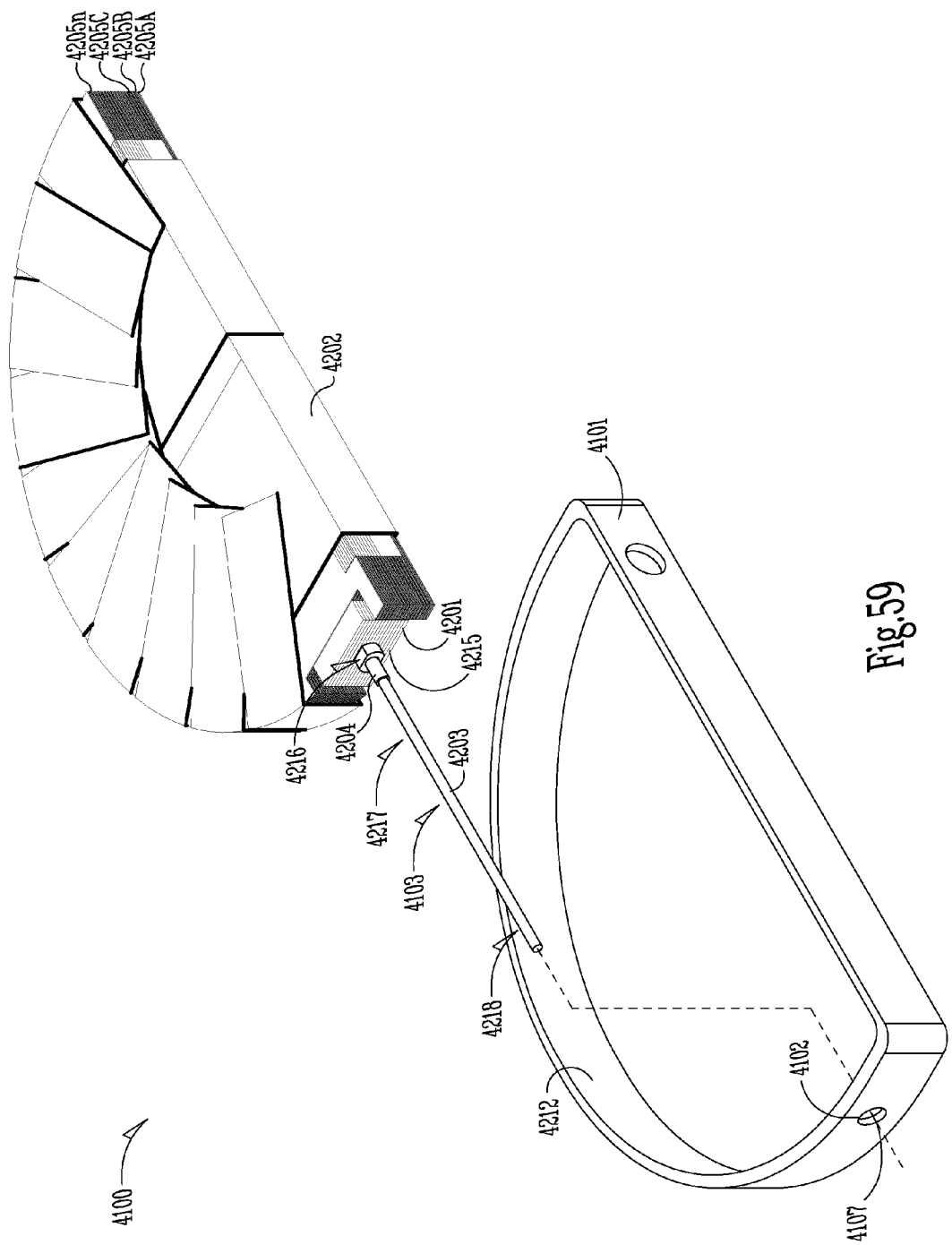
FIG. 59 is an exploded isometric view of the flat capacitor of FIG. 58.
Figure 60:
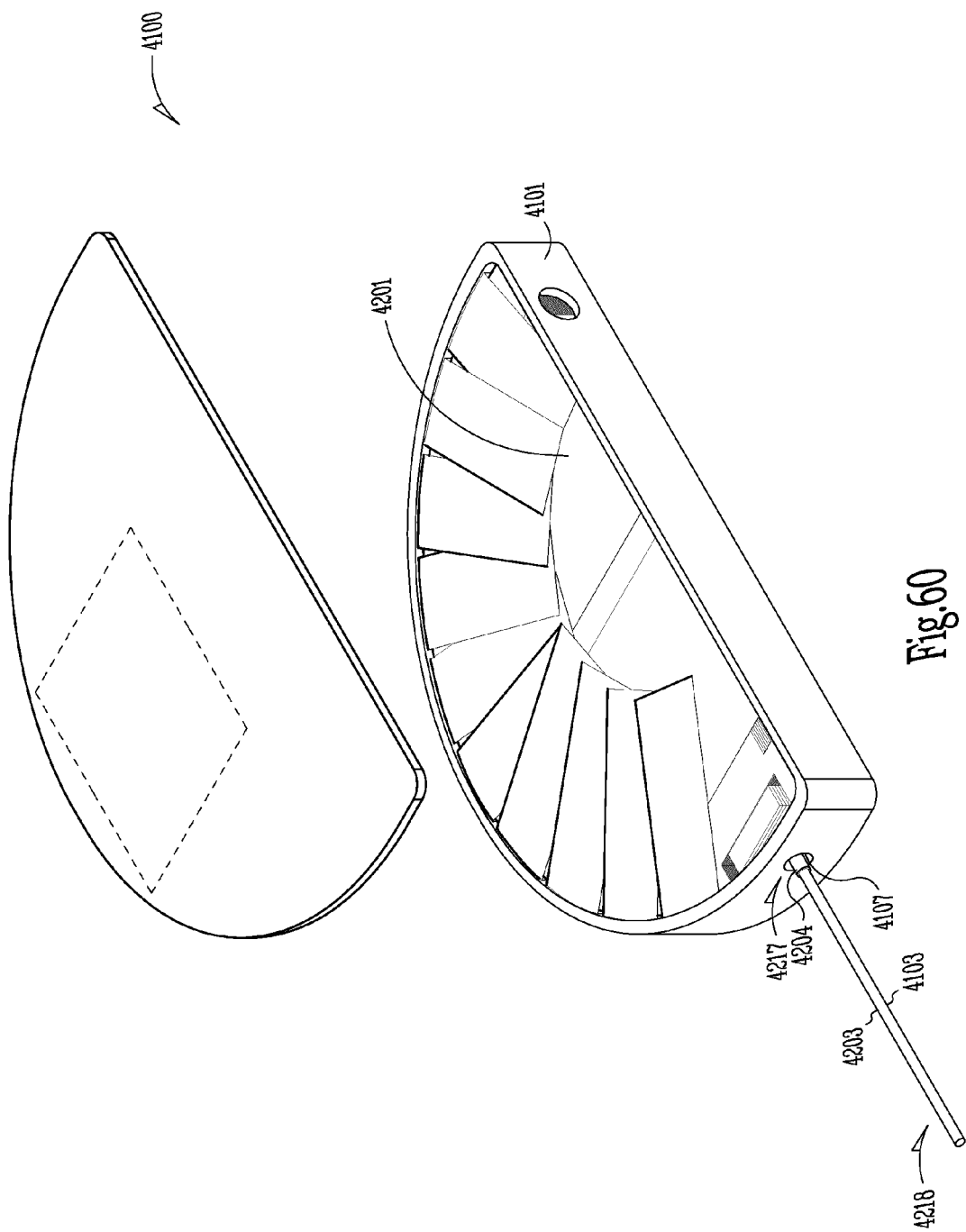
FIG. 60 is another exploded isometric view of the flat capacitor of FIG. 58.

FIGS. 59 and 60 show exploded views of capacitor 4100. Capacitor 4100 includes a capacitor stack 4202 mounted within an internal cavity 4212. The exemplary capacitor stack 4202 includes a plurality of capacitor modules or elements 4205a, 4205b, 4205c, ..., 4205n. Each of elements 4205a-4205n includes a cathode, an anode, and a separator between the cathode and the anode.

In one embodiment, each cathode of capacitor stack 4202 is connected to the other cathodes and to conductive case 4101. Terminal 4104 is attached to case 4101 to provide a cathode connection to outside circuitry. In some embodiments, the cathode is coupled to a feedthrough conductor extending through a feedthrough hole.

In one embodiment, each anode is connected to the other anodes of the capacitor. Attached to the anode of each capacitor element 4205a-4205n is a conductive tab or connection member 4201, as discussed above. In one embodiment, each connection member 4201 includes an edge face 4215 which is substantially perpendicular to the major surface of the anodes. Edge face 4215 provides a conductive surface for connecting each capacitor element 4205a-4205n to feedthrough assembly 4103. The anode connection members 4201 are welded or crimped together and are coupled to feedthrough assembly 4103 for electrically connecting the anode to circuitry outside the case. In some embodiments, the cathode is coupled to a feedthrough assembly and the anode is connected to the case. In other embodiments, both the anode and the cathode are connected to feedthroughs.

In one embodiment, connection members 4201 are edge-welded to each other as discussed above. Edge-welding the connection members provides a flat connection surface 4216, which includes one or more edge faces 4215 of connection members 4201. In some embodiments, connection members 4201 are crimped, soldered, and/or connected by an electrically conductive adhesive.

In one embodiment, feedthrough assembly 4103 includes two members, a feedthrough wire or conductor 4203 and a coupling member 4204. Coupling member 4204 is attached to capacitor stack 4202 at connection surface 4216, and feedthrough conductor 4203 is attached to coupling member 4204. In one embodiment, coupling member 4204 partially extends through feedthrough hole 4107.

Feedthrough conductor 4203 is a conductive member which can include material such as nickel, gold plated nickel, platinum, aluminum, or other conductive metal. Feedthrough conductor 4203 has a proximal end portion 4217 attached to coupling member 4204 and a distal end portion 4218 for attaching to circuitry outside the case, such as defibrillator or cardioverter circuitry. In one embodiment, feedthrough conductor 4203 has a diameter of approximately 0.016" (0.4064 mm). However, other embodiments have feedthrough conductors of different diameters and/or non-circular cross-sections.

Figure 61:
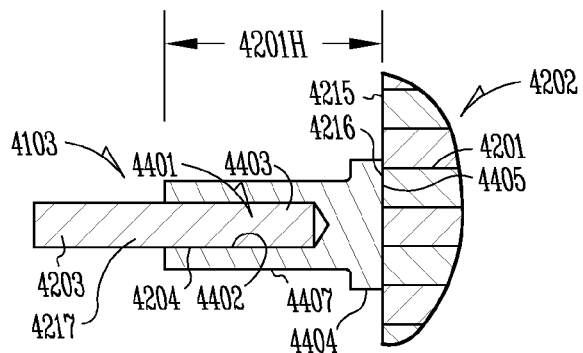
FIG. 61 is a cross-sectional view of the feedthrough assembly of FIG. 58.

FIG. 61 shows a cross-sectional side view of details of one embodiment of feedthrough assembly 4103 and its connection to connection members 4201. As discussed above, in one embodiment, the edge faces 4215 of each connection member 4201 form a substantially flat connection surface 4216 and coupling member 4204 is directly attached to connection members 4201 at surface 4216.

In one embodiment, coupling member 4204 is a high-purity aluminum member which is able to withstand the high voltages generated within the capacitor case. In other embodiments it is made from another conductive material compatible with the capacitor stack. Coupling member 4204 includes a base 4404 and a holding tube 4407. On one side of base 4404 is a planar surface 4405 for attaching to the planar surface 4216 presented by edge-welded connection members 4201.

Figure 63:
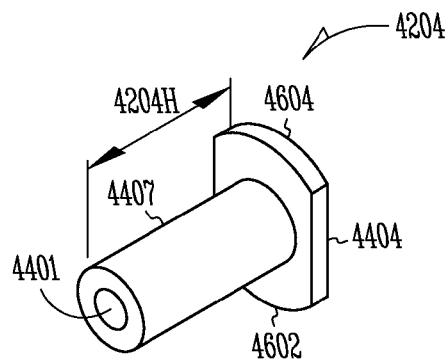
FIG. 63 is an isometric view of an exemplary coupling member in accord with one embodiment of the present subject matter.

FIG. 63 shows additional details of exemplary base 4404. In the exemplary embodiment, base 4404 is substantially rectangular having a pair of opposing rounded or curved ends 4602 and 4604.

Referring again to FIG. 61, in one embodiment, coupling member 4204 is situated so that surface 4405 abuts connection member surface 4216. Coupling member 4204 is laser welded using a butt-weld to surface 4216 of connection members 4201. Alternatively, coupling member 4204 is attached using other means. Butt-welding coupling member 4204 directly to connection members 4201 provides an optimal electrical connection between capacitor stack 4202 and the feedthrough assembly. Moreover, it also provides for a compact capacitor since very little, if any, space is wasted between capacitor stack 4202 and feedthrough assembly 4103. Also, since coupling member 4204 is directly attached to capacitor stack 4202, it helps support feedthrough conductor 4203 while a sealing member 4105, such as an epoxy, is applied to the feedthrough hole area.

Holding tube 4407 is located on the opposing side of base 4404 from surface 4405. Tube 4407 is a cylindrical member having an outer diameter dimensioned to fit within feedthrough hole 4107. Tube 4407 has a mounting section such as mounting hole 4401 defined in part by an inner surface 4402 of holding tube 4406 which is generally perpendicular to base surface 4405. Hole 4401 is located down an axial portion of the tube.

Mounting section or hole 4401 is for receiving proximal end portion 4217 of feedthrough conductor 4203. The surface of feedthrough conductor 4203 contacts inner surface 4402. In one embodiment, hole 4401 is approximately 0.016" (0.4064 mm) in diameter. Alternatively, its diameter can conform with the size of conductor 4203 so that feedthrough conductor 4203 can matably fit within the hole. In one embodiment, coupling member 4204 has a height 204h of approximately 0.085" (2.519 mm). Other embodiments range from 0.050" to 0.100" or higher. Some embodiments provide a height of greater than 0.100".

Figure 62A:
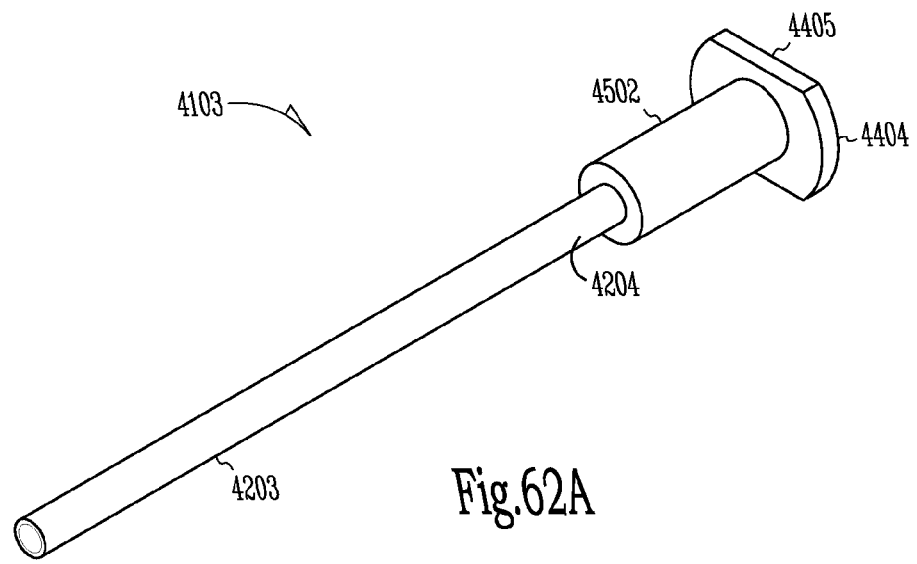
FIG. 62A is an isometric view of the exemplary feedthrough assembly of FIG. 58.
Figure 62B:
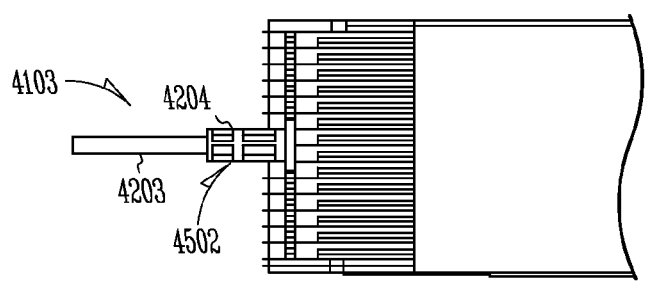
FIG. 62B is a side view of the exemplary feedthrough assembly of FIG. 58.

FIGS. 62A and 62B show an attachment of feedthrough conductor 4203 to coupling member 4204 according to one embodiment. In the present embodiment, feedthrough conductor 4203 and coupling member 4204 are connected at a crimp 4502. Alternatively, they are welded, soldered, glued or interference fit together, as will be discussed below. Example crimp 4502 compresses inner surface 4402 (see FIG. 61) of tube 4407 into mechanical and electrical connection with the surface of portions of feedthrough conductor 4203. In one embodiment, a double crimp is employed. In some embodiments, a single crimp, double crimp, triple crimp or more are used.

In one embodiment, inner surface 4402 of coupling member 4204 is a curved surface, defining an annular connection member. Crimp 4502 compresses and deforms opposing surfaces of annular inner surface 4402 to contact conductor 4203. In one embodiment, the opposing surfaces of inner surface 4402 are separated by a first distance prior to being crimped and separated by a second distance, smaller than the first distance, after being crimped.

Figure 64:
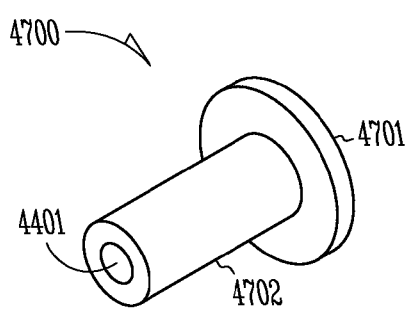
FIG. 64 is an isometric view of another exemplary coupling member in accord with one embodiment of the present subject matter.

FIG. 64 shows another exemplary coupling member 4700. Member 4700 includes a base 4701 and a holding tube 4702. Base 4701 is a circular-shaped base. In one embodiment, base 4701 has a diameter of approximately 0.050" (1.27 mm). In one embodiment (not shown), the base is square shaped.

Figure 65A:
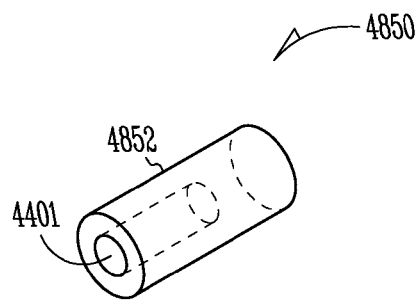
FIG. 65A is an isometric view of another exemplary coupling member in accord with one embodiment of the present subject matter.

FIG. 65A shows another example of a coupling member 4800. Member 4800 does not include a base. In one embodiment, hole 4401 runs completely through holding tube 4802. In one embodiment, one end of tube 4802 has a connection surface and is attached to surface 4216 of connection members 4201. A second end of tube 4802 receives feedthrough conductor 4203.

Figure 65B:
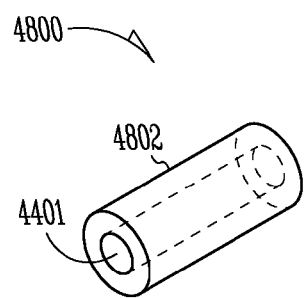
FIG. 65B is an isometric view of another exemplary coupling member in accord with one embodiment of the present subject matter.

FIG. 65B shows another example of a coupling member 4850. Member 4850 does not include a base. In one embodiment, hole 4401 runs only partially through a holding tube 4852. In one embodiment, one end of member 4850 has a connection surface and is attached to surface 4216 of connection members 4201. An end of tube 4802 receives feedthrough conductor 4203.

Figure 66:
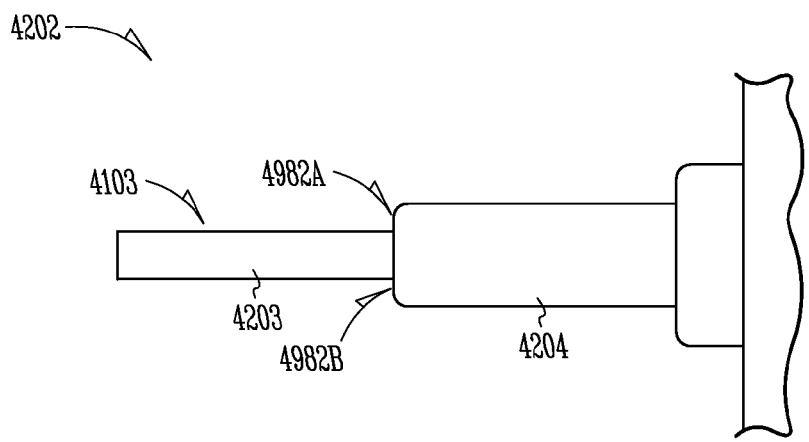
FIG. 66 is a side view of the feedthrough assembly of FIG. 58.

FIG. 66 shows a side view of feedthrough assembly 4103 in which feedthrough conductor 4203 is coupled to coupling member 4204 at one or more arc percussion welding areas, such as areas 4982a and 4982b. An exemplary arc percussion welding machine is manufactured by Morrow Tech Industries of Broomfield, Colo. In this embodiment, the conductor 4203 and coupling members are not crimped together. However, some embodiments include both welding and crimping.

Figure 67:
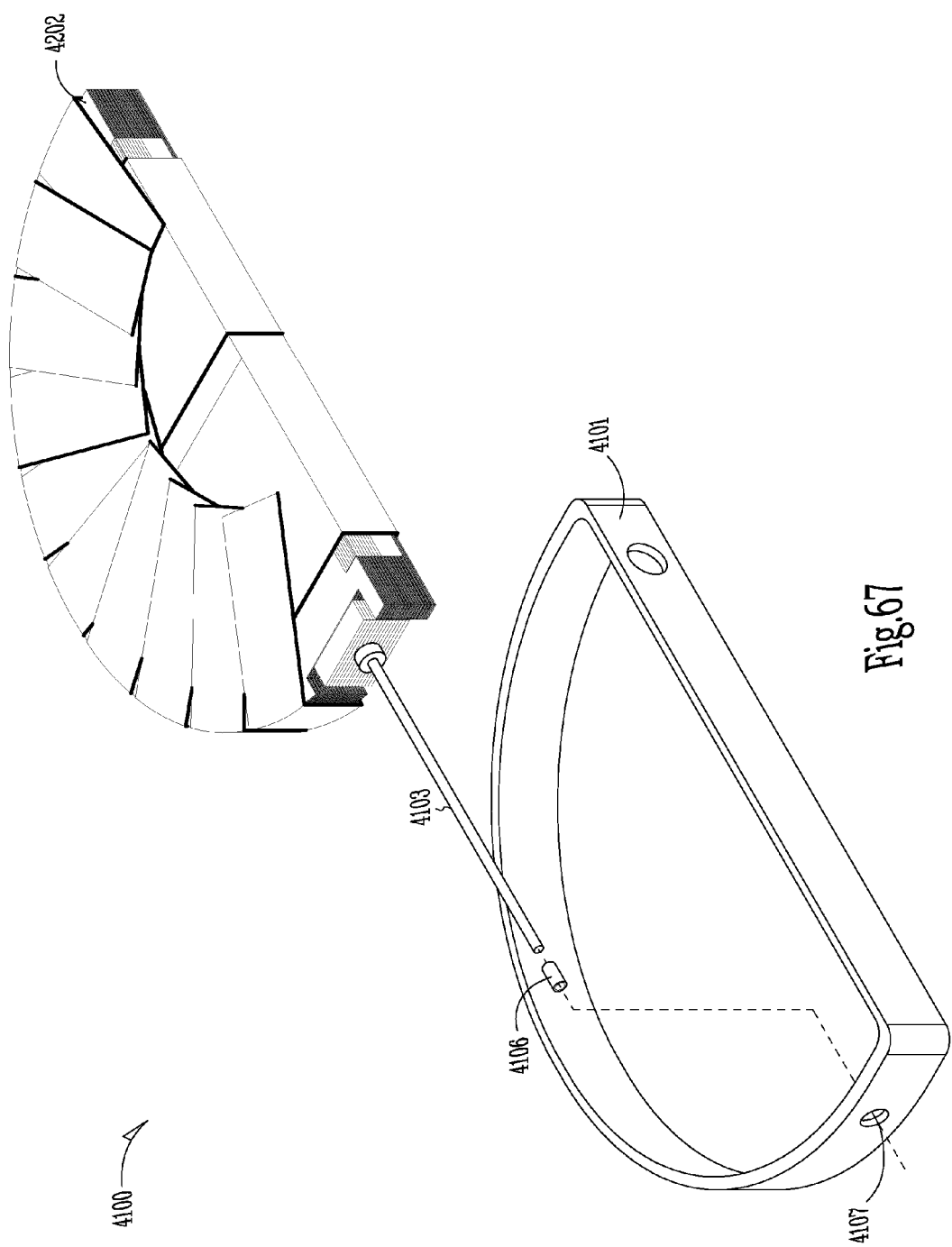
FIG. 67 is an exploded isometric view of a flat capacitor according to one embodiment of the present subject matter.

FIG. 67 shows an exploded view of capacitor 4100 having a sealing member such as a plug 4106 according to one embodiment of the present subject matter. Plug 4106 is insertable into feedthrough hole 4107 of case 4101. In one embodiment, plug 4106 has an outer diameter which is larger than the diameter of feedthrough hole 4107, and the manufacturer inserts it within hole 4107 in an interference fit. When plug 4106 is located within feedthrough hole 4107, the plug seals feedthrough hole 4107 and electrically insulates feedthrough assembly 4103 from case 4101. In some embodiments plug 4106 includes one or more flanges, which will be discussed below.

Figure 68:
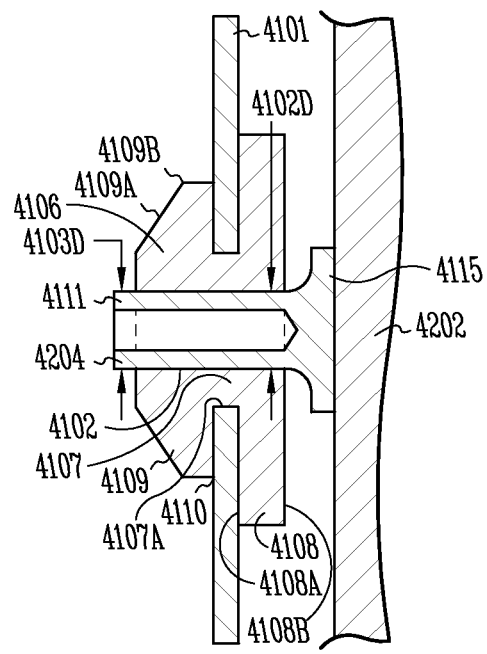
FIG. 68 is a cross-sectional view of the feedthrough assembly of FIG. 67.

FIG. 68 shows a cross-sectional view of plug 4106 assembled with capacitor case 4101. The present example show coupling member 4204 attached to capacitor stack 4202. However, in other embodiments plug 4106 can also be used in capacitors having other types of feedthrough assemblies. In one embodiment, plug 4106 electrically insulates case 4101 from coupling member 4204. Coupling member 4204 has a first end 4115 located in the interior of case 4101 and coupled to capacitor stack 4202. Coupling member 4204 also includes a second end 4111 located exterior to case 4101 for connecting to circuitry, such as defibrillator, or other implantable medical device circuitry. In one embodiment, coupling member 4204 has a feedthrough terminal attached thereto.

In this embodiment, plug 4106 is a double-flanged plug. Plug 4106 includes a first flange 4108. First flange 4108 includes a first surface 4108a which faces the inner surface of case 4101. When the capacitor begins to become pressurized, pressure against a second surface 4108b forces first surface 4108a against the case. Thus, flange 4108 creates a seal against the inner surface of case 4101.

In this embodiment, plug 4106 includes a second flange 4109. Flange 4109 includes a surface which faces the outer surface of case 4101.

Plug 4106 also includes a plug portion 4110 which is located between and defined by first flange 4108 and second flange 4109. Portion 4110 has a smaller diameter than either flange 4108 and/or 4109. Case edge 4107a confronts plug 4106 at portion 4110. In this embodiment, portion 4110 has a normal, unstressed outer diameter approximately equal to the diameter of feedthrough hole 4107. In some embodiments, the unstressed outer diameter is larger than the diameter of feedthrough hole 4107. In some embodiments, the unstressed outer diameter is smaller than hole 4107. As one example, in this embodiment flange 4108 has a diameter of approximately 0.080 inches and portion 4110 has a diameter of approximately 0.060 inches.

Plug 4106 also includes a central passage or hole 4102. In one embodiment, hole 4102 is axially located through the center of plug 4106 and has an unstressed diameter 4102d which is smaller than or equal to a diameter 4103d of a portion of feedthrough member 4103 which is mounted within hole 4102. In various embodiments, diameter 4102d may range from approximately 0.015 inches to approximately 0.033 inches. In other embodiments, diameter 4102d is smaller than 0.015 inches. In some embodiments it is greater than 0.033 inches. Other embodiments vary the hole size depending on the size of the feedthrough conductor used. In some embodiments, when a feedthrough member such as coupling member 4204 is inserted through hole 4102, an interference fit seal is developed between the feedthrough member and the plug. In other embodiments, hydrogen gas can escape along the feedthrough member/plug 4106 border.

In one embodiment, plug 4106 is made from a compressible, elastic material such as rubber, plastic, thermoplastic, or other elastic or elastomeric material. In one embodiment, when plug 4106 is mounted within feedthrough hole 4107 and feedthrough member 4103 is mounted within hole 4102, plug portion 4110 is compressed between assembly 4103 and edge 4107a of feedthrough hole 4107 and the plug exerts a radial force on edge 4107a of the feedthrough hole. This forces or compresses plug 4106 into an interference or compression fit between feedthrough hole edge 4107a and member 4204, thus helping to seal electrolyte solution within case 4101. In other embodiments, the diameter of portion 4110 is smaller than hole 4107 and an interference fit between feedthrough hole edge 4107a and member 4204 is not created.

In one embodiment, as noted above, flange 4108 provides a sealing means for helping seal electrolyte within the case. Accordingly, in some embodiments, when the diameter of portion 4110 is smaller than hole 4107 and an interference fit between feedthrough hole edge 4107a and member 4204 is not created, only flange 4108 provides a sealing means between case 4101 and plug 4106. Advantageously, the seal or seals are formed automatically. Thus, in one embodiment, assembling and tightening a screw or other extraneous hardware is not required to seal the capacitor.

In one embodiment, second flange 4109 provides support for mounting plug 4106 within hole 4107. For instance, when plug 4106 is mounted in hole 4107, flanges 4108 and 4109 each help hold plug 4106 in place once it is mounted, but before the coupling member 4204 is inserted through hole 4102. This aides the manufacturing process.

In one embodiment second flange 4109 includes a tapered section wherein an outer portion 4109a of flange 4109 has a smaller diameter than an inner portion 4109b. The tapered shape of flange 4109 aids in inserting plug 4106 into hole 4107. Some embodiments omit the tapered shape and flange 4109 has a uniform outer diameter. Other embodiments provide a tapered shape for first flange 4108. Other embodiments provide tapered sections on both flanges.

In this embodiment, flange 4108 has a larger diameter than flange 4109. In some embodiments, the two flanges have substantially equal diameters. In further embodiments, flange 4109 has a larger diameter than flange 4108.

Some embodiments omit either or both of flanges 4108 and 4109. For instance, in some embodiments plug 4106 has a generally cylindrical shape. In other embodiments, plug 4106 has an hour-glass shape or other shape which closely fits within feedthrough hole 4107. In some embodiments, plug 4106 is a mass of elastic material with a dimension approximately equal to or larger than the width of feedthrough hole 4107.

In one embodiment, plug 4106 seals the electrolyte within capacitor case 4101, but it does not provide a hermetic seal. Hydrogen is created during consumption of water from the electrolyte and continues to be formed throughout the life of the capacitor. This can cause a hermetically sealed capacitor case to bulge outward from the hydrogen gas production within, thus risking long-term device reliability due to shorting.

Accordingly, in one embodiment plug 4106 permits outgassing of hydrogen gas, thus alleviating any problems. For instance, in one embodiment, flange 4108 creates a seal to the inner wall of the case 4101. A pathway for the gas to escape is then present along the border between coupling member 4204 and plug 4106.

Figure 69:
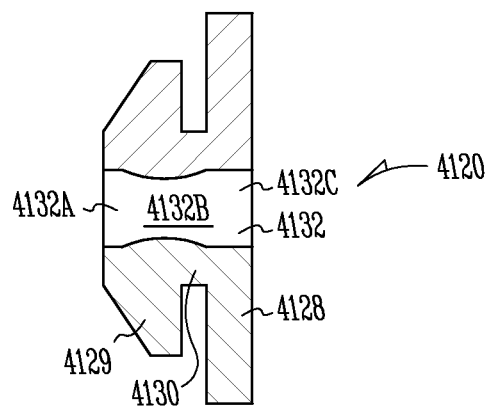
FIG. 69 is a cross-sectional side view showing a feedthrough plug according to one embodiment.

FIG. 69 shows a cross-sectional side view of a plug 4120 according to one embodiment. Plug 4120 includes one or more features of plug 4106 and discussion of unnecessary details will be omitted. Plug 4120 includes a first flange 4128, a second flange 4129, and a portion 4130 between the two flanges 4128 and 4129. In one embodiment, plug 4130 includes a hole 4132. Hole 4132 has a sealing section such as a narrow section 4132b, which is located between two nominal diameter sections 4132a and 4132b. Other embodiments omit section 4132b or move it to either end, thereby omitting sections 4132a or 4132b.

In one embodiment, narrow section 4132b provides an O-ring type interference fit for a feedthrough member such as coupling member 4204. In this embodiment, narrow section 4132b is generally located within second flange 4129. Other embodiments locate the narrow section within central portion 4130. Other embodiments locate the narrow section within first flange 4128. By way of example, in one embodiment, the nominal diameters of sections 4132a and 4132c is approximately 0.032 inches, and the diameter of narrow section 4132b is 0.026 inches.

Referring again to FIG. 67, one method of assembling a capacitor having a plug 4106 is as follows. Plug 4106 is inserted into feedthrough hole 4107 of case 4101. In one embodiment, plug 4106 includes a double-flange construction which helps hold the plug in place once it is mounted. Feedthrough assembly 4103 is attached to capacitor stack 4202 and inserted through inner hole 4102 of plug 4106 while capacitor stack 4202 is placed within the cavity of case 4101. An interference fit between plug 4106 and feedthrough 4103 and between case 4101 and plug 4106 are created. Thus, a seal is formed between the interior of case 4101 and the exterior of case 4101.

Figure 70:
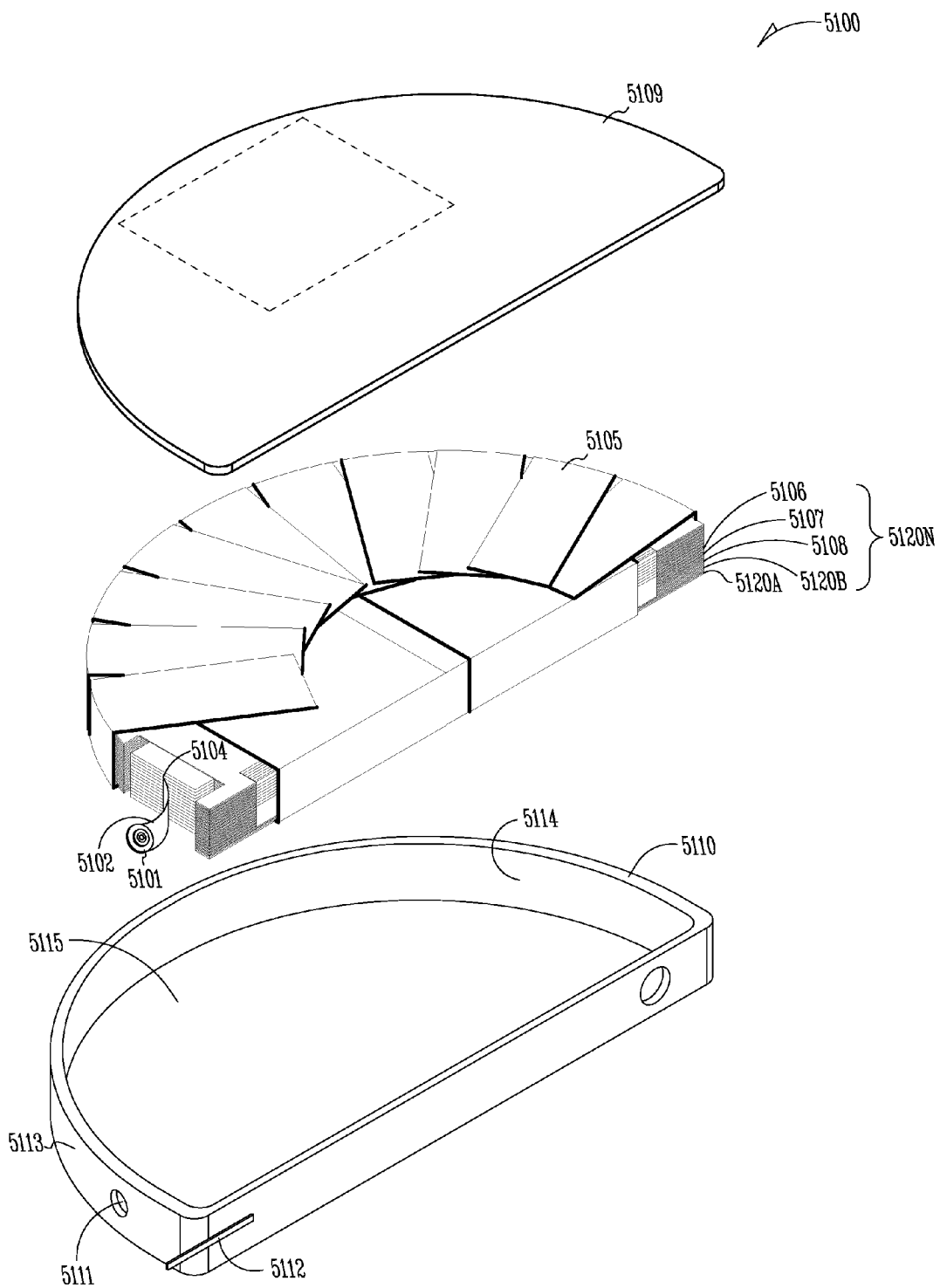
FIG. 70 is an exploded view of a flat capacitor according to one embodiment of the present subject matter.

FIG. 70 shows a feedthrough assembly according to another embodiment of the present subject matter. FIG. 70 shows an exploded view of a flat capacitor 5100 incorporating a feedthrough assembly 5101. Although the present embodiment is described as a flat capacitor, other capacitor forms can take advantage of the feedthrough assembly and the other features discussed in the present description.

Capacitor 5100 includes one or more features of capacitor 100 of FIG. 1 and details will be omitted for the sake of clarity. In the present embodiment, capacitor 5100 includes a feedthrough assembly 5101, a conductor 5102, one or more capacitor element tabs 5104, a capacitor stack 5105, a terminal 5112, and a capacitor housing or case 5113. Case 5113 includes a container portion 5110 and a lid 5109. Container portion 5110 has a cavity for holding capacitor stack 5105. The cavity is defined in part by a bottom side 5115 surrounded by a side wall 5114. When lid 5109 is attached to the container portion of the case, the lid and the bottom side are substantially parallel to each other.

In one embodiment, case 5113 includes a feedthrough port or hole 5111. Alternatively, the case can include one, two, three, four or more holes, depending on other design factors which will be discussed below.

Capacitor stack 5105 is situated within capacitor case 5113. In the exemplary embodiment, capacitor stack 5105 includes one or more capacitor modules or elements 5120a, 5120b, . . . , 5120n. The number of capacitor elements 5120 can vary according to capacitive need and size of a capacitor desired. Each capacitor element 5120a-5120n includes a cathode 5106, an anode 5108, and a separator 5107 sandwiched between cathode 5106 and anode 5108. In some embodiments, other numbers and arrangements of anodes, cathodes, and separators are used.

In one embodiment, attached to each capacitive element 5120a-5120n is a foil connection structure such as a conductive tab 5104, made from aluminum or other suitable material, which electrically connects each anode to the other anodes of capacitor stack 5105. Each tab 5104 of each capacitor element 5120a-5120n is connected to each other tab 5104 and coupled to conductor 5102 for electrically coupling the anode to a component outside the case.

In one embodiment, conductor 5102 is an aluminum ribbon tab and is coupled at one end to anode tabs 5104 and at another end to feedthrough assembly 5101 for electrically coupling capacitor stack 5105 to a component outside the case through hole 5111. Conductor 5102 is coupled to feedthrough assembly 5101 by welding or other coupling means.

In one embodiment, each cathode 5106 is a foil attached to the other cathodes of capacitor stack 5105. In the present embodiment, the cathodes are attached to case 5113. Terminal 5112 is attached to case 5113. In some embodiments, each cathode 5106 is joined to the other cathodes at cathode tabs for providing an external cathode connection. In one embodiment, cathodes 5106 are coupled to a feedthrough assembly extending through a feedthrough hole, such as hole 5111. In various embodiments, the anode is connected to the case and the cathode is connected to a feedthrough assembly, or both anodes and cathodes are connected to feedthrough assemblies.

Figure 71:
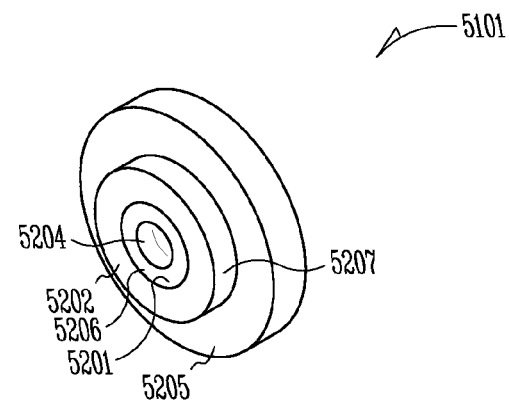
FIG. 71 is an isometric view of the feedthrough assembly of FIG. 70.

FIG. 71 shows a larger view of feedthrough assembly 5101. Feedthrough assembly 5101 includes an inner core or central feedthrough member 5201 for electrically connecting conductor 5102 to an outside component. In one embodiment, central or inner member 5201 is an annular member which comprises a conductive material, such as aluminum, and has a bore or passage 5204 running through it. In one embodiment, passage 5204 extends all the way through feedthrough member 5201. In some embodiments, passage 5204 extends partially through the member.

Feedthrough assembly 5101 also includes an outer member 5202 molded, glued, or otherwise located around central member 5201. In one embodiment, outer member 5202 is an electrically insulating material, such as a plastic or thermoplastic, for insulating the central member 5201 from case 5113. Member 5202 is an annular, flanged member having a cylindrical stepped-shaped structure. In one embodiment, outer member 5202 includes a substantially flat surface 5205 and a second surface 5207 substantially perpendicular to surface 5205.

Figure 72:
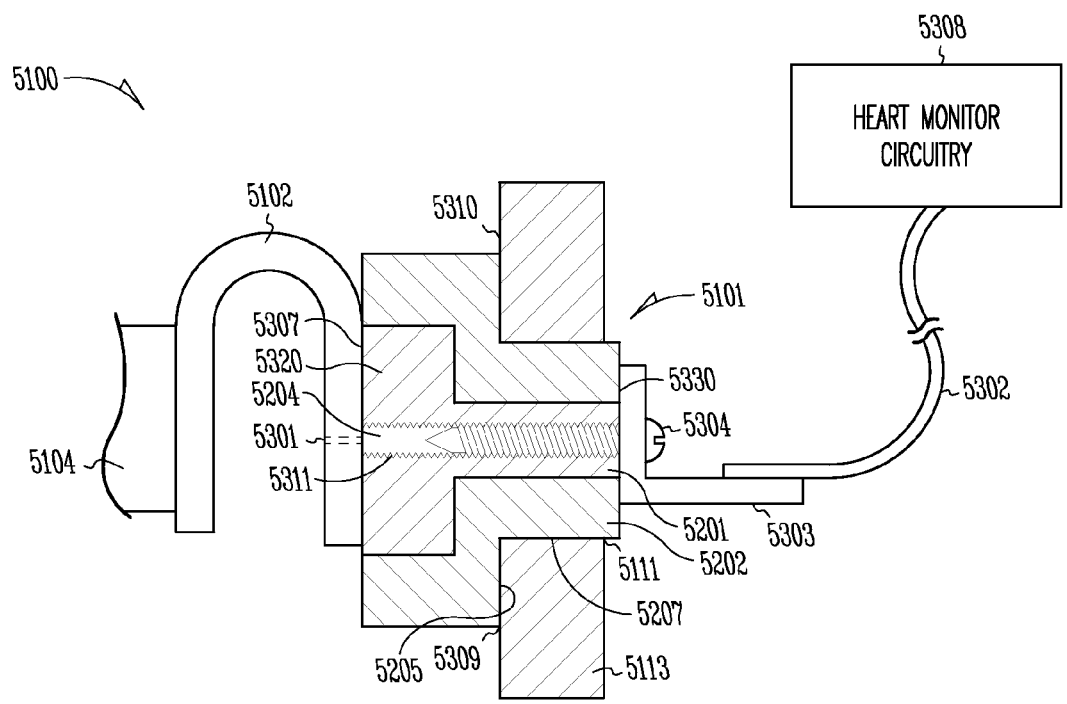
FIG. 72 is a cross-section view of the feedthrough assembly of FIG. 70.

FIG. 72 shows a partial cross-section view of capacitor 5100 connected by feedthrough assembly 5101 to a component, such as heart monitor circuitry 5308. In the present embodiment, outer member 5202 is attached to case 5113 by an epoxy or other adhesive method at areas 5309 and 5310. Some embodiments include threads on surface 5207 and/or form member 5202 from an elastic material that is compressed within hole 5111. In some embodiments, the elastic material is permeable to allow passage of fluids such as hydrogen gas to escape from case 5113. Outer member surface 5205 abuts an inner surface of case 5113 around feedthrough hole 5111 and surface 5207 abuts or confronts an edge surface of the feedthrough hole.

Tabs 5104 are connected to one end of conductor 5102. In various embodiments, conductor 5102 is welded, crimped, or otherwise attached to the tabs. A second end of conductor 102 is welded or crimped or otherwise attached to a substantially flat surface 5307 of conductive central member 5201. In one embodiment, conductor 5102 is folded over itself between tabs 5104 and feedthrough assembly 5101. In some embodiments, the fold is omitted to reduce the space between tabs 5104 and feedthrough assembly 5101. In one embodiment, conductor 5102 is omitted and central member 5201 is directly attached to tabs 5104.

Central member 5201 electrically connects conductor 5102 to outside component 5308. In the exemplary embodiment, central member 5201 is a cylindrical stepped-shaped member having a first annular section and a second annular flange section. Member 5201 has a first end 5320 within case 5113 and a second end 5330 extending through hole 5111. In one embodiment, second end 5330 has a substantially flat end surface which is positioned flush with an outer surface of case 5113. In other embodiments, second end 5330 is partially within feedthrough hole 5111. In some embodiments, second end 5330 protrudes from hole 5111 and extends a distance from case 5113.

In one embodiment, central member passage 5204 includes a mounting section 5311, such as a threaded section. A feedthrough terminal fastener 5304 includes a mounting section (in one embodiment, a threaded section) that corresponds to mounting section 5311 of passage 5204 so that feedthrough terminal fastener 5304 is removably attachable to the central member of feedthrough assembly 5101. In some embodiments, a sealant such as Loctite is placed on the mounting section to provide for a sealed connection.

Terminal fastener 5304 attaches a feedthrough terminal 5303 to feedthrough assembly 5101. Terminal 5303 in turn is attached (for example, soldered or welded) to a connector 5302 which is connected to component 5308. In one embodiment, terminal 5303 is a conductive material, such as aluminum or gold-plated nickel. Other embodiments have other suitable conductive materials. Since terminal fastener 5304 is removable, it allows a defective capacitor to be replaced by a good one.

For instance, if capacitor 5100 were installed in a defibrillator and it was discovered that the capacitor was defective, a user could disengage feedthrough terminal 5303 from the capacitor and mount a new capacitor in place of the defective one. This is in contrast with conventional feedthrough assemblies in which one would have to cut connector 5302 from terminal 5303 and then reweld or re-solder the connector to a new capacitor. Moreover, the conventional design requires an extra length for connector 5302 to allow for replacement. This extra length takes up extra space within the device, for example an implantable defibrillator or cardioverter, including the capacitor. Thus, the exemplary embodiment permits an optimal, minimal length of connector 5302 while still permitting a defective capacitor to be replaced without having to throw the whole device away.

In one embodiment, conductor 5102 includes one or more holes, such as a hole 5301, adjacent to and contiguous with passage 5204. In some embodiments, hole 5301 is as small as a pinhole. In the present embodiment, hole 5301 is aligned with passage 5204 and provides a continuous passage that effectively extends passage 5204 into the interior of case 5113, allowing introduction of an electrolyte solution (or other material) into case 5113 through passage 5204 and hole 5301. Thus, a user can fill case 5113 with electrolyte through an existing feedthrough hole instead of providing and sealing a separate backfill hole. Thus, the present embodiment saves at least one manufacturing step. In some embodiments, conductor 5102 is attached to feedthrough assembly 5101 so that it is slightly offset from passage 5204, thus providing a continuous passage into the interior of case 5113. In some embodiments, conductor 5102 includes two, three, or more holes.

Figure 73:
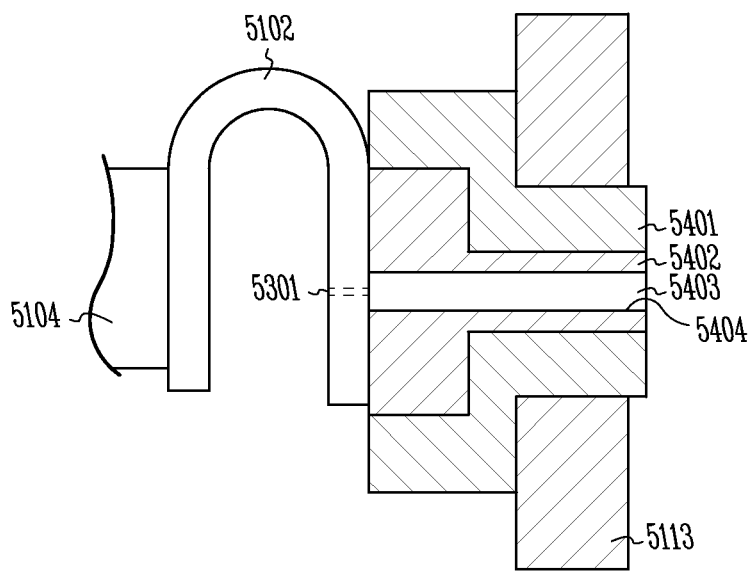
FIG. 73 is a cross-section view of another exemplary feedthrough assembly according to one embodiment of the present subject matter.

FIG. 73 shows a partial cross-section view of a feedthrough assembly 5400 according to another embodiment. Feedthrough assembly 5400 includes a central feedthrough member 5402 and an outer member 5401. In one embodiment, member 5402 is a cylindrical, step-shaped member made from a conductive material such as aluminum. Central member 5401 has a passage 5403 extending through it. Conductor 5102 is attached to member 5402 and includes one or more holes 5301 adjacent to and contiguous with passage 5403 so that an electrolyte solution can be deposited within case 5113 through the passage 5403 and the hole 5301.

In this embodiment, passage 5403 is a non-threaded cylindrical passage adapted to have a terminal fastener (not shown) riveted, interference fitted, glued, or otherwise coupled to it. In one embodiment, a connector from an outside component is directly coupled within passage 5403 by an interference or friction fit. In some embodiments, passage 5403 has a square, triangle, or other shape for receiving a terminal fastener.

Figure 74:
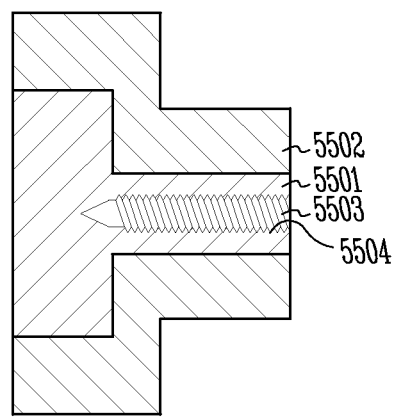
FIG. 74 is a cross-section view of another exemplary feedthrough assembly according to one embodiment of the present subject matter.

FIG. 74 shows a partial cross-section view of a feedthrough assembly 5500 according to another embodiment. Feedthrough assembly 5500 includes a central feedthrough member 5501 and an outer member 5502. In one embodiment, member 5501 is a cylindrical, step-shaped member made from a conductive material such as aluminum. Outer member 5502 is an electrically insulative material, molded, glued, or otherwise placed around conductive central member 5501 to electrically insulate member 5501 from a conductive capacitor case.

In this embodiment, feedthrough member 5501 includes a passage 5503. Passage 5503 extends partially through a central axial portion of the central member. In the exemplary embodiment, passage 5503 is threaded. This provides a mounting portion for removably mounting a threaded member such as a terminal fastener. In some embodiments, passage 5503 is not threaded and a terminal fastener or a terminal is interference fitted, glued or otherwise attached within passage 5503.

Figure 75:
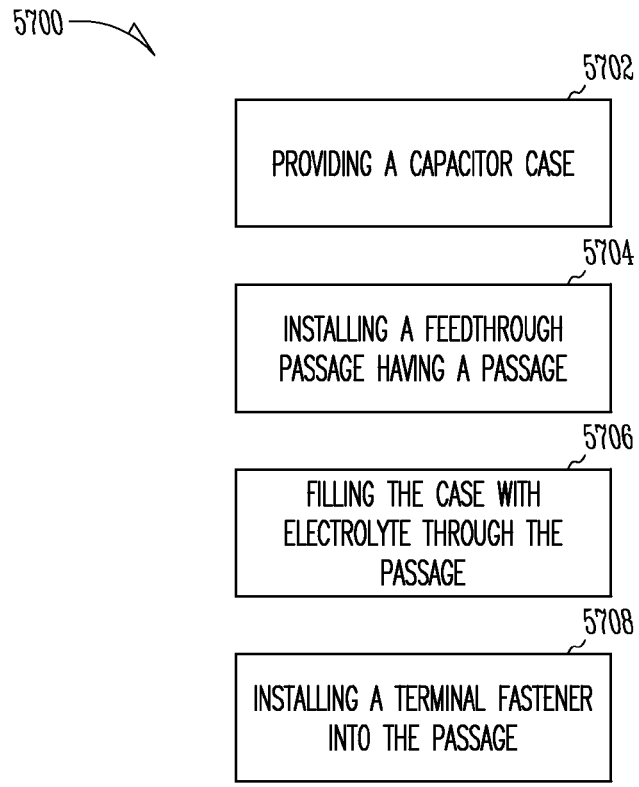
FIG. 75 is a flow-chart of a method for manufacturing an electrolytic capacitor according to one embodiment of the present subject matter.

FIG. 75 shows an example of a method 5700 for manufacturing an electrolytic capacitor according to one embodiment of the present subject matter. Method 5700 will be discussed in reference to exemplary capacitor 5100 of FIGS. 70-72. However, it is understood that the method can be performed on different types of capacitors. In block 5702, method 5700 includes providing a capacitor case 5113 having a hole 5111. In block 5704, the method includes installing feedthrough assembly 5101 at least partially into hole 5111. The feedthrough assembly 5101 includes conductive member 5201 having passage 5204 therethrough. In block 5706, method 5700 includes filling case 5113 with an electrolyte solution through passage 5204. In block 5708, method 5700 includes installing terminal fastener 5304 in passage 5204. The exemplary method saves at least one manufacturing step since the electrolyte is filled through an existing feedthrough hole instead of providing and sealing a separate backfill hole.

Figure 76:
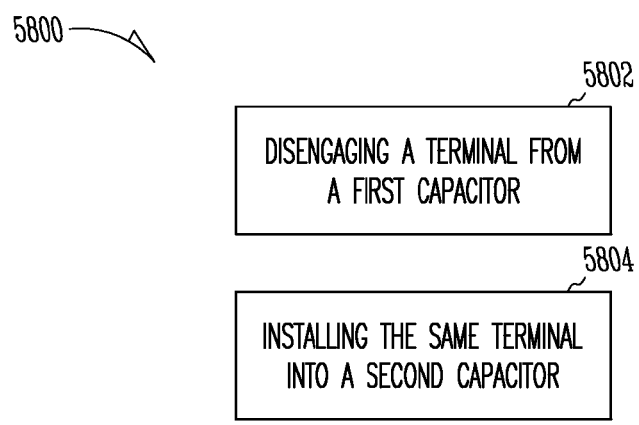
FIG. 76 is a flow-chart of a method for replacing a first capacitor with a second capacitor according to one embodiment of the present subject matter.

FIG. 76 shows an exemplary method 5800 for replacing a first capacitor installed in a medical device with a second capacitor. Again, the method will be discussed in reference to capacitor 5100. In block 5802, the method includes disengaging a terminal 5303 coupled to a medical device 5308 from a feedthrough passage 5204 of the first capacitor 5100. In block 5804, the method includes installing the same terminal 5303 into a feedthrough passage of the second capacitor (not shown). This provides that the capacitor can be replaced instead of having to throw the whole unit away.

Figure 77:
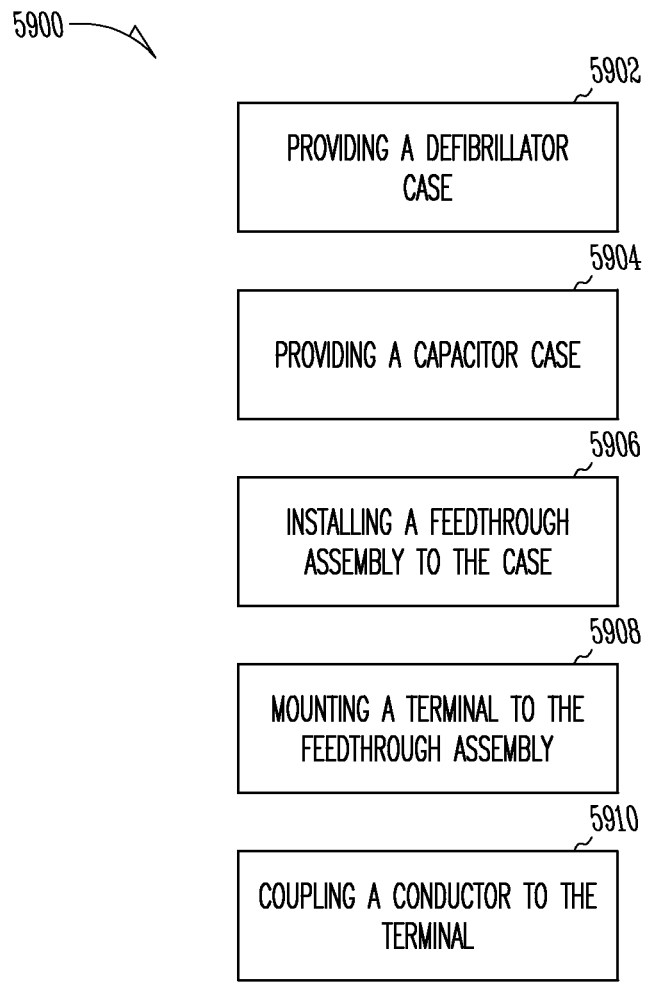
FIG. 77 is a flow-chart of a method for manufacturing an implantable defibrillator according to one embodiment of the present subject matter.

FIG. 77 shows a method 5900 for manufacturing an implantable defibrillator according to one embodiment of the present subject matter. Again, the method will be discussed in reference to capacitor 5100. In block 5902, the method includes providing a defibrillator case having circuitry 5308. In block 5904, the method includes providing a capacitor case 5113 having a hole 5111. In block 5906, the method includes installing feedthrough assembly 5101 at least partially into hole 5111. In the exemplary method, the feedthrough assembly 5101 includes a conductive member 5201 having a passage 5204. In block 5908, the method includes mounting terminal 5303 to passage 5204 using a terminal fastener 5304. In block 5910, the method includes coupling a conductor 5302 coupled to defibrillator circuitry 5308 to terminal 5303.

FIGS. 78-82 show one or more embodiments for coupling a cathode or anode stack to a capacitor case.

Figure 78:
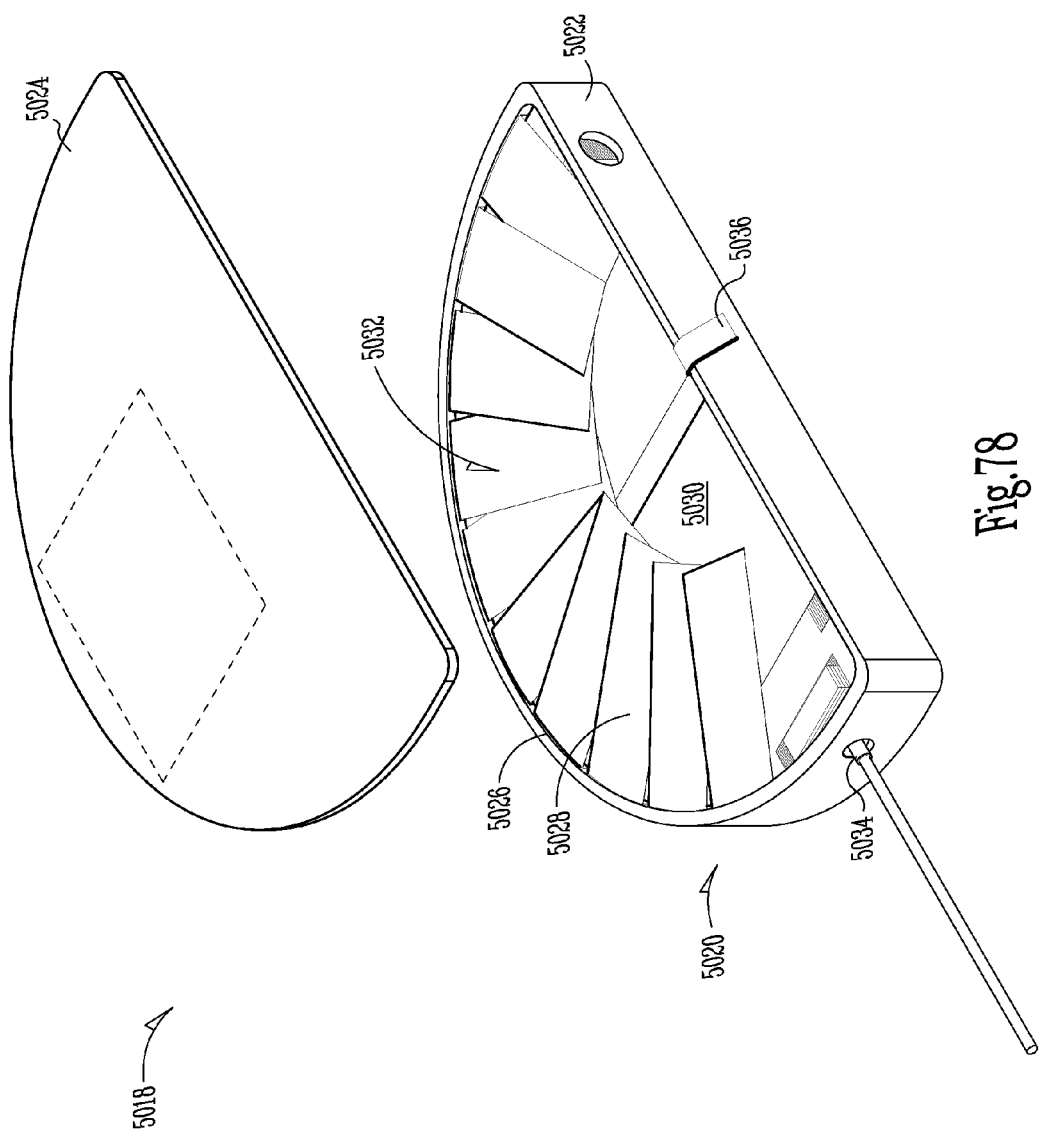
FIG. 78 is an exploded perspective view of a capacitor according to one embodiment of the present subject matter.

FIG. 78 shows a perspective view of a capacitor 5018. Capacitor 5018 includes one or more features described above for capacitor 100 of FIG. 1. Accordingly, certain details will be omitted herein. Capacitor 5018 includes a capacitor container 5020 including a case 5022 and a lid, or cover 5024 overlying case 5022 for placement on an upper rim 5026 of case 5022. A capacitor stack 5028 with a top surface 5030 is enclosed by container 5020 which defines a chamber 5032.

Capacitor stack 5028 includes a plurality of cathode and anode foil layers separated by one or more separators. The anode foil layers are connected together and coupled to a feedthrough conductor 5034. In one embodiment, feedthrough conductor 5034 passes through a hole in case 5022, and conductor 5034 is electrically isolated from case 5022.

The cathode foil layers of stack 5028 are connected together and connected to a conductor 5036. In one embodiment, cathode conductor 5036 is a tab strip which is integral to one of the cathode layers. In other embodiments, cathode conductor 5036 is a strip of aluminum tab stock connected to one or more of the cathode foil layers. Cathode conductor 5036 provides an electrical connection between the cathode layers and case 5022.

Figure 79:
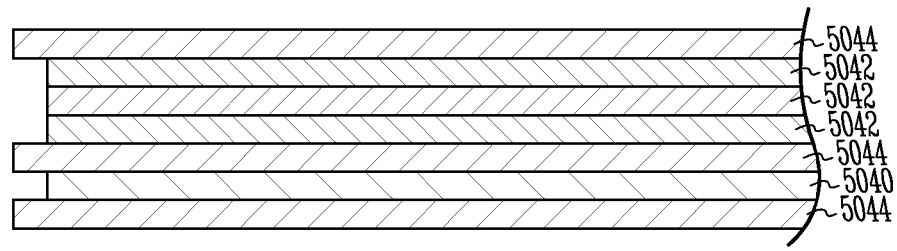
FIG. 79 is a cross sectional view of portions of the capacitive stack of FIG. 78.

FIG. 79 shows a capacitive element 5038 in accord with one embodiment. Capacitor stack 5028 includes a plurality of generally flat capacitive elements 5038. Capacitive element 5038 includes foil layers such as cathode layer 5040 and anode layers 5042 each of whose electrical elements are connected in parallel. In this embodiment, anode layers 5042 form a triple anode structure. Other embodiments include single, double, triple, four, and/or more anode foils.

Figure 80:
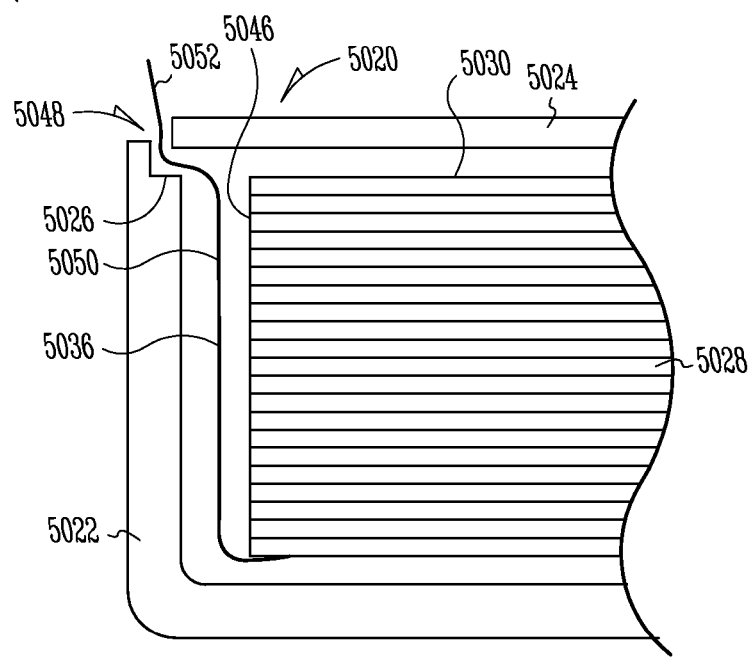
FIG. 80 is a partial cross sectional view of a capacitor with a cathode conductor positioned between the cover and the case according to one embodiment.
Figure 81:
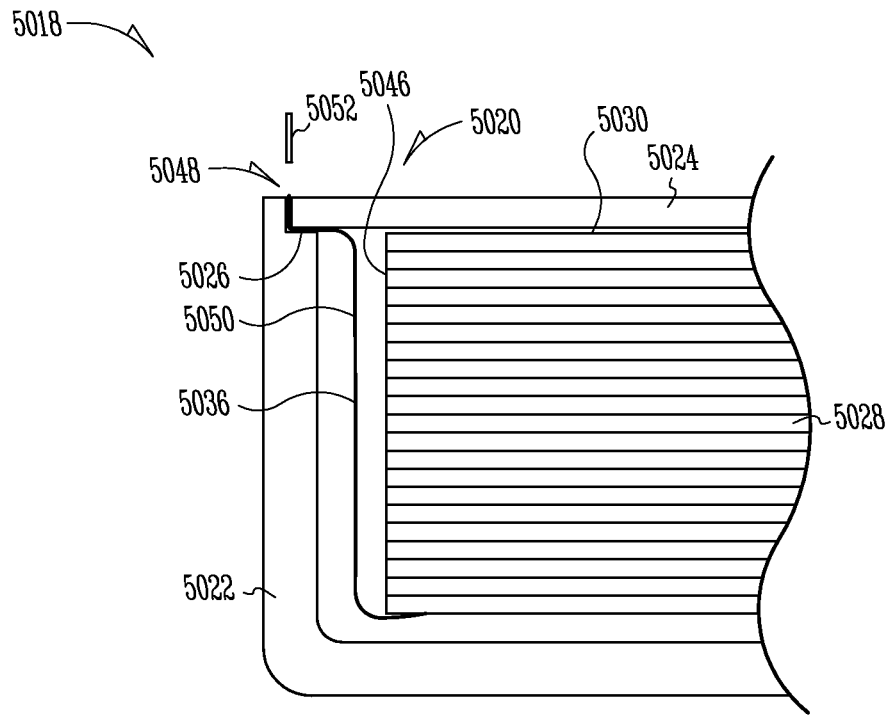
FIG. 81 is a partial cross sectional view of a capacitor with the cathode conductor attached to the cover and the case according to one embodiment.
Figure 82:
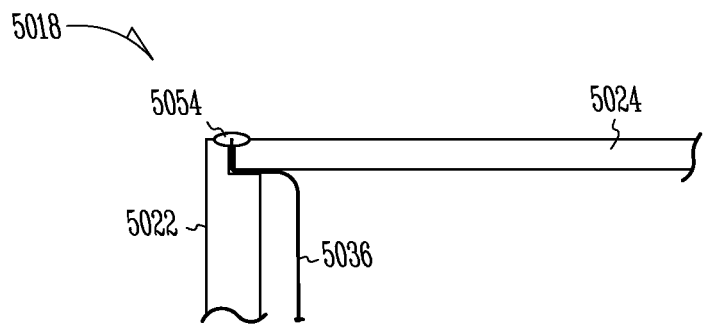
FIG. 82 is a partial cross sectional view of a capacitor with the cathode conductor welded to the cover and the case according to one embodiment.

FIGS. 80-82 show a partial cutaway view of capacitor 5018 during respective manufacturing stages in accord with one or more embodiments of the present subject matter. Capacitor stack 5028 includes top surface 5030 and a lateral face 5046 and includes one or more parallel connected capacitive elements, such as capacitive element 5038 shown on FIG. 79. As discussed above, in one embodiment, the anodes of each capacitive element have respective tabs connected together and welded at their free ends. The welded tabs are then welded (or otherwise fastened or attached) to feedthrough conductor 5034 that passes through case 5022. (See FIG. 78). In some embodiments, an unetched, integral portion of each of one or more anodes is used to weld or attach the anode layers to one another.

In one embodiment, cathode tabs are attached or fastened to cathode conductor 5036. As noted above, in some embodiments cathode conductor 5036 is an integral extension of a cathode foil layer, meaning for example, that the cathode conductor and cathode foil layer are formed from a single piece of foil.

In one embodiment, cathode conductor 5036 extends from capacitor stack 5028 and is positioned and pinched between upper rim 5026 of case 5022 and cover 5024. Cover 5024 and case 5022 form an interface or seam 5048 at upper rim 5026. Cathode conductor 5036 is positioned in interface 5048 between case 5022 and cover 5024. Cathode conductor 5036 is pinched between case 5022 and cover 5024 defining an inner conductor portion 5050 and an outer conductor portion 5052. As shown in FIG. 81, in one embodiment, at least a portion of the outer conductor portion 5052 is trimmed off of the cathode conductor 5036.

In some embodiments, cathode conductor 5036 is welded into place during the base/cover welding process, providing a mechanical and electrical connection to the case 5022 without a separate connection procedure. In contrast, if the cathode conductor is connected to the case in a separate procedure, the extra connection requires that part of the capacitor stack be removed or the case be enlarged to allow space for routing and connecting the conductors, thereby reducing the packaging efficiency of the capacitor. The reduced packaging efficiency ultimately results in a larger capacitor. In some embodiments, conductor 5036 is welded or otherwise fastened to the interior or exterior of cover 5024 or to the exterior of case 5022.

FIG. 82 shows a partial cutaway view of capacitor 5018 with cover 5024 welded to case 5022. Cathode conductor 5036 is positioned between case 5022 and cover 5024 at upper rim 5026. Cathode conductor 5036 is welded in the interface 5048 between cover 5024 and case 5022, providing a mechanical and electrical connection to the container 5020. The welded conductor 5036, cover 5024 and case 5022 are welded together with a single bead 5054. In one embodiment, the bead forms a hermetic seal between the cover 5024 and case 5022.

Among other advantages, one or more of the embodiments described above provide a capacitor structure which reduces the space required for connecting and routing the cathode conductor and thus allows a reduction in the size of the capacitor, or alternatively an increase in its energy storage capacity.

The embodiments described above show the cathode conductor electrically connected to the housing forming a cathodic housing. Alternative embodiments include positioning the anode conductor between the cover and case thereby connecting the anode layers and anode conductor to the housing forming an anodic housing.

An exemplary embodiment of a method to connect a cathode conductor to a capacitor housing is described below. The cathode conductor is connected to the housing by positioning the conductor between the case and the cover; positioning the cover on the case; and attaching the cover to the case so that the conductor is electrically and mechanically connected to the housing. In addition, other embodiments include positioning the conductor between the case and the cover at the upper rim and attaching the cover to the case at the upper rim. In one embodiment, the case and the cover form an interface and the positioning of the conductor between the case and the cover is in the interface. In another embodiment, the attaching the cover to the case comprises welding or soldering the cover to the case. The cathode conductor is welded into place using a single bead during the welding of the cover to the case, eliminating a separate step of connecting the cathode conductor to the case.

Figure 83:
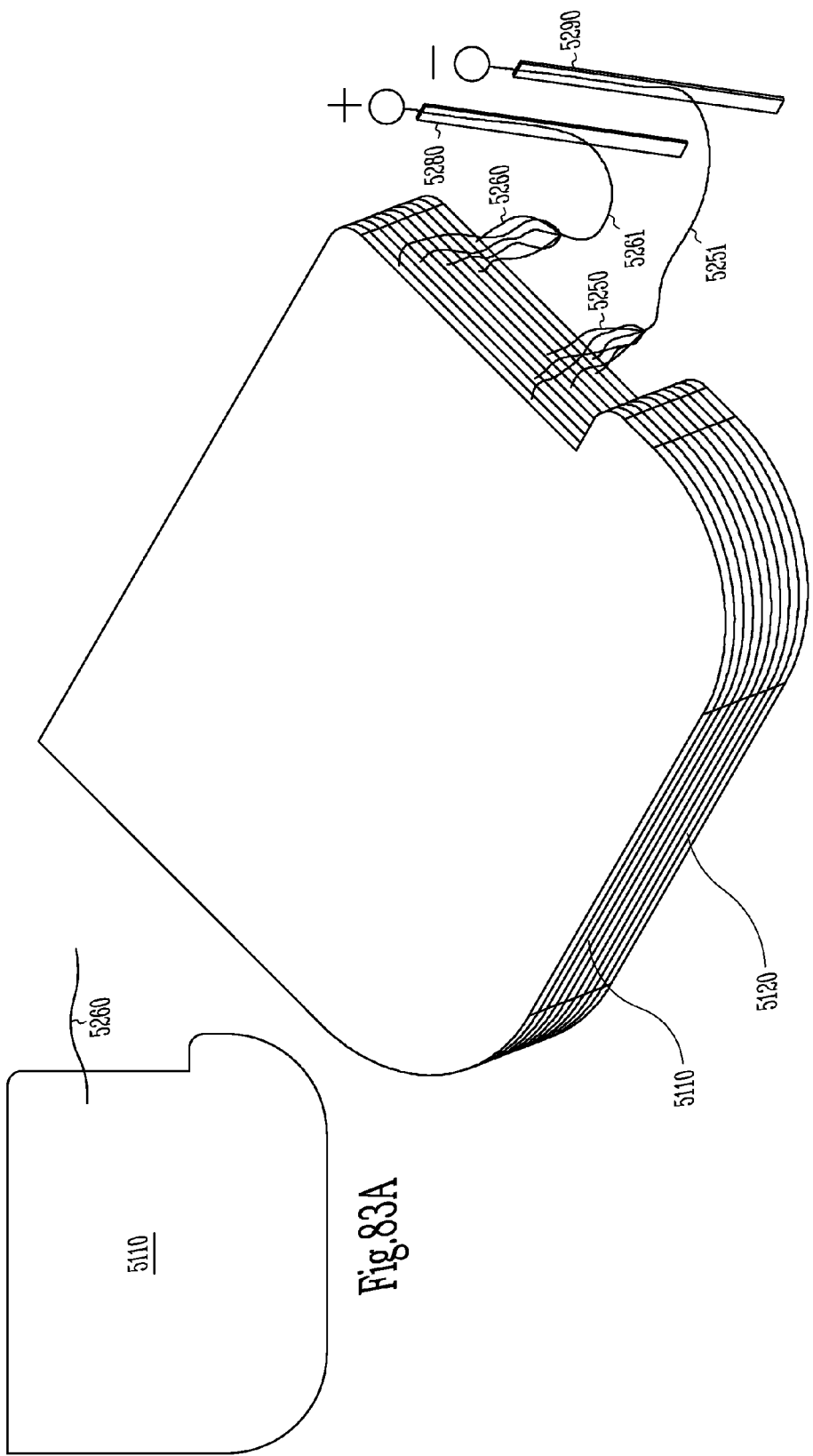
FIG. 83A is a view of a flat capacitor foil with an attached round wire connector according to one embodiment.
FIG. 83B is a perspective view of a flat capacitor showing round wire connectors for interconnecting anode and cathode plates.

One example method of providing internal interconnections and/or external connections is described as follows. FIG. 83A shows a top view of a foil connection according to one embodiment. In this embodiment, a wire connector 5260 is attached to a major surface of an anode layer 5110 along a portion of the wire connector's length. In one embodiment, wire connectors are similarly connected to the cathode layers of the capacitor stack. In one embodiment, wire connector 5250 is made of a high purity aluminum, is a round wire and includes a diameter allowing the desired amount of bending and twisting as the connectors is routed through the capacitor case.

FIG. 83B shows a capacitor in accordance with one embodiment in which one or more round wire connectors 5250 are connected to the cathode layers 5120 and wire connectors 5260 are connected to anode layers 5110. The wire connectors may be made of high purity aluminum and are staked (or otherwise attached such as by welding, brazing, etc.) to the individual cathode and anode layers.

Wire connector 5250 and 5260 connect like types of layers together and can be used to connect the layers to external terminals. In the FIG., the wires connected to the anode layers exit the layers at one common location while the cathode layer wires exit together at a different location. The anode layer wires 5260 and cathode layer wires 5250 are then gathered into corresponding wire bundles 5261 and 5251, respectively. The bundles can then be twisted together into a cable that can be laid in any direction to be routed through feedthroughs 5280 to terminal connections. In the FIG., the anode layers 5110 are electrically connected to positive terminal 5160, and the cathode layers are electrically connected to negative terminal 5150. By directly connecting the round wire connectors to the capacitor layers, there is no need for tabs that add to the space requirements of the capacitor case.

In one embodiment, wire connectors 5250 and/or 5260 are insulated with the insulation removed at the point of bundling in order to electrically connect like types of layers together. In another embodiment, the wires are uninsulated and routed through the case via an insulated feedthrough hole.

Advantageously, in one or more embodiments, the cathode and anode wires can be gathered into bundles and twisted into a cable that can be routed in any direction through a feedthrough of the capacitor case. This allows greater space efficiency and a smaller case for the capacitor.

Figure 84:
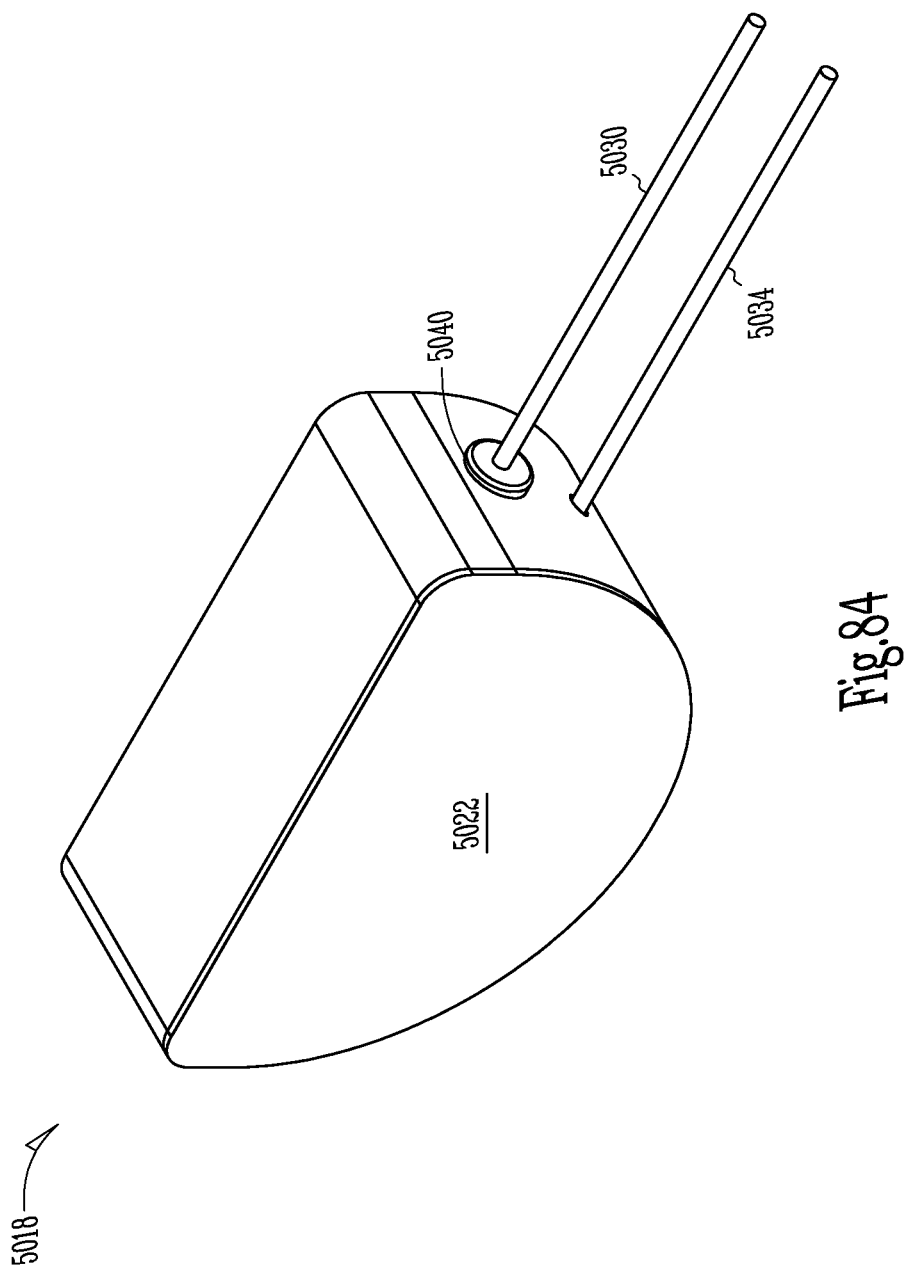
FIG. 84 is a view of a capacitor with an expanded end of a terminal wire attached to a case according to one embodiment.

Referring to FIG. 1, in one embodiment, terminal 104 is attached to case 101 along a side portion of the case. FIG. 84 shows capacitor 5018 having a terminal connection 5030 in accord with another embodiment. In this embodiment, feedthrough conductor 5034 is attached to the anode layers inside the case as described above. The cathode layers are connected to the case in this embodiment, and terminal connector 5030 is attached to the case in an end-on fashion by welding or brazing the end of the wire to the capacitor case.

In one embodiment, terminal connector 5030 includes a body having an end surface which is substantially perpendicular to the body. The end surface is positioned so that the end surface is flushly positioned against the surface of the case and is butt-welded to the case, wherein terminal connector is only attached to the case at its end surface and not along any portions of its body.

In one embodiment, an expanded end 5040 at the end of the wire is provided. The expanded end 5040 in this embodiment is in the shape of a nailhead with a flat surface for attaching to the case. The surface area of the expanded end is sufficient to provide a securely welded connection while minimally altering the footprint of the capacitor case. The overall volume of the device housing can thus be reduced.

Figure 85A:
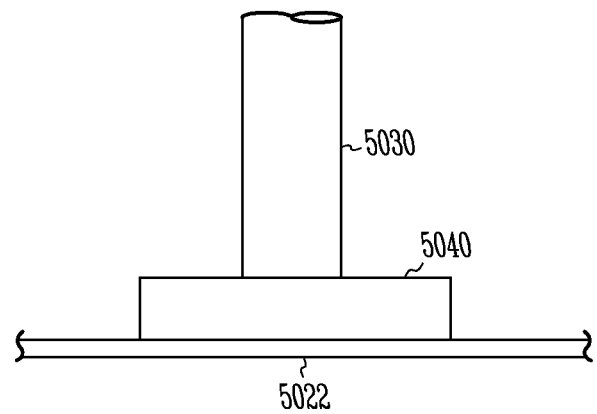
FIG. 85A is a view of a terminal wire attached to a case according to one embodiment.

In FIG. 85A, terminal wire 5030 with an expanded end 5040 at its end is attached directly to a capacitor case 5020 by, for example, arc percussive welding or laser welding.

Figure 85B:
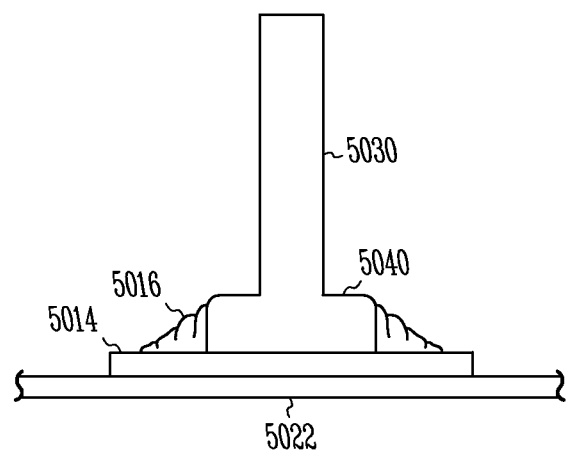
FIG. 85B is a view of a terminal wire attached to a case according to one embodiment.

In FIG. 85B, expanded end 5040 is attached with braze 5016 to a piece of intermediate material 5014 welded to the case 5020. Both methods of attachment result in a low height profile that minimizes the amount of interconnect space required for connection of the capacitor to an external terminal.

In the capacitors described above, the case is electrically connected to the cathode layers to form a negative case. In another embodiment, a terminal wire with an expanded end is attached to an anodic case which is formed by the case inner surface being electrically connected to the anode layers of the capacitor, an example of which will be discussed below. Also, although the subject matter has been described above with reference to electrolytic capacitors, the subject matter may also be used in conjunction with other devices such as batteries or other types of capacitors such as wet tantalum capacitors. The term capacitor, as used herein, should be interpreted to include those devices as well.

FIG. 86 illustrates a flat capacitor 6100 in accordance with one embodiment of the present subject matter. Capacitor 6100 is similar to capacitor 100 of FIG. 1, and as such, some details will be omitted for sake of clarity. Capacitor 6100 includes a case 6110, which contains therein a capacitor assembly 6108, which includes a capacitor stack 6150. In one embodiment, case 6110 is an active case. "Active case" means herein that case 6110 is, in various embodiments, anodic or cathodic. In one embodiment, the case 6110 is manufactured from a conductive material, such as aluminum.

The capacitor stack 6150 includes anode stacks 6200 and cathode stacks 6300, with separator layers interposed therebetween, as is further discussed below. The capacitor stack 6150 further includes a connector 6130 which connects, in one embodiments, the cathode stacks 6300 with active case 6110. In another embodiment, connector connects anodes 6200 to the active case 6110.

The case 6110 further includes two components, a cover 6118 and a bottom 6120, which are coupled together as part of the assembly process. In one option, the cover 6118 and the bottom 6120 are welded together.

By providing an active case, wherein the case acts as an anodic element or a cathodic element, the capacitor 6100 can be made smaller while delivering the same amount of energy.

In one embodiment, the present subject matter provides a capacitor having an active cathodic case which services adjacent anodes. As used herein, "service" means that the case is cathodic in the sense that it not only is connected to the cathode stacks but literally services the anodes which are adjacent to the case. This means the case itself replaces one or two of the end cathodes which are usually present on the two outermost elements of the capacitor stack.

In this embodiment, case 6110 is comprised of at least 98% aluminum. Case 6110 has an inner surface 6112 which includes an upper inner surface 6114 and a lower inner surface 6116. At least a portion of the inner surface 6112 is etched, and in one option, the entire inner surface 6112 is etched. In one example, the inner surface 6112 of the case 6110 is etched in the same way that a cathode conductive layer 6320 (FIG. 90) is etched.

Figure 87:
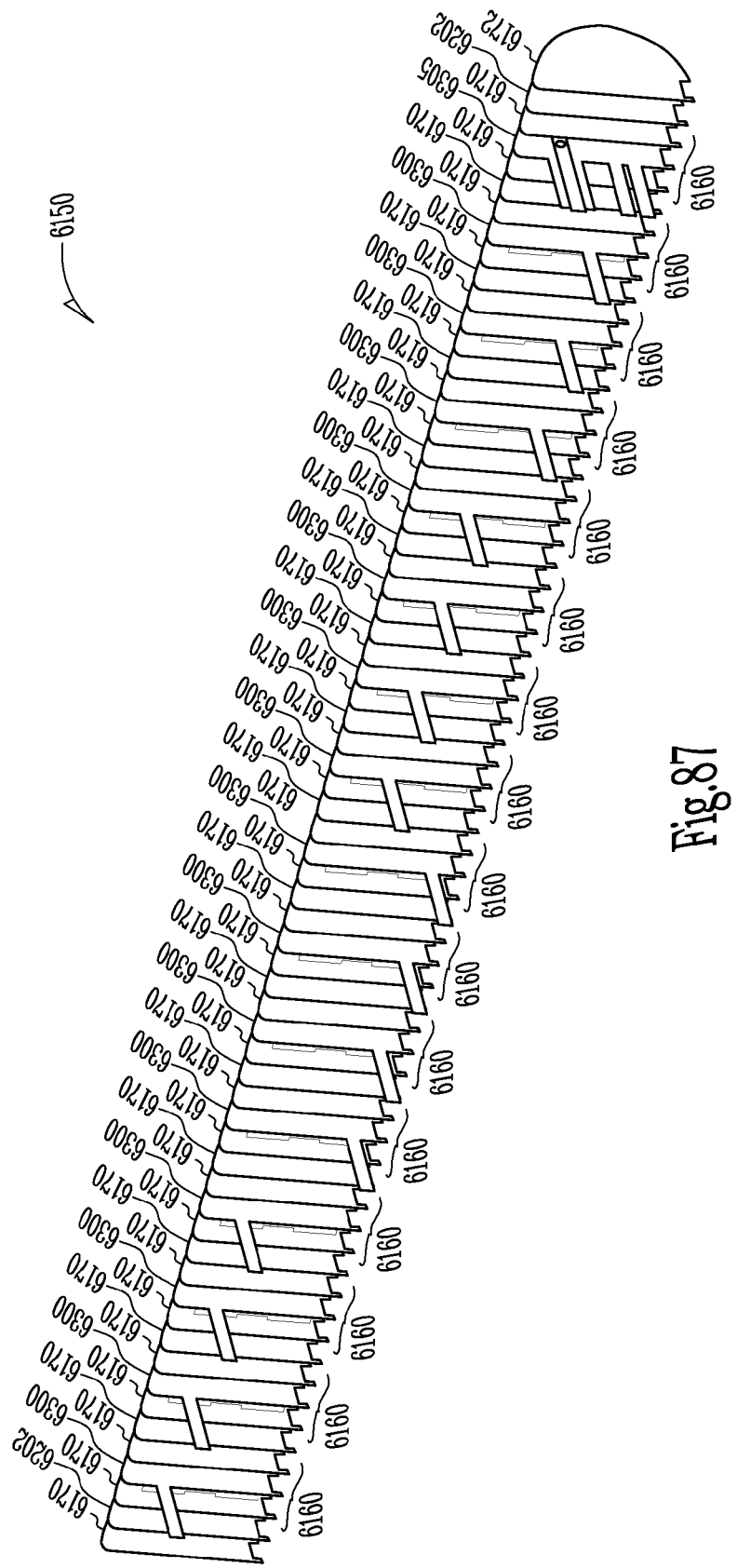
FIG. 87 is an exploded perspective view illustrating a capacitor stack as constructed in accordance with one embodiment.

FIG. 87 illustrates one example of capacitor stack 6150 in greater detail. The capacitor stack 6150 includes a plurality of capacitor elements 6160, each capacitor element 6160 includes at least one anode stack 6200, at least one separator 6170, and one or more cathode stacks 6300. In this embodiment, one of the cathode stacks is a cathode base layer 6305.

Capacitor stack 6150 also includes an end anode stack 6202 and an end separator 6172 which confront an inner surface 6112 of case 6110 (FIG. 86) when stack 6150 is mounted within case 6110.

Each cathode stack 6300 is interconnected with the other cathode stacks in the capacitor stack 6150 and with base cathode layer 6305. The interconnected cathode stacks are electrically coupled with the case 6110 through connection member 6120 of base cathode layer 6305. In this embodiment, case 6110 is an active part of the cathode, as will be discussed further below. In one embodiment, the cathode stack is as described above in FIGS. 43-47. Other embodiments include aluminum tabs attached to each cathode layer. The tabs are connected together and connected to case 6110.

Separator 6170 and 6172 include, but are not limited to, two sheets of paper separator. The separators are, in one embodiment, made from a roll or sheet of separator material. Suitable materials for the separator material include, but are not limited to, pure cellulose or Kraft paper. Other chemically inert materials are suitable as well, such as porous polymeric materials. The separator layers are cut slightly larger than the anode layers (or cathode layers) to accommodate misalignment during the stacking of layers and to prevent subsequent shorting between electrodes of opposite polarity.

The interconnected cathode stack is electrically coupled with the case 6110 (FIG. 86) which has an etched inner surface 6112 (FIG. 86). Capacitor stack 6150 includes an end anode stack 6202. Having an end anode stack 6202 which is serviced by the case 6110 eliminates the need for outer cathode stacks. Since at least one cathode stack 6300 can be removed, this results in a space savings of at least 0.0012 inches (an exemplary cathode thickness). Further, at least one less separator 6170 is needed, resulting in savings of 0.0005 inches per side. In one embodiment, a second cathode stack is removed from the other end of the capacitor stack, resulting in an additional space savings of 0.0012 inches for the foil and 0.0005 for the separator. Thus, an exemplary space saving is 0.0017 inches per side and/or 0.0034 inches for the both sides. These space saving are variable in various embodiments depending on the thickness of foil used for the cathodes. Furthermore, the present capacitor provides for a simplified capacitor having fewer components.

Figure 89:
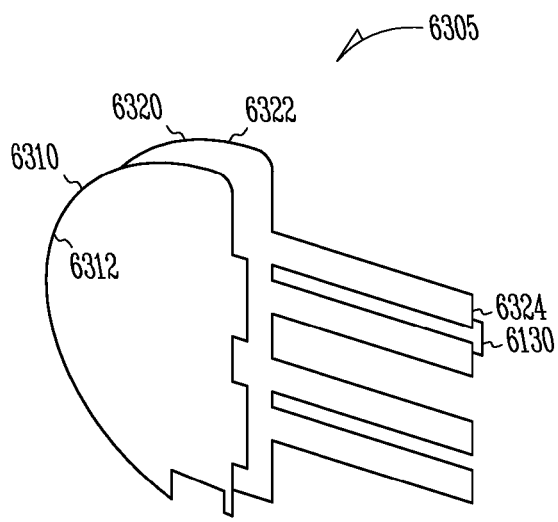
FIG. 89 is an exploded perspective view illustrating a cathode base layer as constructed in accordance with one embodiment.

FIG. 89 illustrates an exploded view of the anode stack 6200 according to one embodiment. The anode stack 6200 includes an anode separator 6210, at least one conductive layer 6220, and an edge connection member or edge clip 6240 coupled with at least one of the conductive layers 6220. In one option, the at least one conductive layer 6220 includes a first conductive layer 6222, a second conductive layer 6224, and a third conductive layer 6226. The first conductive layer 6222 includes a clearance portion 6242 surrounding the edge clip 6240. Each of the conductive layers 6220 includes a major surface 6230 and a side surface 6232.

Figure 90:
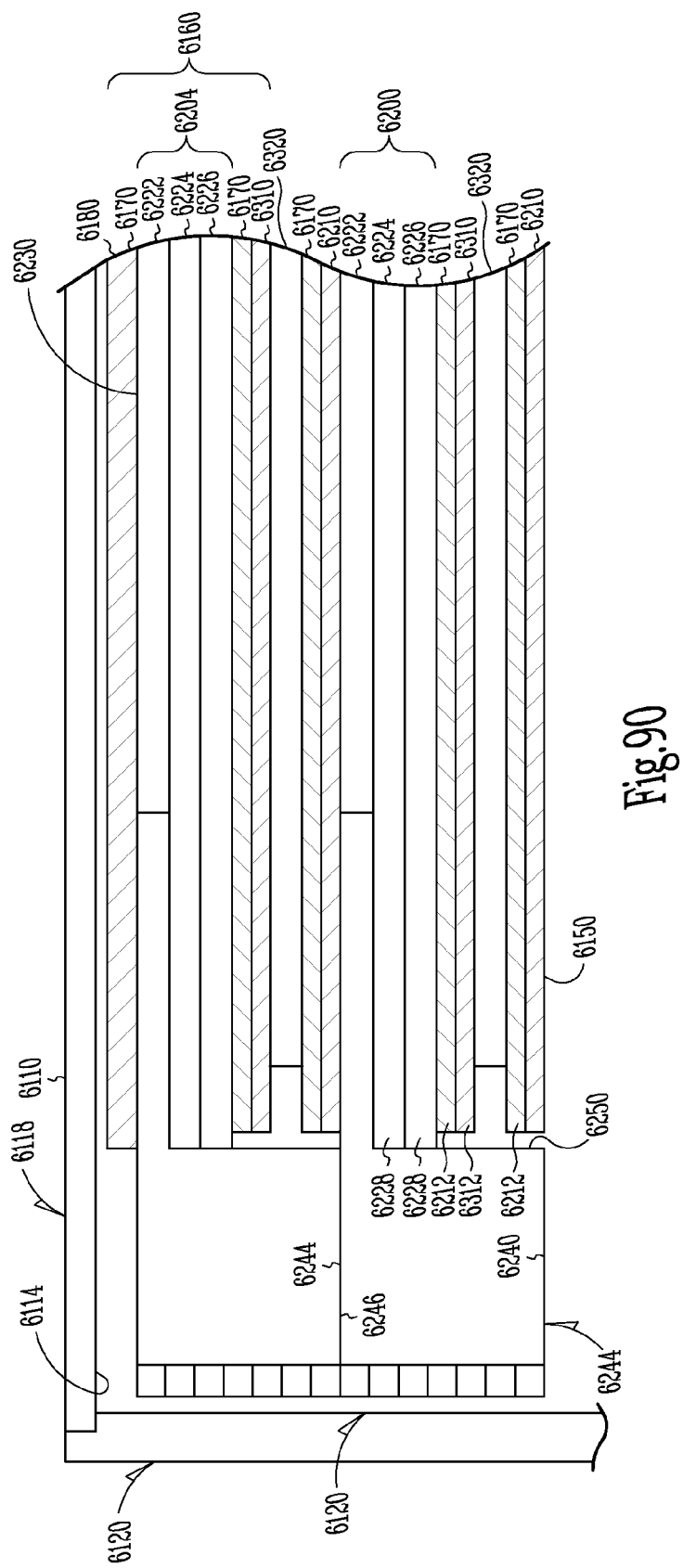
FIG. 90 is a cross-sectional view illustrating a portion of a capacitor as constructed in accordance with one embodiment.

FIG. 90 illustrates an exploded view of cathode base layer 6305 according to one embodiment. Cathode base layer 6305 includes legs 6324, the number of which and location of which are varied depending on the cathode stack 6300. Legs 6324 are for interconnecting base layer 6305 to the other cathodes 6300 of the capacitor stack. Cathode base layer 6305 includes a cathode separator 6310 and a cathode conductive layer 6320. In one embodiment, the cathode conductive layer 6320 has an outer perimeter 6322 inset from the cathode separator edges 6312 so that the edge clip 6240 (FIG. 89) will not contact the cathode conductive layer 6320. Since the outer perimeter 6322 is inset, this can help to prevent a discontinuity on an edge 6228 of the anode stack 6200 (FIG. 89) from making contact with the conductive layer 6320 of the cathode stack 6300. This design also allows for more variations in tolerances which can occur during the manufacturing of the anode stack 6200 and the cathode stack 6300. Attached or integral with cathode 6305 is connection member 6120 for attaching cathode 6300 to case 6110.

Figure 91:
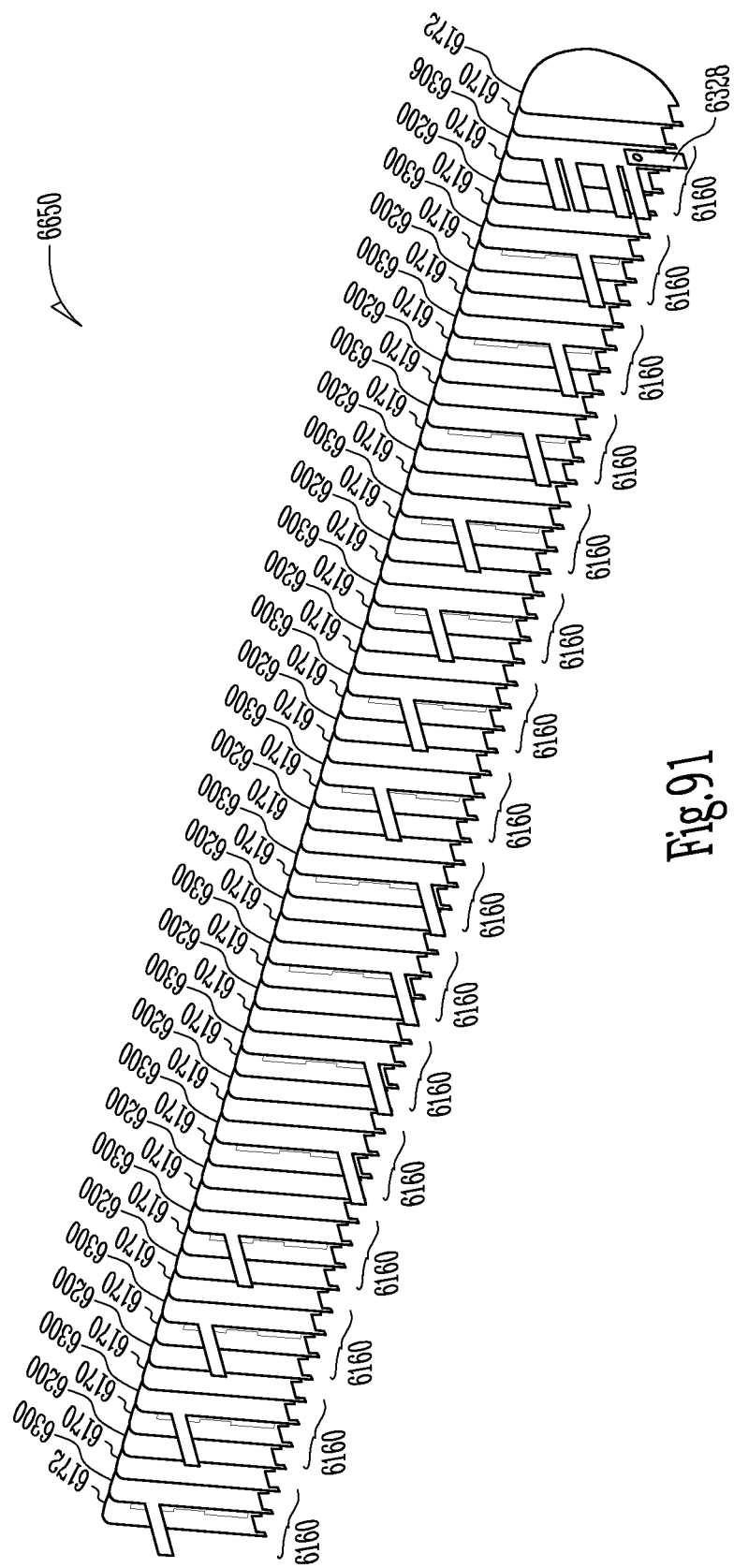
FIG. 91 is an exploded perspective view illustrating a capacitor stack as constructed in accordance with one embodiment.

FIG. 91 illustrates a cross-sectional view of the capacitor stack 6150 within the case 6110. Although the discussion relates to an upper portion of the case, the view of the capacitor stack is substantially the same for a lower portion of the case, and therefore is not repeated. The capacitor stack 6150 includes one or more anode stacks 6200, where each anode stack 6200 includes, for example, a first conductive layer 6222, a second conductive layer 6224, and a third conductive layer 6226. The anode stack 6200 further includes an anode separator 6210. The layers 6222, 6224, 6226 of the anode stack 6200 are coupled together. In one embodiment, the layers are staked together as described above in FIGS. 9-11.

The major surface 6230 of the first conductive layer 6222 of the first anode stack 6204 faces the etched upper inner 6114 surface of the case 6110, separated form case 6110 by separator 6170. An electrolyte 6180 is disposed between the major surface 6230 and the upper inner surface 6114. The electrolyte 6180 facilitates storage of charge between the anode stack 6200 and the case 6110. The etched upper inner surface 6114 of the case 6110 services the anode stack 6200 in the same way that a cathode stack 6300 services the anode stack 6200. In one embodiment, the capacitor stack 6150 includes a first anode stack 6204 having a major surface 6230 facing and adjacent the upper inner surface 6114, and a second anode stack 6206 (FIG. 87) having a major surface 6230 confronting the lower etched inner surface 6116 (FIG. 86), where the case 6110 services both the first anode stack 6204 and the second anode stack 6206.

In one embodiment, an inner surface 6250 of the edge clip 6240 extends along the edges 6228 of the second and third conductive layers 6224, 6226 of the anode stack 6200. The inner surface 6250 of the edge clip 6240 also extends past the separator edge 6212 and the cathode separator edge 6312. The edge clip 6240 also extends along the edge 6212 of the anode separator of an adjacent capacitor element 6160 until making contact and being connected with an adjacent edge clip 6240. A plurality of edge clips stack on top of one another such that a bottom surface 6244 of an edge clip 6240 contacts a top surface 6246 of an edge clip 6240 of an adjacent capacitor element 6160.

The edge clip 6240 allows for greater design flexibility in the choice of materials for the anode conductive layers 6220 as the conductive layers remain essentially flat while the connection between anode stacks 6200 is made. In addition, the edge clip 6240 assists in filling the cross section of the case with anodic surface area, and thus increases the overall percentage of space within the case occupied by anodic surface area. This helps to increase capacitance of the capacitor, and/or allows for the capacitor to be made smaller.

Some embodiments omit edge clips 6240, and interconnect the anode stacks 6200 with tabs which are attached to or integral with each anode stack.

In one embodiment, edge clips 6240 are interconnected and coupled to feedthrough 6280 (FIG. 86), which is insulated from case 6110. In addition, the feed through opening 6282 (FIG. 86) is sealed.

One example of a method for forming a capacitor having an active cathodic case is as follows. The method includes forming and aligning a capacitor stack including at least one anode stack and at least one cathode stack, etching at least a portion of an inner surface of a capacitor case, the inner surface including an upper inner surface and a lower inner surface. The method further includes disposing the capacitor stack in the capacitor case, and an at least one anode stack is adjacent the inner surface of the capacitor case. The method also includes disposing an electrolyte between the at least one anode and the inner surface of the case.

Several options for the method are as follows. For instance, in one embodiment, the method includes etching layers of the anode stack. In another embodiment, the method further includes confronting a major surface of a first anode stack with the upper inner surface of the case. In yet another embodiment, the method includes confronting a major surface of a second anode stack with the lower inner surface of the case. Optionally, the method includes etching an entire inner surface of the case.

In another example of manufacturing the above described cathodic case capacitor, a capacitor case is formed, including a case cover and a case bottom, and the inner surface of the capacitor case is etched. A stack of cathode and anode layers are stacked and aligned to form a capacitor stack. The cathode ledges are welded and folded over the stack. The capacitor stack is taped, and the anode edge clips are welded. An anode feed through is welded to the edge couplers. The capacitor stack is inserted into the capacitor case, and the case cover and cathode leg extension is welded to the case bottom.

Advantageously, the etched inner surface of the case increases cathodic surface area on an existing surface. The etched inner surface allows for reduction of cathode stacks within the case by allowing at least one outer cathode stack to be removed, which in turn allows for the size of the capacitor to be reduced. Alternatively, the anodic surface area within the case can be increased and the total capacitance of the capacitor can be increased.

In one embodiment, the capacitor has an active anodic case. Referring again to FIG. 86, in one embodiment, case 6110 comprises 99.99% aluminum. In another embodiment, the case comprises at least 98% aluminum. In one embodiment, at least a portion of the inner surface 6112 is etched, and in one embodiment, the entire inner surface 6112 is etched.

FIG. 91 illustrates a capacitor stack 6650 according to one embodiment of the present subject matter. Capacitor stack 6650 is mountable in case 6110 similarly to stack 6150.

In this embodiment, capacitor stack 6650 includes a plurality of capacitor elements 6160, each capacitor element 6160, except for the end capacitor elements, includes at least one anode stack 6200, at least one separator 6170, and at least one cathode stack 6300. The capacitor stack 6650 includes end separators 6172. Each cathode stack 6300 is interconnected with the other cathode stacks in the capacitor stack

6650. Each anode stack 6200 is interconnected with the other anode stacks in the capacitor stack 6650.

The at least one separator 6170 and the end separator 6172 include, but are not limited to, a paper separator. The separators are, in one option, made from a roll or sheet of separator material. Suitable materials for the separator material include, but are not limited to, pure cellulose or Kraft paper. Other chemically inert materials are suitable as well, such as porous polymeric materials. The separators layers can be cut slightly larger than the anode layers (or cathode layers) to accommodate misalignment during the stacking of layers and to prevent subsequent shorting between electrodes of opposite polarity.

Figure 88:
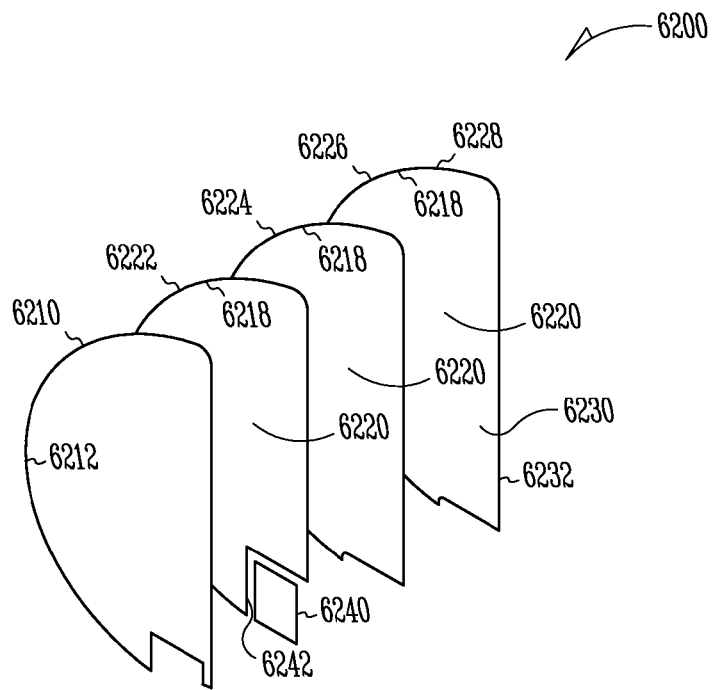
FIG. 88 is an exploded perspective view illustrating an anode stack as constructed in accordance with one embodiment.

Referring again to FIG. 88, in one embodiment, anodes 6200 includes one or more conductive layers 6220. Each of the conductive layers 6220 includes an outer edge surface 6218, which define an outer edge of the capacitor stack 6650 (FIG. 91). In one option, the outer edge surface 6218 of at least one of the conductive layers 6220 is exposed and is electrically coupled with the inner surface 6112 of the case 6110 (FIG. 86), as will be discussed further below.

Figure 92:
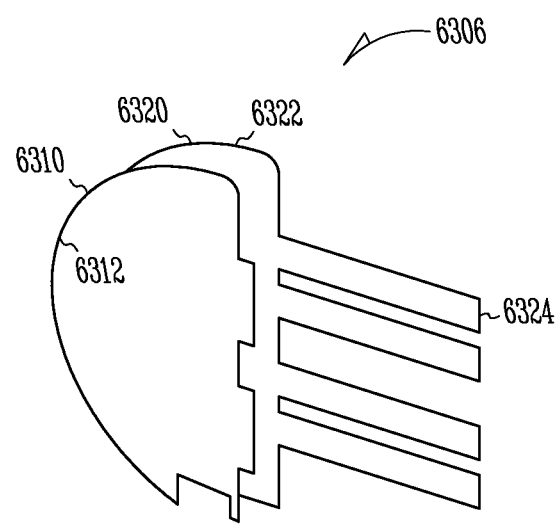
FIG. 92 is an exploded perspective view illustrating a cathode stack as constructed in accordance with another embodiment.

FIG. 92 illustrates an exploded view of a cathode stack 6306 in greater detail. The cathode stack includes legs 6324, the number of which and location of which is varied depending on the cathode stack 6300. The cathode stack 6300 includes a cathode separator 6310 and a cathode conductive layer 6320. The cathode conductive layer 6320 has an outer perimeter 6322 inset from the cathode separator edges 6312 so that the edge clip 6240 (FIG. 88) will not contact the cathode conductive layer 6320. Since the outer perimeter 6322 is inset, this can help to prevent a discontinuity on an edge 6228 of the anode stack 6200 (FIG. 88) from making contact with the conductive layer 6320 of the cathode stack 6300. This design also allows for more variations in tolerances which can occur during the manufacturing of the anode stack 6200 and the cathode stack 6300.

Figure 93:
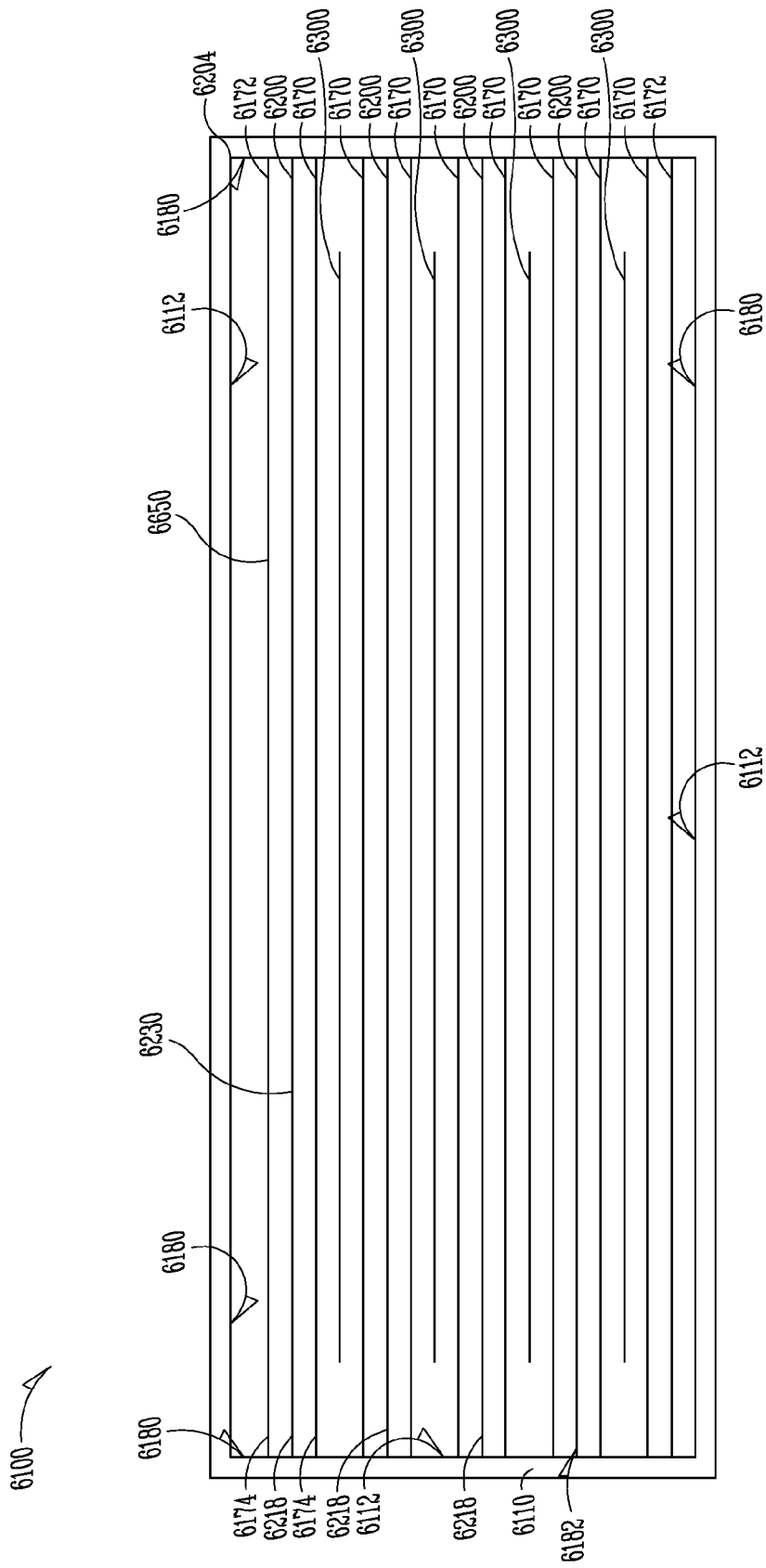
FIG. 93 is a cross-sectional view taken along 8-8 of FIG. 94 illustrating a portion of a capacitor as constructed in accordance with one embodiment.
Figure 94:
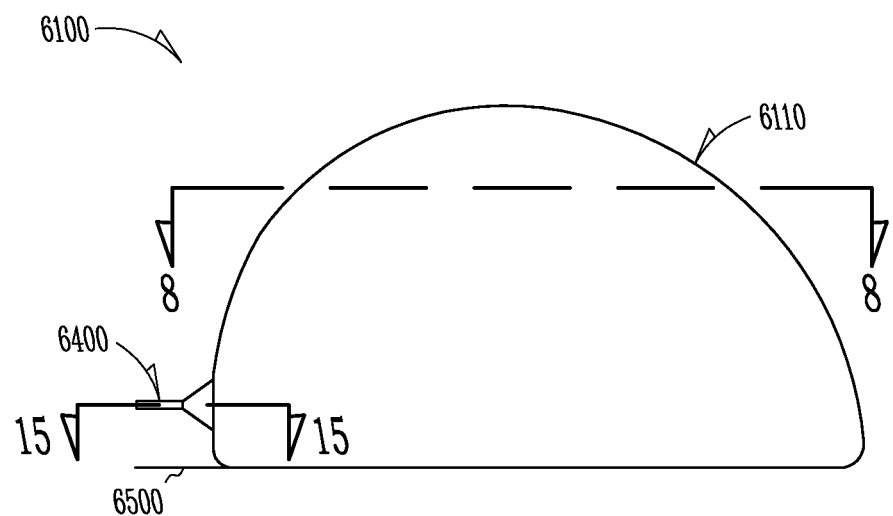
FIG. 94 is a top plan view illustrating a capacitor as constructed in accordance with another embodiment.

FIG. 93 illustrates a cross-sectional view taken along 8-8 of FIG. 94, which shows a capacitor 6100. The capacitor stack 6650 is disposed within the capacitor case 6110. The inner surface 6112 of the capacitor case 6110 includes a dielectric 6180 formed thereon. In this embodiment, the perimeter 6174 of each separator 6170 and 6172 contacts the inner surface 6112 of the case 6110. In addition, the outer perimeter 6322 (FIG. 92) of the cathode stack 6300 is inset from the perimeter 6174 of the separator 6170. In one embodiment, the major surface 6230 of the first anode stack 6204 faces the etched upper inner 6112 surface of the case 6110.

Outer edge surface 6218 of at least one anode stack 6200 contacts the inner surface 6112 of the case 6110. In one option, the outer edge surface 6218 is exposed and electrically coupled with the inner surface 6112 of the case 6110, for example, by intimate contact. In another option, the anode stack 6200 is coupled with the inner surface 6112 of the case 6110 in other manners. For example, the anode stack 6200 is coupled at 6182 with the inner surface 6112 by welding the anode stack 6200 with the inner surface 6112. In another example, the anode stack 6200 is coupled at 6182 with the inner surface 6112 by bonding the anode stack 6200 with the inner surface 6112, for example, using epoxy or other bonding materials.

Figure 95:
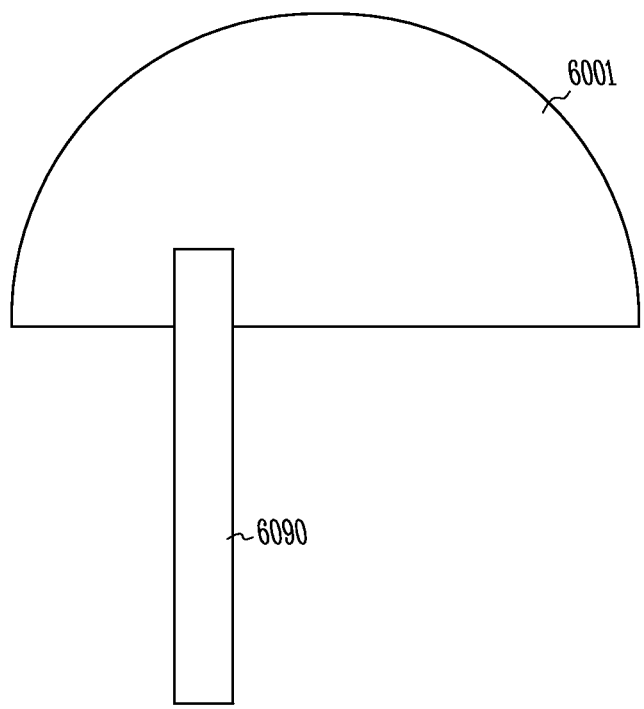
FIG. 95 is a top plan view illustrating an anode as constructed in accordance with one embodiment.

FIG. 95 shows an anode 1001 having a tab connector 6090 according to another embodiment. In this embodiment, one anode in capacitor stack 6650 includes a tab connector 6090. The other anodes in the capacitor stack are interconnected and tab connector 6090 is coupled to case 6110. In some embodiments, more than one anodes have tab connectors 6090. In one embodiment, tab connector is welded to anode 1001.

Figure 96:
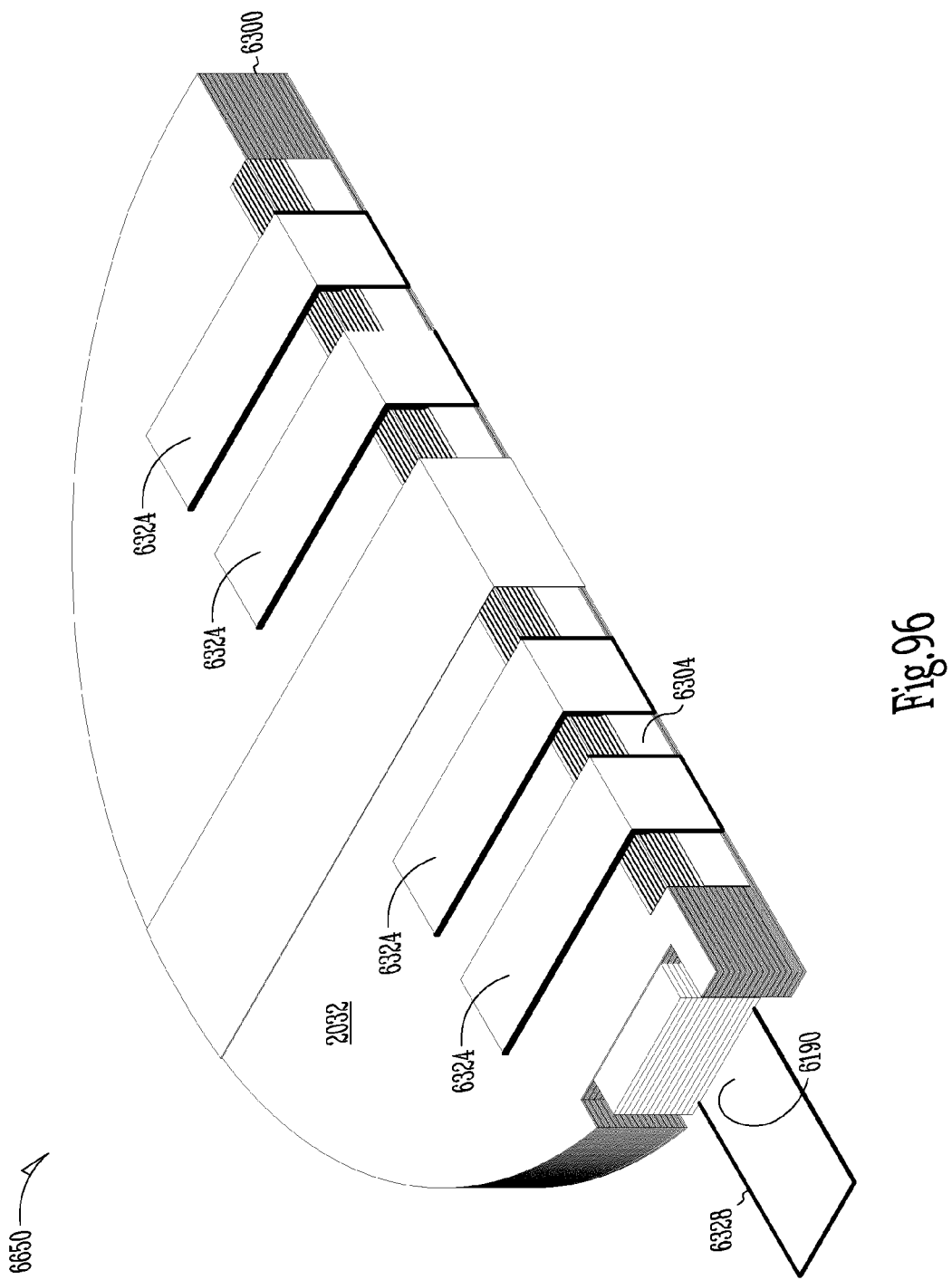
FIG. 96 is a perspective view illustrating a capacitor stack as constructed in accordance with one embodiment.

FIG. 96 illustrates a capacitor stack 6650 including a cathode extension leg 6328. In this embodiment, the cathode extension leg 6328 extends from the bottom cathode stack 6304 below the bottom edge clip 6240. The cathode extension leg 6328 is insulated from the edge clip 6240 by an insulator 6190 included on the inner surface of the cathode extension leg 6328. The cathode extension leg 6328 is folded over the edge clips 6240 and coupled to a feedthrough 6380 (FIG. 86). After connection to the feedthrough 6380, the exposed portion of the cathode extension leg optionally is insulated to prevent contact with the anodic case 6110.

The cathode stacks 6300 include cathode interconnect legs 6324. In an alternative option, a feedthrough 6380 (FIG. 86) is coupled to one of the legs 6324 and the remaining exposed portion is covered by insulator 6192 (FIG. 97).

Figure 97:
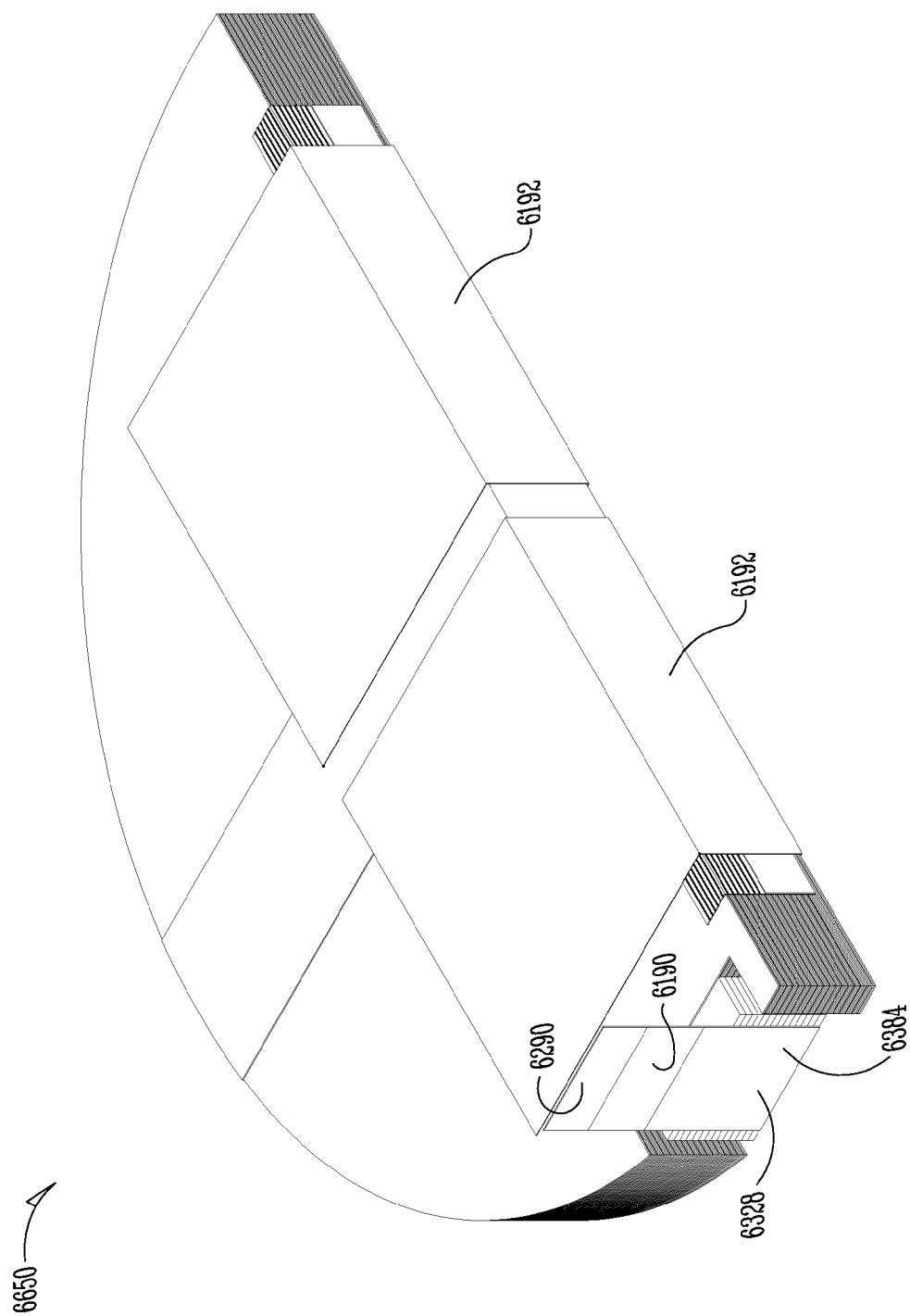
FIG. 97 is a perspective view illustrating a capacitor stack as constructed in accordance with one embodiment.
Figure 98:
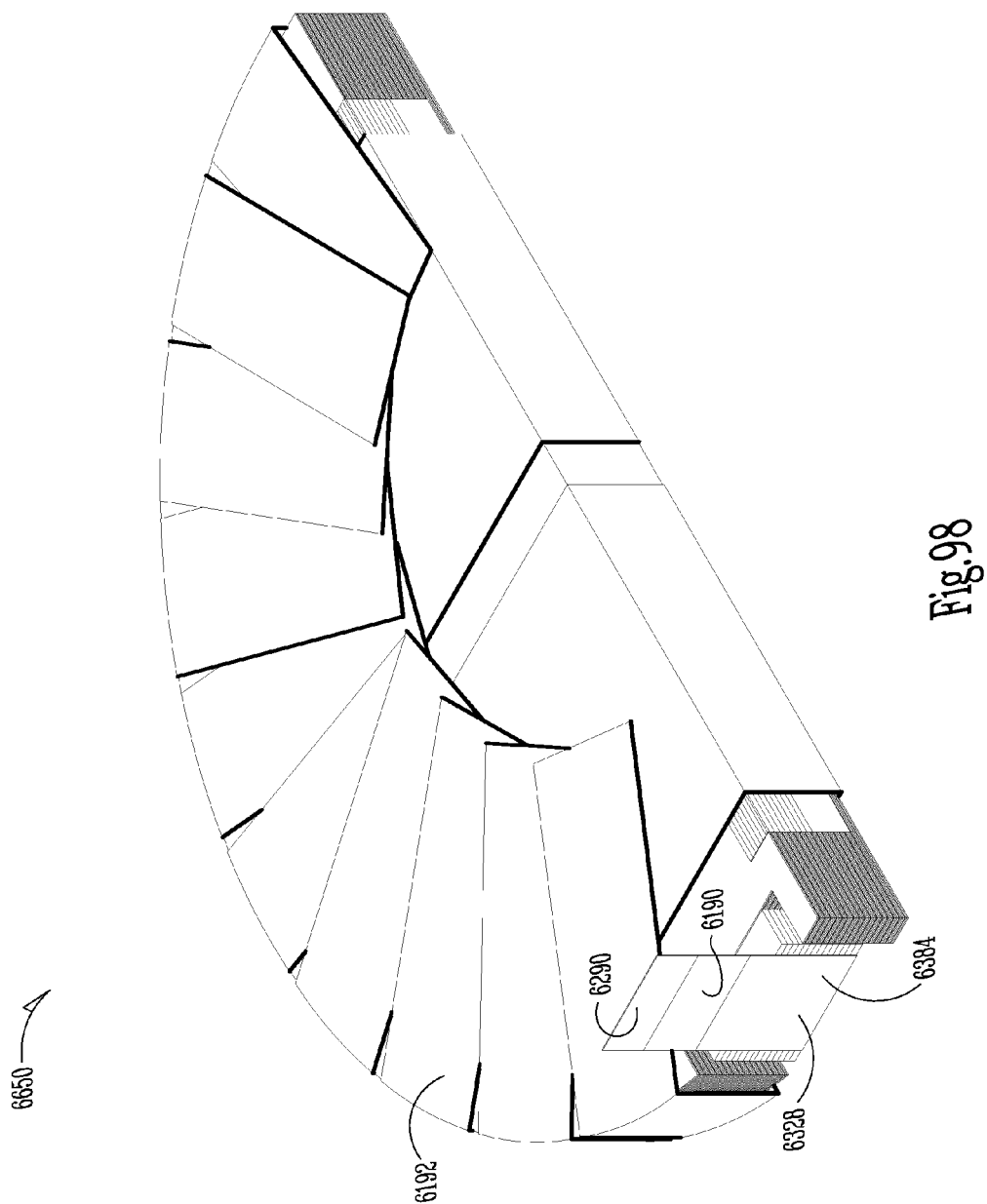
FIG. 98 is a perspective view illustrating a capacitor stack as constructed in accordance with one embodiment.

FIGS. 97 and 98 illustrate the capacitor stack 6650 where the anode stack 6200 (FIG. 91) is coupled with the case 6110 (FIG. 86). The capacitor stack 6650 includes an anode extension leg 6290 coupled to the outer contact surface of the edge clips 6240. The cathode extension leg 6328 is folded over the anode extension leg 6290 and is insulated from the anode extension leg 6290 by insulator 6190. The outer surface of the cathode extension leg 6328 is suitable for receiving a feedthrough connection. After connection to a feedthrough, the exposed portion of the cathode extension leg 6328 is insulated to prevent contact with the anodic case 6110. The capacitor stack 6650 includes insulator 6192 over cathode interconnect legs 6324.

Figure 99:
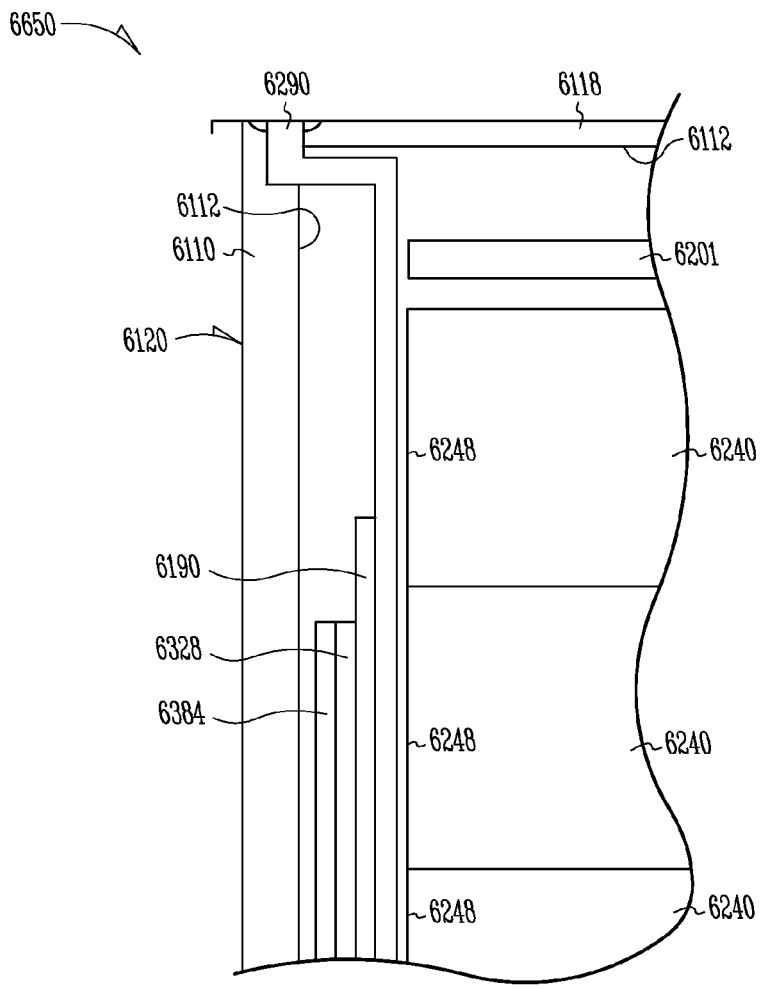
FIG. 99 is a cross-sectional view illustrating a portion of a capacitor as constructed in accordance with one embodiment.

FIG. 99 illustrates a cross-sectional view of a portion of the capacitor stack 6650. In this embodiment, the connection between the edge clips 6240 and the case 6110 is with the anode extension leg 6290. The anode extension leg 6290 is coupled to and extends from the interconnected edge clips 6240. Each edge clip 6240 includes an outer contact surface 6248, which provides a larger contact surface that is more easily attached to an anode extension leg 6290 than existing methods of attachment. The anode extension leg 6290, in one option, is sufficiently ductile to be deformed to extend along the side of the capacitor stack 6150 and between the interface between the case cover 6110 and the case bottom 6120. As mentioned above, the cathode extension leg 6328 folds over the anode extension leg 6290 and is insulated from the anode stacks (FIG. 91) and anode extension leg 6290 by insulator 6190.

Figure 100:
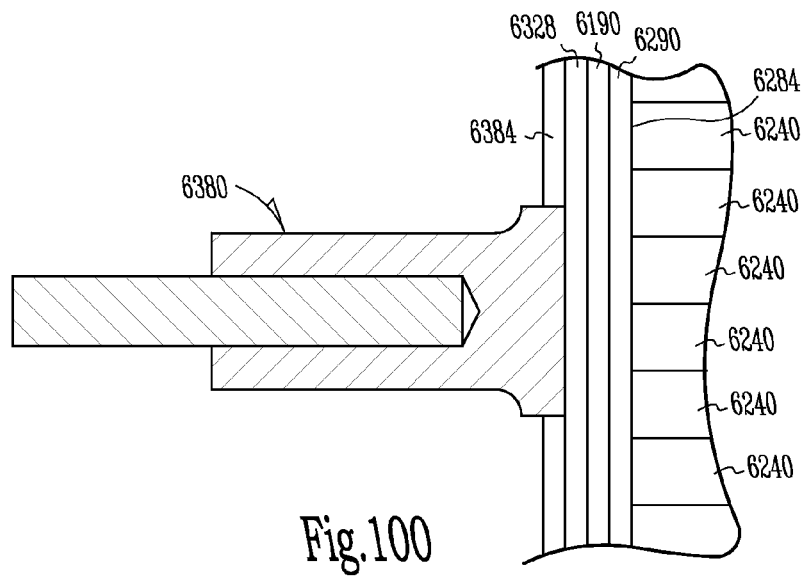
FIG. 100 is a cross-sectional view taken along 15-15 of FIG. 94 illustrating a portion of a capacitor as constructed in accordance with one embodiment.

FIG. 100 shows a cross-section of section 15-15 of FIG. 94. The outer surface of the cathode extension leg 6328 is coupled to a cathode feedthrough 6380. An insulator 6384 is included over the remaining exposed portion of the outer surface of the cathode extension leg 6328. The cathode feedthrough 6380 is welded to the outer surface of the cathode extension leg 6328, and the cathode feedthrough 6380 is insulated from the case 6110 (FIG. 86). The feedthrough opening 6382 (FIG. 86) is sealed.

One aspect of the present embodiment provides a method of manufacturing. In one embodiment, a method includes stacking at least one anode stack including one or more conductive anode layers and an anode separator, stacking at least one cathode stack including one or more conductive cathode layers and a cathode separator, aligning and stacking the at least one anode stack and the at least one cathode stack to form a capacitor stack, disposing the capacitor stack within a capacitor case, and electrically coupling the anode stack with the capacitor case.

Several options for the method are as follows. For example, in one embodiment, the method further includes etching an inner surface of the capacitor case, and/or etching the one or more conductive anode layers. In another embodiment, the method further includes welding the anode stack with the capacitor case, or bonding the anode stack with the capacitor case. In a further embodiment, the method further includes coupling a cathode feedthrough with the cathode stack, and disposing the cathode feedthrough through an opening of the capacitor case. In another embodiment, the method further includes stacking the conductive cathode layer in an offset position from the anode conductive layer, and/or exposing outer edges of the one or more conductive anode layers. In yet another embodiment, the method further includes coupling the exposed outer edges with the capacitor case, and/or welding the exposed outer edges with the capacitor case.

In another example of manufacturing the above described capacitor, a capacitor case is formed, including a case cover and a case bottom, and optionally the inner surface of the capacitor case is etched. A stack of cathode and anode layers are stacked and aligned to form a capacitor stack. The cathode legs are welded and folded over the stack. The capacitor stack is taped, and the anode edge clips are welded. An anode leg is welded to the edge clips, and the cathode feedthrough is welded to the cathode extension leg. The capacitor stack is inserted into the capacitor case, and the case cover and the anode extension leg are welded to the case bottom. An anode ribbon is welded to the case, and the opening for the feedthrough is sealed.

Advantageously, having the case contribute to the effective anodic surface area increases the capacitance of the capacitor without increasing the outer packaging dimensions. Alternatively, it allows for achievement of a given total capacitance with a smaller package. A further benefit is that since the edge of the cathode stack is offset from the anode stack, damage or puncturing of the separator layer is minimized.

Referring again to FIG. 1, in one embodiment, each anode is connected to the other anodes of the capacitor and coupled to feedthrough assembly 103 for electrically connecting the anode to circuitry outside the case. Various example methods of interconnecting the anode foils and/or cathode foils have been discussed. For instance, in some embodiments, interconnections are provided as discussed above for FIGS. 12-15, 43-47, 56-57, and/or 83-84.

FIGS. 101-105 discuss another embodiment for providing interconnections. FIG. 101A shows an anode 7202 according to one embodiment of the present subject matter. Anode 7202 is shown before it is assembled into capacitor stack 7102 as shown in FIG. 1. Anode 7202 includes a main body portion 7204 having one or more connection members 7206. In one embodiment, connection member 7206 includes one or more separate members attached to the anode by welding, staking, or other connection method.

In other embodiments, connection member 7206 is an integral portion of anode 7202, and is punched, laser-cut, or otherwise shaped from the anode foil. In such an embodiment, portions of connection member 7206 are not etched along with the rest of anode 7202. For instance, a chemical mask is put on portions of connection member 7206 to keep those masked portions from becoming etched during the etching process. As will be discussed below, this provides that those unetched, non-porous sections make welding the edges of the anodes to each other easier.

Connection member 7206 includes a proximal section 7208 and distal section 7210. In the embodiment of FIG. 2A, connection member 7206 is an L-shaped member. However, it can also be hook shaped, U-shaped, and/or have other shape. In one embodiment, a portion of a distal section 7210 along its outer edge is unetched, as discussed above.

In one embodiment, proximal section 7208 is connected to main body 7204 and is defined in part by a pair of cut-out portions 7212 and 7214 located on opposing sides of proximal section 7208. Distal section 7210 is connected to a portion of proximal section 7208. In one embodiment, it is integral with proximal section 7208. In some embodiments, distal section 7210 is attached as a separate member. In one embodiment, distal section 7210 is defined in part by a cut-out portion 7216 which is located between main body 7204 and distal section 7210, and a cut-out portion 7218 which separates distal section 7210 from main body 7204.

In this embodiment, connection member 7206 is located within the general perimeter or outline of anode 7202. In other embodiments, connection member extends further from the main body of anode 7202 or connection member 7206 is more internal within the main body of anode 7202.

In some embodiments, each anode foil in capacitor stack 7102 includes an connection member such as connection member 7206. In other embodiments, one or more anode foils in a multi-anode stack have a connection member 7206 while the other anode foils in the multi-anode stack are connected to the anode having the connection member. For instance, in one embodiment, a three-foil anode stack includes one foil having an connection member 7206 and two foils without connection members. The two foils without connection members are welded, staked, or otherwise attached to the foil having the connection member.

FIG. 101B shows a cathode 7302 according to one embodiment of the present subject matter. Cathode 7302 is shown before it is assembled into capacitor stack 7102 as shown in FIG. 1. Cathode 7302 includes a main body portion 7304 having one or more connection members 7306. In one embodiment, connection member 7306 is an integral portion of cathode 7302, and is punched, laser-cut, or otherwise shaped from the anode foil. In one embodiment, connection member 7306 includes one or more separate members attached to the anode by welding, staking, or other connection method.

In one embodiment, connection member 7306 includes a proximal section 7308 and a distal section 7310. In the embodiment of FIG. 101B, connection member 7306 is an L-shaped member. However, additional embodiments include hook shapes, U-shapes, and other shapes.

In one embodiment, proximal section 7308 is connected to main body 7304 and is defined in part by a pair of cut-out portions 7312 and 7314 located on opposing sides of proximal section 7308. Distal section 7310 is connected to a portion of proximal section 7308. In one embodiment, it is integral with proximal section 7308. In some embodiments, distal section 7310 is attached as a separate member. In one embodiment, distal section 7310 is defined in part by a cut-out portion 7316 which is located between main body 7304 and distal section 7310, and a cut-out portion 7318 which separates distal section 7310 from main body 7304.

In this embodiment, connection member 7306 is located within the general perimeter or outline of cathode 7302. In other embodiments, connection member 7306 extends further from the main body of cathode 7302 or connection member 7306 is more internal within the main body of cathode 7302.

FIGS. 102A and 102B show an anode 7202' and a cathode 7302' according to one embodiment of the present subject matter. Anode 7202' and cathode 7302' are shown before they are assembled into capacitor stack 7102 as shown in FIG. 1. Anode 7202' and cathode 7302' are generally similar to anode 7202 and cathode 7302, respectively, except a connection member 7206' does not include a cut-out such as cut-out 7212 of anode 7202 and connection member 7306' does not include a cut-out such as cut-out 7318 of cathode 7302. Other embodiments utilize other shapes and locations for connection members such as connection members 7206, 7206', 7306, and 7306'.

For instance, in various embodiments, connection members 7206 and 7306 may be in different positions along the edges or even within the main body portions of the capacitor foils 7202 and 7302. For instance, in some embodiments, connection members 7206 and 7306 are located along edges 7220 and 7320 of the respective foils 7202 and 7302. In some embodiments, the portions are located along curved edges 7222 and 7322 of the respective foils 7202 and 7302. In other embodiments, the portions may be cut-out within main bodies 7204 and 7304.

In one embodiment, proximal section 7308 of cathode 7302 and proximal section 7208 of anode 7202 are located in different positions (relative to each other) on their respective foils, while distal sections 7210 and 7310 are generally commonly positioned. For instance, in one embodiment connection members 7206 and 7306 of the anode 7202 and the cathode 7302, respectively, are mirror images of each other. In some embodiments, connection members 7206 and 7306 have generally reverse images of each other.

FIG. 103 shows a stack 7402 of one or more alternating anodes 7202 and cathodes 7302. As shown in FIG. 103, connection members 7206 and 7306 are overlaying and underlying each other. As used herein, overlay and underlay refer to the position or location of portions of the foils which are commonly positioned from a top view. In the embodiment of FIG. 103, it is seen that connection members 7206 and 7306 have some commonly positioned portions relative to each other and some portions which are exclusively positioned relative to each other.

For instance, proximal sections 7208 of anodes 7202 are exclusively positioned or located. This means that at least a portion of proximal sections 7208 do not overlay or underlay a portion of cathodes 7203. Likewise, proximal sections 7308 of cathodes 7302 are exclusive portions and include at least a portion not overlaying or underlaying a portion of anode 7202. Conversely, distal sections 7210 and 7310 are commonly positioned and each includes at least a portion overlaying or underlying each another. Cut-out portions 7214 and 7314 are also commonly positioned. Cut-out 7218 is commonly positioned with cut-out 7312 while cut-out 7212 is commonly positioned with cut-out 7318.

When stacked as shown in FIG. 103, the edges of distal sections 7210 and 7310 form a surface 7410. In this embodiment, surface 7410 can generally be described as having a first portion 7410A which fronts the proximal sections 7208 of anodes 7202, a second portion 7410B which fronts common cut-portions 7214 and 7314, and third portion 7410C which fronts the proximal sections 7308 of cathodes 7302.

In this embodiment, distal sections 7210 and 7310 of anode connection member 7206 and cathode connection member 7306 are fully overlaying one another. Fully overlaying means that there are generally no gaps along surface 7410 of stack 7402 when the anodes and cathodes are stacked as in FIG. 103. The fully overlaid structure of stack 7402 provides a complete surface 7410 which provides for ease of edge-welding or otherwise connecting connection members 7206 and 7306 together, as will be described below. Other embodiments leave one or more gaps in surface 7410 when the anodes and cathodes are stacked. For instance, in some embodiments, one or more of distal sections 7210 or 7310 may not reach all the way across front surface 7410.

After being stacked as discussed above, at least portions of connection members 7206 and 7306 are connected to each other. For instance, in one embodiment, portions of distal sections 7210 and 7310 are connected to each other. In one embodiment, distal sections 7210 and 7310 are edge-welded all along surface 7410. In one embodiment, distal sections 7210 and 7310 are only connected along portion 7410A and 7410C of surface 7410. In one embodiment, distal sections 7210 and 7310 are soldered along surface 7410. In some embodiments, portions of distal sections 7310 and 7210 are staked, swaged, laser-welded, or connected by an electrically conductive adhesive. In other embodiments, portions of proximal sections 7208 are connected to each other and/or portions of proximal sections 7308 are connected to each other.

After being connected, portions of connection members 7206 and 7306 are removed or separated so that proximal sections 7208 and 7308 are electrically isolated from each other. As used herein, electrically isolated means that sections 7208 and 7308 are electrically insulated from each other at least up to a surge voltage of capacitor 7100.

Figure 104A:
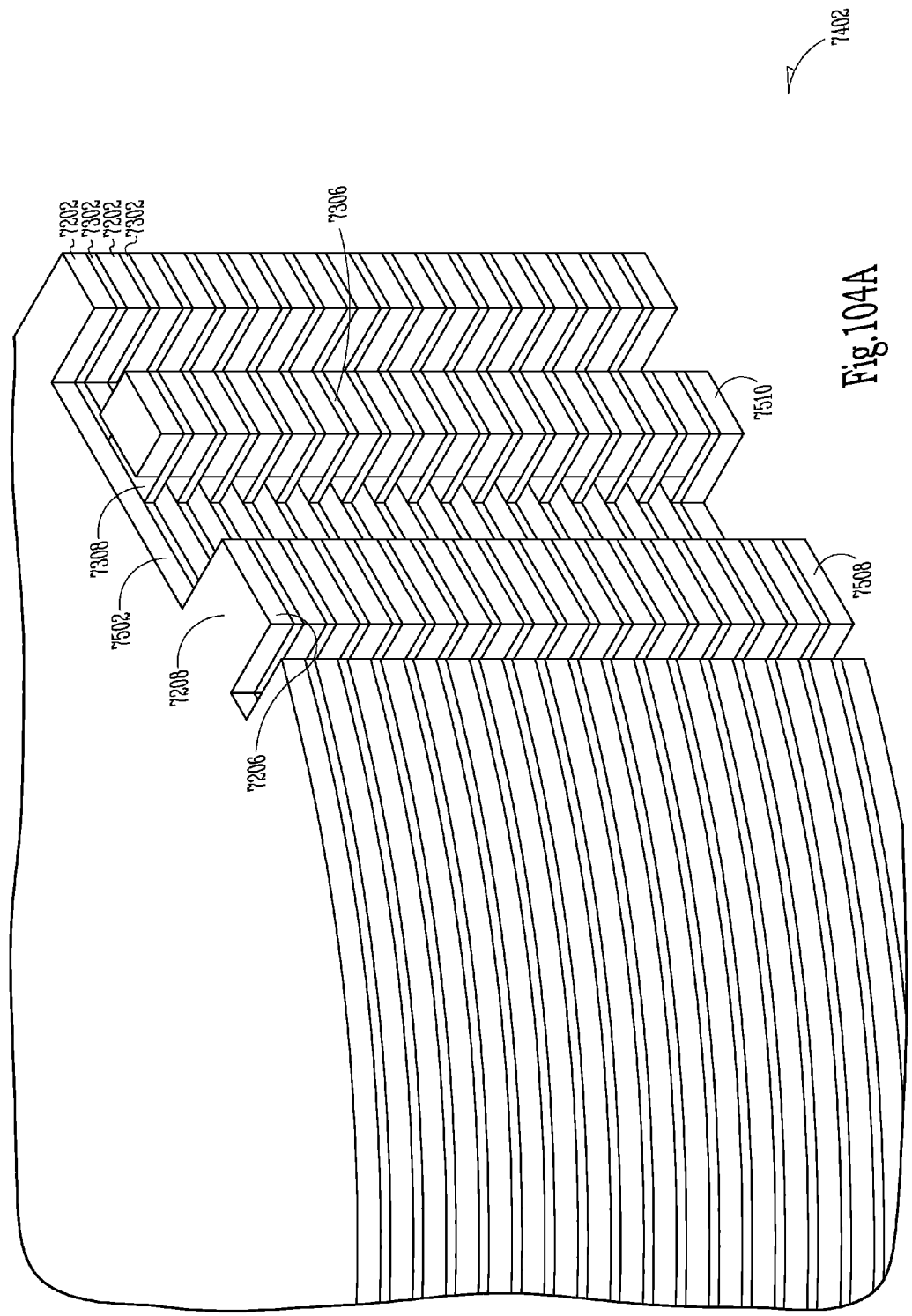
FIG. 104A is a perspective view of the stack of FIG. 103 after the stack has been processed according to one embodiment of the present subject matter.

FIG. 104A shows stack 7402 after portions of distal sections 7210 and 7310 have been removed from the stack, forming a separation 7502 between anode connection members 7206, which together comprise anode connection section 7508, and cathode connection members 7306, which together comprise cathode connection section 7510. Separation 7502 in the present embodiment electrically isolates section 7508 from section 7510. Proximal sections 7308 are still coupled to each other as are proximal sections 7208. In some embodiments, separation 7502 is a thin slice. In some embodiments, separation 7502 is as wide as cut-outs 7214 and 7314, as shown in FIG. 104. In some embodiments, an electrically insulative material is inserted in separation 7502. In various embodiments, separation 7502 is formed by laser cutting, punching, and/or tool or machine cutting.

Figure 104B:
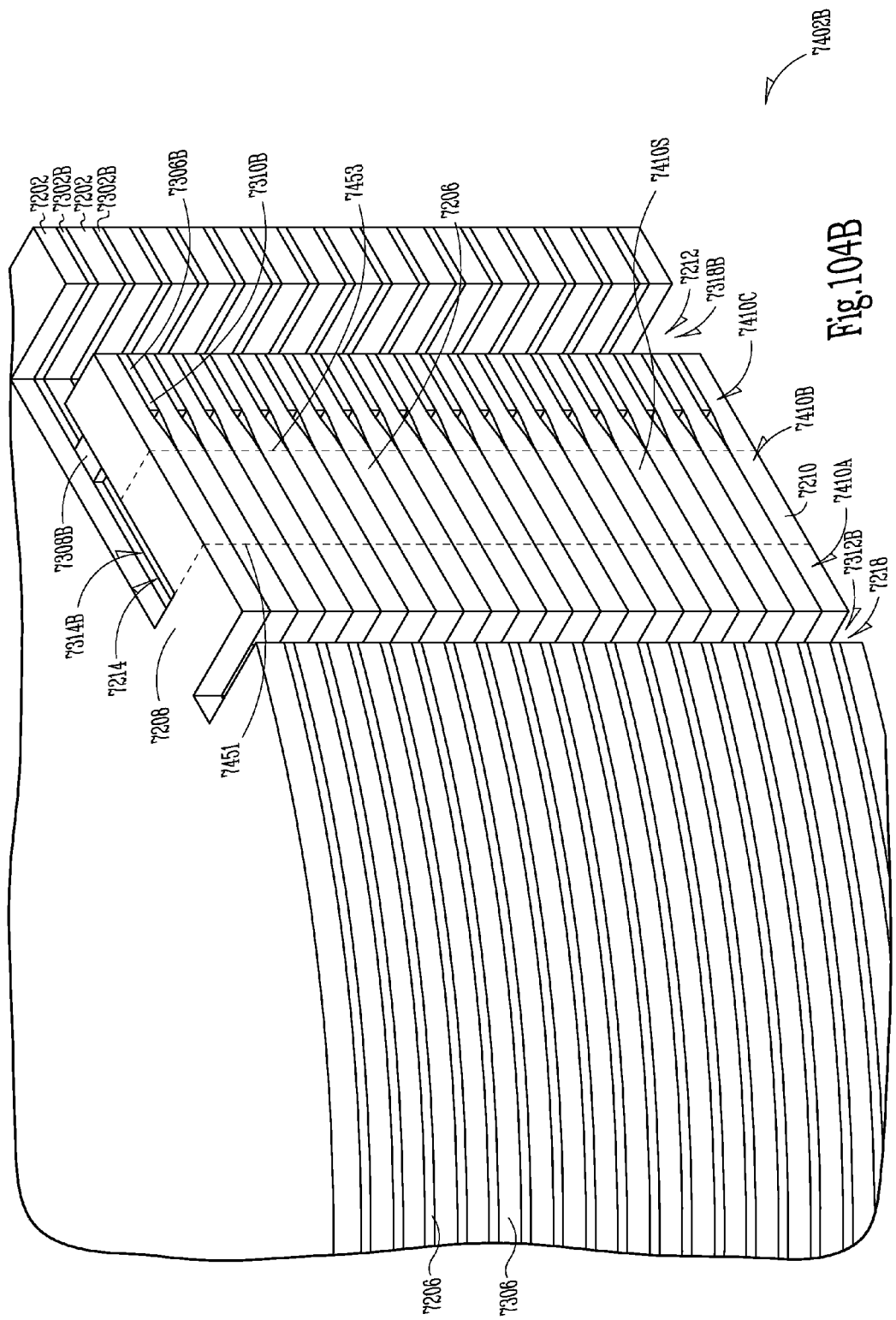
FIG. 104B is a perspective view of a stack of anodes and cathodes according to one embodiment.

FIG. 104B shows a stack 7402B of one or more alternating anodes 7202 and cathodes 7302B, in accordance with one embodiment. Anodes 7202 are as discussed above. In this example, cathodes 7302B can include the features discussed above for other cathodes and the above discussion is incorporated herein. Cathodes 7302B have a shorter distal section 7310B than the example discussed above in FIG. 104A, for example. Distal section 7310B can be L-shaped as discussed above or the connection member can be straight out from the cathode body forming an I-shape. As shown in FIG. 104B, connection members 7206 and 7306B include at least a portion that is overlaying and underlying each other. As noted above, overlay and underlay refer to the position or location of portions of the foils which are commonly positioned from a top view. In the embodiment of FIG. 104B, it is seen that connection members 7206 and 7306B have some commonly positioned portions relative to each other and some portions which are exclusively positioned relative to each other.

For instance, proximal sections 7208 of anodes 7202 are exclusively positioned or located. This means that at least a portion of proximal sections 7208 do not overlay or underlay a portion of cathodes 7302B. Likewise, in one embodiment, proximal sections 7308B of cathodes 7302B are exclusive portions and include at least a portion not overlaying or underlying a portion of anode 7202. Moreover, in this example, distal portion 7310B of cathodes 7302B does not extend across the entire distal portion 7210 of the anodes 7202. Distal sections 7210 and 7310B do include a commonly positioned portion along portion 7410C where each include at least a portion overlaying or underlying each another. Cut-out portions 7214 and 7314B are also commonly positioned. Cut-out 7218 is commonly positioned with cut-out 7312B while cut-out 7212 is commonly positioned with cut-out 7318B.

When stacked as shown in FIG. 104B, the edges of distal sections 7210 and 7310B form a surface 7410S. In this embodiment, surface 7410S can generally be described as having a first portion 7410A which fronts the proximal sections 7208 of anodes 7202, a second portion 7410B which fronts common cut-portions 7214 and 7314B, and third portion 7410C which fronts the proximal sections 7308B of cathodes 7302B.

In this embodiment, distal sections 7210 and 7310B of anode connection member 7206 and cathode connection member 7306B are overlaid relative to each other such as to be not continuous across surface 7410S, with anode connection members 7206 reaching across surface 7410S but cathode connection members 7306B not reaching across the surface. In other embodiments, the reverse can be true and the cathode connection member can reach across while the anode connection member is shorter and does not reach across.

After being stacked as discussed above, at least portions of connection members 7206 and 7306B are connected to each other. For instance, in one embodiment portions of distal sections 7210 and 7310B are connected to each other. In one embodiment, distal sections 7210 and 7310B are edge-welded all along surface 7410S. In one embodiment, distal sections 7210 and 7310B are only connected along portion 7410A and 7410C of surface 7410S. In one embodiment, distal sections 7210 and 7310B are soldered along surface 74105. In some embodiments, portions of distal sections 7310B and 7210 are staked, swaged, laser-welded, or connected by an electrically conductive adhesive. In other embodiments, portions of proximal sections 7208 are connected to each other and/or portions of proximal sections 7308B are connected to each other.

After being connected, portions of connection members 7206 and 7306B are removed or separated so that proximal sections 7208 and 7308B are electrically isolated from each other. As used herein, electrically isolated means that sections 7208 and 7308B are electrically insulated from each other at least up to a surge voltage of capacitor 100 (FIG. 1). For example, dashed lines 7451 and 7453 define an example of an area that can be removed to electrically isolate the anodes and the cathodes. In various embodiments, different areas can be removed. For example, in one embodiment, a portion of the distal ends 7210 of the anodes are removed and the cathode distal sections are not removed at all. In another embodiment, a portion of the commonly positioned section 7410C can be removed. Some examples include removing a portion of the distal section 7210 of the anode connection member 7206 and a portion of the distal section 7310B of the cathode connection member 7306B. Some examples include removing a portion of the distal section 7210 of the anode connection member 7206 such that there remains no material or section of the cathode connection member 7306B adjacent the anode connection member 7206.

Figure 104C:
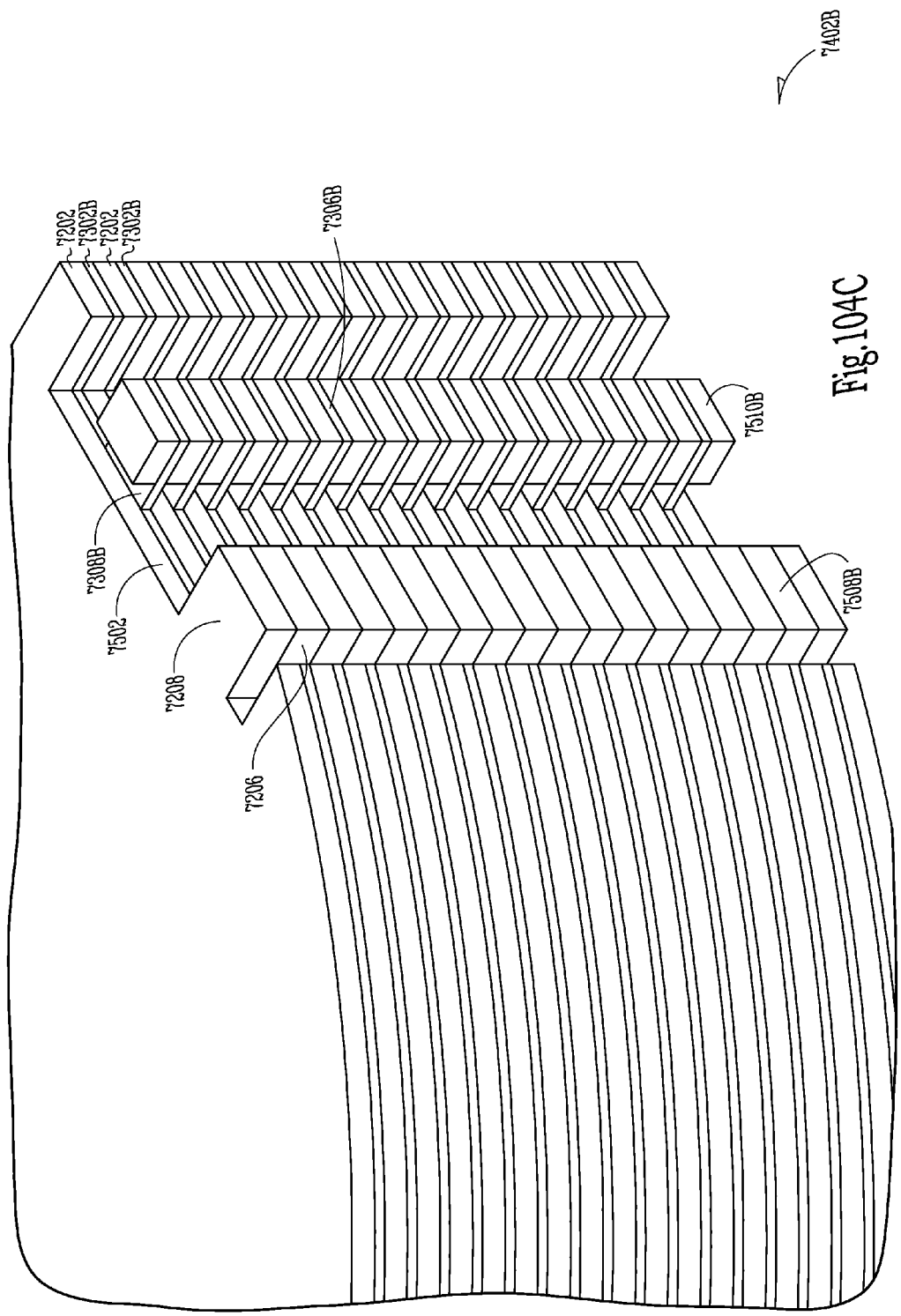
FIG. 104C is a perspective view of the stack of FIG. 5B after the stack has been processed according to one embodiment of the present invention.

FIG. 104C shows stack 7402B after portions of distal sections 7210 have been removed from the stack, forming a separation 7502 between anode connection members 7206, which together comprise anode connection section 7508B, and cathode connection members 7306B, which together comprise cathode connection section 7510B. Separation 7502 in the present embodiment electrically isolates section 7508B from section 7510B. Proximal sections 7308B are still electrically coupled to each other as are proximal sections 7208. In one embodiment, the separation is performed such that cathode connection members 7306B include some anode material between each layer, while anode connection members 7206 do not include any cathode material between the layers.

In some embodiments, separation 7502 is a thin slice. In some embodiments, separation 7502 is as wide as cut-outs 7214 and 7314B, as shown in FIG. 104B. As noted, some examples include removing a portion of the distal section of the anode connection member 7206 such that there remains no portion or material of the cathode connection member adjacent the anode connection members 7206. This is advantageous since in some examples the cathode layers can include a titanium coating, for example. A titanium coating can interfere with the performance of the anodes or can cause an electrical leakage into the weld or connection between the anodes. The present example keeps all cathode material out of the anode side 7508B. In some embodiments, an electrically insulative material is inserted in separation 7502. In various embodiments, separation 7502 is formed by laser cutting, punching, and/or tool or machine cutting.

Figure 105:
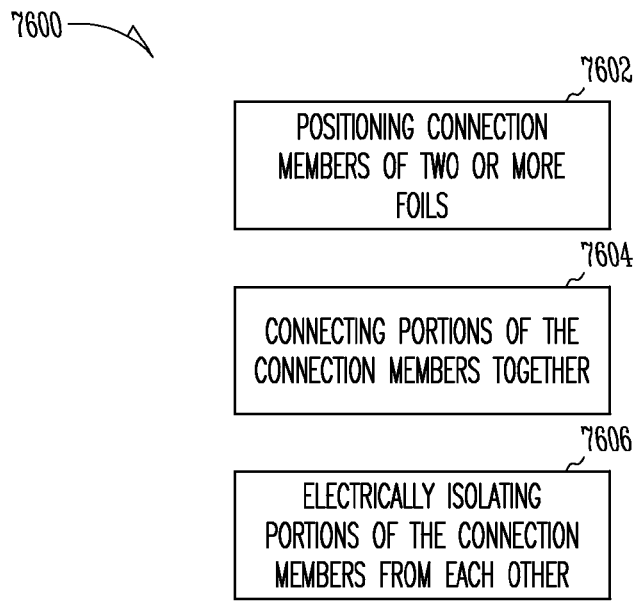
FIG. 105 is a flowchart depicting a method of interconnecting anodes and cathode foils of a capacitor according to one embodiment of the present subject matter.

FIG. 105 shows a flowchart depicting a method 7600 for interconnecting two or more foils of a capacitor according to one embodiment of the present subject matter. Method 7600 includes a block 7602, positioning the connection members of two or more foils, a block 7604, connecting the connection members, and block 7606, electrically isolating portions of the connection members from each other.

In one embodiment, block 7602, positioning the connection members of two or more foils, includes stacking an anode foil having a connection member having a proximal section and a distal section upon a cathode foil having a connection member having a proximal section and a distal section. The foils and connection members are positioned so that the proximal section of the anode foil connection member does not overlay the proximal section of the cathode foil connection member and the distal section of the anode foil connection member at least partially overlays the distal section of the cathode foil connection member.

In one embodiment, block 7604, connecting the connection members, includes connecting the connection member of the anode foil to the connection member of the cathode foil. In one embodiment, this includes connecting the distal section of the anode connection member and the distal section of the cathode connection member at a portion of the anode connection member that overlays (or underlays) the portion of the cathode connection member. In one embodiment, connecting comprises a single, continuous connection process. For instance, a laser weld or staking process is performed which attaches all the anode and cathode foil connection members together during a single, uninterrupted process. In one embodiment, the connection is performed by edge-welding at least a portion of the distal sections of the anode foil and the cathode foil together. One embodiment includes a laser edge-welding process.

Alternatively, in some embodiments, a portion of the stack is welded during a different process or by a different method than the first process. Some embodiments include soldering, staking, swaging, and/or applying an electrically conductive adhesive. In one embodiment, connection members 7206 and 7306 are laser edge-welded to each other by the edge-welding process discussed above.

In one embodiment, block 7606, electrically isolating portions of the connection members from each other, includes removing portions of the anode connection member and the cathode connection member. In one embodiment, the removed portion includes where the cathode connection member overlays (or underlays) a portion of the anode connection member. In one embodiment, this includes removing a portion of the distal sections of the anode connection member and the cathode connection member. In one embodiment, electrically isolating comprises punching-out a portion of the distal section of the anode foil connection member and the distal section of the cathode foil connection member. In one embodiment, electrically isolating includes laser cutting a portion of the distal section of the anode connection member and the distal section of the cathode connection member.

After being processed as discussed above in block 7606, proximal sections 7208 of the connection members of anodes 7202 are still coupled together and proximal sections 7308 of the connection members of cathodes 7302 are still coupled to each other, while the anodes 7202 and cathodes 7302 are electrically isolated from each other. Feedthroughs or other terminal members are then used to couple the anodes and cathodes to outside circuitry. Among other advantages, the present example method reduces the number of processing steps for constructing a capacitor.

One aspect of the present capacitor includes a system for interconnecting anode layers in a flat capacitor stack using vias. In one embodiment, vias are employed to interconnect anode layers. In one embodiment, the vias are made by inserting conductive interconnects which interconnect anode layers without contacting an intervening cathode layer.

Figure 106A:
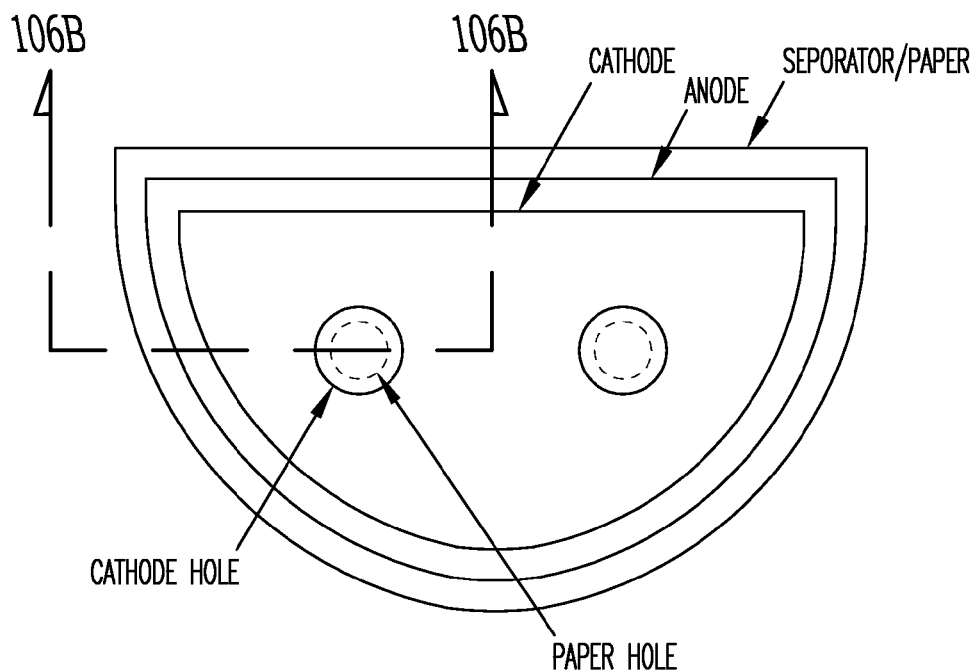
FIG. 106A shows a top view of a capacitor stack according to one embodiment.
Figure 106B:
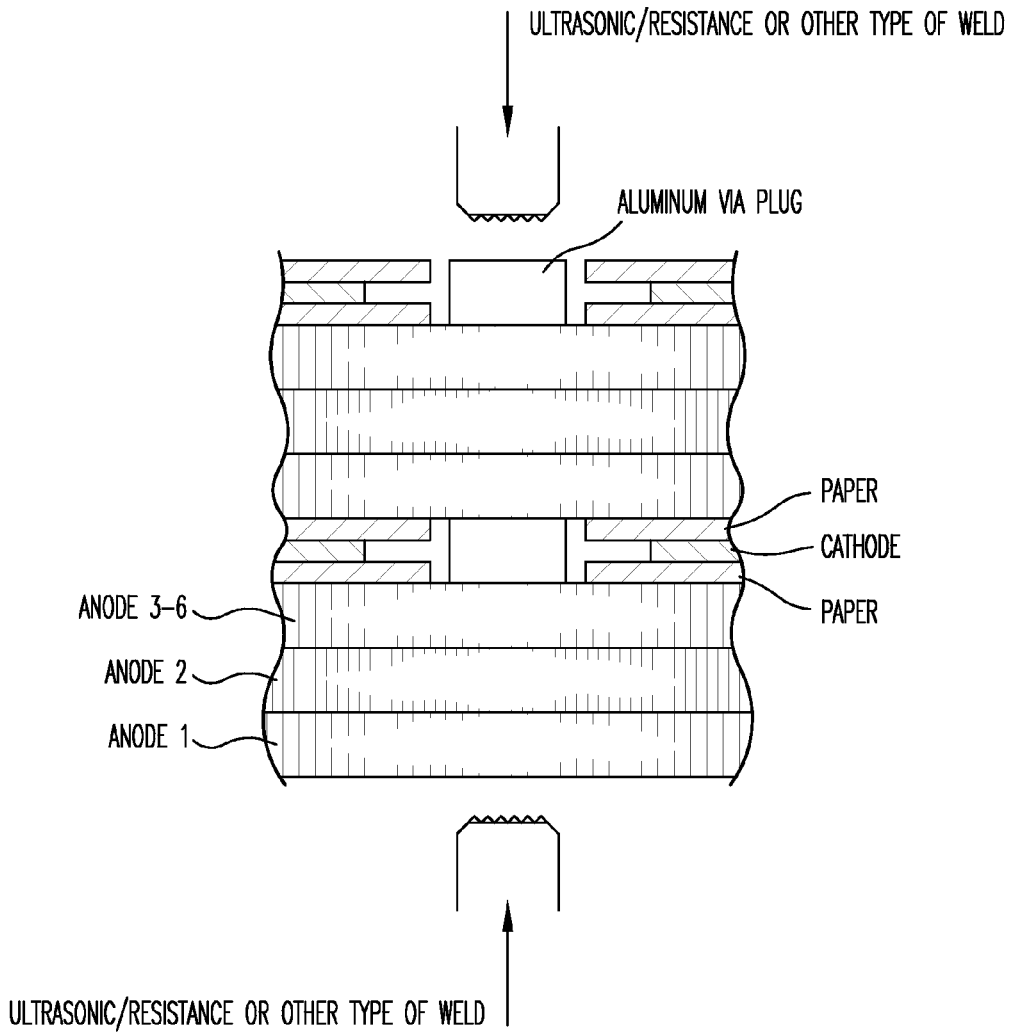
FIG. 106B shows a cross-section of a portion of FIG. 106A.
Figure 106C:
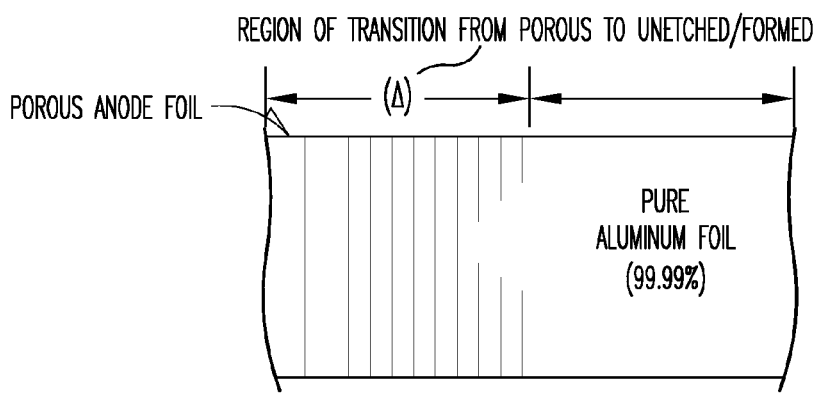
FIG. 106C shows a partially etched anode foil according to one embodiment.

For example, FIG. 106A shows a top view of a cathode and anode layer separated by separator (for example, kraft paper). The cathode layer includes one or more holes which provide ample clearance for a conductive interconnect. The x-section of FIG. 106A, shown in FIG. 106B, shows that the conductive interconnect will interconnect anode layers without contacting an intervening cathode layer. Thus, the cross section of the cathode hole exceeds that of the conductive interconnect to avoid shorting the cathode to the anodes. The conductive interconnect is electrically connected to the anodes by welding, such as ultrasonic, resistance or other types of welding.

One way to facilitate connections is to use a masking process for connection surfaces on the foil to ensure that the masked surfaces are not etched and/or formed. One way to avoid mechanical breakage of the foils is to use a masking technique which provides gradually non-etched portions of the foil to avoid mechanical stresses (e.g. high stress points) due to discontinuities of etching and which provides a suitable region for interconnection of the via to the foil. This is demonstrated by FIG. 106C. The vertical lines show the cross-section of unmasked and masked foil portions. The FIG. shows that foil etching gradually diminishes over the transition from masked portion to unmasked portion. It is noted that the example shows a pure aluminum foil, but that other etchings and foils may be masked without departing from the scope of the present system.

Figure 106D:
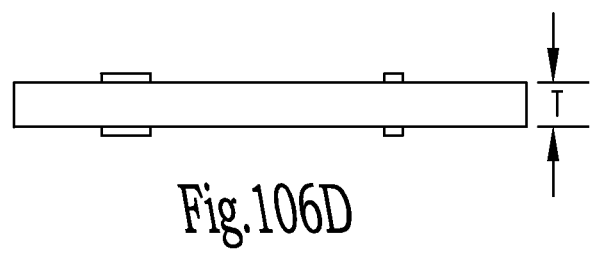
FIG. 106D shows a side view of a foil having masks, according to one embodiment of the present subject matter.
Figure 106E:
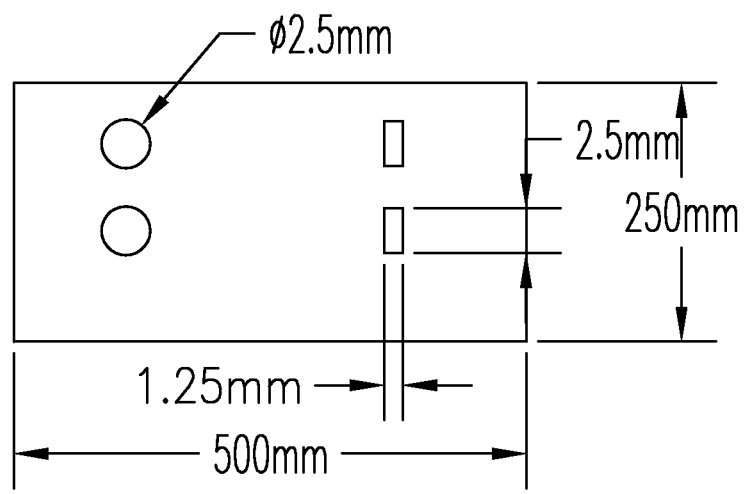

FIG. 106D shows a side view of a foil and positions of the masks for one embodiment of the present system. The top view is provided in FIG. 106E. The positions, shapes and sizes of the masks may vary without departing from the present system, and the demonstrated masks are shown to illustrate the system and are not intended in an exhaustive or exclusive sense. In one embodiment, thickness t is 100 micrometers. However, it is contemplated that other thicknesses may be used without departing from the present system. For example, other thicknesses, including, but not limited to, 50-600 micrometers may be used.

The foil dimensions are shown as 500×250 millimeters, but other sized foils may be employed without departing from the scope of the present system. In one application of the present system, a master roll of foil is masked to provide d-shaped cutouts with accurately placed masks where the conductive interconnects are to contact the foil. In one application, the spacing between foils must be large enough to provide a "web" for processing the cutouts.

Figure 106F:
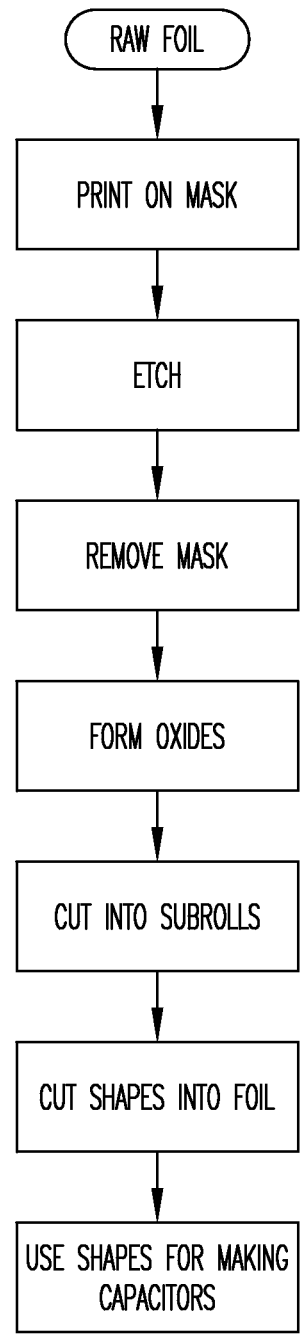

FIG. 106F shows one process for providing one embodiment of a capacitor according to some of the teachings herein. Raw foil is masked by printing the mask on the foil. The masked foil is etched and then the mask is removed. Oxides are formed on the foil and it is then cut into subrolls. The subrolls are processed by cutting shapes for the final capacitor out of the subrolls. The foil shapes are used to make the capacitors.

The cathode foils are processed to accurately place the cathode holes, which correspond to anode mask layers when overlapped. Paper separators are also cut to provide space for the conductive interconnects. In one application, the perimeter of the paper is smaller than that of the cathode to provide a nonconductive guide for the conductive interconnect. In alternate embodiments, an insulator may be used to position the conductive interconnect and to insulate against cathode contact.

It is noted that the conductive interconnects may be connected to formed or unformed portions of the anode layer.

One way to manufacture a capacitor according to the present teachings is to use a robotic assembly method, whereby anodes which are already masked, etched, and formed are stacked, followed by separator material, and then cathode material. In one assembly process, the cathodes are precision punched to provide accurately placed cathode holes. The robot can use the cathode features to accurately place the cathode relative to the anodes. A separator layer and an anode layer are also placed over the cathode using the robot. In embodiments where the conductive interconnect is a metal plug, the robot places the conductive plug accurately prior to the placement of the separator and anode layers. This process may be repeated to provide a stack of anodes of multiple layers interspersed with separator and cathode layers. The robot can also be used to perform the welding steps.

Other types of conductive interconnects may be used without departing from the present system. For example, the conductive interconnects may be made of a non-circular cross section. The conductive interconnects may be made of a suitable metal, such as aluminum. The conductive interconnects may also be made of other materials, including, but not limited to, conductive epoxy, conductive polymer (such as polyimide filled with aluminum), or fused aluminum powder. The metal used in the conductive interconnect should match the anode metal. Other anode metals/interconnect metal pairs may be used including, but not limited to, tantalum, hafnium, niobium, titanium, zirconium, or combinations of these metals.

It is understood that other connections may be performed using the teachings provided herein. For example, it is possible to create a series of interconnections between cathode layers using the teachings provided. Thus, use of the present system is not limited to anode-anode connections.

In one embodiment, the anode layers consist of a plurality of anode foils. In one application is it is possible that a single anode foil is interconnected to a triple anode foil or any multiplicity of anode foil combinations.

In one embodiment an anode layer may include a plurality of parts and/or layers. For example, the anode layer may include two different anode shapes in the same layer to provide a contoured edge. The shapes may be electrically connected to provide an equipotential surface. The use of multiple anode parts for a single layer facilitates the construction of a capacitor of virtually any form factor.

Furthermore, it is possible to weld multiple anode-cathode-anode stacks at different points for different conductive interconnects in one operation. Additionally, depending on the welding process used, several anode/cathode layers can be welded in a single operation.

Some of the benefits of the present system include, but are not limited to, the following: the electrical connection system provides mechanical stability; and alignment to the stack as the layers are being assembled; taping is not required; the assembly is ready for insertion into the capacitor case; surface area is optimized; interior alignment is facilitated using interior features to align the stack layer to layer; edge-welding and/or intra-anode staking may be eliminated; and, in some embodiments, paper gluing may be eliminated.

In one embodiment, a multi-chamber capacitor case is provides. Most implantable medical devices employ two capacitors that are separately charged with an inductive boost converter and connected in series to deliver a shock pulse. Packaging two energy storage capacitors in an implantable medical device housing, however, means fitting two bulky capacitor cases into the housing because each capacitor includes a stack of capacitive elements enclosed in its own case. Simply increasing the number of capacitive elements in the case does not solve the problem, because all of the electrolyte in the case is at the same electrical potential. This prevents the capacitive elements in the case from being connected electrically in series. To provide a series connection, therefore, two separate capacitors with isolated electrolytes must be used. This can be accomplished with greater space efficiency by employing a capacitor case having two (or more) separate compartments for containing separate stacks of capacitive elements.

Figure 107A:
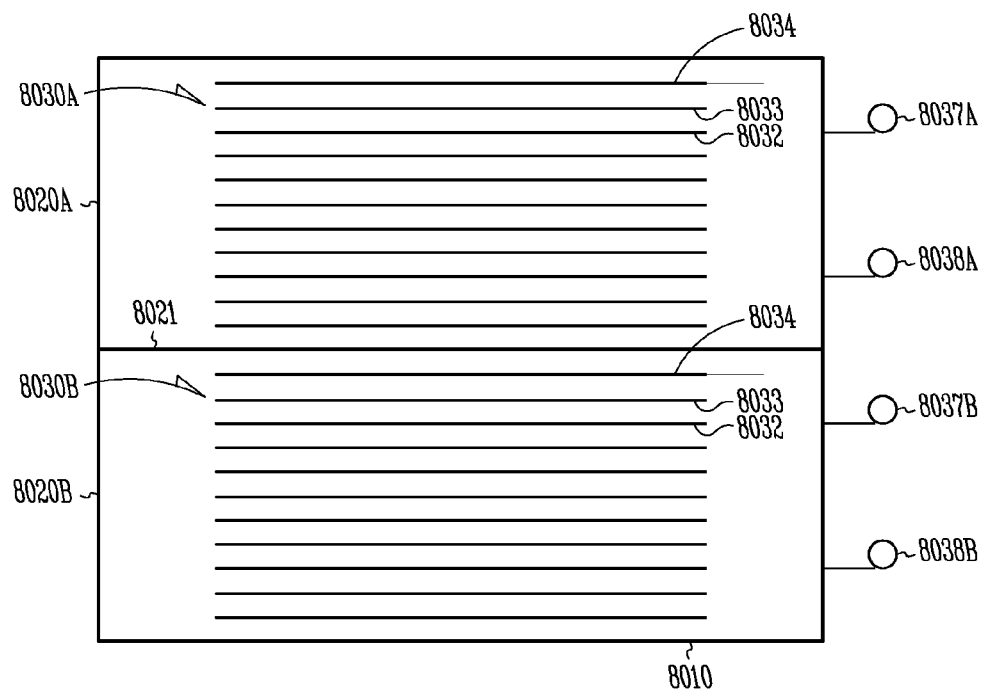

FIG. 107A is a schematic representation of one embodiment of an electrolytic capacitor. A case 8010 has two compartments 8020*a* and 8020*b* for containing two separate stacks 8030*a* and 8030*b* of capacitive elements. The two stacks are stacked vertically in their respective compartments, and a common wall 8021 separates the two compartments. Each capacitive element in a stack includes an anode 8032, a separator 8033, and a cathode 8034 that are arranged in a layered structure, with the separator interposed between the anode and cathodes. An electrolytic ally formed oxide layer on the anode serves as the insulating dielectric for the capacitor. The separator is impregnated with an electrolyte that serves as the cathode for the capacitor, with the cathode plate supplying current to the electrolyte. If the case 8010 is made of a metallic conductive material, an insulating coating can be applied to the inner surface of each compartment to electrically isolate the electrolyte from the case. One means of doing this is to electrolytic ally apply an oxide coating to the inner walls of the compartments.

When a voltage is applied so that the anode plate is made positive relative to the cathode plate, the element acts as a capacitor by dropping a voltage across the oxide layer of the anode plate that is proportional to the charge stored on the plates. Extending tabs from each cathode and anode plate of the stack in compartment 8020*a* are used to electrically connect like types of plates to separate conductors. For instance, the capacitor stack can include tabs which extend from the cathode and anode plates, respectively, as discussed above. Conductors can be connected to the tabs respectively, and be routed via feedthrough holes (i.e., passages in the wall of the case) to connect to a cathode terminal 8037*a* or an anode terminal 8038*a*. A voltage applied to the terminals then sees a capacitance equal to the sum of the capacitances of the capacitive elements in the stack (i.e., the elements are connected in parallel). In a like manner, conductors can be provided for the stack in compartment 8020*b* which are terminated at a cathode terminal 8037*b* and an anode terminal 8038*b*. The two stacks can then be connected together in series by connecting unlike terminals from each stack together. For example, in FIG. 107A, terminal 8038*a* can be connected to terminal 8037*b*. A voltage applied across terminals 8037*a* and 8038*a* then sees a capacitance equal to the desired series connection of the two stacks.

The above description was with reference to a stacked flat type of capacitor. In the case of a cylindrical capacitor, each strip of foil has an attached aluminum tab extending out of the rolled assembly toward the top of the tubular case, which is sealed shut with a lid called a header. Extending from the header are cathode and anode terminals which are connected respectively to the two foils via the aluminum tabs. Two such cylindrical capacitors in separate compartments can then be connected together in series in the same manner as described above.

Figure 107B:
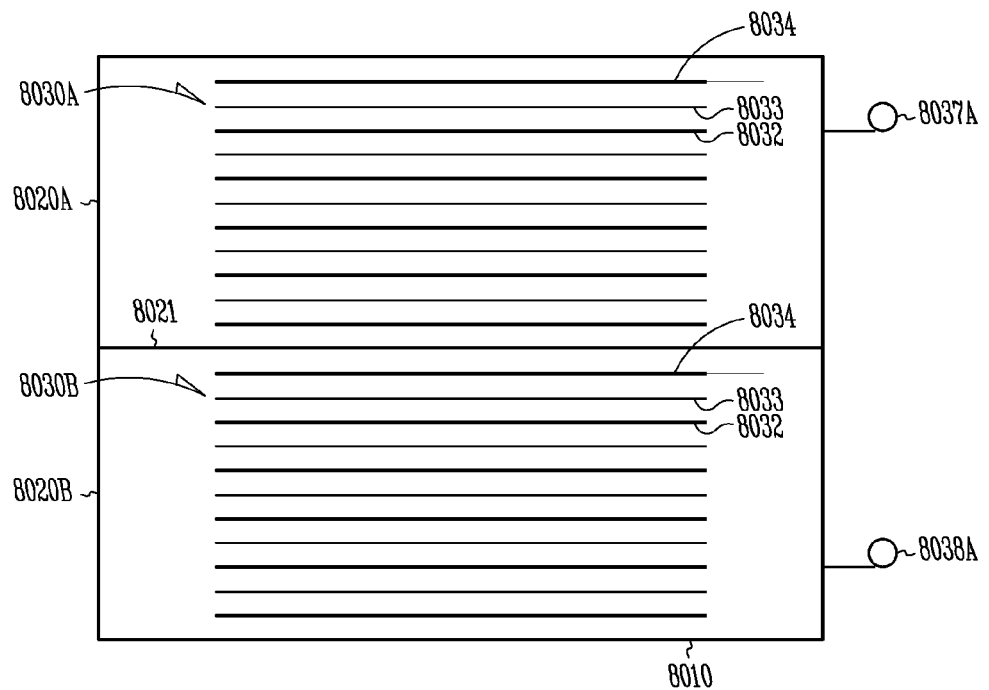

FIG. 107B schematically shows another embodiment where the same reference numerals as in FIG. 107A are used to identify the component parts. In this embodiment, however, the cathode plates of one compartment and the anode plates of the other compartment are connected to a conductive case. That is, instead of connecting unlike terminals from each stack together to provide a series connection, the conductive case is used to electrically connect the stacks of each compartment together. In the example shown in FIG. 107B, the anode terminal of compartment 8020*a* and the cathode terminal of compartment 8020*b* are not brought out external to the case. Instead, the conductors from the anode plates of compartment 8020*a* and the cathode plates of compartment 8020*b* are both electrically connected to the case 8010 which provides a conductive path between the two stacks. As above, the inner surface of each compartment is made non-conductive so as to electrically isolate the electrolyte from the case. An insulating coating may also be applied to the exterior of the case in order to electrically isolate it from the rest of the components in the implantable medical device housing. A voltage applied across terminals 8037*a* and 8038*b* again then sees a capacitance equal to the desired series connection of the two stacks.

Figure 108:
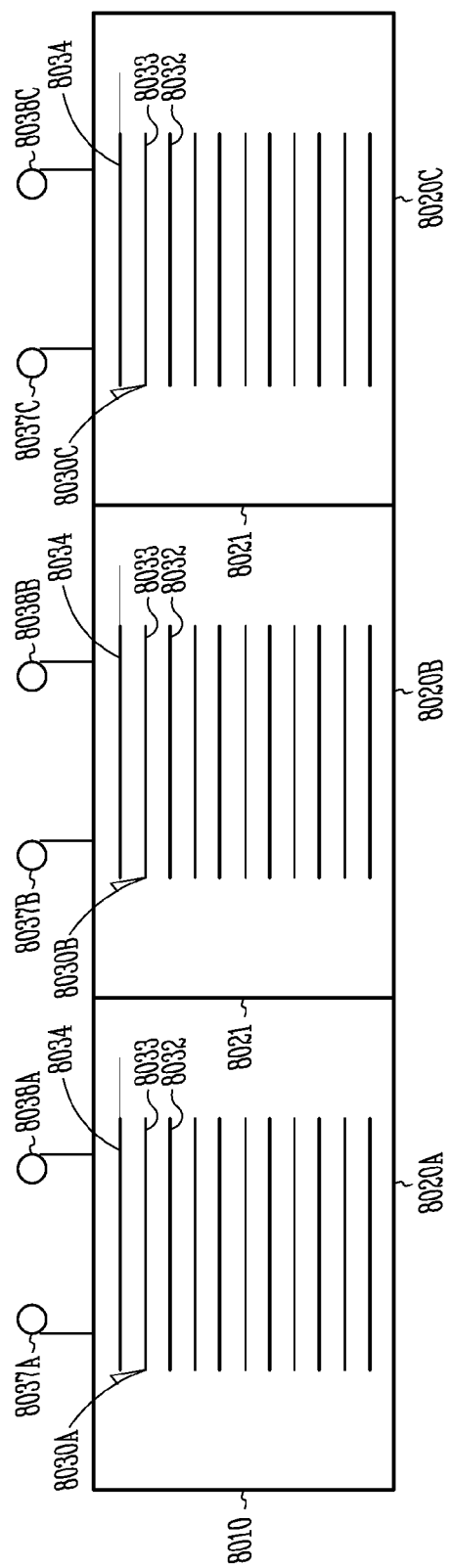

The same principles as described above apply to a capacitor with three or more stacks packaged in a multi-compartment case. FIG. 108 shows another embodiment in which the case 8010 has three compartments 8020*a* through 8020*c* containing separate stacks 8030*a* through 8030*c*, respectively. The stacks in this embodiment are arranged horizontally rather than vertically. The stacks can be electrically connected in series in a manner similar to that described above. In the FIG., a cathode terminal 8037*a* from the stack in compartment 8020*a* can be connected to an anode terminal 8038*b* from the stack in compartment 8020*b*, and a cathode terminal 8037*b* from the stack in compartment 8020*b* can be connected to an anode terminal 8038*c* from the stack in compartment 8020*c*. A voltage applied across the anode terminal 8038*a* from the stack in compartment 8020*a* and the cathode terminal 8037*c* from the stack in compartment 8020*c* then sees a capacitance equal to the series connection of all three stacks.

Figure 109:
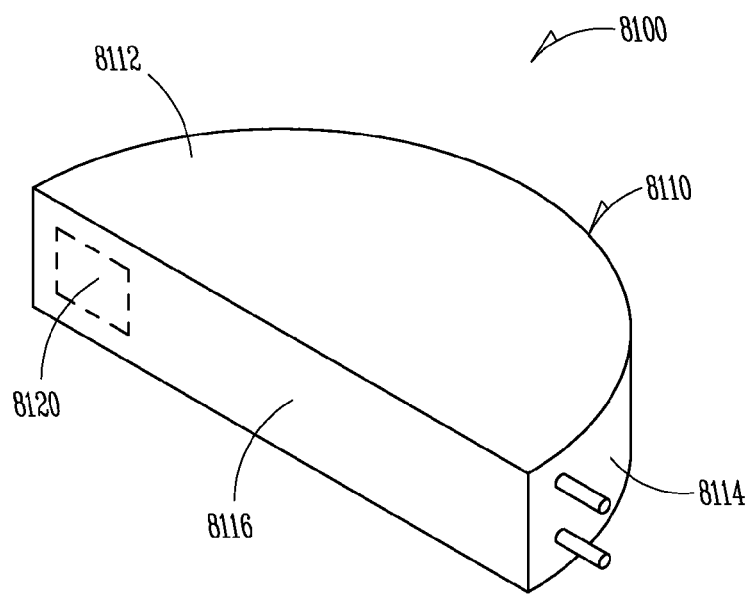

FIG. 109 shows a flat aluminum electrolytic capacitor 8100 according to one embodiment of the present subject matter. Many details of capacitor 8100 are similar to capacitor 8100 described above and will be omitted herein. Capacitor 8100 includes a case 8110 and a generic device 8120 for preventing development of excessive pressure within case 8110. Case 8110, which comprises aluminum and has a D-shape in this exemplary embodiment, includes a planar top face 8112, a generally semicircular or arced back face 8114, and a substantially planar front face 8116. (A planar bottom face is not visible in this view.) Although the exemplary embodiment places device 8120 on front face 8116, other embodiments place device 8120 on any one of the other faces. Thus, the subject matter is not limited to any particular placement of device 8120 on or within the case. Additionally, the subject matter is not limited to any particular case form or composition.

Figure 110:
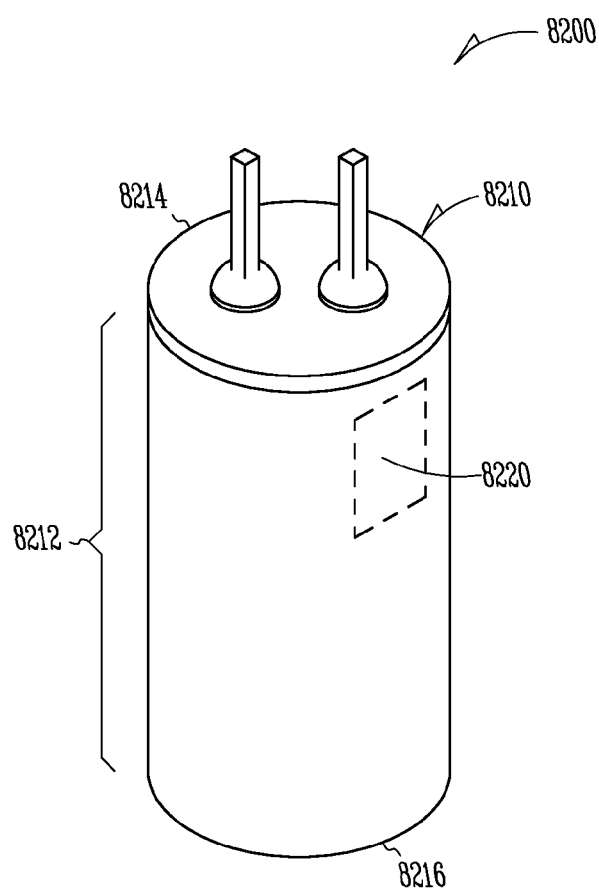

FIG. 110, for example, shows an exemplary cylindrical aluminum electrolytic capacitor 8200 which includes a case 8210 and a generic device 8220 for preventing development of excessive pressure within case 8210. Case 8210, which comprises aluminum in this exemplary embodiment, includes a tubular portion 8212, a top or header 8214, and a bottom 8216. The exemplary embodiment places device 8220 on tubular portion 8212, whereas other embodiments place device 8210 on any one of the other portions, such as on header 8214 or within the case.

Figure 111:
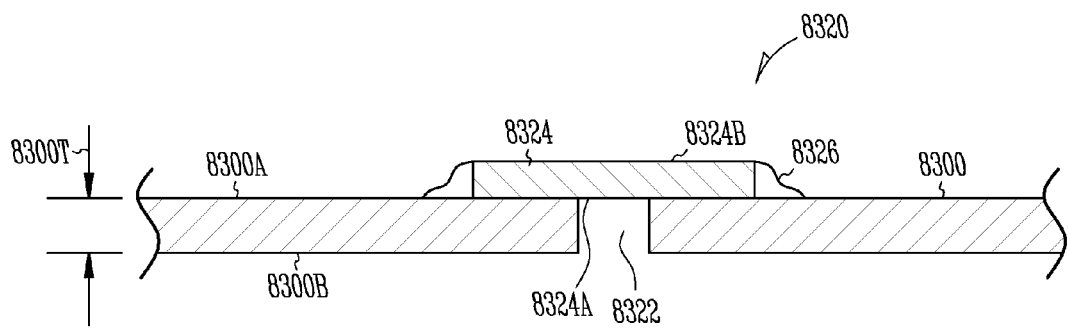

FIG. 111 shows a partial cross-section of an exemplary capacitor case portion 8300, which is not only conceptually representative of any portion of case 8110 or 8210 in FIGS. 109 and 110, but also includes a first exemplary device 8320 for preventing development of excess pressure within case 8110 or 8210. Case portion 8300 includes an exterior surface 8300a and an opposing interior surface 8300b. Interior surface 8300b faces, or confronts, components, such as one or more capacitor elements or modules (not shown), within case 8110 or 8210. Conversely, exterior surface 8300a faces away from the one or more capacitor elements.

Surfaces 8300a and 8300b define a case thickness 8300t, measured in a dimension generally perpendicular to at least one of the surfaces. Case thickness 8300t in the exemplary embodiment is less than 0.015 inches (0.381 millimeters.) Some embodiments use cases as thin as 0.005 inches (0.127 millimeters) or as thick as 0.025 inches (0.635 millimeters.) Other thicknesses are possible without departing from the scope of the present subject matter.

Device 8320 comprises an aperture or hole 8322 within case portion 8300, a membrane 8324 covering hole 8322, and adhesive layer 8326 adhering membrane 8324 to case portion 8300. Hole 8322 extends from exterior surface 8300a to interior surface 8300b and has a length or depth equal to case thickness 8300t. In the exemplary embodiment, hole 8322 is substantially circular and of uniform diameter, for example, 0.050 inches (1.27 millimeters), for the full thickness of case portion 8300. Other embodiments provide linear or non-linear tapered holes with increasing or decreasing diameter from the interior surface to the exterior surface of the case or dual tapered holes with a first portion of increasing diameter and a second portion of decreasing diameter. Still other embodiments also vary the shape and placement of the hole. The hole can be placed with awareness of the implant attitude of the capacitor. Exemplary hole-formation techniques include drilling, cutting, laser cutting, or etching. Thus, the subject matter is not limited to any particular hole geometries, dimensions, or placement.

Membrane 8324, which comprises a semi-permeable material, covers hole 8322, controlling passage of fluids, that is, liquids and/or gases, through hole 8322. Membrane 8324 includes respective interior and exterior surfaces 8324a and 8324b.

In one embodiment, interior surface 8324a abuts exterior surface 8300a of case portion 8300. However, in other embodiments exterior surface 8324b abuts interior surface 8300b, meaning that the membrane is within the case. Exemplary materials for membrane 8324 include a gas-permeable and liquid impermeable polytetrafluoroethylene (PTFE) barrier. This material is permeable to hydrogen gas, which is generally released during normal operation of wet aluminum electrolytic capacitors. Other exemplary membrane materials include silicones, polypropylenes, acetates, and polyester. Still other exemplary materials may be found in Mark Porter, Handbook of Industrial Membrane Technology, Noyes Publications, 1990.

However, the present subject matter is not limited to any particular membrane form, structure, or composition so long as it performs the desired function of preventing excessive pressures within the capacitor case. (As used herein, excessive pressures include, for example, any pressure level that is more likely than not to distort the shape of the capacitor case and/or compromise the intended electrical characteristics of the capacitor. Some cases are known to distort at a pressure of about 15 pounds-per-square inch.) Thus, the scope of the present subject matter, for example, encompasses composite membranes, homogeneous membranes, heterogeneous membranes, organic and inorganic membranes, symmetric and asymmetric membranes.

The exemplary embodiment attaches the membrane to case portion 8300 using adhesive 8326, such as epoxy, on one or more portions of the membrane. For example, the exemplary embodiment places the adhesive at the interface between exterior surface 8300a of case portion 8300 and the peripheral edges of the membrane. Other embodiments place the adhesive in an annular region around hole 8322 between interior surface 8324a of the membrane and exterior surface 8300a of the case.

Additionally, other embodiments, use other types of techniques to secure the membrane in place. Indeed, the membrane could be held in place with a strip of tape or by even wedging it between the capacitor case and an adjacent structure, such as relatively immovable wall or component, such as another capacitor, within an implantable device.

Figure 112:
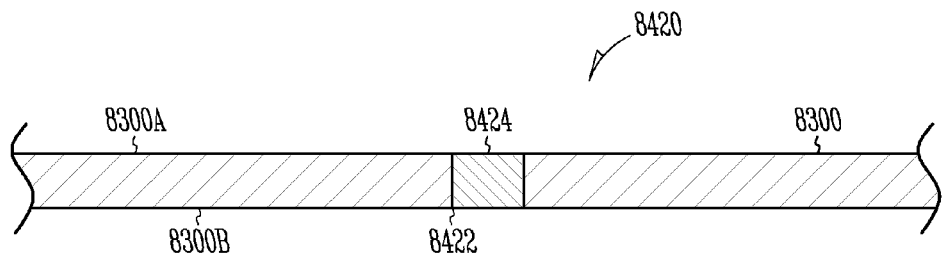

FIG. 112 shows case portion 8300 with a second exemplary device 8420 for preventing development of excess pressure with case 8110 or 8210. In this embodiment, device 8420 includes a hole 8422 and a cylindrical plug or insert 8424 within hole 8422. Plug 8424, which is glued or compression fit into hole 8422, includes a semi-permeable material like that comprising membrane 8324 in FIG. 3. Although plug 8424 takes a cylindrical shape in the exemplary embodiment, it may take any shape or size. Additionally, some embodiments extend a conductor, such as a feedthrough conductor, through plug 8424, allowing hole 8422 to serve as a feedthrough hole, as described above for FIGS. 67-69.

Figure 113:
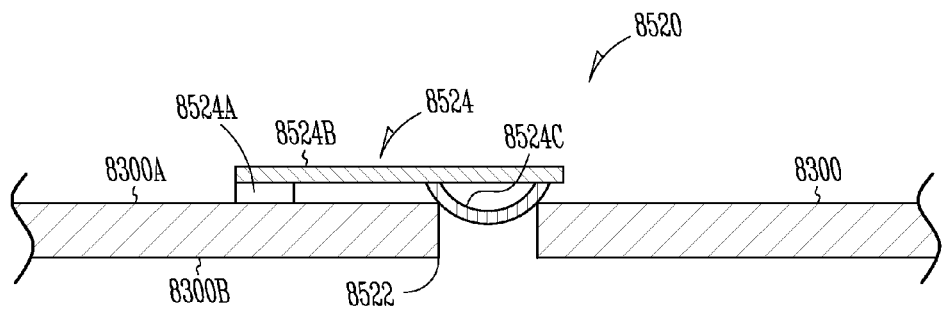

FIG. 113 shows capacitor case portion 8300 outfitted with a second exemplary device 8520 for preventing development of excess pressure within case 8110 or 8210. In this embodiment, device 8520 comprises a hole 8522, and a spring-biased valve 8524 that controls passage of fluids, that is, liquids and/or gases, through hole 8522. Valve 8524 includes a stand-off member 8524a, a cantilever spring 8524b, and a concave or hemispherical valve seat 8524c. Stand-off member 8524a lies adjacent hole 8522 and supports one end of cantilever spring 8524b. The other end of cantilever spring 8524b extends over hole 8522, forcing concave valve seat 8524c, which is generally congruent in shape with hole 8522, to form a seal with the perimeter of the hole. (In some embodiments, valve seat 8524c is composed of a rubber, such as EPDM (Ethylene Propylene Diene Monomer) rubber, and in others it is composed of a semi-permeable material.) The seal opens with an interior pressure of, for example, 5, 10, or 15 pounds-per-square inch.

Although the present embodiment places valve 8524 on exterior surface 8300*a*, other embodiments may place the valve on interior surface 8300*b*. Other embodiments also use other valve assemblies. For example, some embodiments omit stand-off member 8524*a* and attach an end of the cantilever spring directly to the exterior surface. Other embodiments place a valve at the end of tube or other fluid passage connected to the hole to allow greater flexibility in valve placement away from the case. Other embodiments may use electronic micro-machined valves actuated by the charge-and-fire or therapeutic, circuitry of an implantable device.

Figure 114:
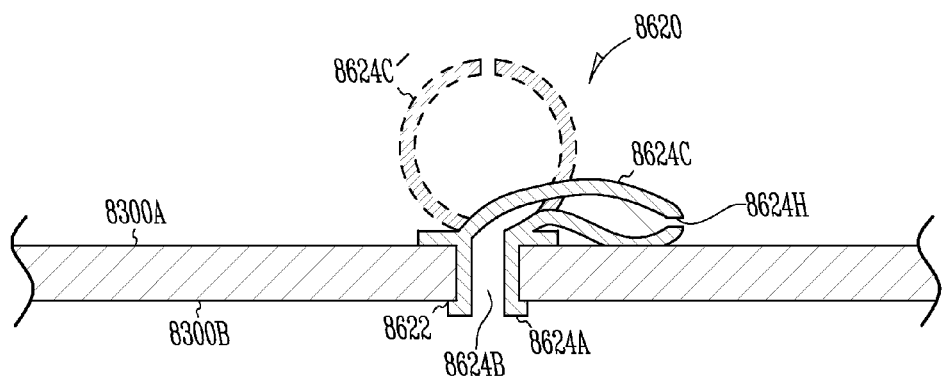

FIG. 114 shows capacitor case portion 8300 outfitted with a third exemplary device 8620 for preventing development of excess pressure within case 8110 or 8210. In this embodiment, device 8620 includes a hole 8622 and an expandable bung 8624 that controls passage of fluids, that is, liquids and/or gases, through hole 8622. Expandable bung 8624 includes a cylindrical plug portion 8624*a* that has an interference or compression fit with hole 8622, an axial passage 8624*b* that extends through plug portion 8624*a*, and an expandable (or inflatable) bladder portion 8624*c* that connects through passage 8624*b* to the interior of capacitor case 8110 or 8210. Bladder portion 8624*c* includes an optional hole 8624*h*.

The present embodiment forms expandable bung 8624 from an elastic material such as a natural or synthetic rubber. However, other embodiments use other materials such as polymers, fluoropolymers, and other pliable synthetics.

In operation, bladder portion 8624*c* expands as gases from the interior of case 8110 or 8210 enter it through passage 8624*b* to assume the form as 8624*c*', which approximates a 0.100-inch-radius sphere. The added volume of bladder portion 8624*c* reduces the pressure in the capacitor case. Hole 8624*h* in the bladder allows gas to escape, thereby further reducing the pressure in the case. In one embodiment, hole 8624*h* has a diameter or width smaller than that of axial passage 8624*b* which ensures different fluid flow rates into and out of bladder portion 8624*c*. Among other advantages, one or more embodiments described above provide devices for preventing excessive pressures from developing within the capacitor cases.

Figure 115:
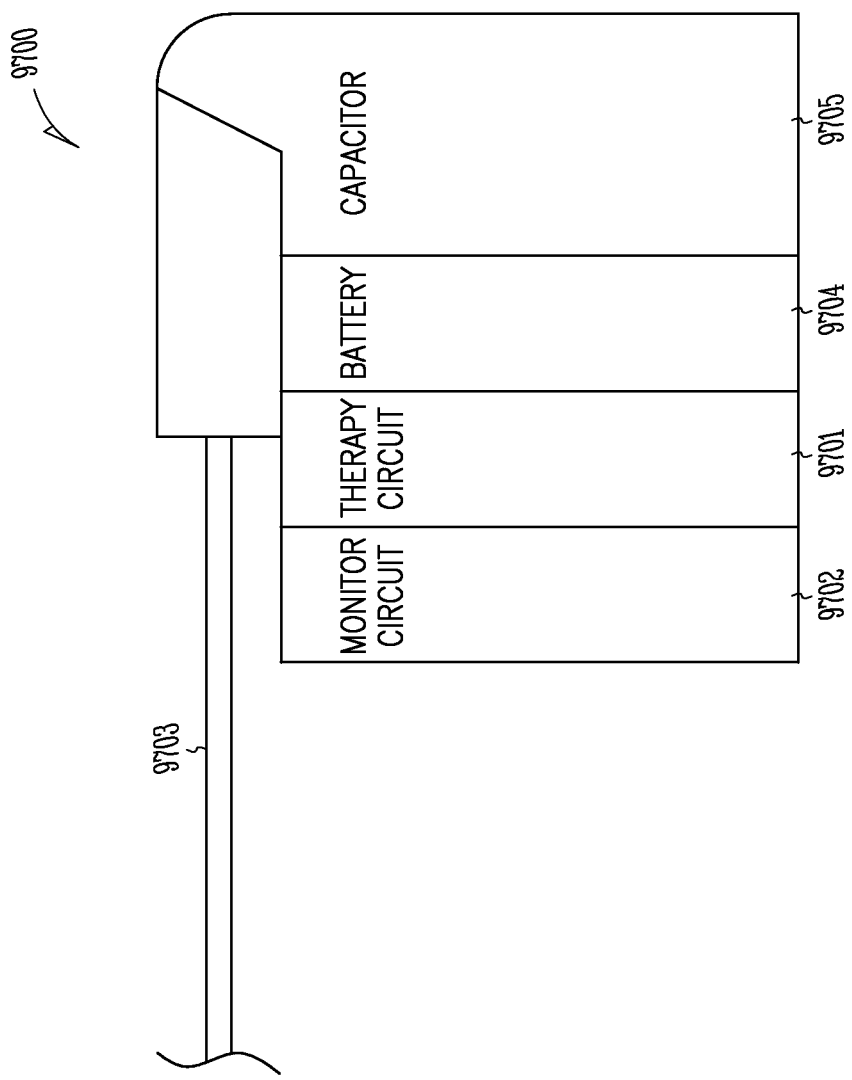

FIG. 115 shows one of the many applications for capacitors incorporating one or more teachings of the present subject matter: an implantable medical device or apparatus 9700. As used herein, this includes any implantable device for providing therapeutic stimulus to a heart muscle. Thus, for example, the term includes pacemakers, defibrillators, cardioverters, congestive heart failure devices, and combinations and/or permutations thereof. Implantable medical device 9700 includes a lead system 9703, which after implantation electrically contact strategic portions of a patient's heart. Shown schematically are portions of device 9700 including a monitoring circuit 9702 for monitoring heart activity through one or more of the leads of lead system 9703, and a therapy circuit 9701 for delivering electrical energy through one or more of the leads to a heart. Device 9700 also includes an energy storage component, which includes a battery 9704 and incorporates at least one capacitor 9705 having one or more of the features of the capacitors described above.

FIGS. 116A-116C illustrate a graph representing characteristics of various embodiments of a capacitor, according to the present subject matter. The teachings of the present subject matter include a process for producing a capacitor which exhibits the traits illustrated by the graph. Among the various properties demonstrated by the graph are practical limitations tied to various aspects of capacitor design. Overall, the graph is useful to illustrate aspects which aid in selection and development of improved capacitors.

The graph includes a three dimensional curve representing energy delivered in joules, voltage in volts, and volume in cubic centimeters. Depending on which aspects of the graph are analyzed, various trends are apparent.

For example, FIG. 116A demonstrates embodiments in which a capacitor delivers improved energy in the range of about 465V to about 565V. The graph illustrates both the relationship between voltage and energy delivered, and volume and energy delivered. From reading and understanding the graph, it is apparent that higher voltages enable higher energy delivered, and that a higher capacitor volume enables higher energy delivered. The particular shape of the curves, and the energy delivered, are, in part, functions of the surface shape of the capacitor. For example, embodiments including capacitors with increased surface area due to etching, which have a dielectric formed on the surface area without substantial reduction in the surface area, provide more energy per volumetric unit. Additionally, embodiments which have increased dielectric thickness enable higher voltages, which also result in higher available energy levels. The present subject matter reveals varying preferential ranges considering these criteria.

For example, one embodiment of the present subject matter is adapted to deliver an electrical pulse at a voltage of between approximately 490 volts and approximately 540 volts. Another embodiment is adapted to deliver an electrical pulse at approximately 515 volts. In some embodiments, a compromise is necessary to achieve the preferred performance. For example, in embodiments where approximately 515 volts is chosen as the operating voltage, an electrolyte which is unable to withstand higher voltages is used. In varying embodiments, an electrolyte which is unable to operate at the peak of the voltages curve evident in the graph is chosen because of technology limitations and cost limitations. However, it is to be understood that the present subject matter encompasses embodiments which operate at the voltages demonstrated by the graph, and the examples included in these teachings are provided solely for illustration, and are not exhaustive or exclusive.

Additionally, the present subject matter includes embodiment adapted to deliver from about 5.3 joules per cubic centimeter of capacitor stack volume to about 6.3 joules per cubic centimeter of capacitor stack volume. Also, the present subject matter teaches embodiments adapted to deliver from about 5.5 joules per cubic centimeter of capacitor stack volume to about 6.1 joules per cubic centimeter of capacitor stack volume. One embodiment is adapted to deliver about 5.8 joules per cubic centimeter of capacitor stack.

FIG. 116B shows a top view of a graph representing various properties of one capacitor embodiment of the present subject matter. The graph illustrates, in part, the relationship between voltage and energy delivered.

FIG. 116C includes a view of the graph which demonstrates the relationship, in part, between volume and energy delivered. In varying embodiments, the graph teaches that volumetric energy density, measured in joules per volt, increases when volume is minimized for a required energy delivered.

Thus, by reading and understanding the information provided by the graph, it is possible to produce a capacitor with an improved packaging density, including, in part, improved volumetric energy density.

As referenced in the discussion for FIGS. 106A-106F, portions of the electrode are masked prior to etch, in various embodiments. FIG. 117 illustrates one example of a mask applied to the electrode of the present subject matter. In varying embodiments, a mask is applied to one or both sides of the electrode. For example, line 9802 defines a portion of an electrode shape which is punched from a sheet, in varying embodiments of the present subject matter. Applied to the sheet are a first mask 9804 and a second mask 9806. In varying embodiments, including the embodiment pictured, masked portions eclipse the eventual shape of the electrode, represented by electrode shape 9802.

For example, the sheet includes a first major surface which is visible, and a hidden second major surface substantially parallel to the first. In varying embodiments, a first pattern of mask 9804 is applied to the first surface, and a second pattern of mask 9806 is applied to the second surface.

In varying embodiments, the first pattern of mask 9804 and the second pattern of mask 9806 are shaped differently. In one example, the first and second pattern have different shapes, and cover varying areas of the sheet. For example, pattern 9804 covers a first area of electrode shape 9802, and pattern 9806 covers a second area of electrode shape 9802, and the first area covered by pattern 9804 of electrode shape 9802 is larger than the second area covered by pattern 9806 of electrode shape 9802.

It should be noted that in varying embodiments, the shape of pattern 9804 and the shape of pattern 9806 are chosen to assist in manufacturing. For example, in varying embodiments, electrode shape 9802 is cut from a sheet of etched and anodized electrodes. When a single sheet is populated with multiple electrodes, in varying embodiments, the choice of shape for pattern 9804 and pattern 9806 can aid in associated manufacturing steps.

In varying embodiments, transition line 9808 is skew to transition line 9810. Varying examples increase the bending stress at the transition between etched foil and non-etched foil, and by positioning the transition line 9808 and 9810 in varying configurations, the bending stress of the electrode 9802 is more evenly distributed about the foil, which, in some embodiments, reduces instances of cracking and breaking.

FIGS. 118A-118F illustrate varying patterns of mask for application to a foil, according to various embodiments of the present subject matter. In varying embodiments, the mask can populate the pattern 9804 or the pattern 9806 illustrated in FIG. 117. It should be noted that the line 9902 described in varying examples is equivalent to the line 9808 of pattern 9804, and line 9810 of pattern 9806.

FIG. 118A illustrates an example of a mask constructed out of a pattern of rounded square shapes arranged proximal to each other. In varying embodiments, the shapes cover approximately 80% of the surface onto which they are printed, proximal the line 9902. Line 9902 defines, and the area proximal the line, define a transition zone between masked electrode and non-masked electrode. By angling the line 9902 in relation to other lines which define the mask, the pattern includes a varied interface at line 9902. The pattern at line 9902 resembles a set of steps.

Through the angle at line 9902, the pattern reduces instances of electrode breakage proximal to the transition zone. For example, in some embodiments, the electrode is etched and exhibits undercutting at the border between a masked portion and a non-masked portion. Parallel to this border is an axis which approximately bisects the undercut. Undercutting, in varying embodiments, results in a portion of the electrode which is weak while bending along the axis which bisects the length of the undercut. However, in varying embodiments, the undercut portion of the electrode is strong when bending orthogonal to an axis bisecting the length of the undercut. Thus, undercutting increases bending stress more in certain directions. By arranging the masking patter in the manner illustrated, the undercut portions of the electrode can be controlled to improve the flexibility of the electrode which reduces instances of breaking or cracking.

FIG. 118B illustrates an example of a mask constructed out of a pattern of rounded squares arranged proximal to each other. In varying embodiments, line 9902 defines an area across which elongate shapes span. It is apparent upon reading and understanding these teachings that the elongate shapes can be constructed out of rounded blocks, and that the elongate shapes can be defined in other fashions.

In varying embodiments, the mask includes exposed area 9908. In one example, exposed area 9908 is sized such that undercutting at the exposed area 9908 during etch does not substantially weaken the electrode under bending stress.

FIG. 118C illustrates one example of a halftone suitable for strengthening an electrode at the juncture between a masked portion and an unmasked portion. In one embodiment, the halftone is comprised for smaller rounded blocks 9904, and larger rounded blocks 9906. In one embodiment, the reach of the halftone is defined by a line 9902, and is limits to a transition zone proximal to the line 9902. In additional embodiments, the halftone is not defined as such.

In varying embodiments, the halftone transitions from covering approximately 80% of the electrode at the masked transition zone, to covering approximately 60% of the electrode at the masked transition zone. In varying embodiments, this can be accomplished with rounded blocks placed proximal to each other, and in additional embodiments, it is accomplished with other shapes arranged in a predictable pattern, such as a grid, or in a random pattern.

FIG. 118D illustrates an example of a halftone suitable for strengthening an electrode at the junction between a masked portion and an unmasked portion.

FIG. 118E illustrates an example of a pattern useful for strengthening an electrode in the region of a transition from a masked area to an unmasked area, according to various embodiments of the present subject matter. By including a sinusoidal shape which spans the line 9902, the instances of undercutting which are parallel to the bending line (the bending line is approximately parallel to transition line 9902) are minimized.

FIG. 118F illustrates a pattern for strengthening an electrode in an area where undercutting is put in bending stress, according to various embodiments of the present subject matter. In varying embodiments, the pattern is comprised of elongate shapes 9910. In varying embodiments, the elongate shapes demonstrate an improved resistance to cracking and breaking when the etched foil is subjected to bending stresses which are proximal the transition line 9902.

FIG. 119 shows a process for producing a foil 9950 with a partially etched area, according to various embodiments of the present subject matter. In varying examples, the process includes depositing a curable mask onto a foil 9952. For example, in one embodiment, the mask is deposited on a foil using a computer controlled mask dispensing system. In one example, ink is deposited using an ink jet process.

The control systems shown and described here can be implemented using software, hardware, and combinations of software and hardware. As such, the term "system" is intended to encompass software implementations, hardware implementations, and software and hardware implementations.

In various embodiments, the methods provided above are implemented as a computer data signal embodied in a carrier wave or propagated signal, that represents a sequence of instructions which, when executed by a processor, cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Additional embodiments cure the mask onto the foil 9954. Examples of curable mask include ink, and photoresist. In varying embodiments, the curable mask is cured to the foil. For example, in one embodiment, ink is deposited on the foil, and then is baked to the foil in an oven. Baking, in some embodiments, exposes the curable mask to radiant heat energy, which can increase hardness or the curable mask, and which also can decrease the time needed for curing. In varying embodiments, the oven is adapted to cure the curable mask without affecting the foil otherwise.

In varying embodiments, the foil is etched 9956, and the mask protects the foil from the etchant. Etching, in varying embodiments, is described in the discussion associated with FIG. 17, but in other embodiments, variations of the etching process are used.

Varying examples of the process then remove the mask 9958. Removing the mask, in one embodiment, includes submerging the foil with mask in a solution adapted to dissolve the mask.

Some embodiments anodize the foil 9960. Anodization, in one embodiment, is accomplished by the process discussed in the teachings associated with FIG. 17. However, these teachings should not be understood to be exhaustive or exclusive, and other methods of forming a dielectric on a foil are within the scope of the present subject matter. Additionally, it should be noted that other examples anodize the foil while the mask is in place.

Varying embodiments cut the anodized foil into shapes 9962, and in some examples, the foil shapes are then assembled into a capacitor 9964.

FIG. 120 shows a flat capacitor 10100, according to one embodiment of the present subject matter. Capacitors must include at least one anode element and at least one cathode element, but are not constrained to one shape by design. Capacitors which are substantially planar, in various embodiments, offer a geometry which is beneficial for packaging. Substantially planar capacitors offer additional benefits as well, such as improved performance and manufacturing efficiency. It should be noted, however, that although capacitor 10100 is D-shaped and substantially planar, in varying embodiments, the capacitor is shaped differently, including other symmetrical or asymmetrical shapes.

Capacitor 10100 includes a case, which in some embodiments includes at least two components; a substantially flat surface and connected sidewalls which form a cup-shaped receptacle, and a substantially flat cover. In various embodiments, the case has one or more openings, and the cover conforms to one of the openings. In one embodiment, the cover is located approximately parallel to substantially planar surface 10102. In one embodiment, the case 10114 includes a curvature 10116 which allows the case to be placed in receptacles which conform to the curvature. Among other benefits, the case is useful to retain electrolyte in capacitors using a fluidic electrolyte. In other words, various examples of the present subject matter comprise flat capacitors with a number of electrodes stacked and placed in a case, with the case filled with electrolyte.

It should be noted that in various embodiments, the case and cover include openings which are formed, in part, by features present in one or both the cover and the case. For example, in one embodiment, the cup-shaped receptacle includes a semi-circle shaped edge discontinuity, and the cover includes a semi-circle edge discontinuity, and when they are assembled, they form a circle shaped opening in a case.

In accordance with the design requirement of retaining electrolyte, in various examples, the case and the cover mate to form a seal. Varying embodiments use welding to join the case and the cover. For example, in one embodiment, the cover is laser welded to the case 10114. In one embodiment, the weld is performed by an approximately 1064 nm Yag laser weld with an energy range of approximately 2.5 joules to 3.5 joules. Other embodiments use mechanical locks to join the cover and case, or various forms of adhesive. Some embodiments use a combination of known joining methods, including crimping combined with welding. Preferred designs form a seal between the case and the cover which resists the flow of electrolyte.

In various embodiments, the capacitor of the present invention includes an anode conductor 10104 and a cathode conductor 10106. In various embodiments, these conductors connect the anode of the capacitor stack and the cathode of the capacitor stack with electronics which are located external to the capacitor. In various embodiments, one or both of these conductors are electrically isolated from the capacitor case. In one example, the case 10114 of the capacitor is electrically conductive and comprises a portion of the cathode. This exemplary variant is manufactured from aluminum, and connected to the cathode of the capacitor stack using a connection means internal to the case 10114. In other embodiments, the case is manufactured using a nonconductive material, such as a ceramic or a plastic. It should be noted that the case can also comprise a portion of the anode.

In embodiments where the capacitor case forms part of a set of capacitor electrodes, one way to economically connect a conductor to the desired portions of the capacitor stack is to connect the conductor directly to the exterior of the case. In various embodiments, attaching an electrode to the case is facilitated by a plate. One example uses a plate 10110 which is electrically conductive, and which is laser welded to the case 10114, placing the plate 10110 in electrical communication with the case 10114. In one embodiment, the weld is performed by an approximately 1064 nm Yag laser weld with an energy range of approximately 1.5 joules to 2.5 joules. The seal formed by welding a plate to a case, in various embodiments, is sufficient to restrict the flow of electrolyte. In one example, cathode conductor 10106 is arc percussion welded to the plate 10110. The result of this process is that the conductor is placed in electrical communication with the capacitor stack located inside the case. In other words, in one embodiment, the cathode conductor 10106 is percussion welded to the plate 10110, which is laser welded to the case 10114, which is in electrical communication with the cathode of the capacitor stack placed inside the case 10114.

Additionally, in various examples, the plate includes an aperture sealed by a plug. In one example, a plug 10108 is laser welded to the plate 10110. In one embodiment, the weld is performed by an approximately 1064 nm Yag laser weld with an energy range of approximately 1.5 joules to 2.5 joules. In varying embodiments, the plug and aperture are used to fill the capacitor case with electrolyte. The seal formed by welding the plug to the plate is, in some examples, sufficient to restrict the flow of electrolyte.

Varying embodiments of the present subject matter include a conductor feedthrough in the case. In various embodiments, a feedthrough enables a conductor to provide a conductive path from the exterior of the case to the interior of the case without conducting electricity to the case. An exemplary embodiment includes a cathodic case 10114 and uses a feedthrough to put the anode of the capacitor stack in electrical communication with electronics external to the case 10114, in a manner isolated from the cathodic case. The example uses the anode conductor 10104, which passes through the feedthrough, to conduct electricity. Because the feedthrough passageway comprises a hole in the case, in embodiments where the capacitor is filled with electrolyte, the feedthrough passageway must be sealed. To seal the feedthrough passage, various examples include a curable resin disposed between the case and the conductor, the curable resin conforming to the feedthrough passage, and resisting the flow of electrolyte. In one example, the curable resin 10112 is an epoxy conforming to the feedthrough passageway and bonded to the anode conductor 10104 and the case 10114. Varying embodiments form a hermetic seal.

Overall, the present subject matter enables various improvements over the current art. For example, by eliminating the need to pass one or more conductors through the case by directly connecting the conductor to the plate, the cost of capacitor manufacturing can be reduced, and complexity affecting reliability and manufacturing can be reduced. By using a plate, a capacitor design can include a case of varying thicknesses. In one embodiment, the thickness of the insert plate is 0.030 inches. In varying embodiments, insert plates run from approximately 0.020 inches thick to 0.040 inches thick. In varying embodiments, the insert plate is combined with a case this is approximately 0.010 inches thick. Additionally, in one embodiments, a case which is from about 0.008 inches thick to about 0.015 inches thick.

For example, in one embodiment, the plate mounts coplanar to the exterior of the case, but extends into the capacitor deeper than does the thickness of the case 10114. One benefit of this design is that a welding process for connecting a conductor to the case may be used which requires material thickness greater than that of the case 10114. For example, one embodiment uses arc percussion welding with parameters which are sufficient to weld a conductor to the plate 10110, but which would damage the case 10114 if the conductor were welded to the case 10114. In other words, the present subject matter allows using a capacitor with a case which is too thin for some metal bonding processes, but which is otherwise sufficient to satisfy other requirements of the case, such as retaining electrolyte and a capacitor stack. This design, in various embodiments, allows for a reduction in case thickness and mass, without sacrificing welding options available for connecting the conductor to the capacitor, ultimately providing for a smaller capacitor, and therefore, for a smaller implantable device.

FIG. 121 illustrates a close up view 10200 of the plate and plug of FIG. 120, according to one embodiment of the present subject matter. In various embodiments, the capacitor includes case 10114. In one embodiment, the case includes a curvature 10116 which is adapted to allow the capacitor to be placed in a similarly shaped receptacle. The example also includes a cathode conductor 10106, an anode conductor 10104, an curable resin 10112, a plate 10110, and a plug 10108. Additionally, various embodiments include an aperture which extends from the exterior of the case to the interior of the case, and which, in some examples, passes through the plate.

In one exemplary embodiment, plate 10110 is welded to case 10114 forming a seal which restricts the flow of electrolyte. Similarly, the aperture 10414 is sealed and resists the flow of electrolyte by welding the plug 10108 to the plate 10110, in various embodiments of the present subject matter.

It should be noted that in other embodiments of the present subject matter, the plate is fastened to the case with other fastening means, including a physical lock such as threads. Additionally, the plug 10108 is fastened to the plate with alternate fastening means, such as threads. These and other types of fastening designs are within the scope of the present subject matter, and the list enumerated here is not intended to be limiting.

FIG. 122 illustrates an exploded view of a capacitor 10100, according to one embodiment of the present subject matter. In various embodiments, cup shaped receptacle 10314 includes a feedthrough passageway 10308 which is formed in a sidewall of the cup shaped receptacle 10314. Additionally, a cover 10204 is adapted for conforming to an opening in the cup shaped receptacle 10314 of the case 10114. The feedthrough passageway 10308, in various embodiments, is useful to allow the passage of a conductor which connects external circuitry at one end to a capacitor stack at the other. Additionally, in various embodiments, a paper isolating element 306 is placed proximal to the feedthrough passageway 10308, and internal to the case. For example, in one embodiment, the anode conductor 10104 passes through the case and connects to the anode of the capacitor stack 10302. In some embodiments, case 10114 includes two or more feedthrough passageways.

Internal to various embodiments of the assembled capacitor is a terminal 10304, which is connected to the capacitor stack 10302 and to one of the group including the cup shaped receptacle 10314, the cover 10204, or both the cup shaped receptacle 10314 and the cover 10204. In various embodiments, a connection between the terminal 10304 and the cover 10204 is formed by pinching the terminal 10304 during assembly of the capacitor stack 10302, the cup-shaped receptacle 10314, and the cover 10204. Various embodiments connect terminal 10314 to the electrode stack 10302 using additional means, such as welding.

In one example, the cathode conductor 10106 is connected to the plate 10110, which is connected to the cup shaped receptacle, which is connected to terminal 10304, which is connected to the cathode of the capacitor stack 10302. Additionally, a plug 10108 is attached to the plate 10110.

The capacitor stack 10302, in various embodiments, is constructed in a shape which approximates the interior space in the receptacle, in order to reduce unused space, which can reduce capacitor size, and concomitantly, device size. One method of reducing device size includes choosing components in the capacitor stack to adjust the physical dimensions of the capacitor stack 10302. For example, in one embodiment, anode layers are added or subtracted from the stack, resulting in a capacitor stack 10302 which matches the interior volume of a particular case. In this exemplary embodiment, the capacitor stack includes 20 cathode layers, and 58 anode layers, but it should be understood that other embodiments include different numbers of elements.

FIG. 123A illustrates the front view of a plate 10110, according to one embodiment of the present subject matter. In various embodiments, the plate 10110 includes an aperture 10414. Some embodiments include an aperture 10414 with a first portion 10202, and a second portion 10206. Various embodiments of the first portion 10202 and the second portion 10206 comprise coaxial cylindrical shapes with varying diameters. Additionally, various embodiments of the plate include a first major surface 10410.

In various embodiments, the plate 10110 is shaped like an irregular pentagon with three rounded adjacent apexes which are approximately 90 degrees, and two rounded adjacent apexes which are obtuse angles. However, it should be noted that other plate shapes are within the scope of the present subject matter.

FIG. 123B illustrates a cross section of a side view of a plate 10110, according to one embodiment of the present subject matter. The view cuts the plate 10110 through the aperture 10414. In various embodiments, the aperture 10414 includes a first portion 10202. Various examples of the aperture 10414 are shaped like a counterbore, with the first portion 10202 comprising a larger diameter, the second portion comprising a smaller diameter, and the difference between the two diameters comprising a substantially planar step shape defined by the concentric circles of the perimeters of the first and second portions. In various embodiments, the first portion 10202 opens to the first major surface 10410. In additional embodiments, the first portion 10202 has a depth of t1, and the second portion 10206 has a depth which is the distance of the depth t1 subtracted from the thickness of the plate 10110.

In various embodiments, the aperture is adapted to mate with a plug, as is demonstrated by the plate 10110 and the plug 108 of the exemplary illustration of FIG. 121. In various embodiments, the plug 10108 roughly matches the shape defined by the first portion 10202 of the aperture 10414. In embodiments using the plug to form a seal with the aperture, a plug is selected which includes a thickness which is approximately equal to the thickness t1. In various embodiments, the surface of the plug is roughly coplanar with the surface of the plate once installed. Various examples of the present subject matter affix the plug to the plate 10110 using welding, an interference fit, adhesive, threads, or various additional forms of attachment. On embodiment uses laser welding. In one embodiment, the weld is performed by an approximately 1064 nm Yag laser weld with an energy range of approximately 1.5 joules to 2.5 joules. In various embodiments, the plate is adapted to mate with an opening in a case 10114, as illustrated in the example of FIG. 120. For instance, in one embodiment, the plate is shaped to restrict its passage through an opening in the case 10114. Accordingly, one example of the plate includes a step 10402 which divides the plate into a first section with a first major surface 10410, and a second section with a second major surface 10412. In one embodiment, the first major section 10410 is sized for passage through an opening in a case 10114, and the second major section is sized so that it cannot pass through the same opening. In one embodiment, the face of the step 10402 is positioned proximal to an interior surface of case 10114, and is further positioned proximal to an opening in the case 10114.

In various embodiments, the plate includes a thickness t2. In various embodiments, the thickness t2 is selected to match the thickness of a capacitor case, including the case illustrated in the example of FIG. 120. In examples where t2 matches the thickness of a capacitor case, the major face 10110 is coplanar with the exterior of a capacitor case when the plate 10110 is attached to the capacitor case. It should be noted that the relationship between t1 and t2 is not intended to be exhaustive or exclusive, and it provided solely for illustration.

Generally, the thickness of the plate 10110 depends on the type and nature of the contents of the capacitor. In general, a thickness is chosen which is compatible with desired manufacturing processes. For example, in embodiments where a conductor is welded to the plate 10110, a plate thickness is chosen which will result in a final plate shape, after welding, which is substantially similar to the shape of the plate prior to the welding process. In other words, in various embodiments, the thickness of the plate is selected to minimize warpage due to thermal stress applied to the plate 10110 due to various processes, including welding.

In general, the plate can be manufactured by machining, powdered metallurgy, or by stamping. Additional forming processes are also within the scope of the present subject matter. In various embodiments, the transition between the first portion 10202 of the aperture and the second portion of the aperture 10206 is designed with the objective of enabling laser welding. In some examples, enabling a laser weld requires that the transition include step shapes which are largely perpendicular. Varying embodiments of a laser welding process require a step shape to limit laser energy from extending beyond the welding area.

FIG. 124 shows a side view of conductor 10106 attached to a plate 10110 with a first major face 10410, according to one embodiment of the present subject matter. In various embodiments, the conductor 10106 includes a wire 10510 and a coupling member 10512, and one or more arc percussion welding areas, 10506, 10508, 10502 and 10504. In various embodiments, the wire 10510 is attached to the coupling member 10512 using a crimping process, a welding process, or other processes. In one embodiment, the coupling member 10512 is arc percussion welded to the wire at one or more areas. In various examples, areas 10506 and 10508 are used for applying an arc-percussion weld. Additionally, the coupling member 10512 is arc-percussion welded to a plate 10110 in various embodiments, and in one embodiment the coupling member 10512 is arc percussion welded at areas 10502 and 10504. Because of the nature of arc percussion welding, the mating region between the plate 10110 and the coupling member 10512 must be chosen to enable a desired form of weld. In one example, coupling member 10512 and plate 10110 include substantially planar faces which are adapted to mate with each other.

An exemplary arc percussion welding machine is manufactured by Morrow Tech Industries of Broomfield, Colo. In this embodiment, the conductor 510 and coupling members are not crimped together. However, some embodiments include both welding and crimping.

It should be noted that in some embodiments, the wire 10510 and the coupling member are one piece. Additionally, it should be noted that other forms of conductor 10106 which are adapted for percussion welding to a plate 10110 are within the scope of the present subject matter.

FIG. 125 shows a cross-sectional side view of details of one embodiment of feedthrough assembly 10620. In some examples, a means is available for connecting the capacitor stack contained in the case to electronics which are located outside of the case. In some of these embodiments, the connecting means is of one polarity, and the capacitor case is of another polarity. In these embodiments, it is necessary to provide a structure for allowing electricity to pass through the case wall without contacting the case wall. In various embodiments, the feedthrough assembly 10620 provides one embodiment adapted for providing this. In varying examples, the feedthrough assembly 10620 includes a feedthrough passageway 10308 which is drilled, molded, punched, or otherwise formed in a portion of a sidewall of the case 10114. Additionally, in some embodiments, the feedthrough passageway is located in a plate, or is located partially in a case and partially in a plate. For example, in one embodiment, one half of a feedthrough passageway is located in a plate or cover and one half of a feedthrough passageway is located in a case.

In some embodiments, the feedthrough assembly 10620 includes an anode conductor 10104 which is attached to the anode of the capacitor. Varying embodiments of the capacitor anode include one or more anode members 10608 which are coupled to anode conductor 10104 for electrically connecting the anode to circuitry outside the case 10114. In one embodiment, anode members 10608 are edge-welded to each other. Edge-welding the anode members 10608, in various embodiments, provides a flat connection surface 10410. In some embodiments, anode members 10608 are crimped or soldered, and in further embodiments, the anode members 10608 are connected by an electrically conductive adhesive or by other means.

In some embodiments, a wire 10604 is coupled to a coupling member 606, forming, in part, an anode conductor 10104. Various embodiments of the present subject matter include attaching the wire 10604 to the coupling member 10606 using soldering, welding, crimping, and other methods sufficient to connect the wire 10604 to the coupling member 10606, in varying embodiments. In one embodiment, anode conductor 10104 is a single, substantially unified metallic crystalline member.

In one embodiment, coupling member 10606 is a high-purity aluminum member which is able to withstand the high voltages generated within the capacitor case. In other embodiments it is made from another conductive material compatible with the capacitor stack 10302. In various embodiments, one side of the coupling member 10606 includes a planar surface for attaching to the planar surface 10610 presented by edge-welded capacitor stack 10608.

In one embodiment, coupling member 10606 is laser welded to surface 10610 of capacitor stack 10302 using a butt-weld. Alternatively, coupling member 10606 is attached using other means. Butt-welding coupling member 10606 directly to capacitor stack 10302 provides an electrical connection between capacitor stack 10302 and the conductor. Also, since coupling member 10606 is directly attached to capacitor stack 10302, it supports the conductor while a curable resin 10112, such as an epoxy, is applied to the feedthrough passageway area.

In one embodiment, feedthrough passageway 10308 is in part defined by an edge which is tapered to improve the surface area available to a bonding agent. Curable resins bond to surfaces, and as such, can create a larger bonding areas when applied to a larger surface area. A larger bond, in various embodiments, is more robust, reliable, and is less likely to permit leaks. Additionally, in one embodiment, a larger bonding area can increase the distance between the coupling member and the case by including a larger feedthrough passage. Accordingly, increased area can reduce instances of unwanted arcing. A tapered edge, in various embodiments, includes these benefits.

For example, in one embodiment, a feedthrough passageway includes an inbound narrowing sidewall 10624 extending to a lip 10622. In various embodiments, a cavity is defined by the sidewall 10624, the coupling member 10606, and an isolating element 10306. A curable resin 10112, in various embodiments, is disposed in the cavity and hardened, and serves to insulate the case 10114 from the anode conductor 10104, and further serves as a seal to resist the flow of electrolyte 10602. For example, in one embodiment, the conductor is an uninsulated anode conductor 10104 connected to the anode of the capacitor stack, the anode conductor 10104 passing through a feedthrough passageway 10308 in a cathodic case 10114. In this exemplary embodiment, a curable resin 10112 is used to seal electrolyte 10602 into the capacitor, and is further used to insulate the anodic elements, such as the coupling 10606, from the cathodic elements, such as the case 10114. In one example, the curable resin 10112 is a hardened two-part quick-setting thermal-set epoxy.

In one embodiment, an isolating element 10306 is combined with the conductor 10104, the feedthrough passageway 10308, and the curable resin 10112. This combination, in various embodiments, in useful for restricting the flow of electrolyte 10602, curable resin 10112, or both. In various embodiments, the isolating element 10306 is a paper washer which assists in limiting the flow of curable resin 10112 to a desired area. One benefit of using an isolating element 10306 to restrict the flow of a curable resin, such as epoxy, is that the epoxy is less likely to flow into other locations within the capacitor, which can adversely affect capacitor performance.

In varying embodiments, the feedthrough passageway 10308 is assembled to the capacitor stack and seals to the capacitor stack surface 10610, and in additional embodiments, the feedthrough passageway 10308 seals to the coupling member 10606. In one embodiment, the feedthrough passageway 10308 includes a lip 10622 adapted for forming a circular seal with the coupling member 10606. In various embodiments, because of the nature of assembly, including imperfect manufacturing tolerances and imperfect surface finishes, the effectiveness of the seal formed between the feedthrough passageway 308 and the coupling member 10606 is limited. To increase the effectiveness of the seal, in various embodiments, an isolating element 306 is located between the feedthrough passageway 10308 and the coupling member 10606 which is compressible, and which resists the flow of electrolyte and resists the flow of epoxy. In one embodiment, the isolating element 10306 is constructed from paper which is of a thickness which can absorb manufacturing irregularities, such as surface finish irregularities and manufacturing tolerance irregularities, while providing a seal.

In additional embodiments, the isolating element 10306 is useful for providing electrical insulation between the case 10114 and the anode conductor 10104. In one embodiment, the isolating element is made from separator paper. For example, in various embodiments, the case is cathodic, and an anodic coupling 10606 must be electrically isolated from the case 10114 for the capacitor to function. Additionally, in various embodiments, to reduce the size of the capacitor, the anode conductor 10104 and the case 10114 are placed near one another. Therefore, in various embodiments, to reduce instances of arc between the case and the anodic conductor 10104, an insulative element 10306 is disposed between the case 10114 and the anode conductor 10104.

In various embodiments, a curable resin 10112 is any of numerous clear to translucent yellow or brown, solid or semi-solid, viscous substances of plant origin, such as copal, rosin, and amber, used principally in lacquers, varnishes, inks, adhesives, synthetic plastics, and pharmaceuticals. Additionally, curable resin 10112 includes any of numerous physically similar polymerized synthetics or chemically modified natural resins including thermoplastic materials such as polyvinyl, polystyrene, and polyethylene and thermosetting materials such as polyesters, epoxies, and silicones that are used with fillers, stabilizers, pigments, and other components to form plastics. It should be noted that the sealing members listed here are not a complete list of the sealing members within the scope of the present subject matter. For example, various examples include sealing members which provide a non-hermetic seal, and one embodiment includes a substantially elastic plug.

It should be noted that the embodiments enumerated here, in which an anode conductor passes through a feedthrough assembly, are only examples of the present subject matter. Additional embodiments include a cathode conductor passing through a passageway in an anodic capacitor case. Further, additional embodiments include multiple feedthrough passages, and some include a case which is neither anodic nor cathodic.

FIG. 126 shows a method 10700 for manufacturing an implantable cardioverter defibrillator according to one embodiment of the present subject matter. In various embodiments, the method includes providing a capacitor receptacle with at least two openings 10702. For example, various embodiments include a cup-shaped receptacle, with a major surface and side-walls extending from the surface and forming a dish-shaped volume. In one embodiment, the receptacle side-walls include two openings: a first opening which is adapted for mating with a plate, and a second opening which is adapted for mating with a cover. In various embodiments, the receptacle is a conductive metal, and in one embodiment, the receptacle is aluminum.

In various embodiments, the method includes attaching a plate to one of the openings in the receptacle 10704. In various examples, the plate is sized for mating with the first opening. In some examples, the plate is substantially planar, and cannot pass through the first opening when positioned approximately parallel to the sidewall which includes the opening. Additionally, in various embodiments, the plate is sized thicker than the sidewall of the receptacle. In embodiments where the sidewall is not of a uniform thickness, the plate is thicker than at least part of the sidewall proximal to the opening to which the plate is attached.

Varying embodiments attach the plate using a welding process. In one embodiment, the plate is attached using a laser welding process. In other embodiments, the plate is attached to the receptacle using other means, such as threads or a mechanical lock. In various forms, attaching the plate to the receptacle forms a seal, and in some embodiments the seal resists the flow of electrolyte.

Various embodiments of the present subject matter include a plate adapted for attachment of a terminal. Various embodiments include attaching a terminal to the plate 10706. For example, in various embodiments, a terminal is welded to the plate. In one embodiment, a terminal is percussion welded to the plate. In various embodiments, the parameters of the percussion weld require a plate of a minimum thickness, and the plate is sized to approximate that thickness. By sizing the plate to approximately match the required parameters of the welding process, only a portion of the capacitor case is produced at that thickness, allowing the remaining portions, which are not welded to, to be thicker or thinner. In one embodiment, a thinner receptacle is used, which results, in various embodiments, in a capacitor which is smaller and lighter.

In various examples, a capacitor stack is placed in the capacitor receptacle through the second opening 10708. Additionally, various embodiments include attaching a cover to the second opening 10710. Attaching the cover includes, in various embodiments, includes welding the cover to the receptacle. In one embodiment, a seal is created using a laser welding process which resists the flow of electrolyte.

Various embodiments also include filling the receptacle with electrolyte 10712, and sealing the receptacle to resist the flow of electrolyte 10714. For example, in one embodiment, an aperture provides access to the interior volume formed by attaching the plate and the cover to the receptacle. In various embodiments, the aperture is the only access to the interior of the capacitor case which does not resist the flow of electrolyte. In various embodiments, the method of the present subject matter includes filling the volume with electrolyte. For example, in various embodiments, the volume is filled, and later pressurized to encourage the escape of gasses from the interior volume of the capacitor. In one embodiment, the gases escape through the aperture. Various embodiments include sealing the aperture after the capacitor has been filled with electrolyte to resist the flow of electrolyte.

FIG. 127 shows a method 10800 for manufacturing an implantable cardioverter defibrillator, according to one embodiment of the present subject matter. For example, in various embodiments, a receptacle is provided with a first opening and a second opening 10802. In some embodiments, a plate is inserted 10804 into the receptacle and attached 10806 to the first opening. In one embodiment, the plate is substantially planar and is sized so that it cannot pass through the first opening when positioned approximately parallel to the plate formed by the perimeter of the opening.

In various embodiments, the plate includes an aperture. In one embodiment, the plate is inserted and attached to the receptacle, a capacitor stack is installed in the receptacle 10808, and a cover is attached to the receptacle 10810. The exemplary embodiment is assembled forming a seal which resists the flow of electrolyte, excluding the aperture. Various examples which are sealed to resist the flow of electrolyte are filled with electrolyte 10812, which substantially impregnates the interior volume of the capacitor case. Various examples use a pressure differential to encourage the impregnation of the interior volume of the capacitor with electrolyte.

Various examples plug the aperture with a member 10814, which can be attached in a number of ways, including welding, interference fit, threading, and other means suitable for forming a sealed attachment. In one embodiment, the aperture is sealed by laser welding a disc shaped plug into a similarly shaped counterbore in the aperture.

FIG. 128 shows a method 10900 for manufacturing an implantable cardioverter defibrillator according to one embodiment of the present subject matter. In various embodiments, the method of the present subject matter includes assembling a stack with at least one terminal 10902. In various embodiments, a paper isolating element 306 is assembled to the terminal 10904. In one exemplary embodiment of the present subject matter a paper washer is inserted onto a terminal which is shaped like a boss.

In various embodiments, the assembled capacitor stack is placed into a receptacle with a first opening and a second opening 10906. Various examples of the method of the present subject matter include aligning the terminal with the first receptacle opening. One example includes aligning the terminal with the first receptacle opening so that the terminal passes at least part of the way through the receptacle opening.

Various embodiments attach a cover to the second receptacle opening 10909. Various embodiments include attaching the cover using a welding process, including laser welding. Additional embodiments include attaching the cover with various additional methods, including using mechanical locks, rivets, fasteners, or other forms of fastening methods. In various embodiments, attaching the cover to the second receptacle opening includes forming a seal between the cover and the receptacle. In one example, the seal is adapted for resisting the flow of electrolyte.

In various embodiments, a sealing member is used to seal the terminal to the first opening 10910. For example, in various embodiments, an epoxy is used to seal the space between the terminal and the first opening. In one exemplary embodiment of the present subject matter the paper isolating element 10306 is adapted to interface with the first opening and the terminal to form a seal which is adapted to localize the epoxy proximal to the interface between the paper insert, the terminal, and the second opening. In other words, the paper isolating element 10306 is adapted to limit the epoxy to wetting proximal to the terminal, the first opening, and the paper insert.

It should be noted that the methods of the present subject matter, in various embodiments, include inserting the assembled capacitor into an implantable medical device suited for delivering electrical stimulation to a patient. In one embodiment, the method of the present subject matter includes installing a capacitor in a implantable cardioverter defibrillator which is adapted for implant in a patient, and which is also adapted to deliver high voltage pulses to a patient in order to promote cardiac wellness. For example, in various embodiments, one method of the present invention includes providing a defibrillator case having circuitry disposed in the case. Additionally, various embodiments include implanting an implantable cardioverter defibrillator in a patient. Also, some examples include connecting the cardiac system of a patient to the implantable cardioverter defibrillator. In one example, circuitry in the capacitor controls the discharge of electrical energy from the capacitor to the patient. Overall, in various embodiments, the method of the present invention enables improved delivery of electrical stimulation to a patient using an implantable cardioverter defibrillator.

Overall, the present subject matter offers multiple advantages. First, the present subject matter features capacitor designs which are compact and lightweight due to improved volumetric energy density. Smaller capacitors can enable smaller implantable medical devices, which tend to increase patient comfort. Additionally, increasingly effective capacitors can do the work of two less effective capacitors, reducing size and complexity of devices using capacitors. Reduced complexity can increase reliability and reduce manufacturing costs.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments, will be apparent to those of skill in the art upon reviewing the above description. The scope of the present subject matter should be determined with reference to the appended claims, along with the full scope of equivalents to which such claims are entitled.

What is claimed is:

1. A method of producing an apparatus for use in a patient, comprising:
    etching an anode foil;
    anodizing the anode foil;
    assembling the anode foil, at least one cathode foil and one or more separators into a capacitor stack adapted to deliver from about 5.3 joules per cubic centimeter of capacitor stack volume to about 6.3 joules per cubic centimeter of capacitor stack volume, with the capacitor adapted to deliver maximum energy for a defibrillation pulse at a voltage of between about 465 volts to about 620 volts;
    inserting the stack into a capacitor case;
    inserting the capacitor case into a device housing adapted for implant in a patient;
    connecting the capacitor to a component; and
    sealing the device housing.

2. The method of claim 1, wherein anodizing the anode foil includes forming a hydrous oxide layer on an aluminum foil.

3. The method of claim 1, wherein anodizing the anode foil includes forming a dielectric layer with a thickness of less than approximately 1200 nanometers.

4. The method of claim 1, wherein anodizing the anode foil includes forming a dielectric layer from about 600 nanometers to about 800 nanometers thick.

5. The method of claim 1, further comprising:
    forming a hydrous oxide layer on the anode foil;
    anodizing the anode foil in a bath containing an aqueous solution of approximately 10 to approximately 120 grams per liter boric acid and approximately 2 to approximately 50 parts per million phosphate as electrolyte at a pH of 4.0 to 6.0 and a temperature of approximately 85 degrees Celsius to approximately 95 degrees Celsius, whereby said foil can be anodized to approximately 760 V without scintillation; and
    interrupting the anodizing process to stabilize the anode foil in a mildly alkaline bath.

6. The method of claim 4, wherein the anodization occurs from approximately 600 volts to approximately 760 volts.

7. The method of claim 5, wherein the anodization occurs from about 650 volts to about 720 volts.

8. The method of claim 6, wherein the anodization occurs from about 670 volts to about 710 volts during formation.

9. The method of claim 4, wherein the resistivity of said electrolyte is approximately 1500-3600 ohm-centimeters.

10. The method of claim 4, wherein the phosphate is phosphoric acid.

11. The method of claim 4, wherein the pH of the aqueous solution of approximately 10 to approximately 120 grams per liter is attained by the addition of a reagent selected from one of the group including ammonium and alkali metal hydroxides and ammonium and alkali metal salts.

12. The method of claim 10, wherein said reagent is selected from the group consisting of sodium hydroxide and borax.

13. The method of claim 4, wherein the mildly alkaline bath includes an approximately 0.001 to approximately 0.05M borax solution having a pH of approximately 8.5 to approximately 9.5 and a temperature of at least 80 degrees Celsius.

14. The method of claim 12, wherein the borax solution is buffered by approximately 0.005 molar to approximately 0.05 molar sodium carbonate solution.

15. The method of claim 13, wherein interrupting includes removing the anode foil from the bath more than once, and dipping the anode in the mildly alkaline bath at least twice.

16. A method of producing an apparatus for use in a patient, comprising:
    etching an substantially planar anode;
    anodizing the substantially planar anode;
    assembling into a substantially flat capacitor stack the substantially planar anode, at least one substantially planar cathode and one or more separators electrically isolating the substantially planar anode from the substantially planar cathode, the substantially flat capacitor stack being adapted to deliver from about 5.3 joules per cubic centimeter of capacitor stack volume to about 6.3 joules per cubic centimeter of capacitor stack volume, with the capacitor adapted to deliver maximum energy for a defibrillation pulse at a voltage of between about 465 volts to about 620 volts; and
    inserting the substantially flat capacitor stack into a conductive capacitor case having at least one electrically insulated feedthrough adapted to electrically interconnect the capacitor stack;
    inserting the capacitor case into a device housing;

electrically connecting the capacitor to a component; and hermetically sealing the device housing.

17. The method of claim 16, wherein anodizing the cathode includes coating an aluminum substrate with a cathode coating including titanium oxide.

18. The method of claim 16, wherein anodizing the anode includes forming a dielectric layer from about 600 nanometers to about 800 nanometers thick.

19. A method of producing an apparatus for use in a patient, comprising:
- etching an substantially planar anode;
- anodizing the substantially planar anode from approximately 600 volts to approximately 760 volts until an aluminum oxide ($Al_2O_3$) layer from about 600 nm to about 800 nm forms;
- assembling the substantially planar anode, at least one substantially planar cathode and one or more separators into a substantially flat capacitor stack adapted to deliver from about 5.3 joules per cubic centimeter of capacitor stack volume to about 6.3 joules per cubic centimeter of capacitor stack volume, with the capacitor adapted to deliver maximum energy for a defibrillation pulse at a voltage of between about 465 volts to about 620 volts; and
- inserting the substantially flat capacitor stack into a capacitor case having at least one feedthrough adapted to electrically interconnect the capacitor stack;
- inserting the capacitor case into a device housing adapted for implant in a patient;
- electrically connecting the capacitor to a component; and sealing the device housing.

20. The method of claim 19, further comprising stacking a plurality of substantially planar anodes s with a plurality of substantially planar cathode s until the substantially flat capacitor stack has a mass of between approximately 10.7 grams and approximately 11.8 grams.

* * * * *